(12) United States Patent
Larson

(10) Patent No.: US 10,918,423 B2
(45) Date of Patent: Feb. 16, 2021

(54) SPINE-ANCHORED TARGETING SYSTEMS AND METHODS FOR POSTERIOR SPINAL SURGERY

(71) Applicant: Howmedica Osteonics Corp., Mahwah, NJ (US)

(72) Inventor: Jeffrey John Larson, Coeur d'Alene, ID (US)

(73) Assignee: Howmedica Osteonics Corp., Mahwah, NJ (US)

(*) Notice: Subject to any disclaimer, the term of this patent is extended or adjusted under 35 U.S.C. 154(b) by 59 days.

(21) Appl. No.: 15/735,480

(22) PCT Filed: Jun. 10, 2016

(86) PCT No.: PCT/US2016/036976
§ 371 (c)(1),
(2) Date: Dec. 11, 2017

(87) PCT Pub. No.: WO2016/201292
PCT Pub. Date: Dec. 15, 2016

(65) Prior Publication Data
US 2018/0153592 A1   Jun. 7, 2018

Related U.S. Application Data

(60) Provisional application No. 62/253,280, filed on Nov. 10, 2015, provisional application No. 62/240,231, (Continued)

(51) Int. Cl.
*A61B 17/70* (2006.01)
*A61B 90/50* (2016.01)
(Continued)

(52) U.S. Cl.
CPC .......... *A61B 17/7074* (2013.01); *A61B 17/88* (2013.01); *A61B 90/11* (2016.02); *A61B 90/50* (2016.02); *A61B 17/1757* (2013.01)

(58) Field of Classification Search
CPC ............ A61B 17/7074; A61B 17/1757; A61B 17/7023; A61B 17/7001; A61B 17/7004;
(Continued)

(56) References Cited

U.S. PATENT DOCUMENTS 373,362 A   11/1887 Hamilton
1,382,783 A   6/1921 Howard
(Continued)

FOREIGN PATENT DOCUMENTS

JP   2004514528 A   5/2004
JP   2011500280 A   1/2011
(Continued)

OTHER PUBLICATIONS

International Search Report for Appl. No. PCT/US2016/036976 dated Sep. 2, 2016.
(Continued)

*Primary Examiner* — Tessa M Matthews
(74) *Attorney, Agent, or Firm* — Lerner, David, Littenberg, Krumholz & Mentlik, LLP

(57) ABSTRACT

A monopedicular targeting system for posterior spinal surgery includes a first joint component, a fastener for affixing the first joint component to a single pedicle, a positioning arm having a second joint component for mating with the first joint component to form a first joint having three rotational degrees of freedom, and a connector for coupling the spinal surgery device to the positioning arm. The connector has a third joint component that mates with a fourth joint component of a spinal surgery device to form a second joint having three rotational degrees of freedom. A mono-
(Continued)

pedicular targeting method for posterior spinal surgery includes affixing a fastener to a single pedicle and adjusting three translational degrees of freedom and three rotational degrees of freedom of a posterior spinal surgery device with respect to a pedicle of a vertebra by manipulating joints of a manipulator connecting the spinal surgery device to the fastener.

18 Claims, 68 Drawing Sheets

Related U.S. Application Data filed on Oct. 12, 2015, provisional application No. 62/174,342, filed on Jun. 11, 2015.

(51) Int. Cl.
*A61B 90/11* (2016.01)
*A61B 17/88* (2006.01)
*A61B 17/17* (2006.01)

(58) Field of Classification Search
CPC ............ A61B 17/7014; A61B 17/7025; A61B 17/7032; A61B 17/7041; A61B 17/7049; A61B 17/7064; A61B 90/50
See application file for complete search history.

(56) References Cited

U.S. PATENT DOCUMENTS

| | | |
|---|---|---|
| 1,397,090 A | 11/1921 | Dimas |
| 1,440,401 A | 1/1923 | May |
| 1,460,697 A | 7/1923 | Bendlin |
| 3,278,207 A | 10/1966 | Barash et al. |
| 3,858,578 A | 1/1975 | Milo |
| 4,143,652 A | 3/1979 | Meier et al. |
| 4,946,458 A | 8/1990 | Harms et al. |
| 5,344,422 A | 9/1994 | Frigg |
| 5,865,730 A | 2/1999 | Fox et al. |
| 6,013,027 A | 1/2000 | Khan et al. |
| 6,036,641 A | 3/2000 | Taylor et al. |
| 6,193,652 B1 | 2/2001 | Berky et al. |
| 6,210,325 B1 | 4/2001 | Bartie et al. |
| 6,234,961 B1 | 5/2001 | Gray |
| 6,241,655 B1 | 6/2001 | Riess |
| 6,315,718 B1 | 11/2001 | Sharratt |
| 6,331,158 B1 | 12/2001 | Hu et al. |
| 6,364,883 B1 | 4/2002 | Santilli |
| 6,394,951 B1 | 5/2002 | Taylor et al. |
| 6,506,149 B2 | 1/2003 | Peng et al. |
| 6,663,563 B1 | 12/2003 | Sharratt |
| 6,758,808 B2 | 7/2004 | Paul et al. |
| 6,758,809 B2 | 7/2004 | Briscoe et al. |
| 6,860,877 B1 | 3/2005 | Sanchez et al. |
| 6,866,628 B2 | 3/2005 | Goodman et al. |
| 6,994,669 B1 | 2/2006 | Gannoe et al. |
| 7,137,949 B2 | 11/2006 | Scirica et al. |
| 7,182,731 B2 | 2/2007 | Nguyen et al. |
| 7,311,664 B2 | 12/2007 | Goodman et al. |
| 7,399,272 B2 | 7/2008 | Kim et al. |
| 7,479,104 B2 | 1/2009 | Lau et al. |
| 7,655,012 B2 | 2/2010 | DiPoto et al. |
| 7,736,307 B2 | 6/2010 | Hu et al. |
| 7,753,844 B2 | 7/2010 | Sharratt et al. |
| 7,927,343 B2 | 4/2011 | Hill et al. |
| 8,016,835 B2 | 9/2011 | Birkmeyer et al. |
| 8,382,048 B2 | 2/2013 | Nesper et al. |
| 8,460,172 B2 | 6/2013 | Meyer et al. |
| 8,460,310 B2 | 6/2013 | Stern |
| 8,469,032 B2 | 6/2013 | Farnum |
| 8,485,484 B2 | 7/2013 | Kronner et al. |
| 8,496,661 B2 | 7/2013 | Moore et al. |
| 8,808,176 B2 | 8/2014 | Menendez et al. |
| 8,814,919 B2 | 8/2014 | Barrus et al. |
| 9,078,635 B2 | 7/2015 | Menendez et al. |
| 9,307,891 B2 | 4/2016 | Carter et al. |
| 9,307,972 B2 | 4/2016 | Lovell et al. |
| 9,622,795 B2 | 4/2017 | Reitblat et al. |
| 2002/0077531 A1 | 6/2002 | Puchovsky et al. |
| 2002/0087161 A1 | 7/2002 | Randall et al. |
| 2003/0083555 A1 | 5/2003 | Hunt et al. |
| 2004/0127903 A1 | 7/2004 | Schlapfer et al. |
| 2004/0230202 A1 | 11/2004 | Tromanhauser et al. |
| 2005/0101954 A1 | 5/2005 | Simonson |
| 2005/0215862 A1 | 9/2005 | Larson et al. |
| 2005/0251192 A1 | 11/2005 | Shluzas et al. |
| 2006/0195017 A1 | 8/2006 | Shluzas et al. |
| 2006/0247651 A1 | 11/2006 | Roehm et al. |
| 2007/0055291 A1 | 3/2007 | Birkmeyer et al. |
| 2007/0162010 A1* | 7/2007 | Chao .................. A61B 17/7077 606/86 A |
| 2008/0071145 A1 | 3/2008 | Bjork et al. |
| 2008/0125788 A1* | 5/2008 | Cohen ................ A61B 17/7076 606/104 |
| 2008/0195154 A1 | 8/2008 | Brown et al. |
| 2008/0269757 A1 | 10/2008 | McMinn |
| 2008/0312692 A1 | 12/2008 | Brennan et al. |
| 2009/0062857 A1* | 3/2009 | Ramsay ............. A61B 17/1735 606/246 |
| 2010/0030377 A1 | 2/2010 | Unsworth |
| 2010/0137914 A1 | 6/2010 | Ritland |
| 2010/0137920 A1 | 6/2010 | Hammill, Sr. et al. |
| 2010/0191066 A1 | 7/2010 | Koysh et al. |
| 2010/0262196 A1 | 10/2010 | Barrus et al. |
| 2010/0286486 A1 | 11/2010 | Parker et al. |
| 2011/0160772 A1 | 6/2011 | Arcenio et al. |
| 2012/0116468 A1 | 5/2012 | Beverland et al. |
| 2012/0143269 A1 | 6/2012 | Ichelmann et al. |
| 2012/0330417 A1 | 12/2012 | Zipnick |
| 2013/0023735 A1 | 1/2013 | Brown et al. |
| 2014/0039556 A1* | 2/2014 | Rutschmann ...... A61B 17/7002 606/266 |
| 2014/0088649 A1* | 3/2014 | Refai ................... A61B 17/013 606/256 |
| 2014/0296650 A1 | 10/2014 | Weisshaupt et al. |
| 2014/0350346 A1 | 11/2014 | Oberlander et al. |
| 2015/0209119 A1 | 7/2015 | Theodore et al. |
| 2015/0313585 A1 | 11/2015 | Abidin et al. |
| 2016/0051241 A1 | 2/2016 | Vogtherr et al. |
| 2016/0262810 A1* | 9/2016 | Meyer ............... A61B 17/7076 |
| 2017/0065269 A1 | 3/2017 | Thommen et al. |
| 2019/0209154 A1* | 7/2019 | Richter ............. A61B 1/00045 |

FOREIGN PATENT DOCUMENTS

| | | |
|---|---|---|
| JP | 2012525890 A | 10/2012 |
| WO | 2012015668 A1 | 2/2012 |

OTHER PUBLICATIONS

Australian Search Report for Application No. 2016274981, dated Jan. 16, 2020, 1 page.

\* cited by examiner

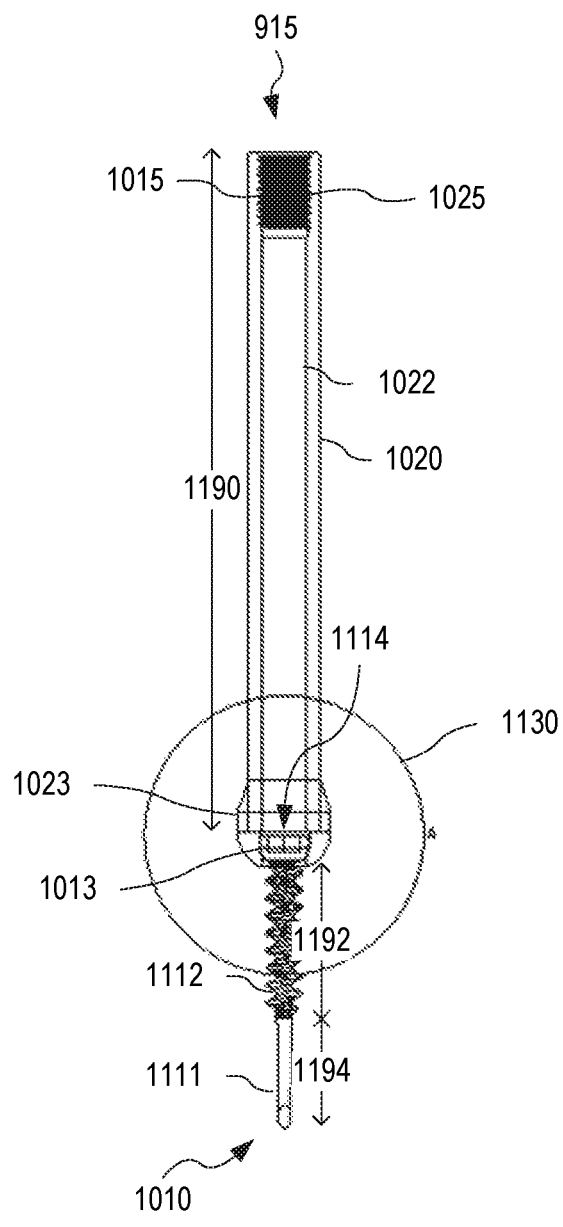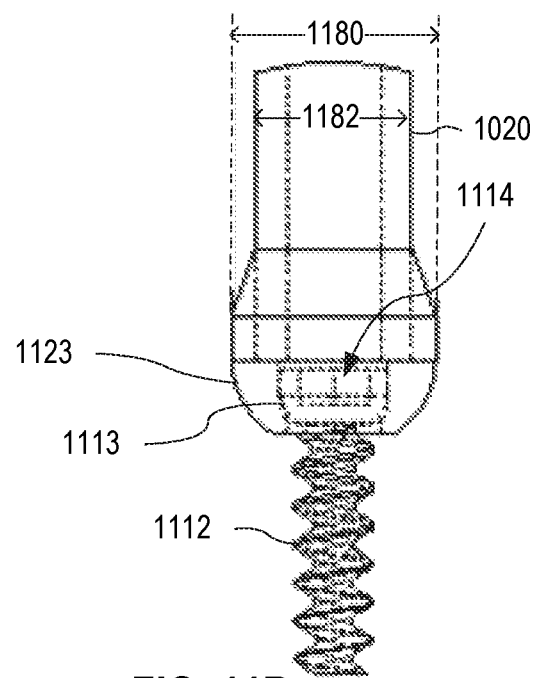
FIG. 11A
FIG. 11B

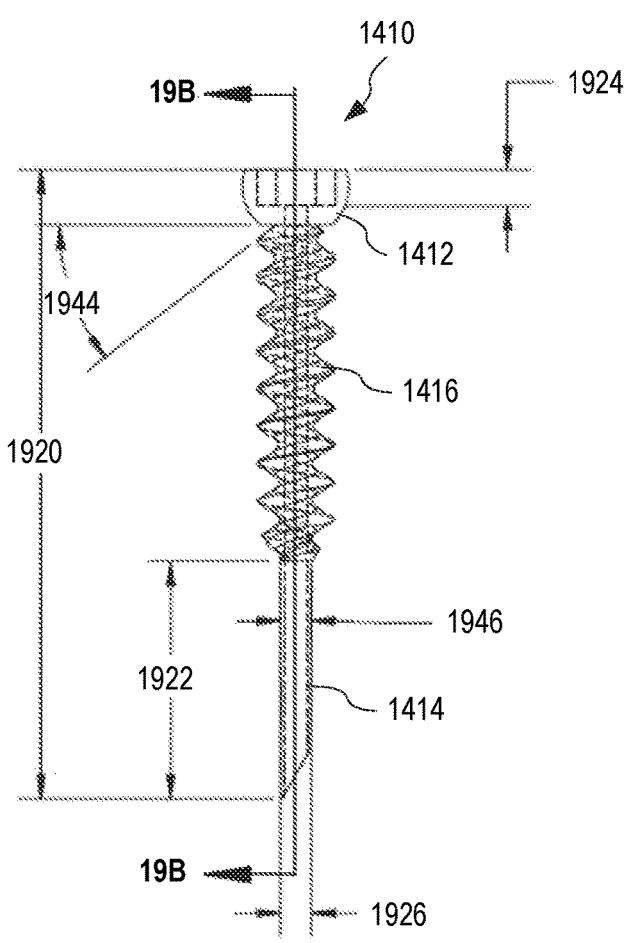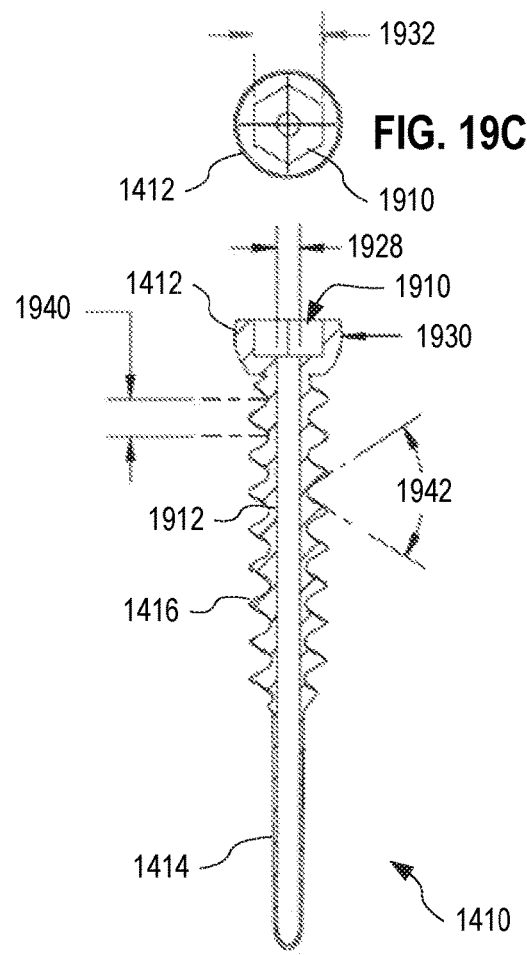
FIG. 19A
FIG. 19B

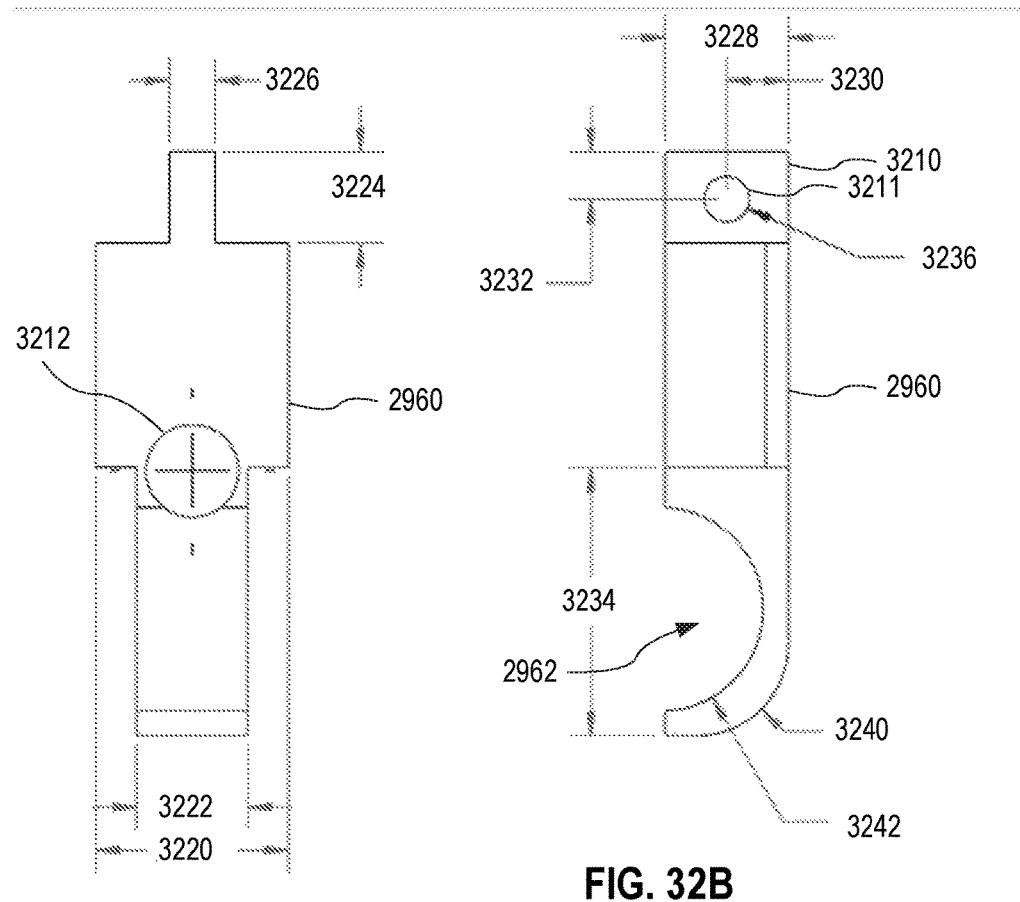
FIG. 32A
FIG. 32B
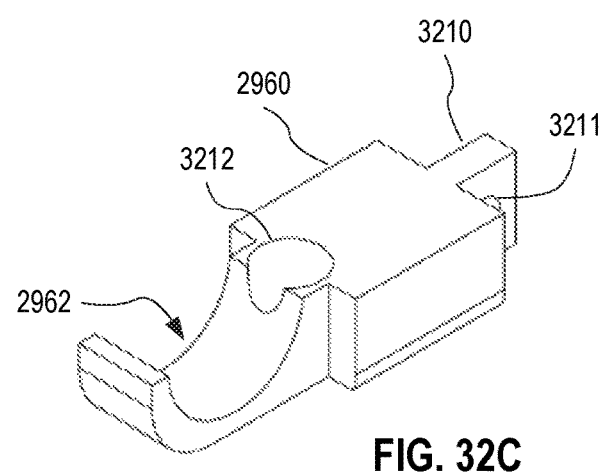
FIG. 32C

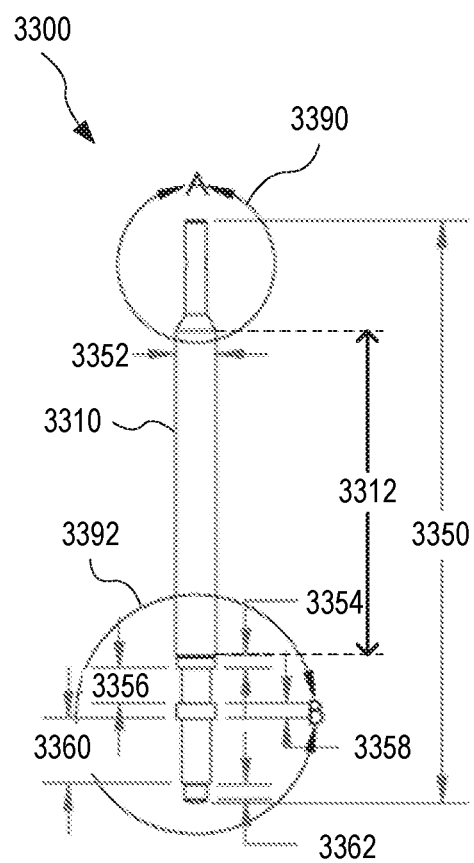
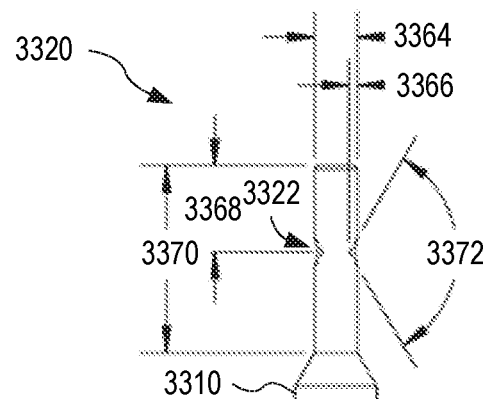
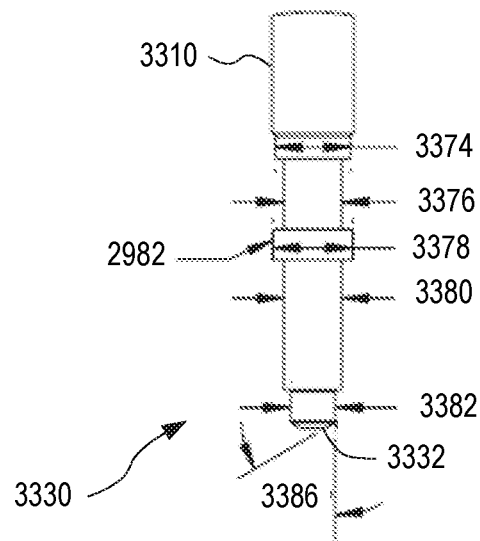
FIG. 33A
FIG. 33B
FIG. 33C

SPINE-ANCHORED TARGETING SYSTEMS AND METHODS FOR POSTERIOR SPINAL SURGERY

CROSS-REFERENCE TO RELATED APPLICATIONS

The present application is a national phase entry under 35 U.S.C. § 371 of International Application No. PCT/US2016/036976 filed Jun. 10, 2016, published in English, which claims priority from U.S. Provisional Patent Application No. 62/174,342 filed Jun. 11, 2015, U.S. Provisional Patent Application No. 62/240,231 filed Oct. 12, 2015, and U.S. Provisional Patent Application No. 62/253,280 filed Nov. 10, 2015, all of which are incorporated herein by reference in their entireties.

BACKGROUND

In surgery of the thoracic spine and the lumbar spine, the area of interest is usually accessed from the posterior (back) side of the patient. The physician makes an incision in the skin, and retracts muscles and other intervening tissue to access the spinal segment or spinal segments requiring surgery. In some cases, the surgeon may further remove bone material from one or more spinal segments to gain access to a deeper lying region. In the example of transforaminal lumbar interbody fusion, wherein two lumbar spine segments are fused together, the surgeon may remove a portion of the facet joints between the two lumbar spine segments, such that an opening between the nerve roots exciting and passing through the spine deep to the facet joints may be used to better access the disc space.

In conventional open spine surgery, the incision is generally about 3-6 inches long and the blood loss and recovery time are significant. On the other hand, "minimally invasive" surgery with posterior access may be performed using an incision as small as one inch and patients may be discharged the day of or the day after surgery. Such minimally invasive procedures utilize retraction devices for holding aside skin, muscles, and other intervening tissue. These retraction devices are anchored to two or more vertebrae, or to an external system such as a fixture mounted to the operating table.

SUMMARY

In an embodiment, a monopedicular targeting system for posterior spinal surgery includes a first joint component, a fastener for affixing the first joint component to a single pedicle of a vertebra, a positioning arm having a second joint component for mating with the first joint component to form a first joint having three rotational degrees of freedom, and a connector for coupling a spinal surgery device to the positioning arm. The connector has a third joint component that mates with a fourth joint component of the spinal surgery device to form a second joint having three rotational degrees of freedom.

In an embodiment, a monopedicular targeting method for posterior spinal surgery includes affixing a fastener to a single pedicle of a vertebra, anchoring a spinal surgery device to the pedicle via a manipulator attached to the fastener, and adjusting the manipulator to define, with three translational degrees of freedom and three rotational degrees of freedom relative to the pedicle, the position and orientation of the spinal surgery device to posteriorly target a surgery location.

In an embodiment, a monopedicular targeting system for posterior spinal surgery includes a manipulator for holding a spinal surgery device and manipulating three translational and three rotational degrees of freedom of the spinal surgery device with respect to an anchoring location of the manipulator. The monopedicular targeting system further includes a fastener for anchoring the manipulator to a single pedicle of a vertebra.

In an embodiment, a monopedicular targeting method for posterior spinal surgery includes coupling a spinal surgery device to a percutaneous pedicle screw via a connector, to anchor the spinal surgery device to a single pedicle of a vertebra.

In an embodiment, a spine-anchored targeting system for posterior spinal surgery includes a first joint component, a fastener for affixing the first joint component to a portion of a patient selected from the group consisting of a structure of spine of the patient and a pelvis of the patient, a positioning arm having a second joint component for mating with the first joint component to form a first joint having three rotational degrees of freedom, and a connector for coupling a spinal surgery device to the positioning arm, the connector having a third joint component that mates with a fourth joint component, for mounting to the spinal surgery device to form a second joint having three rotational degrees of freedom.

In an embodiment, a spine-anchored targeting method for posterior spinal surgery includes affixing a fastener to a portion of a patient selected from the group consisting of a structure of spine of the patient and a pelvis of the patient, anchoring a spinal surgery device to the portion of the patient via a manipulator attached to the fastener, and adjusting the manipulator to define, with three translational degrees of freedom and three rotational degrees of freedom relative to the portion of the patient, position and orientation of the spinal surgery device to posteriorly target a surgery location.

In an embodiment, a spine-anchored targeting system for posterior spinal surgery includes a manipulator for holding a spinal surgery device and manipulating three translational and three rotational degrees of freedom of the spinal surgery device with respect to an anchoring location of the manipulator, and a fastener for anchoring the manipulator to a portion of a patient selected from the group consisting of a structure of spine of the patient and a pelvis of the patient.

BRIEF DESCRIPTION OF THE DRAWINGS

FIGS. 11A and 11B are cross sectional views showing a positioning arm and a fastener of the monopedicular targeting system of FIG. 9, when the positioning arm is coupled with the fastener, according to an embodiment.

FIGS. 19A-C show, in further detail, one exemplary embodiment of a fastener of the monopedicular targeting system of FIGS. 14A-C.

FIGS. 32A-C show, in further detail, one exemplary embodiment of a second clamp subpart of the monopedicular targeting system of FIGS. 29A-C.

FIGS. 33A-C show, in further detail, one exemplary embodiment of a locking driver of the monopedicular targeting system of FIGS. 29A-C.

DETAILED DESCRIPTION OF THE EMBODIMENTS

Figure 1A:
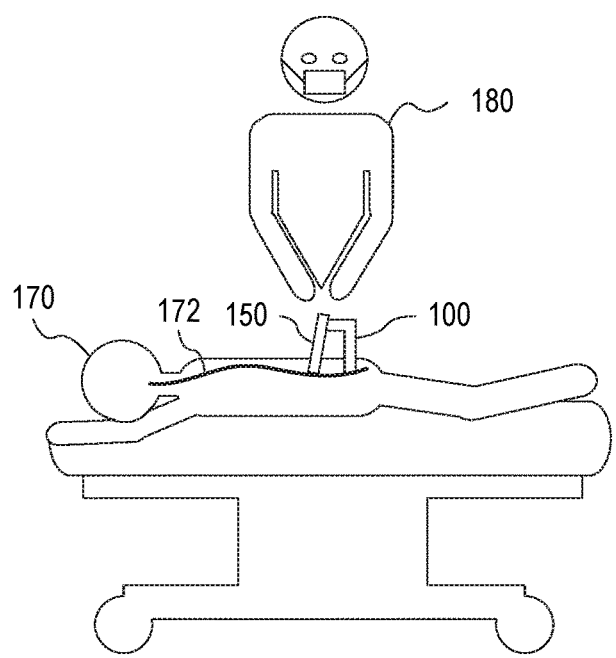
FIGS. 1A, 1B, and 1C illustrate a monopedicular targeting system for posterior spinal surgery, according to an embodiment.
Figure 1B:
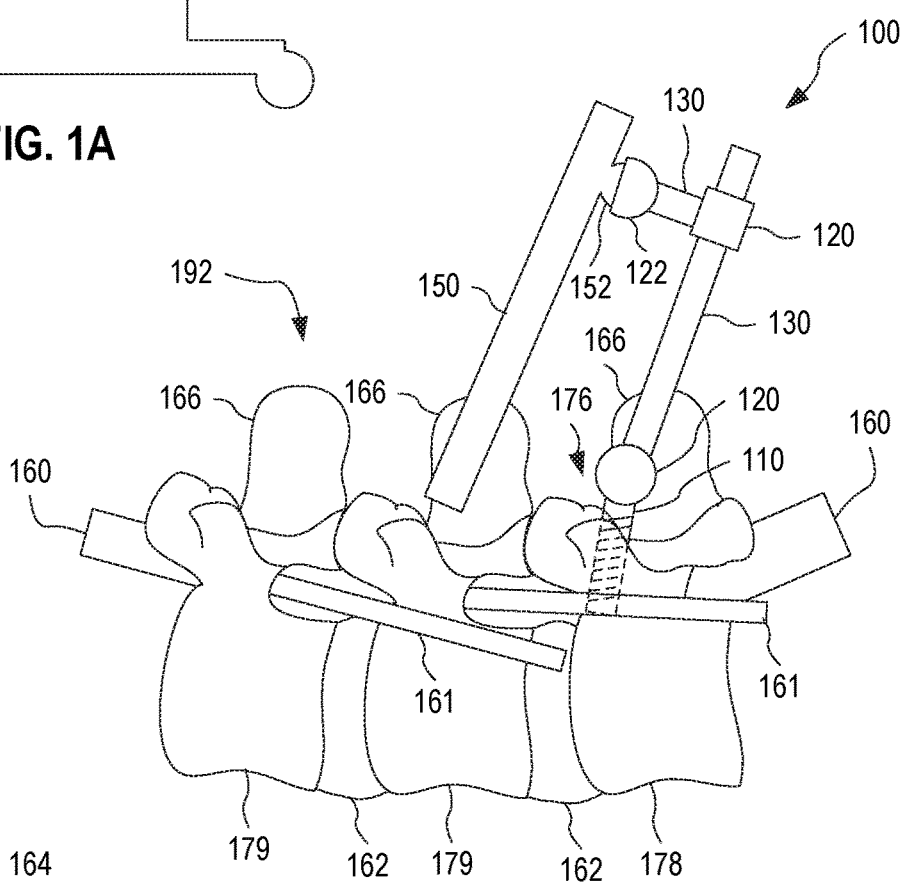
Figure 1C:
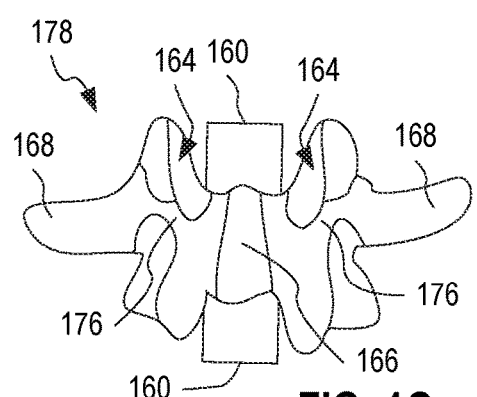

FIGS. 1A, 1B, and 1C illustrate one exemplary monopedicular targeting system 100 for posterior spinal surgery. FIG. 1A shows monopedicular targeting system 100 in one exemplary use scenario. FIG. 1B shows monopedicular targeting system 100 in further detail as implemented in the use scenario of FIG. 1A and in lateral view. FIG. 1C shows, in posterior view, exemplary locations for affixing monopedicular targeting system 100 to a pedicle. FIGS. 1A-C are best viewed together.

Monopedicular targeting system 100 is anchored to a single pedicle 176 of a vertebra 178 of spine 172 of a patient 170 from posterior side 192 of spine 172. Monopedicular targeting system 100 is configured to hold a spinal surgery device 150, and aids a surgeon 180 with performing posterior spinal surgery on spine 172 near pedicle 176. In one example, spinal surgery device 150 is a retractor for retracting tissue of patient 170 to access a surgery location of spine 172. In another example, spinal surgery device 150 is a device used to perform at least a portion of the surgery on spine 172 after retracting the intervening tissue, such as a robot, a drill, an osteotome, a curette, a rongeur, a rasp, a device/cage applier, a graft applier, or another spinal surgery device known in the art.

Herein, a "surgeon" may refer to one or more humans, a robotic system, a system including Haptic technology, and/or a combination thereof.

As shown by FIG. 1B, vertebra 178 (and other vertebrae 179 of spine 172) has two pedicles 176. Each pedicle 176 is approximately anterior to a corresponding facet joint surface 164 of vertebra 178. For clarity of illustration, FIGS. 1B and 1C indicate spinous process 166 of each of vertebra 178 and vertebrae 179, spinal cord 160 (or alternatively thecal sac 160), nerve roots 161, and intervertebral discs 162. FIG. 1C further indicates transverse processes 168. Monopedicular targeting system 100 is anchored to only a single pedicle 176 of vertebra 178. Pedicle 176 may be inferior or superior to the portion of spine 172 needing surgery by spinal surgery device 150. Without departing from the scope hereof, pedicle 176 may be a pedicle of the sacrum (not shown in FIG. 1B) of patient 170.

Since monopedicular targeting system 100 is affixed to pedicle 176, adverse effect of patient movement is eliminated or reduced. This is a significant improvement over systems that are affixed to an external system such as the operating table. Monopedicular targeting system 100 allows six degrees of freedom for placement of spinal surgery device 150 with respect to pedicle 176, such that the targeted surgery location may be accessed along a range of trajectories. Within certain range limitations, monopedicular targeting system 100 is capable of placing spinal surgery device 150 at any position and at any orientation with respect to pedicle 176. This allows surgeon 180 to choose an optimal trajectory for targeting a surgery location at spine 172. Additionally, in one embodiment, monopedicular targeting system 100 may be locked to maintain this optimal trajectory, even in the presence of movement of patient 170. In another embodiment, joints of monopedicular targeting system 100 have sufficient resistance against movement to remain stable without actively locking the joints. Generally, monopedicular targeting system 100 enables precise and stable targeting of a surgery location of spine 172, while being less bulky and requiring less hardware than prior art systems.

Monopedicular targeting system 100 is well suited for minimally invasive posterior spinal surgery, for example of the lumbar or thoracic spine. In one implementation, a small incision of about two centimeters or less is made at pedicle 176 to affix monopedicular targeting system 100 to pedicle 176, and another small incision, for example of order 2-4 centimeters, is made at the surgery location of spine 172. In another example, a single incision of a few centimeters is made to access both pedicle 176 and the surgery location of spine 172. Monopedicular targeting system 100 may facilitate less risk, less surgery time, reduced blood loss, less soft tissue trauma, and faster discharge of patient 170, as compared to both conventional open surgery and minimally invasive surgery utilizing two or more pedicles for anchoring a retractor.

Monopedicular targeting system 100 includes a fastener 110. In use, fastener 110 is affixed to pedicle 176. Fastener 110 may be a screw, a pin, a combined awl and tap, a percutaneous screw, a pedicle screw, or another type of fastener known in the art. Herein, a "pedicle" screw refers to a screw that may be left in spine 172 permanently (or at least long-term). In one-level transforaminal lumbar interbody fusion, four pedicle screws are inserted into the four respective pedicles associated with a spinal segment. To help stabilize the spinal segment, the two left pedicle screws are connected by one rod and the two right pedicle screws are connected by another rod. In two-level transforaminal lumbar interbody fusion, an additional pair of pedicle screws are attached to the left and right pedicles of an adjacent vertebra. To help stabilize the two spinal segments, the three left pedicle screws are connected by one rod and the three right pedicle screws are connected by another rod. In each additional level of surgery, an additional pair of pedicle screws are attached to the left and right pedicles of the additional vertebra and these additional pedicle screws are included in the rod construct used to connect all of the pedicle screws of each side.

Monopedicular targeting system 100 further includes a joint component 122 that is configured to mate with a joint component 152 that is included in spinal surgery device 150, permanently coupled with spinal surgery device 150, or removably coupled with spinal surgery device 150. Joint components 122 and 152 are configured to mate to form a joint with three rotational degrees of freedom. In one embodiment, joint components 122 and 152 are configured to mate to form a spherical joint. Joint components 122 and 152 may be a ball and a socket, respectively, or a socket and a ball, respectively.

Figure 9:
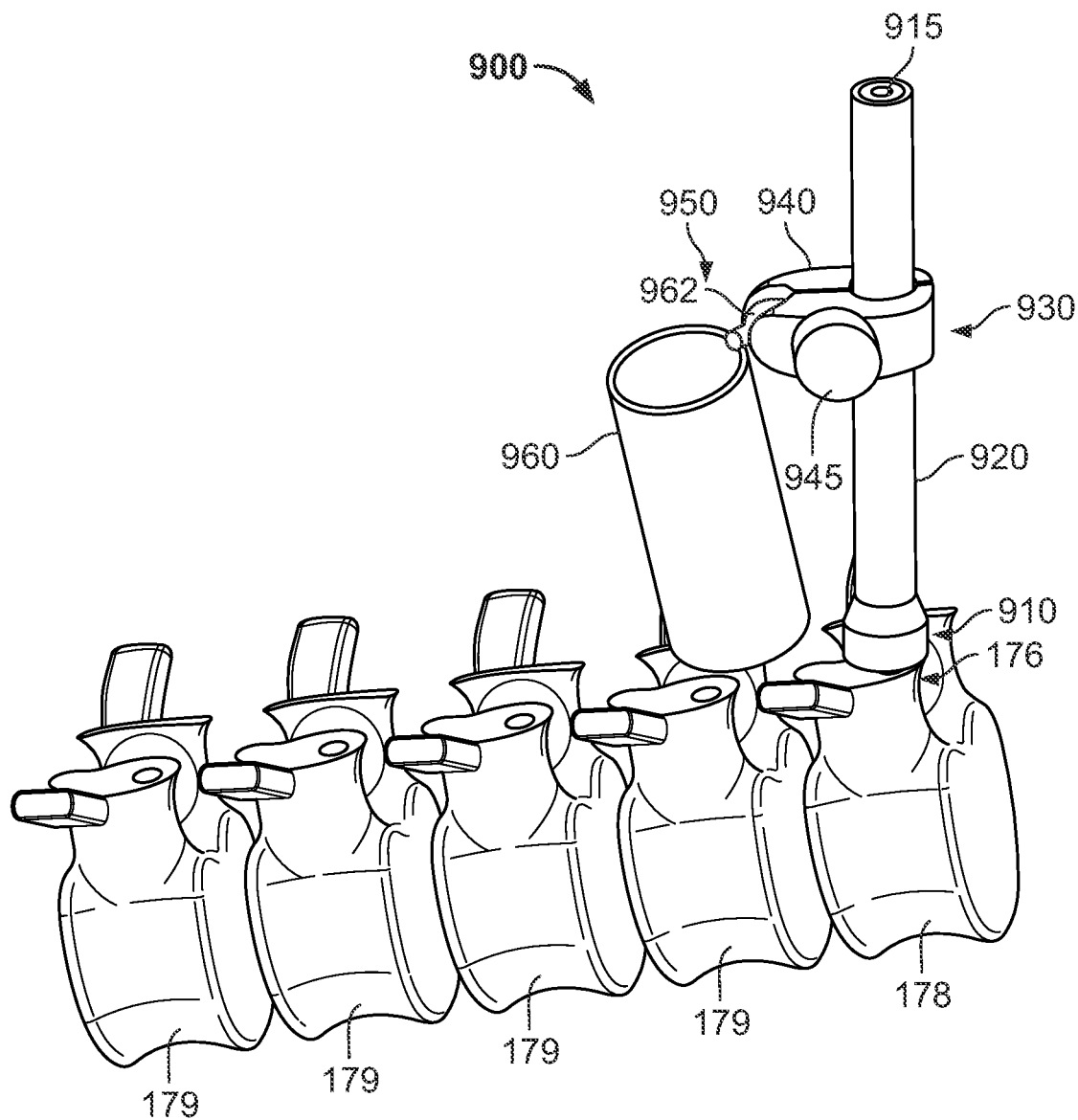
FIG. 9 illustrates, in perspective view, a monopedicular targeting system for posterior spinal surgery when affixed to a pedicle, according to an embodiment.
Figure 14A:
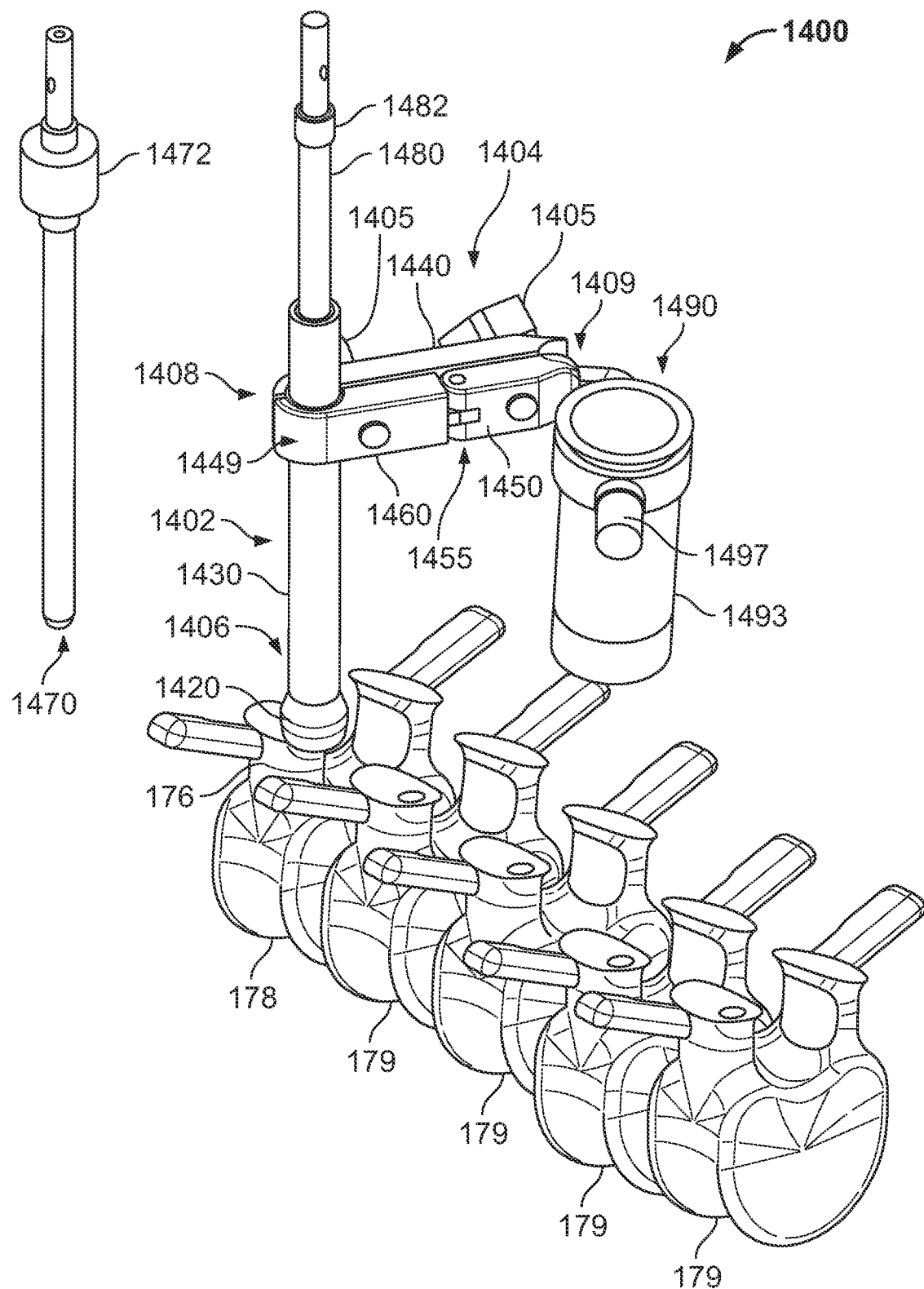
FIGS. 14A-C illustrate another monopedicular targeting system for posterior spinal surgery, according to an embodiment.
Figure 14B:
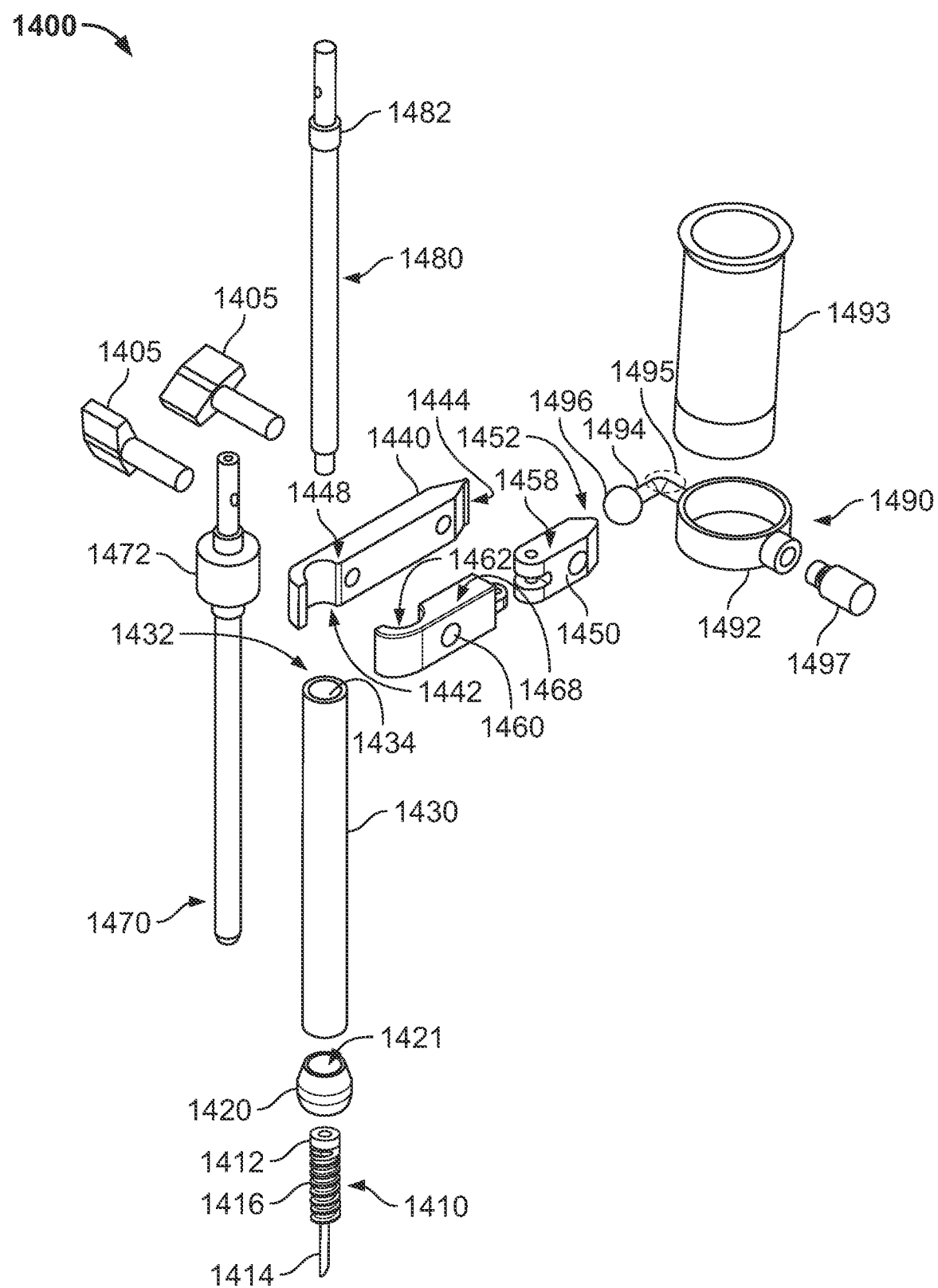
Figure 14C:
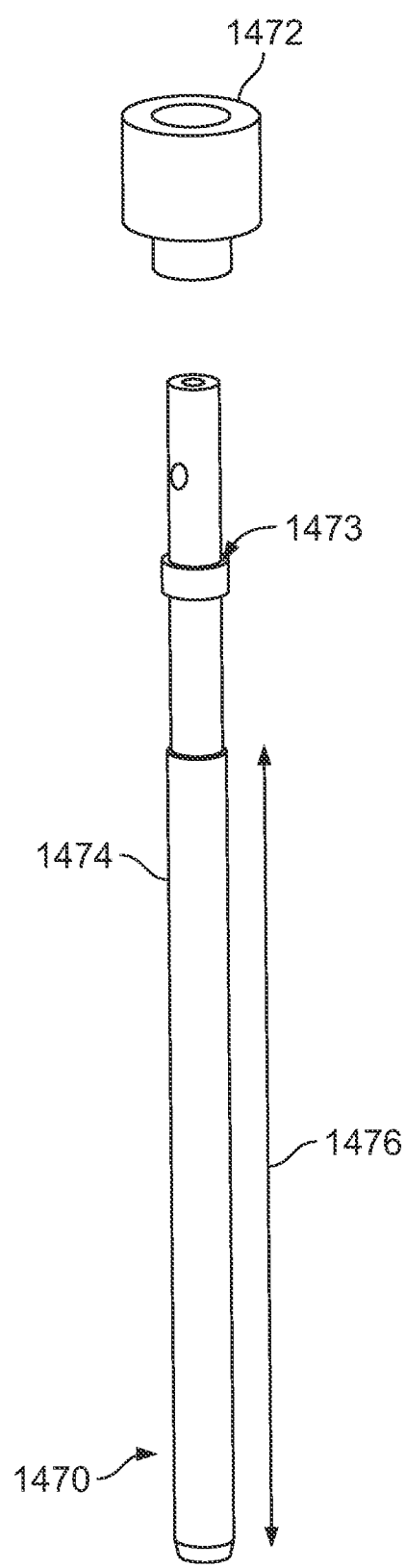

FIGS. 14A-C below illustrate one embodiment, wherein an embodiment of joint component 152 is removably coupled with an embodiment of spinal surgery device 150. FIG. 9 below illustrates one embodiment, wherein an embodiment of joint component 152 is included, or permanently coupled with, an embodiment of spinal surgery device 150. Regardless of how joint component 152 is coupled with (or included in) spinal surgery device 150, a connecting arm may exist between joint component 152 and the operating portion of spinal surgery device 150. For example, this connecting arm is angled to improve flexibility of positioning of spinal surgery device 150 and improve imaging access to the targeted surgery location (see for example FIGS. 14A-C, 29A-C, 42A, and 42B). It is understood that, throughout this disclosure, an embodiment of joint component 152 permanently coupled with (or included in) an embodiment of spinal surgery device 150 may be replaced by an embodiment of joint component 152 removably coupled with an embodiment of spinal surgery device 150, and vice versa.

Herein, a "joint component" refers to a portion of a joint, such that two joint components may be connected to form a joint that allows the two joint components to move relative to each other. For example, two joint components may be a ball and a socket, which mate with each other to form a spherical joint. In another example, two joint components are a protrusion and a receptacle, which mate with each other to form a joint with three rotational degrees of freedom. In yet another example, two joint components are a cylinder and an element with a through hole, which mate with each other to form a cylindrical joint. In a further example, one joint component fits over another joint component to form a telescoping joint. The coupling between two joint components to form a joint is, for example, mechanical and/or magnetic, and may be configured to have a friction between the two joint components. In addition, a "joint" need not be formed by connecting two joint components. In one example, a joint may be a pliable material such that two elements, attached to two different portions of the pliable material, may move relative to each other. Herein, a "spherical joint" refers to a joint that has three rotational degrees of freedom and that has no translational degrees of freedom in excess of those associated with manufacturing tolerances. A spherical joint is, for example, a protrusion and a receptacle mated with each other, or a ball and a socket mated with each other, wherein the ball does not need to be a complete ball but includes a portion of a ball.

Monopedicular targeting system 100 includes a plurality of connectors 130 and joints 120 that cooperate with the joint formed by joint components 122 and 152 to provide three translational degrees of freedom and three rotational degrees of freedom of spinal surgery device 150 with respect to fastener 110. Thus, when fastener 110 is affixed to pedicle 176 and spinal surgery device 150 is connected to joint component 122, monopedicular targeting system 100 anchors spinal surgery device 150 to pedicle 176 while allowing three translational degrees of freedom and three rotational degrees of freedom of spinal surgery device 150 with respect to pedicle 176.

In the exemplary embodiment shown in FIG. 1B, monopedicular targeting system 100 includes two joints 120 and two connectors 130. A first connector 130 is configured to connect with fastener 110 via a first joint 120, and a second connector 130 is configured to mate with the first connector 130 via a second joint 120. In one example of this embodiment, joint 120 between fastener 110 and the first connector 130 has three rotational degrees of freedom, joint 120 between the first and second connectors 130 has a translational degree of freedom, and the joint formed by joint components 122 and 152 has three rotational degrees of freedom.

It is understood that the present disclosure is not limited to the particular embodiment shown in FIG. 1B. For example, monopedicular targeting system 100 may include a different number of joints 120 and connectors 130 to provide three translational degrees of freedom and three rotational degrees of freedom for spinal surgery device 150 with respect to pedicle 176.

Figure 2A:
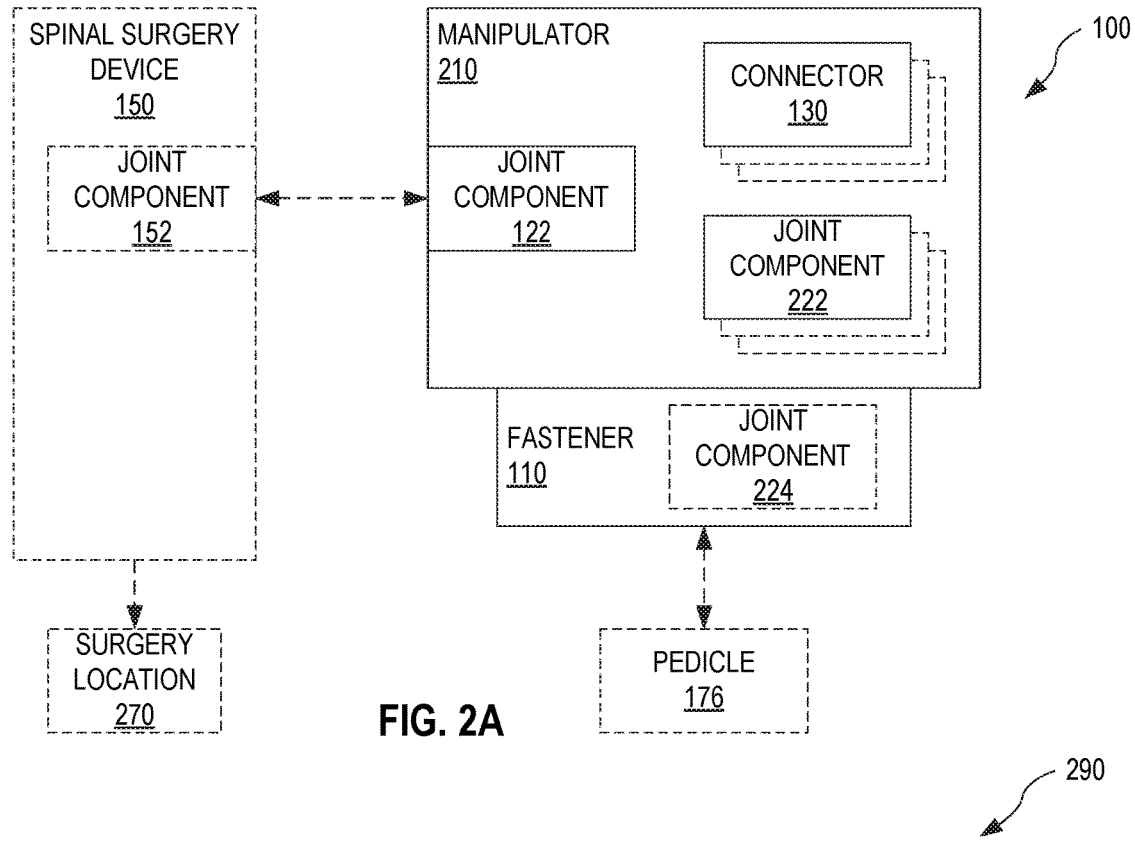
FIG. 2A is a block diagram illustrating a more general embodiment of the monopedicular targeting system of FIG. 1.

FIG. 2A is a block diagram illustrating a more general embodiment of monopedicular targeting system 100. Monopedicular targeting system 100 includes fastener 110 and a manipulator 210. Manipulator 210 includes joint component 122, one of more connectors 130, and one or more additional joint components 222. Optionally, fastener 110 includes a joint component 224 that is configured to mate with a joint component 222 to form a joint at the interface between fastener 110 and manipulator 210. Although not shown in FIG. 2A, connector(s) 130 may implement joint components 122 and 222, without departing from the scope hereof.

As discussed in reference to FIGS. 1A-C, fastener 110 is configured to be affixed to pedicle 176, and joint component 122 is configured to interface with joint component 152 of spinal surgery device 150 to target a surgery location 270. In certain embodiments, monopedicular targeting system 100 includes at least a portion of spinal surgery device 150. For example, monopedicular targeting system 100 may include joint component 152.

Monopedicular targeting system 100 may be provided to a user in assembled form or in a form that requires at least some assembly to be performed by a user. For example, monopedicular targeting system 100 may be provided to a user as separate fastener 110 and separate connector(s) 130, wherein connector(s) 130 implement joint component 122 and 222. The user then assembles these separate components. Additionally, fastener 110 may be provided to a user as two or more separate parts, which are to be assembled by the user to form fastener 110, without departing from the scope hereof. For example, fastener 110 may be provided as a threaded member and a non-threaded member, wherein the threaded member is configured to connect with a connector 130.

Figure 2B:
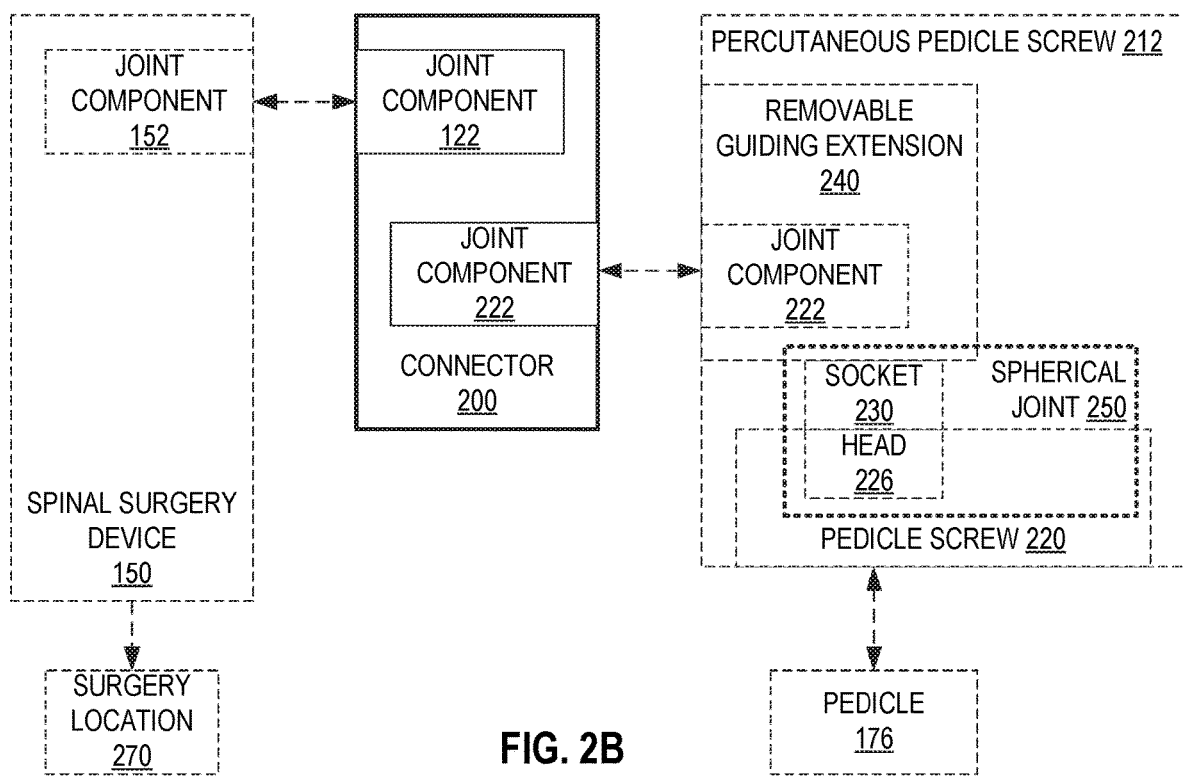
FIG. 2B is a block diagram illustrating a connector configured to couple with a percutaneous pedicle screw to form an exemplary monopedicular targeting system, according to an embodiment.

FIG. 2B is a block diagram illustrating one exemplary connector 200 configured to couple with a percutaneous pedicle screw 212 to form one exemplary monopedicular targeting system 290. Monopedicular targeting system 290 is an embodiment of monopedicular targeting system 100. Monopedicular targeting system 290 may further include at least a portion of spinal surgery device 150.

Percutaneous pedicle screw 212 may be an off-the shelf percutaneous pedicle screw produced by a third party vendor, or a custom made item supplied together with connector 200. Exemplary vendors supplying percutaneous pedicle screw suitable for implementation as percutaneous pedicle screw 212 include, but are not limited to, Stryker, DePuy Synthes, NuVasive, Globus, K2 Medical, Medtronic, Biomet, and Zimmer Spine. Percutaneous pedicle screw 212 includes (a) a pedicle screw 220 for screwing into pedicle 176, (b) a socket 230 (such as a "tulip" as known in the art) that forms a spherical joint 250 with a head 226 of pedicle screw 220, and (c) a removable guiding extension 240 of socket 230. Removable guiding extension 240 extends outside patient 170 when pedicle screw 220 is fastened to pedicle 176 and generally serves to guide a tool or other hardware to pedicle screw 220, socket 230, or a location near pedicle 176. Removable guiding extension 240 may be both removable and reinsertable or, alternatively, be removable only in a irreversible manner and thus not reinsertable. When no longer needed, removable guiding extension 240 may be removed from socket 230, for example by breaking a relatively fragile connection between removable guiding extension 240 and socket 230, by unscrewing removable guiding extension 240 from socket 230, or by undoing a pressure fit connection between removable guiding extension 240 and socket 230. Pedicle screw 220 is an embodiment of fastener 110, head 226 is an embodiment of joint component 224, socket 230 is an embodiment of joint component 222, and removable guiding extension 240 is an embodiment of connector 130 implementing joint component 222.

Herein, the term "percutaneous pedicle screw" is not limited to devices inserted into patient 170 percutaneously. Throughout the present disclosure, a "percutaneous pedicle screw" may be inserted into patient 170 percutaneously or non-percutaneously, for example as commonly done in open surgery procedures.

Connector 200 implements (a) joint component 122, configured to mate with joint component 152 to form a joint with three rotational degrees of freedom, and (b) a joint component 222 configured to mate with a joint component 222 of removable guiding extension 240 to form a joint having at least a translational degree of freedom. Thus, connector 200 is capable of cooperating with percutaneous pedicle screw 212 and joint component 152 to provide three translational and three rotational degrees of freedom for spinal surgery device 150 with respect to pedicle 176 when percutaneous pedicle screw 212 is affixed to pedicle 176. Connector 200 cooperates with removable guiding extension 240 and socket 230 to form an embodiment of manipulator 210.

Connector 200 facilitates multipurpose use of percutaneous pedicle screw 212 of monopedicular targeting system 290. After utilizing monopedicular targeting system 290 to position spinal surgery device 150 to target surgery location 270, surgeon 180 may, for example after detaching connector 200 from percutaneous pedicle screw 212, detach removable guiding extension 240 from socket 230, while leaving pedicle screw 220 in place in pedicle 176. Pedicle screw 220 may then be used for another purpose, for example for stabilizing a spinal segment by attaching a rod to pedicle screw 220 and another pedicle screw fastened to an adjacent pedicle on the same side of spine 172.

In an embodiment, joint component 122 of connector 200 mates with joint component 152 to form a spherical joint. In an embodiment, joint component 222 of connector 200 may attach to joint component 222 of percutaneous pedicle screw 212 at a variable distance from socket 230. Optionally, the joint formed between joint components 222 of connector 200 and percutaneous pedicle screw 212 further has a rotational degree of freedom and is, for example, a cylindrical joint.

Without departing from the scope hereof, connector 200 may be supplied together with one or more adapters such that joint component 222 of connector 200 may be coupled to one or more respective percutaneous pedicle screws having differently sized or shaped joint component 222.

As discussed in further detail below in reference to FIGS. 56-59, monopedicular targeting system 100 is readily extended to spine-anchored targeting systems that each have the same functionality as monopedicular targeting system 100 but may be anchored to a different structure of spine 172 or to a pelvis of patient 170. Such spine-anchored targeting systems may be used in posterior spinal surgery of the cervical, thoracic, and/or lumbar spine of patient 170.

Figures 3A, 3B:
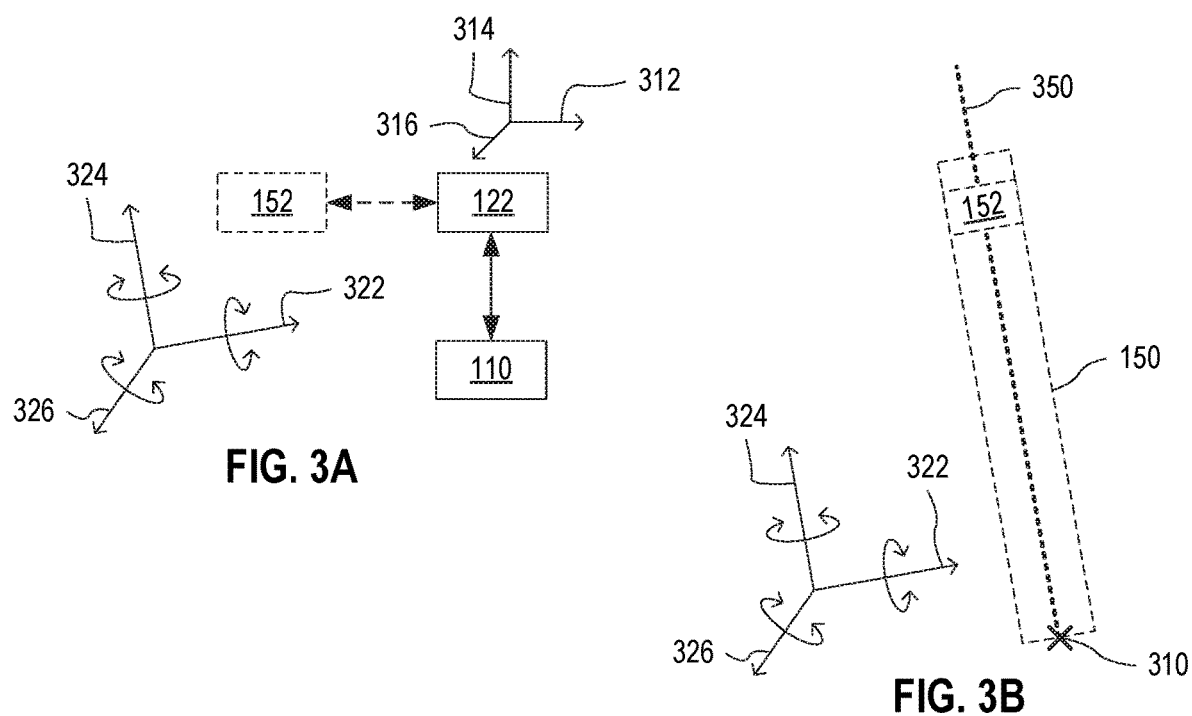
FIGS. 3A and 3B illustrate motion of a manipulator of the monopedicular targeting system of FIGS. 1A-C and a spinal surgery device connected to this manipulator, according to an embodiment.

FIGS. 3A and 3B illustrate exemplary motion of manipulator 210 and spinal surgery device 150 connected to manipulator 210. FIGS. 3A and 3B are best viewed together. Manipulator 210 is capable of translating joint component 122 with respect to fastener 110 in at least three orthogonal directions 312, 314, and 316, or alternately in at least three other directions that span a three-dimensional space. These translational degrees of freedom result in three translational degrees of freedom of position 310 of spinal surgery device 150 with respect to fastener 110. Although shown in FIG. 3B as being at one end of spinal surgery device 150, position 310 may be referenced to a different portion of spinal surgery device 150, such as the position of the center of spinal surgery device 150.

When joint component 152 of spinal surgery device 150 is connected to joint component 122, joint component 152, and thus spinal surgery device 150, is capable of rotating about at least three orthogonal axes 322, 324, and 326, or alternately about at least three other axes that span a three-dimensional space. In one example, axes 322, 324, and 326 are parallel to directions 312, 314, and 316, respectively. In another example, at least one of axes 322, 324, and 326 is not parallel to any one of directions 312, 314, and 316. These rotational degrees of freedom result in three rotational degrees of freedom of an orientation 350 of spinal surgery device 150 with respect to fastener 110. Although shown in FIG. 3B as being a longitudinal axis of spinal surgery device 150, orientation 350 may be referenced to a different axis of spinal surgery device 150, such as an axis associated with an operational part of spinal surgery device 150.

Without departing from the scope hereof, the diagrams of FIGS. 3A and 3B apply also to monopedicular targeting system 290, in which case fastener 110 and joint component 122 in FIGS. 3A and 3B represent pedicle screw 220 and joint component 122 of connector 200, respectively.

Figure 4A:
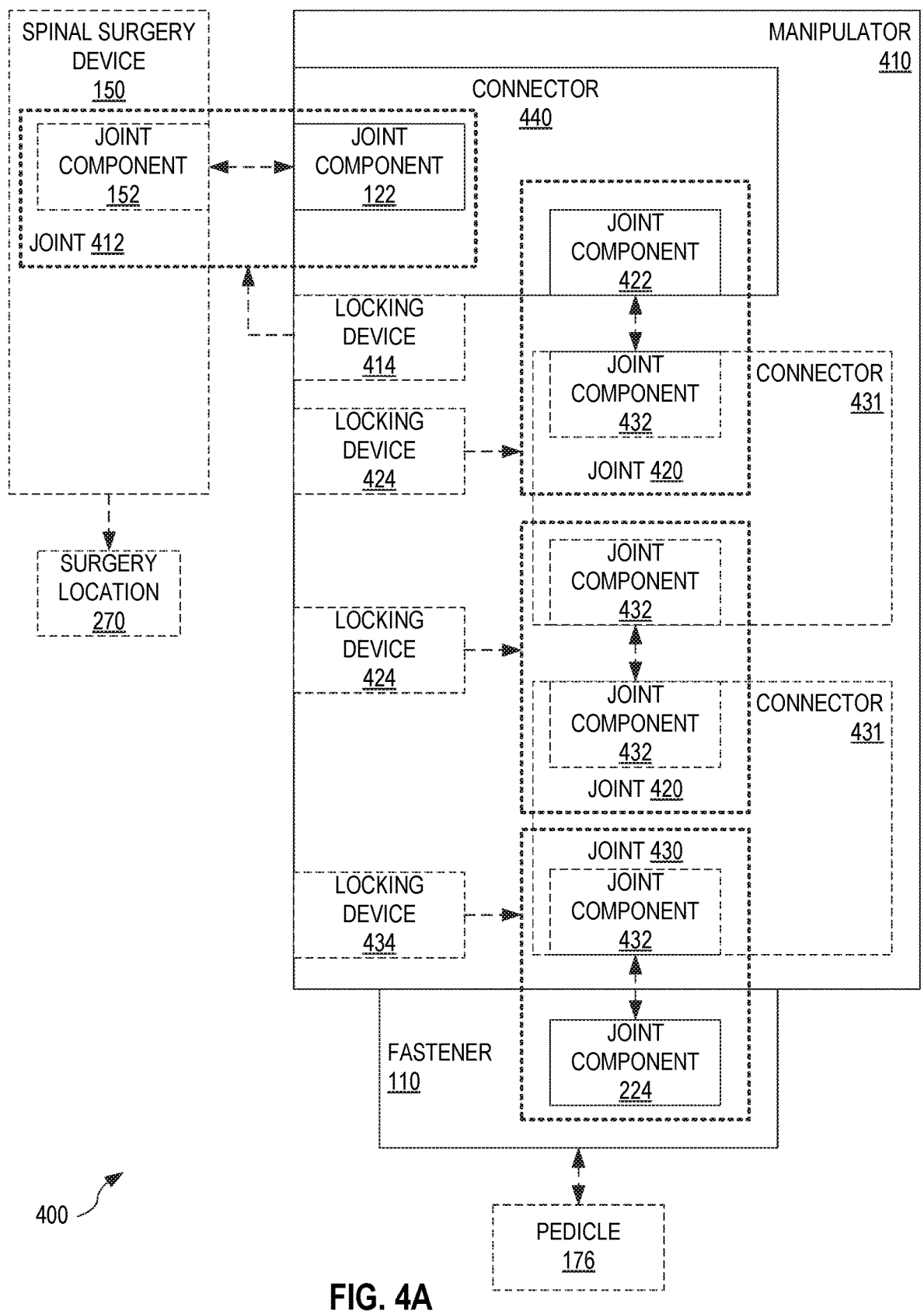
FIG. 4A illustrates a monopedicular targeting system, for posterior spinal surgery, which includes a manipulator that has joint components implemented in one or more connectors, according to an embodiment.

FIG. 4A illustrates one exemplary monopedicular targeting system 400, for posterior spinal surgery, including a manipulator 410 that has joint components implemented in one or more connectors. Monopedicular targeting system 400 is an embodiment of monopedicular targeting system 100, and manipulator 410 is an embodiment of manipulator 210.

Monopedicular targeting system 400 includes fastener 110 and manipulator 410. Fastener 110 includes joint component 224. Manipulator 410 includes one connector 440 that implements a joint component 422 and joint component 122. Joint component 122 is configured to mate with joint component 152 to form a joint 412 between manipulator 410 and spinal surgery device 150. Joint 412 has three rotational degrees of freedom and is, for example, a spherical joint. Joint component 422 is an embodiment of joint component 222, and connector 440 is an embodiment of connector 130.

In one embodiment, manipulator 410 includes an additional connector 431. Additional connector 431 is an embodiment of connector 130 and includes two joint components 432 for mating with joint component 422 and 224, respectively, to form joints 420 and 430, respectively.

In another embodiment, manipulator 410 includes two additional connectors 431. In this embodiment, a joint component 432 of a first additional connector 431 is configured to mate with joint component 422 to form a first joint 420, a joint component 432 of a last additional connector 431 is configured to mate with joint component 224 to form a joint 430, and a joint component 432 of the first additional connector 431 is configured to mate with a joint component 432 of the last additional connector 431 to form a second joint 420. Although FIG. 4A only shows two additional connectors 431, manipulator 410 may include three of more additional connectors 431 without departing from the scope hereof. For example, additional connectors 431 in excess of two may be inserted between the first and last connectors 431 (connected to connector 440 and fastener 110, respectively) to form additional intermediate joints 420.

In yet another embodiment, manipulator 410 does not include any additional connectors 431, and joint component 422 is configured to mate with joint component 224 to form joint 430.

Optionally, manipulator 410 includes a locking device 414 that may be engaged to lock joint 412 in a desired configuration. Manipulator 410 may also include a locking device 434 that may be engaged to lock joint 430 in a desired configuration. For each joint 420, manipulator 410 may include a locking device 424 that may be engaged to lock a respective joint 420 in a desired configuration. Each of locking devices 414, 424, and 434 is a fastener, for example. Without departing from the scope hereof, one or more of locking devices 414, 424, and 434 may be configured to act on one or more of connectors 440 and 431, instead of joints 412, 420, and/or 430, to lock the position of one or more of connectors 440 and 431.

Monopedicular targeting system 400 may be provided to a user in assembled form or in a form that requires at least some assembly to be performed by a user. For example, monopedicular targeting system 400 may be provided to a user as separate fastener 110, separate connector 130, and optionally separate connectors 431, which are to be assembled by the user. Additionally, fastener 110 may be provided to a user as two or more separate parts, which are to be assembled by the user to form fastener 110, without departing from the scope hereof. For example, fastener 110 may be provided as a threaded member and a non-threaded member, wherein the threaded member is configured to be affixed to pedicle 176 and the non-threaded member includes joint component 224. Monopedicular targeting system 400 may include at least a portion of spinal surgery device 150.

As discussed in further detail below in reference to FIGS. 56-59, monopedicular targeting system 400 is readily extended to spine-anchored targeting systems that each have the same functionality as monopedicular targeting system 400 but may be anchored to a different structure of spine 172 or to a pelvis of patient 170. Such spine-anchored targeting systems may be used in posterior spinal surgery of the cervical, thoracic, and/or lumbar spine of patient 170.

Figure 4B:
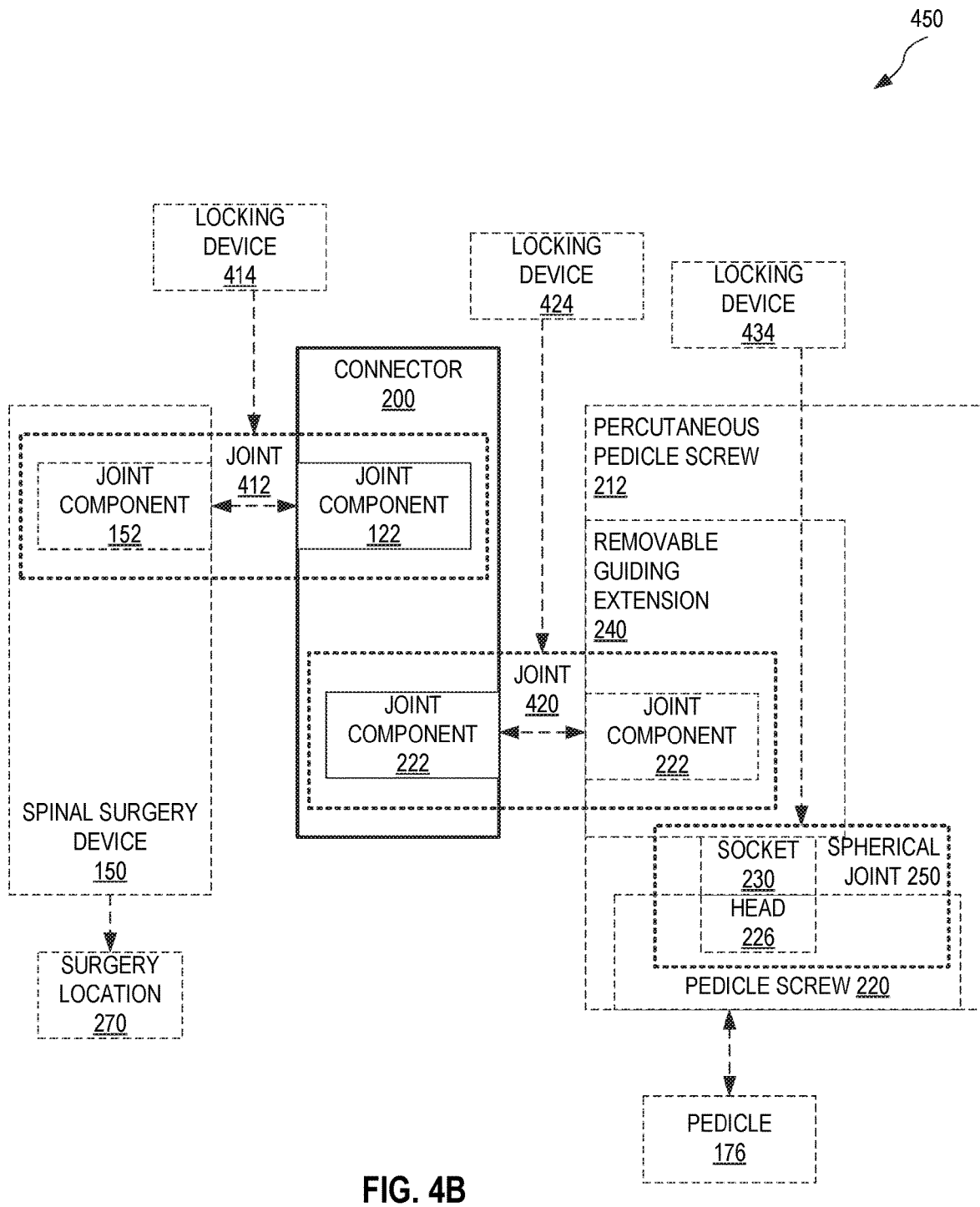
FIG. 4B illustrates a connector as implemented in one exemplary monopedicular targeting system that also utilizes a percutaneous pedicle screw, according to an embodiment.

FIG. 4B illustrates connector 200 as implemented in one exemplary monopedicular targeting system 450 that also utilizes percutaneous pedicle screw 212. Monopedicular targeting system 450 is an embodiment of monopedicular targeting systems 290 and 400. Monopedicular targeting system 450 includes connector 200 and percutaneous pedicle screw 212 and may further include at least a portion of spinal surgery device 150.

In monopedicular targeting system 450, joint component 122 is configured to mate with joint component 152 to form joint 412. Likewise, joint component 222 of connector 200 is configured to mate with joint component 222 of removable guiding extension 240 to form joint 420. In certain embodiments, connector 200 is configured to couple to locking devices 414 and 424 configured to lock joints 412 and 420, respectively. In one example, one or both of locking devices 414 and 424 are included in connector 200 or supplied to a user together with connector 200.

Monopedicular targeting system 450 may include one or more of locking devices 414, 424, and locking device 434, wherein locking device 434 is configured to lock spherical joint 250. Spherical joint 250 is an embodiment of joint 430.

Figure 4C:
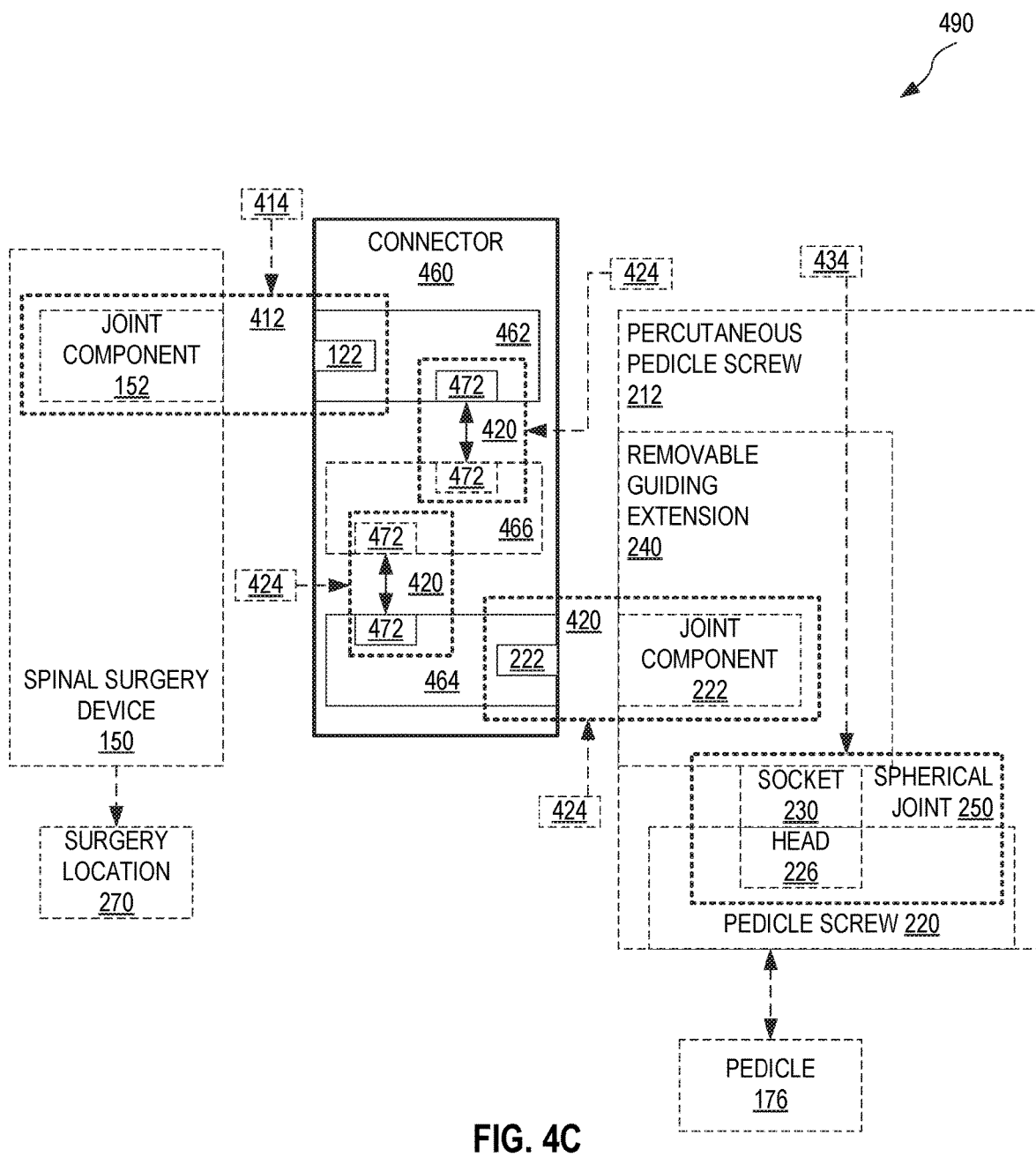
FIG. 4C illustrates another connector as implemented in one exemplary monopedicular targeting system that also utilizes a percutaneous pedicle screw, according to an embodiment.

FIG. 4C illustrates one exemplary connector 460 configured to cooperate with percutaneous pedicle screw 212 to form one exemplary monopedicular targeting system 490. Connector 460 is an embodiment of connector 200, which further includes at least one additional joint. Monopedicular targeting system 490 is an embodiment of monopedicular targeting systems 400 and 450.

Connector 460 includes sub-connectors 462, 464 and, optionally, one or more additional sub-connectors 466. For clarity of illustration, only one additional sub-connector 466 is shown in FIG. 4C. Sub-connector 462 is an embodiment of connector 440. Each of sub-connectors 464 and 466 is an embodiment of connector 431. Sub-connector 462 includes joint component 122 and a joint component 472. Sub-connector 464 includes a joint component 472 and a joint component 222 that is configured to mate with joint component 222 of percutaneous pedicle screw 212 to form joint 420 as discussed in reference to FIG. 4B. Each optional sub-connector 466 includes two joint components 472 configured to mate with two joint components 472 of two other sub-connectors included in connector 460 to form two respective joints 420. Each joint component 472 is an embodiment of joint component 432. Each joint 420 may be coupled with a respective locking device 424. Connector 460 may include each such locking device 424, or be supplied to a user with each such locking device 424.

Figure 5A:
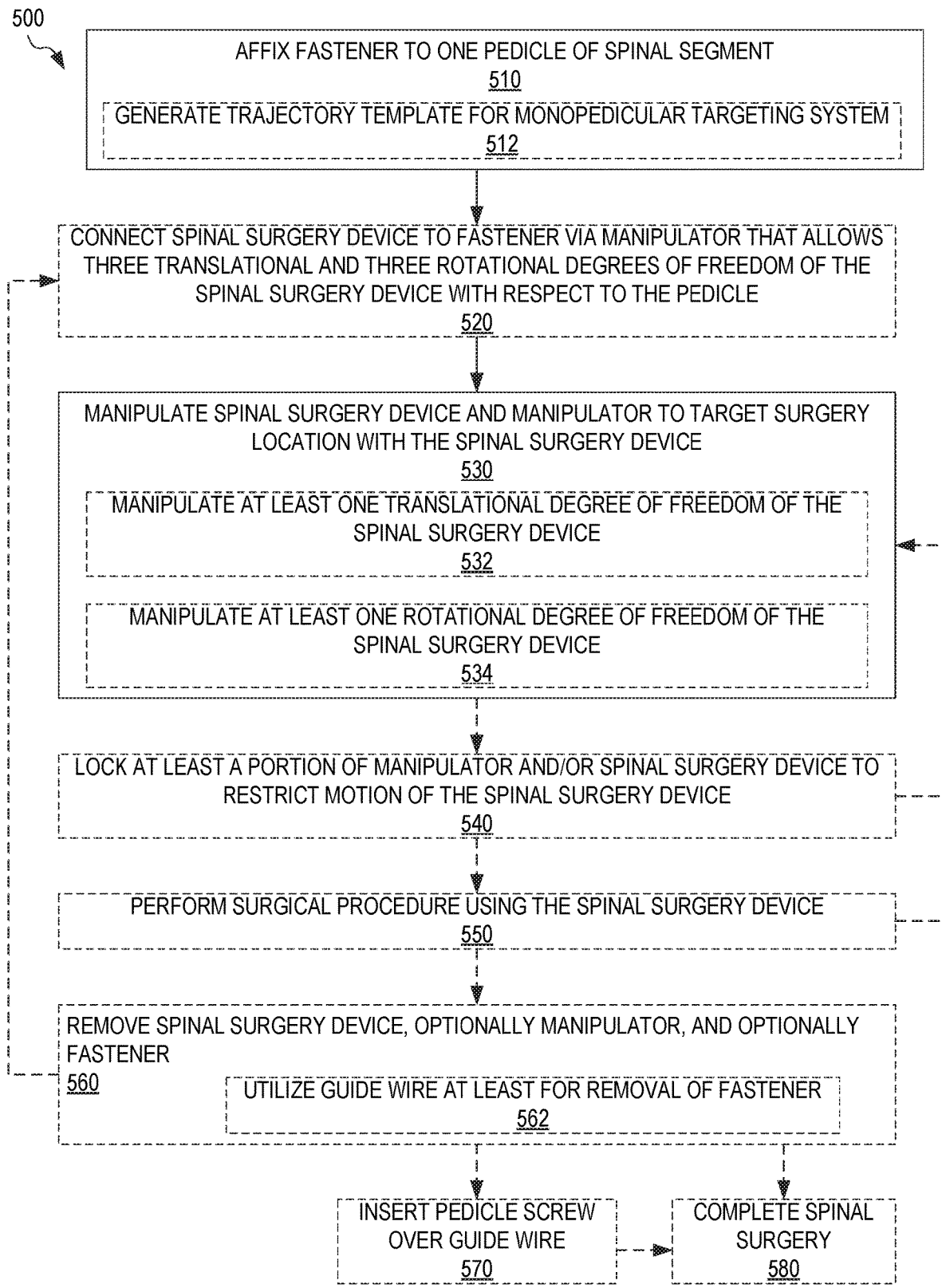
FIG. 5A illustrates a monopedicular targeting method for posterior spinal surgery, according to an embodiment.

FIG. 5A illustrates one exemplary monopedicular targeting method 500 for posterior spinal surgery. Method 500 includes anchoring a monopedicular targeting system to pedicle 176 of patient 170 and using the monopedicular targeting system in posterior spinal surgery of patient 170. The monopedicular targeting system is configured to hold spinal surgery device 150 while allowing three translational degrees of freedom and three rotational degrees of freedom for spinal surgery device 150 with respect to pedicle 176 of patient 170. Method 500 may be used to install monopedicular targeting system 100 and may apply monopedicular targeting system 100 to perform posterior spinal surgery.

In a step 510, a fastener is affixed to one pedicle of a spinal segment. Step 510 may utilize devices known in the art, such as a drill, a tap, a jamshidi needle, and/or a guide wire. The fastener may be cannulated or a non-cannulated. In one example, step 510 utilizes a guide wire for guiding a cannulated fastener into position in pedicle 176. In an embodiment, step 510 includes a step 512 of generating a trajectory template for the monopedicular targeting system. For example, step 512 may include locating pedicle 176 using fluoroscopy and/or other navigation tools to generate the trajectory template. This trajectory template is used in step 510 to select an optimal trajectory for the fastener into pedicle 176. The trajectory template is generated at least partly based upon an anticipated optimal trajectory of spinal surgery device 150 and geometric properties of the monopedicular targeting system that relate the trajectory of the fastener to the trajectory of spinal surgery device 150. In one example of step 510, surgeon 180 affixes fastener 110 to pedicle 176. Surgeon 180 or a computer system may generate a trajectory template for fastener 110, which may be at least partly based upon an anticipated optimal trajectory of spinal surgery device 150 and geometrical properties of monopedicular targeting system 100 when used to anchor spinal surgery device 150 to fastener 110.

In one embodiment, the monopedicular targeting system, including fastener 110, is preassembled and also connected to spinal surgery device 150 prior to step 510. In another embodiment, method 500 includes a step 520 of connecting spinal surgery device 150 to the fastener of step 510 via a manipulator that allows three translational degrees of freedom and three rotational degrees of freedom for spinal surgery device 150 with respect to pedicle 176 to which the fastener is affixed. In one example of step 520, surgeon 180 connects spinal surgery device 150 to manipulator 210, which, in this example, is pre-connected to fastener 110. In another example of step 520, surgeon 180 connects manipulator 210 to fastener 110, and connects spinal surgery device 150 to manipulator 210. In yet another example of step 520, surgeon 180 connects a portion of manipulator 210 to another portion of manipulator 210 that is pre-connected to fastener 110, and connects spinal surgery device 150 to manipulator 210.

A step 530 manipulates spinal surgery device 150 and a manipulator of the monopedicular targeting system to target a surgery location 270 of patient 170 with spinal surgery device 150, wherein spinal surgery device 150 is anchored to pedicle 176 via the manipulator and the fastener of step 510. In one embodiment, step 530 includes at step 532 of manipulating at least one translational degree of freedom of spinal surgery device 150 with respect to pedicle 176. In another embodiment, step 530 includes at step 534 of manipulating at least one rotational degree of freedom of spinal surgery device 150 with respect to pedicle 176. In one example of step 530, a surgeon 180 manipulates manipulator 210 and spinal surgery device 150, anchored to pedicle 176 via manipulator 210 and fastener 110, to target surgery location 270 with spinal surgery device 150. Surgeon 180 may manipulate one, two, or three translational degrees of freedom and/or one, two, or three rotational degrees of freedom of spinal surgery device 150 with respect to pedicle 176.

In an embodiment, method 500 includes a step 540 of locking the position and orientation of at least a portion of the manipulator, used in step 530, and/or spinal surgery device 150 to at least restrict motion of spinal surgery device 150 with respect to pedicle 176. In one example of step 540, surgeon 180 engages one or more of locking devices 414, 424, and 434 to lock one or more of joints 412, 420, and 430 in a desired configuration, respectively, so as to at least restrict motion of spinal surgery device 150. For example, surgeon 180 may engage each implemented locking device to fully lock the position and orientation of spinal surgery device 150 with respect to pedicle 176. As needed, method 500 may return to step 530 from step 540 to adjust the position and/or orientation of spinal surgery device 150.

Optionally, method 500 further includes a step 550 of performing a surgical procedure using spinal surgery device 150 as positioned in step 530. In one example of step 550, spinal surgery device 150 is a retractor that retracts tissue of patient 170 to provide access to surgery location 270. In another example of step 550, spinal surgery device 150 is a tool for operating on spine 172 of patient 170, for example a tool used to remove tissue from patient 170 or insert hardware or implants into patient 170. As needed, method 500 may return to step 530 from step 550 to adjust the position and/or orientation of spinal surgery device 150, and optionally perform step 540 to re-restrict motion of spinal surgery device 150.

In an optional step 560, method 500 removes spinal surgery device 150. In one example of step 560, surgeon 180 removes spinal surgery device 150 from monopedicular targeting system 100. As needed, method 500 may return to step 520 from step 560 to connect a different spinal surgery device 150 to monopedicular targeting system 100 so as to anchor this different spinal surgery device 150 to pedicle 176. Step 560 may also include removing the manipulator or at least a portion of the manipulator when no longer needed. In one such example of step 560, surgeon 180 disconnects manipulator 210 from fastener 110. In another such example of step 560, surgeon 180 removes a portion of manipulator 210 sufficient to enable subsequent removal of fastener 110. Additionally, step 560 may include extracting the fastener from pedicle 176. In one such example of step 560, surgeon 180 extracts fastener 110 from pedicle 176, for example after disconnecting spinal surgery device 150 and, optionally, at least a portion of manipulator 210.

In one embodiment, step 560 includes a step 562 of utilizing a guide wire for removal of the fastener and, optionally, at least a portion of the manipulator. When step 560 implements step 562, a guide wire is inserted into the fastener through a cannulation of the fastener, and the fastener is removed along the guide wire. The guide wire may pass through at least a portion of the manipulator such that both the fastener and the at least a portion of the manipulator are removed along the guide wire. In one example of step 560 implemented with step 562, surgeon 180 inserts a guide wire into a cannulation of fastener 110 and extracts fastener 110 from pedicle 176 along the guide wire. In another embodiment, step 560 removes the fastener without use of a guide wire.

Embodiments of method 500 that include step 562 may further include a step 570 of inserting a pedicle screw into pedicle 176 along the guide wire. This allows the surgeon to take advantage of the existing trajectory of the fastener inserted in step 510, and also the hole made by this fastener in pedicle 176, when inserting the pedicle screw. The pedicle screw may have diameter in the range between 3.5 and 7 millimeters. In one embodiment, the pedicle screw has greater diameter than the fastener inserted in step 510, such that contact between the pedicle screw and pedicle 176 is not compromised by damage to pedicle 176 incurred by the fastener inserted in step 510. In one example, fastener 110 has outer diameter of about four millimeters, while the pedicle screw has outer diameter of about six millimeters. In another example, the pedicle screw diameter is greater by the diameter of fastener 110 by about 1-3 millimeters. Embodiments of method 500 that do not include step 562 may perform step 570 without use of a guide wire.

Optionally, method 500 includes a step 580 of completing the spinal surgery procedure after step 560 or after step 570. Step 580 may utilize methods known in the art.

One implementation of method 500 utilizes monopedicular targeting system 450. In this implementation, step 510 includes affixing percutaneous pedicle screw 212 to pedicle 176, optionally along a trajectory determined in step 512. In step 520, spinal surgery device 150 is attached to removable guiding section 240 via connector 200. Step 530 manipulates at least some degrees of freedom of spherical joint 250, joint 420, and joint 412 to target surgery location 270 with spinal surgery device 150. If implemented, step 540 utilizes one or more of locking devices 414, 424, and 434 to lock at least a portion of monopedicular targeting system 450 in a desired configuration before performing a surgical procedure in step 550 using spinal surgery device 150. If implemented, step 560 includes removing spinal surgery device 150 and connector 200, while leaving in percutaneous pedicle screw 212. This implementation does not require step 570. In step 580, percutaneous pedicle screw 212 may serve another purpose for the spinal surgery procedure. For example, a rod may be inserted into patient 170 via removable guiding section 240, placed in socket 230 and in a similar socket of a percutaneous pedicle screw affixed to an adjacent pedicle on the same side of spine 172, and secured to socket 230 and a similar socket affixed to the adjacent pedicle. This implementation of method 500 eliminates the need for removing a non-pedicle screw fastener to replace this fastener with a pedicle screw, and thereby both simplifies the workflow and minimizes potential damage to pedicle 176.

Without departing from the scope hereof, method 500 (without step 570) may utilize a spine-anchored targeting system anchored to a different structure of spine 172 than pedicle 176, or to a pelvis of patient 170, to perform posterior spinal surgery of the cervical, thoracic, and/or lumbar spine of patient 170. Such spine-anchored targeting system are discussed further in reference to FIGS. 56-59 below.

Figure 5B:
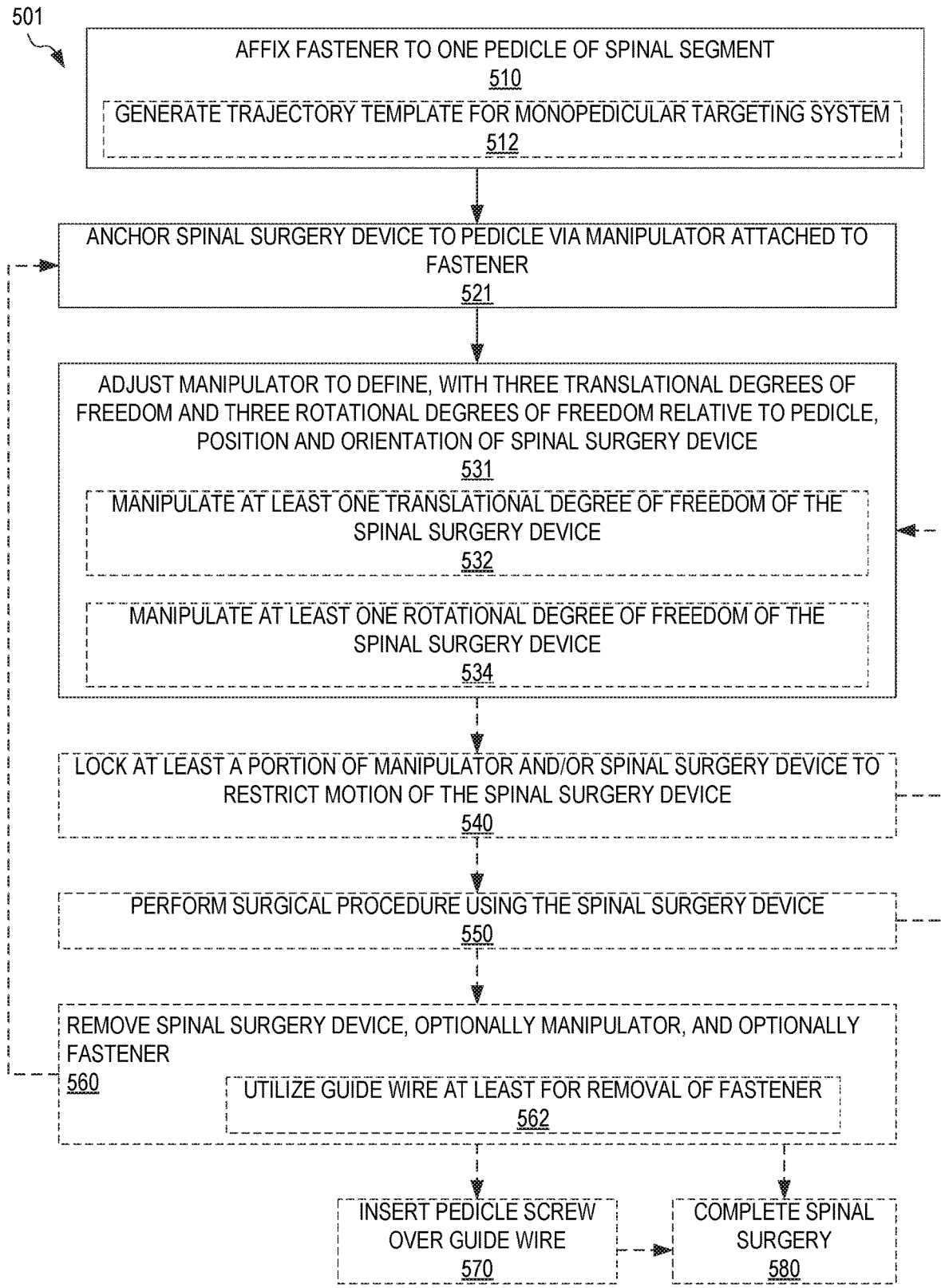
FIG. 5B illustrates another monopedicular targeting method for posterior spinal surgery, according to an embodiment.

FIG. 5B illustrates another exemplary monopedicular targeting method 501 for posterior spinal surgery. Method 501 is similar to method 500 except for optional step 520 and step 530 being replaced by steps 521 and 531, respectively.

In step 521, spinal surgery device 150 is anchored to pedicle 176 via a manipulator attached to the fastener. In one example of step 521, surgeon 180 connects spinal surgery device 150 to manipulator 210, which, in this example, is pre-connected to fastener 110. In another example of step 521, surgeon 180 connects manipulator 210 to fastener 110, and connects spinal surgery device 150 to manipulator 210. In yet another example of step 521, surgeon 180 connects a portion of manipulator 210 to another portion of manipulator 210 that is pre-connected to fastener 110, and connects spinal surgery device 150 to manipulator 210. In a further example of step 521, surgeon 180 uses connector 200 to connect spinal surgery device 150 to percutaneous pedicle screw 212.

Step 531 adjusts the manipulator to define, with three translational degrees of freedom and three rotational degrees of freedom relative to pedicle 176, the position and orientation of spinal surgery device 150 to target a surgery location 270 of patient 170 with spinal surgery device 150. Step 531 may include one or both of steps 532 and 534. Surgeon 180 may manipulate one, two, or three translational degrees of freedom and/or one, two, or three rotational degrees of freedom of spinal surgery device 150 with respect to pedicle 176. In one example of step 531, surgeon 180 manipulates manipulator 210 and spinal surgery device 150, anchored to pedicle 176 via manipulator 210 and fastener 110, to target surgery location 270 with spinal surgery device 150. In another example of step 531, surgeon 180 manipulates one or more degrees of freedom of spherical joint 250, joint 412, and joint 420 of monopedicular targeting system 450 to target surgery location 270 with spinal surgery device 150, anchored to pedicle 176 via connector 200 and percutaneous pedicle screw 212.

Without departing from the scope hereof, method 501 (without step 570) may utilize a spine-anchored targeting system anchored to a different structure of spine 172 than pedicle 176, or to a pelvis of patient 170, to perform posterior spinal surgery of the cervical, thoracic, and/or lumbar spine of patient 170. Such spine-anchored targeting system are discussed further in reference to FIGS. 56-59 below.

Figure 5C:
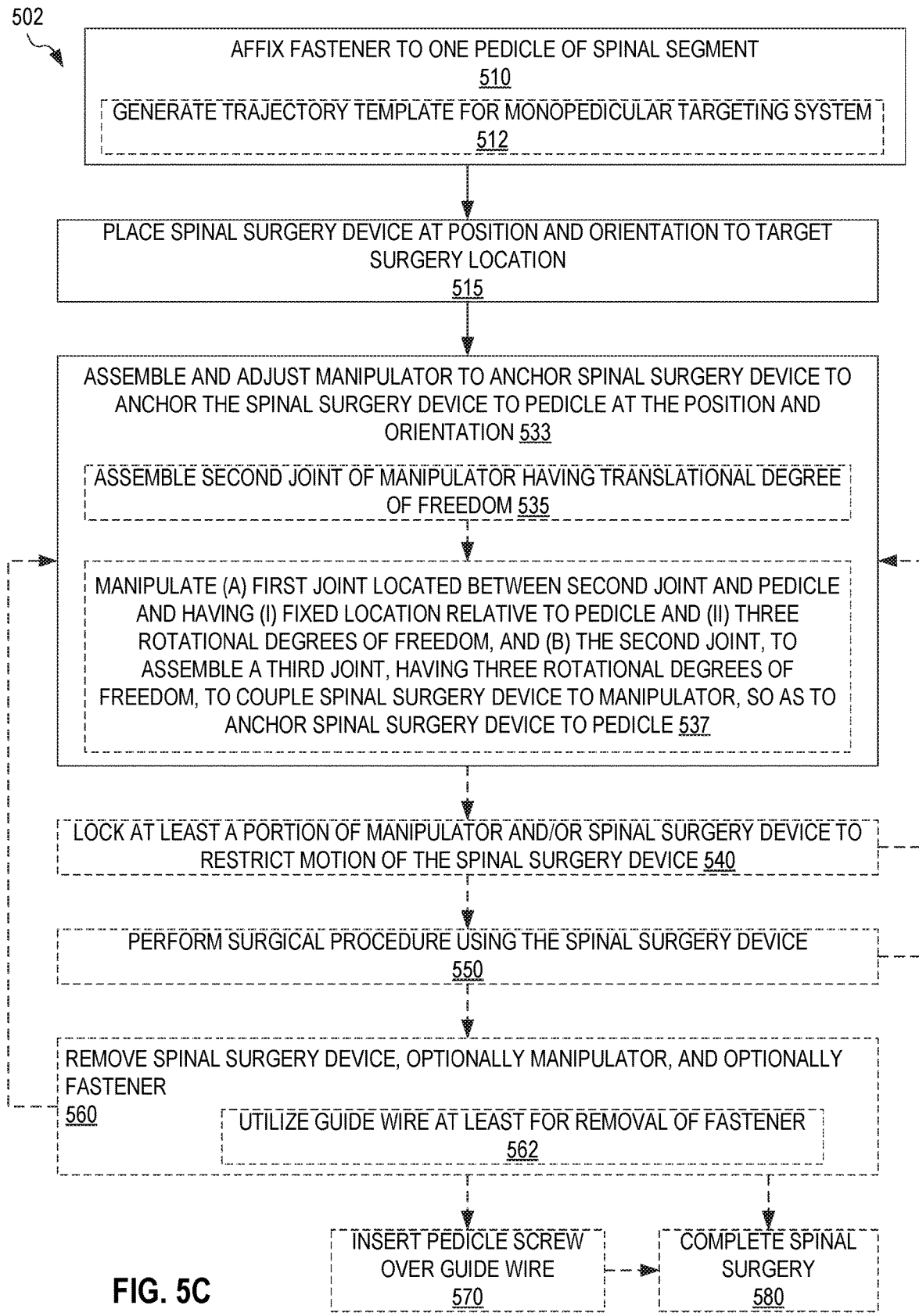
FIG. 5C illustrates yet another monopedicular targeting method for posterior spinal surgery, according to an embodiment.

FIG. 5C illustrates yet another exemplary monopedicular targeting method 502 for posterior spinal surgery. Method 502 is similar to method 501 except for steps 521 and 531 being replaced by steps 515 and 533.

In step 515, surgeon 180 places spinal surgery device 150 at a position and orientation suitable for targeting surgery location 270. Step 515 is performed prior to anchoring spinal surgery device 150 to pedicle 176 via a manipulator.

In step 533, surgeon 180 assembles and adjusts a manipulator to anchor spinal surgery device 150 to pedicle 176 while maintaining, or at least approximately maintaining the position and orientation of spinal surgery device 150 obtained in step 515. Step 533 may include steps 535 and 537. In step 535, surgeon 180 assembles a second joint of the manipulator having a translational degree of freedom. In one example of step 535, surgeon 180 assembles a joint 420 of manipulator 410. In another example of step 535, surgeon 180 assembles joint 420 of monopedicular targeting system 450. In step 537, surgeon 180 manipulates (a) a first joint located between the second joint and pedicle 176 and (b) the second joint, in order to assemble a third joint to couple spinal surgery device to manipulator, so as to anchor spinal surgery device to pedicle. The first joint has fixed location relative to pedicle and three rotational degrees of freedom, and the third joint has three rotational degrees of freedom.

Without departing from the scope hereof, method 502 may include further manipulation of the manipulator to adjust the position and/or orientation of spinal surgery device 150 after step 533.

Without departing from the scope hereof, method 502 (without step 570) may utilize a spine-anchored targeting system anchored to a different structure of spine 172 than pedicle 176, or to a pelvis of patient 170, to perform posterior spinal surgery of the cervical, thoracic, and/or lumbar spine of patient 170. Such spine-anchored targeting system are discussed further in reference to FIGS. 56-59 below.

Figure 5D:
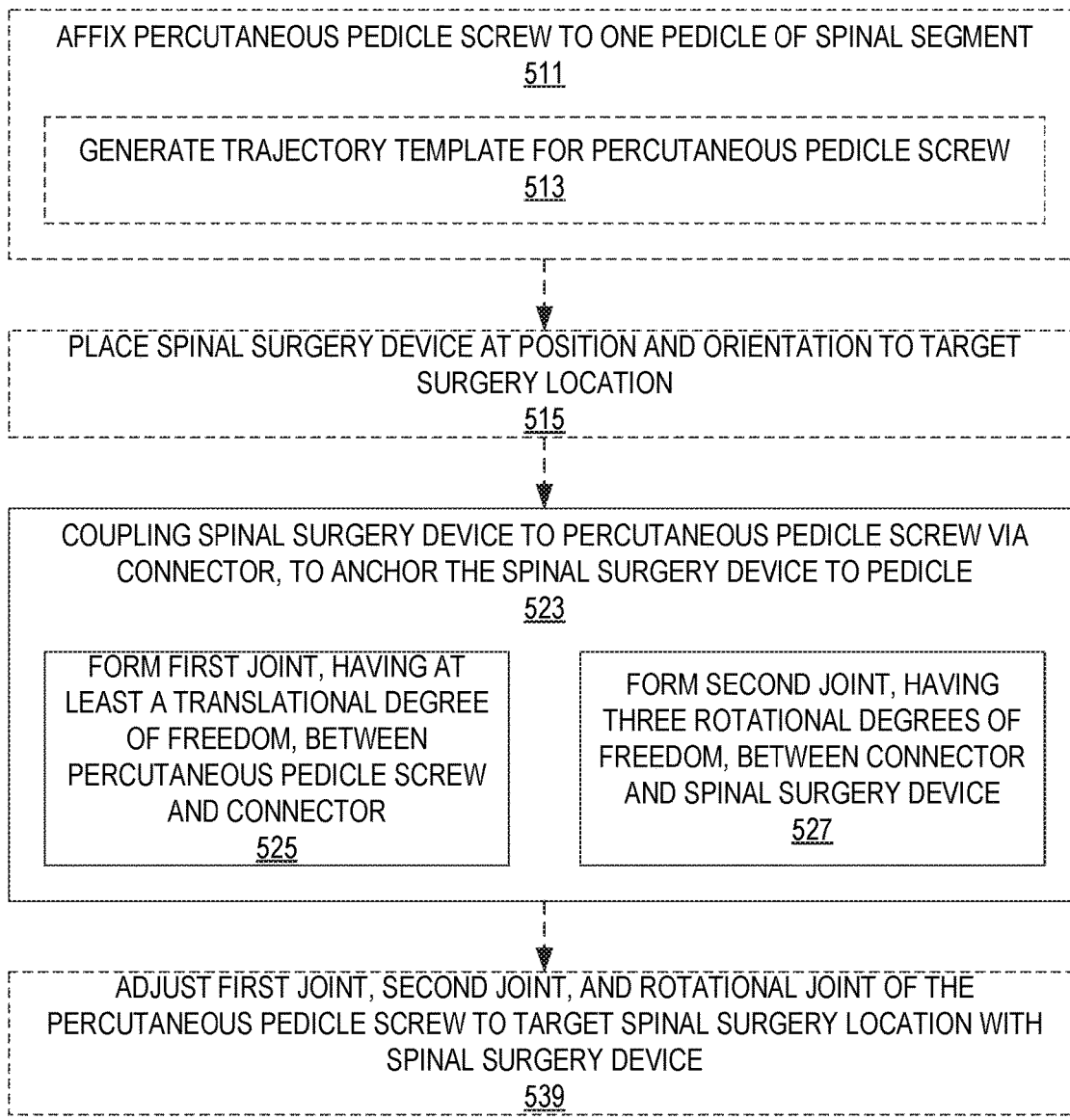
FIG. 5D illustrates a monopedicular targeting method for posterior spinal surgery, which utilizes the connector of FIG. 2B to anchor a spinal surgery device to a pedicle via a percutaneous pedicle screw, according to an embodiment.

FIG. 5D illustrates one exemplary monopedicular targeting method 503 for posterior spinal surgery, which utilizes connector 200 to anchor spinal surgery device 150 to pedicle 176 via percutaneous pedicle screw 212. Method 503 is an embodiment of a portion of each of methods 500, 501, and 502.

In an optional step 511, surgeon 180 affixes a percutaneous pedicle screw 212 to pedicle 176. Step 511 may include a step 513 of generating a trajectory template for percutaneous pedicle screw 212. Step 513 is step 512 applied to percutaneous pedicle screw 212. Step 511 is an embodiment of step 510.

In a step 523, surgeon 180 couples spinal surgery device 150 to percutaneous pedicle screw 212 via connector 200 to anchor spinal surgery device 150 to pedicle 176. Step 523 includes steps 525 and 527. In step 525, surgeon 180 couples connector 200 to percutaneous pedicle screw 212 to form a joint 420 therebetween. In step 527, surgeon 180 couples connector 200 to spinal surgery device 150 to form joint 412. Step 523 is an embodiment of (a) step 520 optionally combined with step 530, (b) step 521 optionally combined with step 531, and (c) step 515.

In one embodiment, method 503 includes a step 539, wherein surgeon 180 adjusts one or more degrees of freedom of joint 412, joint 420, and/or spherical joint 250 to target surgery location 270 with spinal surgery device 150. Step 539 is an embodiment of each of steps 530 and 531. In another embodiment, method 503 includes step 515 prior to step 523, such that step 539 may be unnecessary.

Figure 6A:
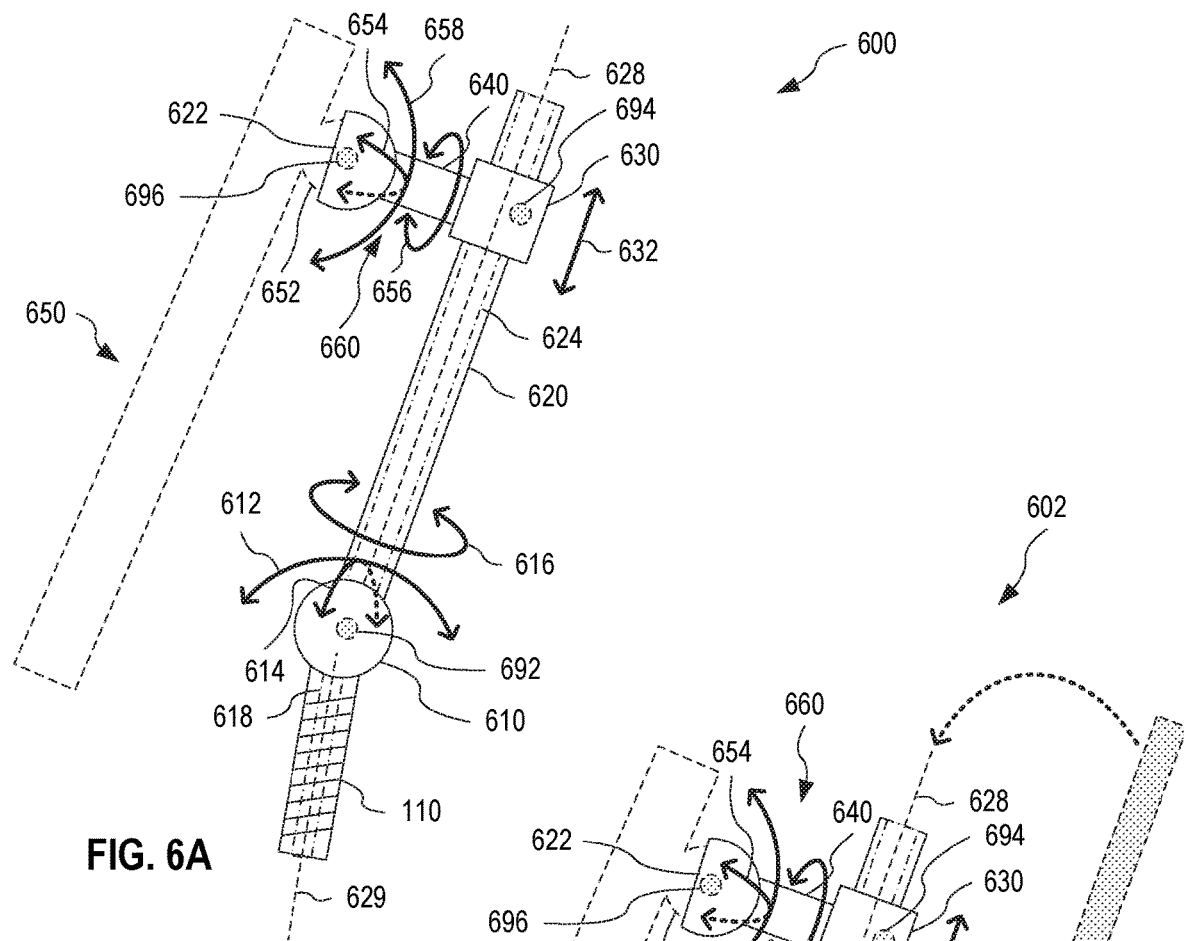
FIG. 6A illustrates a monopedicular targeting system that, when assembled, forms a spherical joint, a joint with at least a translational degree of freedom, and a spherical joint component configured to mate with a spherical joint component of a spinal surgery device, according to an embodiment.

FIG. 6A illustrates one exemplary monopedicular targeting system 600 that, when assembled, forms (a) a spherical joint 610, (b) a joint 630 having at least a translational degree of freedom, and (c) a spherical joint component 622 configured to mate with a spherical joint component 652 of a spinal surgery device 650. Spinal surgery device 650 is an embodiment of spinal surgery device 150, which implements joint component 152 as a spherical joint component. Monopedicular targeting system 600 is an embodiment of monopedicular targeting system 400, which implements one connector 431, joint 430, and one joint 420. Spherical joint component 622 is an embodiment of joint component 122, joint 610 is an embodiment of joint 430, and joint 630 is an embodiment of joint 420. Monopedicular targeting system 600 may be used to perform any of methods 500, 501, 502, and 503.

Monopedicular targeting system 600 includes fastener 110, a positioning arm 620 configured to connect with fastener 110 via spherical joint 610, and a connector 640 configured to connect with positioning arm 620 via joint 630. Connector 640 further implements spherical joint component 622. Joint 610 has three rotational degrees of freedom as indicated by orthogonal rotation directions 612, 614, and 616. Without departing from the scope hereof, joint 610 may be able to rotate in directions not shown in FIG. 6. Joint component 622 is configured to mate with joint component 652 to form a joint having three rotational degrees of freedom as indicated by orthogonal rotation directions 658, 654, and 656. Without departing from the scope hereof, this joint may be able to rotate in directions not shown in FIG. 6.

Joint 630 has a translational degree of freedom along positioning arm 620 as indicated by direction 632. Positioning arm 620 has a longitudinal axis 628 extending from joint 610 through joint 630. In the exemplary embodiment shown in FIG. 6, positioning arm 620 has substantially constant cross section, orthogonal to longitudinal axis 628, for the full length of positioning arm except for the portion of positioning arm 620 implementing a joint component of joint 610. Connector 640 may connect with positioning arm at any location associated within this substantially constant cross section. Thus, the distance between spherical joint 610 and the spherical joint formed when mating joint component 622 with joint component 652 may be adjusted in the dimension spanned by direction 632.

Without departing from the scope hereof, only a section of positioning arm 620 along longitudinal axis 628 may have a substantially constant cross section, and connector 640 may connect with positioning arm within this section. Likewise, at least a portion of positioning arm 620 may be curved such that longitudinal axis 628 is curved.

In an embodiment, positioning arm 620, or at least a section thereof having substantially constant cross section orthogonal to longitudinal axis 628, is cylindrical. In this embodiment, joint 630 is a cylindrical joint that further allows rotation of connector 640 about longitudinal axis 628.

Spherical joint 610 and joint 630 cooperate to provide three translational degrees of freedom of joint component 622 with respect to fastener 110, as illustrated for joint component 122 in FIG. 3A. The spherical joint formed when mating joint component 622 with joint component 652 provides three rotational degrees of freedom for spinal surgery device 150 with respect to fastener 110, as illustrated in FIG. 3B.

In an embodiment, positioning arm 620 is cannulated and has a cannulation 624 that extends for the full length of positioning arm 620 from the end of positioning arm 620 associated with spherical joint 610 to the opposite end of positioning arm 620. Cannulation 624 may serve to allow access to fastener 110 through positioning arm 620. Optionally, fastener 110 has a cannulation 618. Cannulation 618 may fit a guide wire such that fastener 110 may be inserted into pedicle 176 along a guide wire. In embodiments of monopedicular targeting system 600 that include both cannulation 624 and cannulation 618, positioning arm 620 may be connected to fastener 110 prior to inserting fastener 110 into pedicle 176 along a guide wire. In such embodiments, monopedicular targeting system 600 may be fully assembled, and optionally connected with spinal surgery device 650, prior to inserting fastener 110 into pedicle 176 along the guide wire.

Monopedicular targeting system 600 may include one or more locking devices 692, 694, and 696, for locking in a desired configuration one or more of joint 610, joint 630, and the joint formed by mating joint components 622 and 652, respectively. Locking device 692 is an embodiment of locking device 434, locking device 694 is an embodiment of locking device 424, and locking device 696 is an embodiment of locking device 414. Without departing from the scope hereof, two or more of locking devices 692, 694, and 696 may be implemented in a single locking device. Each of locking devices 692, 694, and 696 may be hand-actuated and/or actuated by a tool.

Monopedicular targeting system 600 may be provided to a user in assembled form or in a form that requires at least some assembly to be performed by a user. For example, monopedicular targeting system 600 may be provided to a user as separate fastener 110, separate positioning arm 620, and separate connector 640, which are to be assembled by the user. In another example, monopedicular targeting system 600 is provided to a user with positioning arm 620 and fastener 110 connected to each other via joint 610, but with connector 640 separate therefrom. Additionally, fastener 110 may be provided to a user as two or more separate parts, which are to be assembled by the user to form fastener 110, as discussed in reference to monopedicular targeting system 100.

As discussed in further detail below in reference to FIGS. 56-59, monopedicular targeting system 600 is readily extended to spine-anchored targeting systems that each have the same functionality as monopedicular targeting system 600 but may be anchored to a different structure of spine 172 or to a pelvis of patient 170. Such spine-anchored targeting systems may be used in posterior spinal surgery of the cervical, thoracic, and/or lumbar spine of patient 170.

Figure 6B:
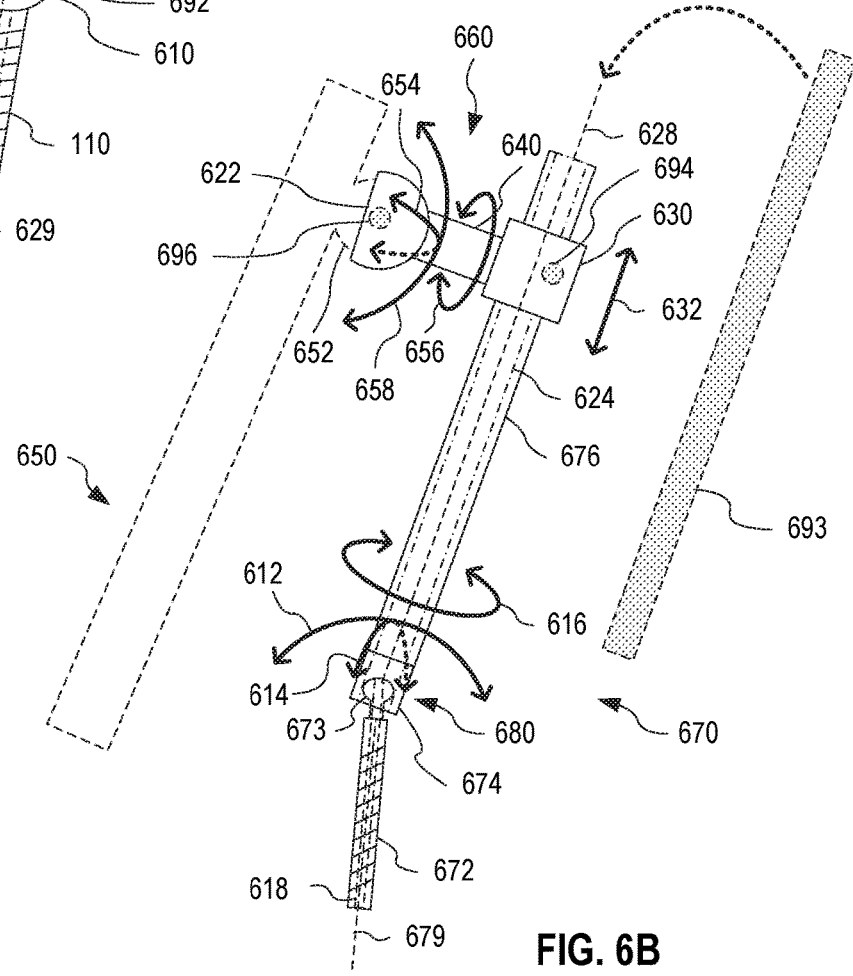
FIG. 6B illustrates a monopedicular targeting system that is based upon a percutaneous pedicle screw and a connector, according to an embodiment.

FIG. 6B illustrates one exemplary monopedicular targeting system 602 that is based upon a percutaneous pedicle screw 670 and a connector 660. Connector 660 is configured to connect spinal surgery device 650 to percutaneous pedicle screw 670 affixed to pedicle 176. Monopedicular targeting system 602 is an embodiment of monopedicular targeting system 450 and of monopedicular targeting system 600. Connector 660 is an embodiment of connector 200. As compared to monopedicular targeting system 600 (as shown in FIG. 6A), positioning arm 620, joint 610, and fastener 110 are replaced by percutaneous pedicle screw 670.

Percutaneous pedicle screw 670 is an embodiment of percutaneous pedicle screw 212 and includes (a) a pedicle screw 672 with a head 673, (b) a socket 674 forming a spherical joint 680 with head 673, and (c) a removable guiding extension 676. Pedicle screw 672, head 673, socket 674, spherical joint 680, and removable guiding extension 676 are embodiments of pedicle screw 220, head 226, socket 230, spherical joint 250, and removable guiding extension 240, respectively. Removable guiding extension 676 includes cannulation 624 extending from the end of removable guiding extension 676 most distant from socket 674 at least to head 673. Optionally, pedicle screw 672 includes cannulation 618. Spherical joint 680 has three rotational degrees of freedom as discussed for joint 610.

Removable guiding extension 676 and socket 674 form an embodiment of positioning arm 620. Connector 660 includes (a) connector 640, (b) a joint component 622, and (c) a joint component of joint 630 configured to slide along removable guiding extension 676, along direction 632, as discussed for joint 630 and positioning arm 620 in reference to FIG. 6A.

In one embodiment, removable guiding extension 676 is coupled with socket 674 in a manner that allows for attaching removable guiding extension 676 to socket 674 and detaching removable guiding extension 674 from socket 674. In one example, removable guiding extension 676 is threaded into socket 674 and may be removed from socket 674 by unscrewing it therefrom. In another embodiment, removable guiding extension 676 is connected to socket 674 via a fragile connection and may be broken off of socket 674 by breaking the fragile connection. In one example, removable guiding extension 676 is integrally formed with socket 674. Removable guiding section 676 may be substantially cylindrical. Alternatively, at least a portion of removable guiding section 676 includes only a portion of a cylindrical shape. In one such example, removable guiding section 676 may be one or more (for example two) break-off blades oriented along axis 628, and cannulation 624 may be accessed both from the end of removable guiding section 676 most distant from socket 674 and through openings between the two break-off blades.

Monopedicular targeting system 602 may implement locking device 692 as a locking driver 693 in the shape of a shaft that fits within cannulation 624 and engages with socket 674 and/or removable guiding section 676 to apply pressure on head 673 to lock spherical joint 680 in a desired configuration. In one embodiment, locking driver 693 is configured to stabilize break-off blades of removable guiding extension 676 to prevent inadvertent break-off of these break-off blades when locking connector 660 to removable guiding section 676 using locking device 694. For example, the outer diameter of locking driver 693 may be sufficiently close to the inner diameter of cannulation 624 to counteract inwards pressure applied by locking device 694. Locking driver 693 may be hand-actuated and/or actuated by a tool. Without departing from the scope hereof, locking driver 693 may be replaced by an alternative implementation of locking device 692. For example, such an alternative implementation of locking device 692 may be adapted to the specific properties of a third party percutaneous pedicle screw.

Without departing from the scope hereof, connector 660 may be supplied as a stand-alone item configured to cooperate with a third party percutaneous pedicle screw 670 and a third party spinal surgery device 650 to target surgery location 270. Connector 660 is an embodiment of connector 200.

Figure 7A:
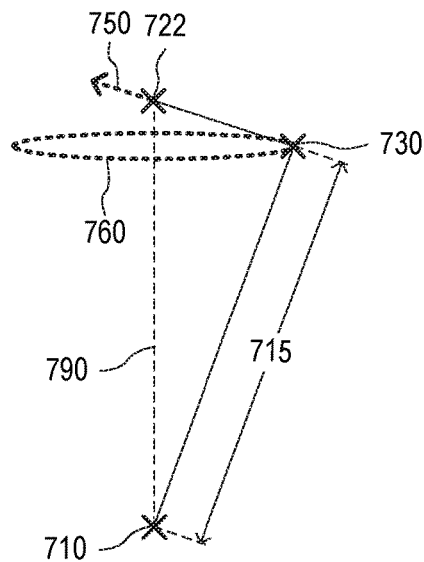
FIGS. 7A and 7B illustrate an additional rotational degree of freedom for the monopedicular targeting systems of FIGS. 6A and 6B, according to an embodiment.
Figure 7B:
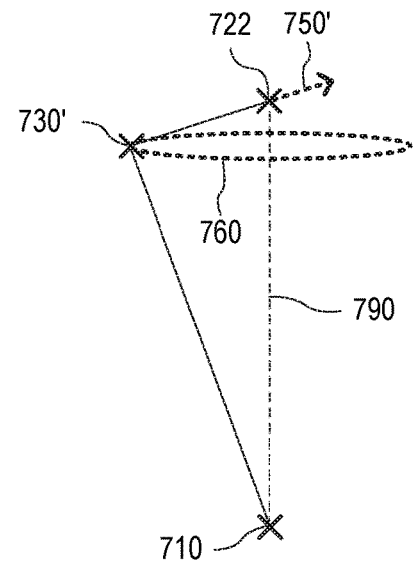

FIGS. 7A and 7B illustrate an additional rotational degree of freedom for monopedicular targeting systems 600 and 602. FIGS. 7A and 7B are best viewed together.

Point 710 indicates the location of joint 610 (or joint 680) and point 722 indicates the location of joint component 622. Given fixed points 710 and 722, joint 630 may move along a circular trajectory 760 such that the direction in which joint component 622 faces away from positioning arm 620 (or removable guiding extension 676) may be rotated about the axis 790 defined by points 710 and 722. FIG. 7A shows one exemplary facing direction 750 of joint component 622 when joint 630 is located at a position 730 along circular trajectory 760. FIG. 7B shows a different exemplary facing direction 750' of joint component 622 when joint 630 is located at a different position 730' along circular trajectory 760. This additional rotational degree of freedom may be achieved at a range of distances 715 between joint 610 (or joint 680) and joint 630.

The freedom to vary the facing direction of joint component 622, as illustrated in FIGS. 7A and 7B, enhances the ability to achieve a desired trajectory for spinal surgery device 650.

Figure 7C:
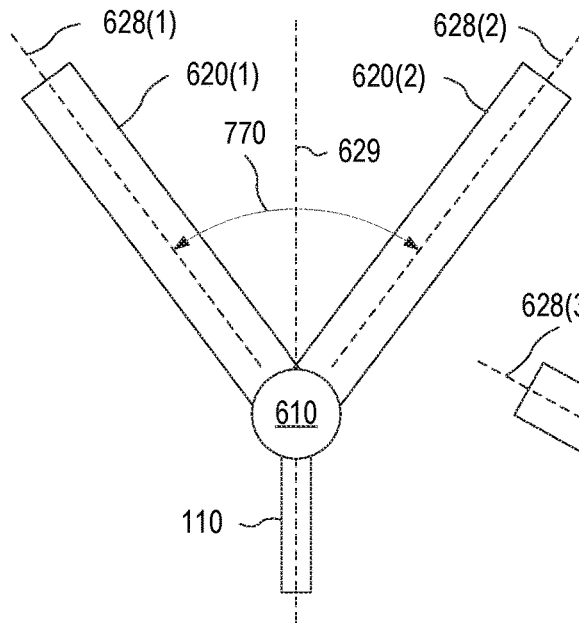
FIG. 7C illustrates the angular range of a spherical joint of the monopedicular targeting systems of FIGS. 6A and 6B, wherein the spherical joint is implemented as a symmetric joint, according to an embodiment.

FIG. 7C illustrates one exemplary angular range of joint 610 of monopedicular targeting system 600, wherein joint 610 is implemented as a symmetric joint having the same angular range for rotation about any axis orthogonal to longitudinal axis 629 of fastener 110. FIG. 7C is a side view of fastener 110, joint 610, and positioning arm 620, for two different orientations of positioning arm 620 relative to longitudinal axis 629. One extreme orientation of positioning arm 620 is indicated as positioning arm 620(1) having longitudinal axis 628(1). An opposite extreme orientation of positioning arm 620 is indicated as positioning arm 620(2) having longitudinal axis 628(2). Joint 610 has angular range 770. In one embodiment, angular range 770 is in the range from 40 degrees to 60 degrees (such that the angular range away from the longitudinal axis of fastener 110 is in the range from 20 degrees to 30 degrees). In another embodiment, angular range 770 is at least 70 degrees to provide greater flexibility for the position and orientation of spinal surgery device 650 with respect to pedicle 176. In one such example, angular range 770 is between 70 degrees and 75 degrees.

Figure 7D:
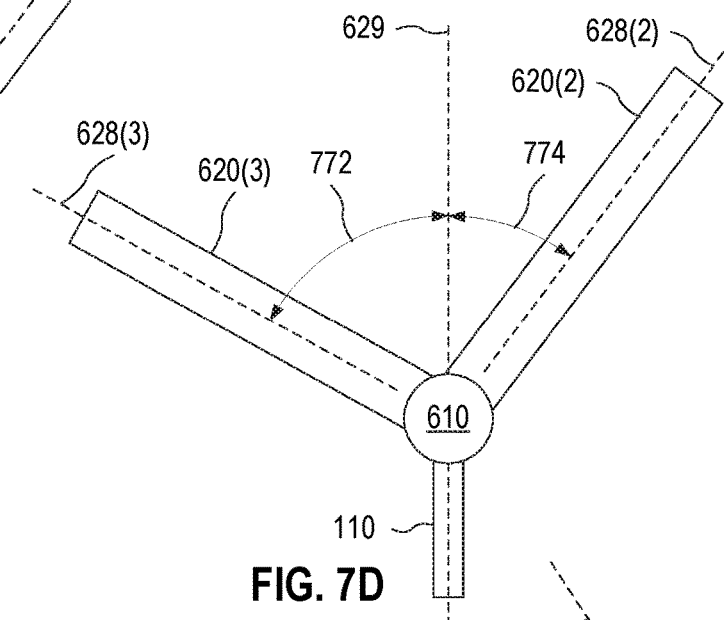
FIGS. 7D and 7E illustrate the angular range of a spherical joint of the monopedicular targeting systems of FIGS. 6A and 6B, wherein the spherical joint is implemented as an asymmetric joint having expanded angular range in certain directions, according to an embodiment.
Figure 7E:
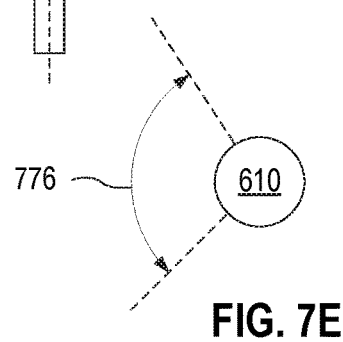

FIGS. 7D and 7E illustrate one exemplary angular range of joint 610 of monopedicular targeting system 600, wherein joint 610 is implemented as an asymmetric joint having expanded angular range in some directions. FIG. 7D is a side view of fastener 110, joint 610, and positioning arm 620, for two different orientations of positioning arm 620 relative to longitudinal axis 629. FIG. 7E is a cross-sectional view of joint 610 with the viewing direction being along longitudinal axis 629. FIGS. 7D and 7E are best viewed together.

Joint 610 has expanded angular range within a directional range indicated in FIG. 7E as angular section 776. In one use scenario, monopedicular targeting system 600 is used to contralaterally target surgery location 270 with spinal surgery device 650 and joint 610 is advantageously oriented such that angular section 776 faces spine 172. Outside angular section 776, joint 610 has the same angular range as the symmetric embodiment illustrated in FIG. 7C. Extreme orientation of positioning arm 620, indicated as positioning arm 620(2) having longitudinal axis 628(2), falls outside angular section 774 and has an angular range 774 away from longitudinal axis 629. Angular range 774 is half of angular range 770. Another extreme orientation of positioning arm 620 is indicated as positioning arm 620(3) having longitudinal axis 628(3). This extreme orientation is within angular section 776. Within angular section 776, joint 610 has angular range 772 away from longitudinal axis 629. Angular range 772 is greater than angular range 774. In one embodiment, angular range 772 exceeds angular range 774 by between 10 degrees and 35 degrees. In one example, angular section 776 has angular extent in the range between 70 degrees and 150 degrees in the plane of FIG. 7E.

Herein, "contralateral" refers to the opposite side of spine 172, such that, e.g., a surgery location 270 is contralaterally targeted from the right side of spine 172 with monopedicular targeting system 100 affixed to a pedicle 176 on the left side of spine 172. In contrast, "ipsilateral" refers to the same side of spine 172, such that, e.g., a surgery location 270 is ipsilaterally targeted from the left side of spine 172 with monopedicular targeting system 100 affixed to a pedicle 176 on the left side of spine 172.

Without departing from the scope hereof, the diagrams of FIGS. 7C-E apply also to monopedicular targeting system 602, in which case fastener 110, joint 610, and positioning arm 620 in FIGS. 7C-E represent pedicle screw 672, joint 680, and removable guiding section 676, respectively.

Figure 8A:
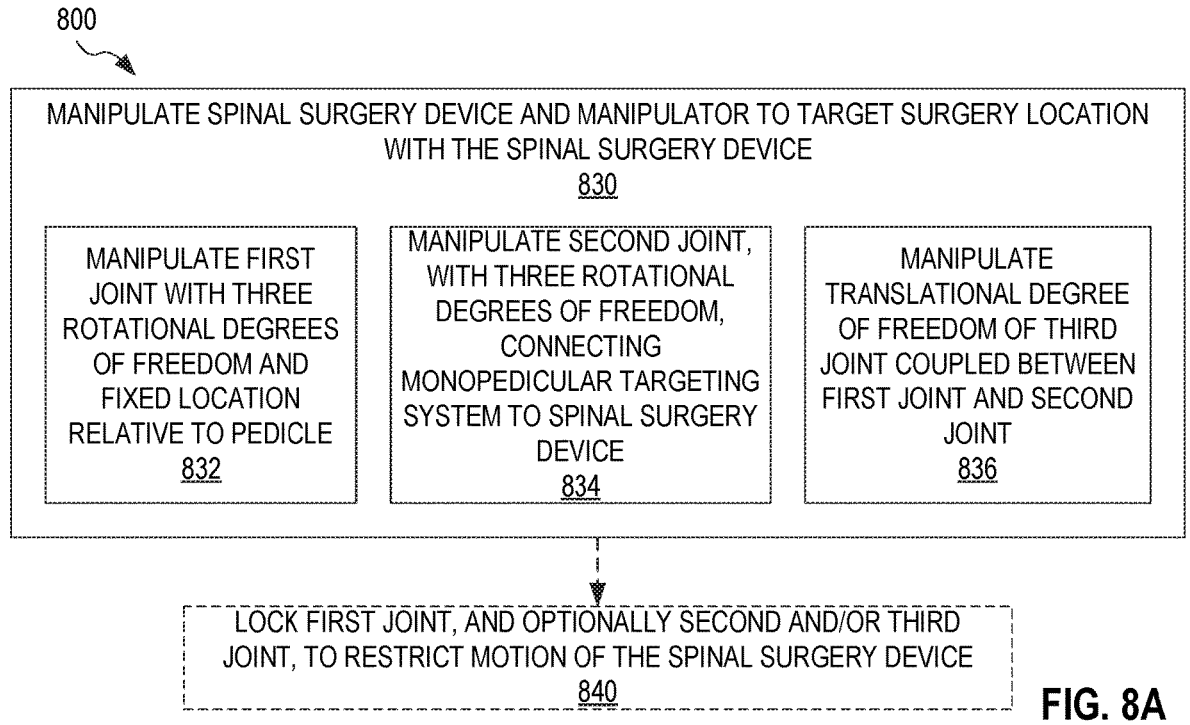
FIG. 8A illustrates a method for manipulating a monopedicular targeting system for posterior spinal surgery, according to an embodiment.

FIG. 8A illustrates one exemplary method 800 for manipulating a monopedicular targeting system for posterior spinal surgery. Method 800 is an embodiment of a portion of each of methods 500 and 501, and may be implemented in either or both of methods 500 and 501. Method 800 is performed by monopedicular targeting system 600 or 602, for example.

A step 830 manipulates a monopedicular targeting system, affixed to pedicle 176, and spinal surgery device 650 anchored to pedicle 176 via the monopedicular targeting system, such as monopedicular targeting system 600 or 602. Step 830 is an embodiment of each of steps 530 and 531. Step 830 includes steps 832, 834, and 836.

Step 832 manipulates a first joint of the monopedicular targeting system. This first joint has three rotational degrees of freedom and has fixed location relative to pedicle 176. In one example of step 832, surgeon 180 manipulates spherical joint 610 of monopedicular targeting system 600. In another example of step 832, surgeon 180 manipulates spherical joint 680 of monopedicular targeting system 602.

Step 834 manipulates a second joint with three rotational degrees of freedom. This second joint connects spinal surgery device 650 to the monopedicular targeting system. In one example of step 834, surgeon 180 manipulates the spherical joint formed by joint components 622 and 652 of monopedicular targeting system 600 or 602.

Step 836 manipulates a translational degree of freedom of a third joint of the monopedicular targeting system. This third joint is coupled between the first joint and the second joint. In one example of step 836, surgeon 180 manipulates joint 630 of monopedicular targeting system 600 or 602.

In an embodiment, method 800 further includes a step 840 of locking the first joint and, optionally, one or both of the second and third joints to at least restrict motion of spinal surgery device 650 relative to pedicle 176. Step 840 is an embodiment of step 540. In one example of step 840, surgeon 180 engages locking device 692 to lock spherical joint 610, or engages locking driver 693 to lock spherical joint 680. Surgeon 180 may further engage one or both of locking devices 694 and 696 to lock joint 630 and the joint formed by mating joint components 622 and 652, respectively.

Figure 8B:
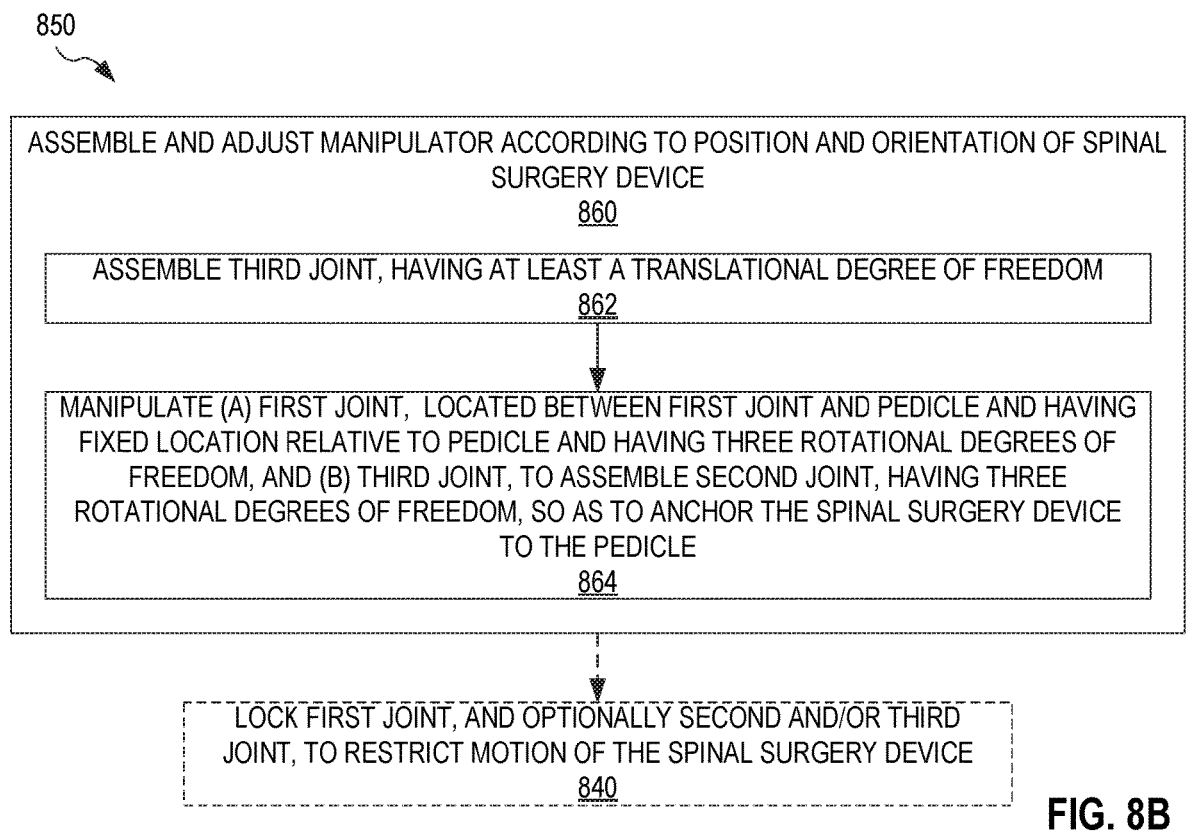
FIG. 8B illustrates a method for coupling a spinal surgery device to a pedicle while maintaining the position and orientation of the spinal surgery device relative to the pedicle, according to an embodiment.

FIG. 8B illustrates one exemplary method 850 for coupling spinal surgery device 150 to pedicle 176 while maintaining the position and orientation of spinal surgery device 150 relative to pedicle 176. Method 850 may be implemented as step 523 of method 503 or as step 533 of method 502.

In a step 860, method 850 assembles and adjusts a manipulator according to position and orientation of spinal surgery device 150 relative to pedicle 176. Step 860 includes steps 862 and 864. Step 862 assembles the third joint discussed above in reference to FIG. 8A. In one example of step 862, surgeon 180 assembles joint 630 of monopedicular targeting system 600 or 602. Step 864 manipulates the first joint (discussed above in reference to FIG. 8A) and the third joint to assemble the second joint (discussed above in reference to FIG. 8A), so as to anchor spinal surgery device 150 to pedicle 176 while maintaining the position and orientation of spinal surgery device 150 relative to pedicle 176. In one example of step 864, surgeon 180 manipulates joint 610 of monopedicular targeting system 600 and joint 630 of monopedicular targeting system 600 to assemble the spherical joint formed by joint components 622 and 652. In another example of step 864, surgeon 180 manipulates joint 680 of monopedicular targeting system 602 and joint 630 of monopedicular targeting system 602 to assemble the spherical joint formed by joint components 622 and 652.

Optionally, method 850 further includes step 840.

Figure 10:
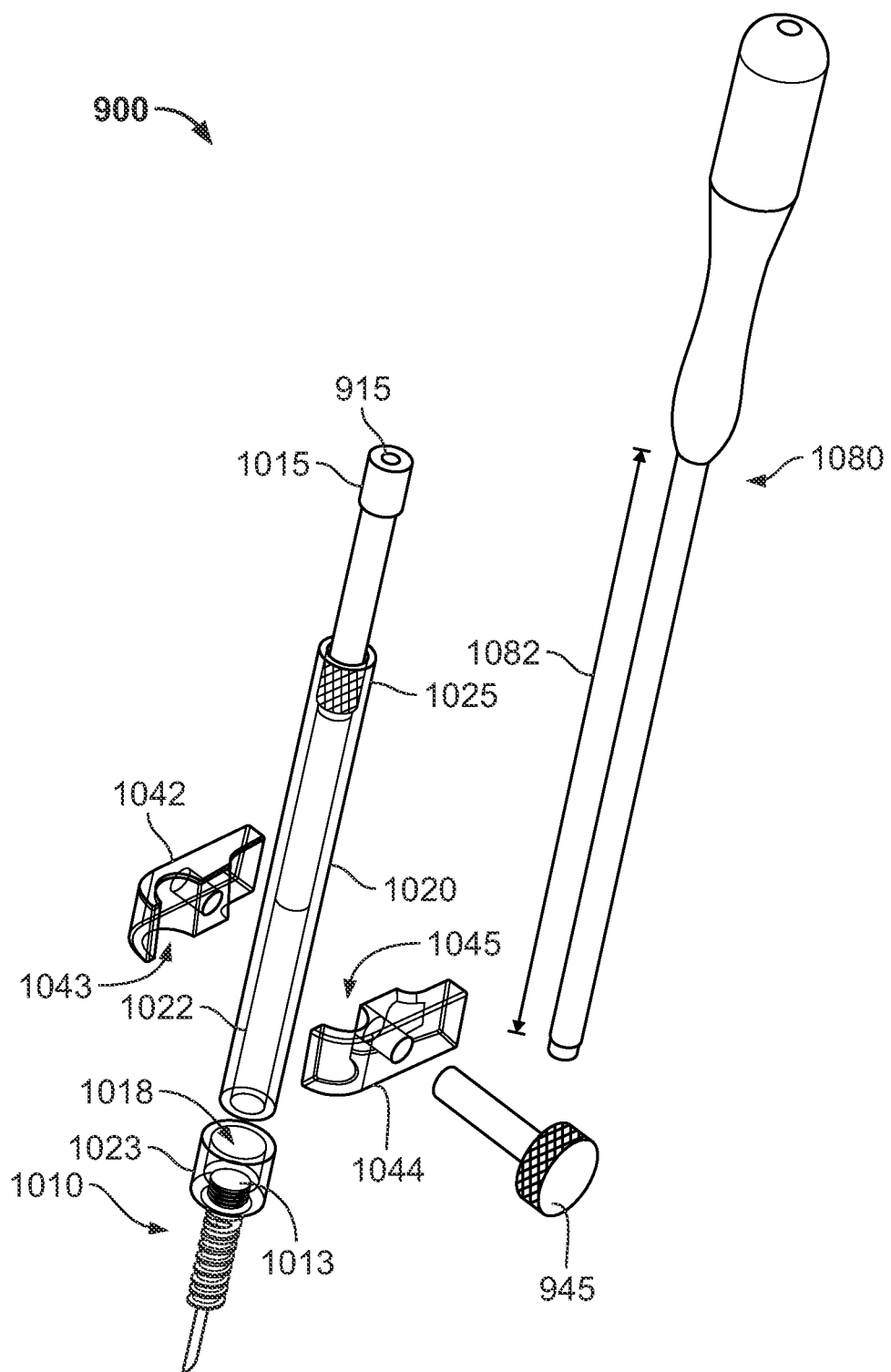
FIG. 10 shows the monopedicular targeting system of FIG. 9 in exploded view together with a driver used to lock a joint of the monopedicular targeting system of FIG. 9, according to an embodiment.

FIGS. 9 and 10 illustrate one exemplary monopedicular targeting system 900 for posterior spinal surgery, which is an embodiment of monopedicular targeting system 600. Monopedicular targeting system 900 may be used to perform any of methods 500, 501, and 502. FIG. 9 shows monopedicular targeting system 900 in perspective view when affixed to pedicle 176. FIG. 10 shows monopedicular targeting system 900 in exploded view together with a driver used to screw a fastener of monopedicular targeting system 900 into pedicle 176. FIGS. 9 and 10 are best viewed together.

Monopedicular targeting system 900 includes a fastener 1010 (not visible in FIG. 9), a positioning arm 920, and a clamp 940. Fastener 1010, positioning arm 920, and clamp 940 are embodiments of fastener 110, positioning arm 620, and connector 640, respectively. Clamp 940 is also an embodiment of connector 200.

Positioning arm 920 includes (a) a cylinder 1020 with a cannulation 1022 and (b) a socket 1023. Socket 1023 has an opening 1018 that is configured to accept cylinder 1020. In one embodiment, cylinder 1020 is permanently affixed in socket 1023 to form positioning arm 920. For example, cylinder 1020 may be welded in place in socket 1023. In another embodiment, cylinder 1020 and socket 1023 are configured such that cylinder 1020 may be removably placed in socket 1023. For example, cylinder 1020 may have external threads (not shown) and socket 1023 may have internal threads (not shown), such that cylinder 1020 may be threaded into socket 1023.

Fastener 1010 has a head 1013 that includes a portion of a ball. Head 1013 forms an embodiment of joint component 224, and socket 1023 forms an embodiment of joint component 432. Head 1013 and socket 1023 are configured to mate to form a ball-and-socket joint 910. Joint 910 is an embodiment of joint 610. Joint 910 may have angular range as discussed for joint 610 in reference to FIGS. 7C-E.

Clamp 940 includes two clamp parts 1042 and 1044. Clamp part 1042 has a groove 1043, and clamp part 1044 has a groove 1045. Clamp parts 1042 and 1044 are configured to be brought together with grooves 1043 and 1045 around cylinder 1020 to form a cylindrical joint 930. Grooves 1043 and 1045 cooperate to form an embodiment of joint component 622. Cylindrical joint 930 is an embodiment of joint 630. Clamp 940 may be mounted on cylinder 1020 at any position along the length of cylinder 1020, except for that placed within socket 1023. A portion of clamp 940, away from grooves 1043 and 1045, is configured to mate with a protrusion 962 of a spinal surgery device 960 to form a spherical joint 950. Spherical joint 950 is an embodiment of the spherical joint formed by joints components 622 and 652. In one implementation, clamp 940 has full length no greater than 25 millimeters, for example about 18 millimeters, in direction orthogonal to the longitudinal axis of cylinder 1020. This length is practical for performing an ipsilateral spinal surgery procedure.

Spinal surgery device 960 is an embodiment of spinal surgery device 650 and protrusion 962 is an embodiment of joint component 652. Although shown in FIG. 9 as being a tubular retractor with a ball shaped protrusion 962, spinal surgery device 960 may be another type of spinal surgery device, and protrusion 962 may have a different shape, without departing from the scope hereof. Also without departing from the scope hereof, clamp 940 may have a protrusion, instead of grooves 1043 and 1045, that mates with a receptacle of spinal surgery device 960, instead of protrusion 962, to form spherical joint 950.

Monopedicular targeting system 900 further includes a locking driver 915 in the shape of a shaft that may be inserted into cylinder 1020 through cannulation 1022 to press on head 1013 through socket 1023. Cylinder 1020 has internal threads 1025 and locking driver 915 has external threads 1015, such that locking driver 915 may be threaded into cylinder 1020. Contact between internal threads 1025 and external threads 1015 cooperate with pressure between head 1013 and locking driver 915 to lock joint 910. Locking driver 915 is an embodiment of locking device 692.

Monopedicular targeting system 900 also includes a locking fastener 945 that may be inserted through one of clamp parts 1042 and 1044 to be screwed into another one of clamp parts 1042 and 1044 to tighten clamp parts 1042 and 1044 together over cylinder 1020 and protrusion 962, so as to lock both of joints 930 and 950. Locking fastener 945 implements both locking device 694 and 696.

One or more portions of monopedicular targeting system 900 or spinal surgery device 960 may have anti-glare or glare reducing surfaces. In one embodiment, wherein spinal surgery device 960 is implemented as a tubular retractor, the inside surface of the tubular retractor may have anti-glare or glare reducing properties. For example, the tubular retractor may be anodized metal. Furthermore, one or more portions of monopedicular targeting system 900 or spinal surgery device 960 may be translucent to radiation used for imaging of surgery location 270, such that these portions do not interfere with imaging-based visualization of surgery location 270.

Optionally, monopedicular targeting system 900 includes a screwdriver 1080. Screwdriver 1080 fits through cannulation 1022, when locking driver 915 is not located in cannulation 1022. Screwdriver 1080 may be used, through positioning arm 920 to screw fastener 1010 into pedicle 176. After screwing fastener 1010 into pedicle 176, screwdriver 1080 may be removed from cylinder 1020, such that joint 910 is free to rotate, and such that locking driver 915 may be inserted into cylinder 1020. Screwdriver 1080 has length 1082 sufficient to reach head 1013 through cannulation 1022. In one example, length 1082 is in the range between 3 and 6 inches. Although not shown in FIG. 10, monopedicular targeting system 900 may further include a shorter version of screwdriver 1080, suitable for actuating locking driver 915.

In certain embodiments, monopedicular targeting system 900 includes spinal surgery device 960.

Monopedicular targeting system 900 may be provided to a user in assembled form or in a form that requires at least some assembly to be performed by a user. For example, monopedicular targeting system 900 may be provided to a user as shown in FIG. 10, optionally with cylinder 1020 permanently affixed in socket 1023 and with fastener 1010 connected to socket 1023.

As discussed in further detail below in reference to FIGS. 56-59, monopedicular targeting system 900 is readily extended to spine-anchored targeting systems that each have the same functionality as monopedicular targeting system 900 but may be anchored to a different structure of spine 172 or to a pelvis of patient 170. Such spine-anchored targeting systems may be used in posterior spinal surgery of the cervical, thoracic, and/or lumbar spine of patient 170.

FIGS. 11A and 11B are cross sectional views showing exemplary embodiments of positioning arm 920 and fastener 1010 in more detail, when positioning arm 920 is coupled with fastener 1010 via joint 910. FIG. 11A shows all of positioning arm 920 and fastener 1010. FIG. 11B is a close-up of portion 1130. FIGS. 11A and 11B are best viewed together.

Fastener 1010 includes a non-threaded portion 1111 furthest from head 1013, and a threaded portion 1112 between non-threaded portion 1111 and head 1013. Thus, fastener 1010 is a combined awl/tap. Non-threaded portion 1111 has a length 1194, and threaded portion 1112 has a length 1192. In an example, each of lengths 1192 and 1194 are in the range between 0.5 and 1.5 inches, respectively. Head 1013 includes a receptacle 1114 that matches driver 1080. In an alternate embodiment, fastener 1010 is a pedicle screw and may be left in spine 172 after removal of all other parts of monopedicular targeting system 900.

Cylinder 1020 has length 1190. Length 1190 is such that monopedicular targeting system 900 with spinal surgery device 960 has sufficient reach to reach surgery location 270 from pedicle 176. In one example, length 1190 is in the range between 3 and 5 inches, which is a practical length for reaching a spinal segment associated with, or adjacent to, vertebra 178. In another example, length 1190 is in the range between 5 and 10 inches, which may be practical for reaching a spinal segment that is near but not adjacent vertebra 178.

Cylinder 1020 may have diameter 1182 in the range between 0.3 and 0.7 inches, and socket 1023 may have diameter 1180 in the range between 0.35 and 1.0 inches.

Figure 12A:
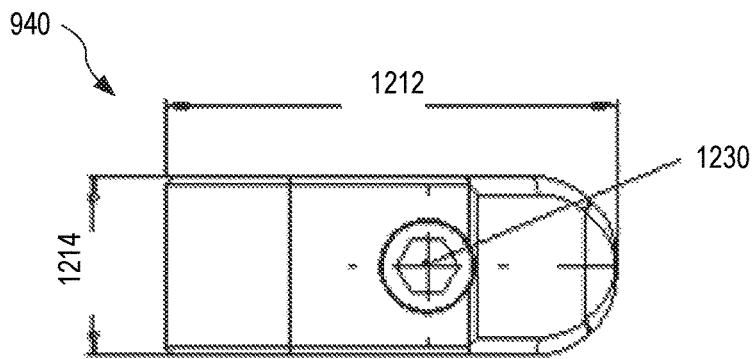
FIGS. 12A and 12B show, in orthogonal views, a clamp of the monopedicular targeting system of FIG. 9, according to an embodiment.
Figure 12B:
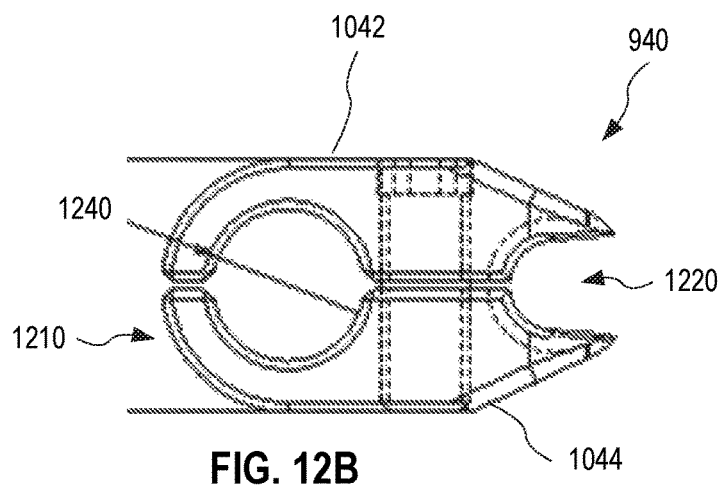

FIGS. 12A and 12B show, in orthogonal views, one exemplary embodiment of clamp 940 in further detail. FIGS. 12A and 12B are best viewed together. When clamp parts 1042 and 1044 are in near-contact, as shown in FIG. 12B, the diameter 1240 of the opening formed by grooves 1043 and 1045 is similar to diameter 1182 of cylinder 1020, such that clamp 940 may clamp tight onto cylinder 1020. Also when clamp parts 1042 and 1044 are in near-contact, as shown in FIG. 12B, clamp parts 1042 and 1044 form a receptacle 1220 for mating with protrusion 962 of spinal surgery device 960.

In an exemplary implementation, each clamp part 1042 and 1044 has length 1212, from the end associated with positioning arm 920 to the end associated with spinal surgery device 960, in the range from 20 to 50 millimeters. This range of length 1212 is practical for accommodating grooves 1043 and 1045, receptacle 1220 and locking fastener 945 and is suitable for targeting a surgery location 270 close to pedicle 176, such as an ipsilateral side of the nearest intervertebral disc. In embodiments intended for targeting a surgery location 270 further from pedicle 176, such as a contralateral side of the nearest intervertebral disc, length 1212 may be in the range from 50 to 100 millimeters.

Figure 13A:
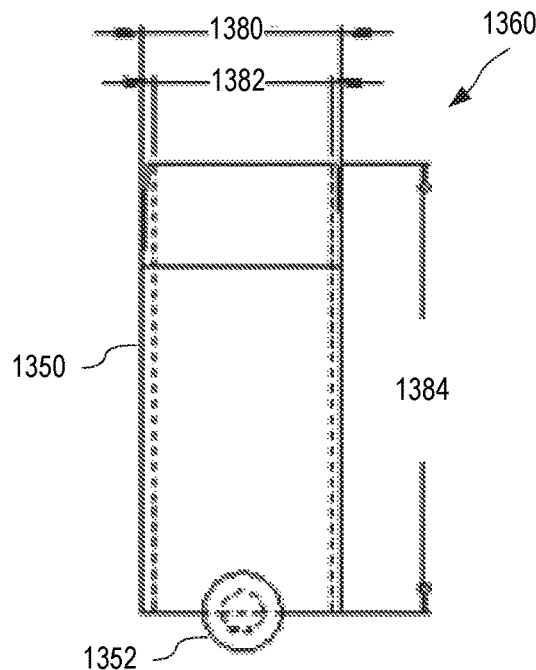
FIGS. 13A and 13B show, in orthogonal cross sectional views, a tubular retractor, according to an embodiment.
Figure 13B:
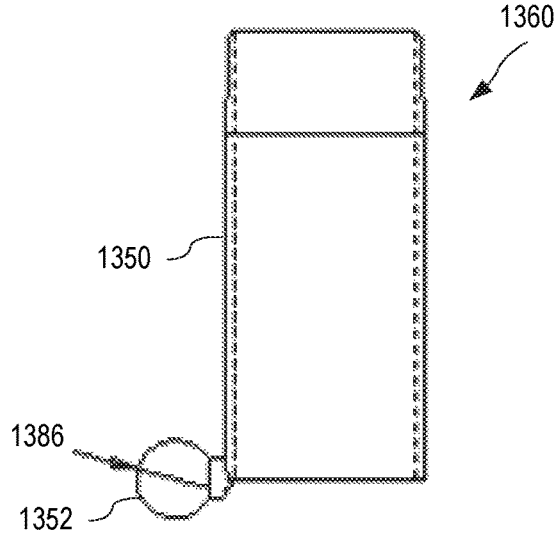

FIGS. 13A and 13B show, in orthogonal cross sectional views, one exemplary tubular retractor 1360 that is an embodiment of spinal surgery device 960. Tubular retractor 1360 retracts tissue of patient 170 to provide access to surgery location 270. Tubular retractor 1360 includes a cylinder 1350 and a ball 1352. Ball 1352 is an embodiment of protrusion 962.

Cylinder 1350 has outer diameter 1380, inner diameter 1382, and length 1384. In an example, outer diameter 1380 is in the range between 15 and 40 millimeters, for example between 20 and 30 millimeters or between 16 and 26 millimeters, and inner diameter 1382 is approximately 1-3 millimeters less than outer diameter 1380. These values of diameters 1380 and 1380 are appropriate for exposing a typical surgery location 270 while providing sufficient room to access surgery location 270. Length 1384 may be in the range from 30 to 90 millimeters, such as between 50 and 60 millimeters. This value of length 1384 is suitable for retracting the tissue between spine 172 and the skin surface of patient 170, without extending so far above the skin surface of patient 170 that cylinder 1350 imposes unnecessary restriction of movement of surgery tools inserted through cylinder 1350 to operate on surgery location 270.

Optionally, the outer diameter of tubular retractor 1360, at the end of tubular retractor 1360 most distant from ball 1352, is tapered to ease insertion of tubular retractor 1360 into the tissue of patient 170.

Ball 1352 has a diameter 1386. In one example, diameter 1386 is similar to the diameter of cylinder 1020, for example in the range between 0.3 and 0.7 inches.

Without departing from the scope hereof, cylinder 1350 may have non-circular cross section. For example, the cross section of cylinder 1350 may be elliptical or oval, or have the shape of a polygon such as a triangle, a rectangle, a square, a pentagon, a hexagon, or an octagon. Additionally, cylinder 1350 may be composed of multiple separable pieces. In one such implementation, one of the multiple separable pieces may be removable, for example to change the shape and/or size of tubular retractor 1360 or to form a window in tubular retractor 1360.

FIGS. 14A-C illustrate another exemplary monopedicular targeting system 1400 for posterior spinal surgery, which is an embodiment of monopedicular targeting system 600 and of monopedicular targeting system 400. Monopedicular targeting system 1400 may be used to perform any of methods 500, 501, and 502. FIG. 14A shows monopedicular targeting system 1400 in assembled form, affixed to pedicle 176, and coupled with a spinal surgery device 1493 for targeting a surgery location 270 from a contralateral working direction. FIG. 14B shows monopedicular targeting system 1400 in exploded view. FIG. 14C shown a screw driver in exploded view. FIGS. 14A-C are best viewed together.

Monopedicular targeting system 1400 includes a fastener 1410, a positioning arm 1402, and a connector 1404. Fastener 1410, positioning arm 1402, and connector 1404 are embodiments of fastener 110, positioning arm 620, and connector 640, respectively. Connector 1404 is also an embodiment of connector 200.

Positioning arm 1402 includes a cylinder 1430 with a cannulation 1432 and a socket 1420. Socket 1420 has an opening 1421 that is configured to accept cylinder 1430. In one embodiment, cylinder 1430 is permanently affixed in socket 1420 to form positioning arm 1402. For example, cylinder 1430 may be welded in place in socket 1420. In another embodiment, cylinder 1430 and socket 1420 are configured such that cylinder 1430 may be removably placed in socket 1420. For example, cylinder 1430 may have external threads (not shown) and socket 1420 may have internal threads (not shown), such that cylinder 1430 may be threaded into socket 1420.

Fastener 1410 has a head 1412 that includes a portion of a ball. Head 1412 forms an embodiment of joint component 224, and socket 1420 forms an embodiment of joint component 432. Head 1412 and socket 1420 are configured to mate to form a ball-and-socket joint 1406. Joint 1406 is an embodiment of joint 610. Joint 1406 may have angular range as discussed for joint 610 in reference to FIGS. 7C-E. Fastener 1410 is shown in FIGS. 14A-C as a tap awl with a non-threaded section 1414, most distant from head 1412, and a threaded section 1416 adjacent non-threaded section 1414. Without departing from the scope hereof, fastener 1410 may a different type of fastener.

Connector 1404 includes two clamp parts 1440 and 1449. Clamp part 1449 is implemented as clamp subparts 1450 and 1460. Clamp part 1440 has a groove 1442, and clamp part 1449 has a groove 1462. Clamp parts 1440 and 1449 are configured to be brought together with grooves 1442 and 1462 around cylinder 1430 to form a cylindrical joint 1408. Cylindrical joint 1408 is an embodiment of joint 630. Connector 1404 may be mounted on cylinder 1430 at any position along the length of cylinder 1430, except for that placed within socket 1420. Receptacles 1444 and 1452 (not directly visible in FIGS. 14A and 14B) of clamp parts 1440 and 1449, respectively, are configured to mate with a protrusion 1496 of a coupler 1490 to form a spherical joint 1409. Coupler 1490 is configured to removably couple with a spinal surgery device 1493. Spherical joint 1409 is an embodiment of the spherical joint formed by joints components 622 and 652.

Connector 1404, as shown in FIGS. 14A and 14B, has length compatible with contralaterally targeting a surgery location 270. However, connector 1404 may be shorter than shown in FIG. 14 to ipsilaterally target a surgery location 270 at a spine segment adjacent pedicle 176, without departing from the scope hereof. Likewise, connector 1404 may be longer than shown in FIGS. 14A and 14B to target a more distant surgery location 270.

Spinal surgery device 1493 is an embodiment of spinal surgery device 650 and protrusion 1496 is an embodiment of joint component 652. Although FIGS. 14A and 14B show spinal surgery device 1493 as being a tubular retractor and protrusion 1496 as being a ball shaped protrusion, spinal surgery device 1493 may be another type of spinal surgery device, and protrusion 1496 may a different shape, without departing from the scope hereof. Also without departing from the scope hereof, connector 1404 may have a protrusion, instead of grooves 1442 and 1462, that mates with a receptacle of coupler 1490, instead of protrusion 1496, to form spherical joint 1409.

Without departing from the scope hereof, spinal surgery device 1493 may be a tubular retractor of non-circular cross section. For example, the cross section may be elliptical or oval, or have shape of a polygon such as a triangle, a rectangle, a square, a pentagon, a hexagon, or an octagon. Additionally, this tubular retractor may be composed of multiple separable pieces. In one such implementation, one of the multiple separable pieces may be removable, for example to change the shape and/or size of the tubular retractor or to form a window in the tubular retractor.

Monopedicular targeting system 1400 further includes a locking driver 1480 that may be inserted into cylinder 1430 through cannulation 1432 to press on head 1412 through socket 1420. Cylinder 1430 has internal threads 1434 and locking driver 1480 has external threads 1482, such that locking driver 1480 may be threaded into cylinder 1430. Contact between internal threads 1434 and external threads 1482 cooperate with pressure between head 1412 and locking driver 1480 to lock joint 1406 in a desired configuration. Locking driver 1480 is an embodiment of locking device 692. Although not shown in FIGS. 14A-C, monopedicular targeting system 1400 may include a tool for actuating locking driver 1480.

Monopedicular targeting system 1400 also includes two locking fasteners 1405 that may be inserted through one of clamp parts 1440 and 1449 to be screwed into another one of clamp parts 1440 and 1449 to tighten clamp parts 1440 and 1449 together over cylinder 1430 and protrusion 1496, so as to lock both of joints 1408 and 1409 in a desired configuration. Locking fasteners 1405 implement locking devices 694 and 696. Clamp part 1449 includes two clamp subparts 1450 and 1460 with a hinge 1455 therebetween. Clamp subpart 1450 includes receptacle 1452. Clamp subpart 1460 includes groove 1462. Hinge 1455 facilitates mutually independent locking of joints 1408 and 1409.

Coupler 1490 includes protrusion 1496, a ring 1492, a connecting arm 1494 that connects protrusion 1496 to ring 1492, and a locking fastener 1497 configured to fasten ring 1492 to spinal surgery device 1493. Connecting arm 1494 has an angled section 1495 that allows monopedicular targeting system 1400 to contralaterally target a surgery location 270 without blocking an anterior-posterior imaging pathway to surgery location 270. In addition, connecting arm 1494 provides additional flexibility for positioning of spinal surgery device 1493. In the embodiment shown in FIGS. 14A and 14B, angled section 1495 has a 90 degree angle. However, the angle of angled section 1495 may be in the range between 60 degrees and 120 degrees, or in the range between 45 and 135 degrees, without departing from the scope hereof. Also without departing from the scope hereof, ring 1492 may be replaced by a differently shaped element configured to couple with a spinal surgery device different from spinal surgery device 1493 shown in FIGS. 14A and 14B. Furthermore, ring 1492 may be replaced by another component that need not be configured to wrap around spinal surgery device 1493 but may attach to spinal surgery device 1493 through other means. For example, ring 1492 may be replaced by a component that is screwed onto spinal surgery device 1493, or press fit into an appropriate receptacle of spinal surgery device 1493.

Protrusion 1496 may have etching to enhance friction at joint 1409.

Although shown in FIGS. 14A and 14B as including two straight sections, connecting arm 1494 may, in an alternate embodiment, include no straight sections or only one straight section. For example, connecting arm 1494 may be composed of angled section 1495 alone, wherein angled section 1495 is directly coupled to ring 1492 and protrusion 1496.

Although shown in FIGS. 14A and 14B as screws with finger holds, locking fasteners 1405 and 1497 may be configured for actuation by a tool, without departing from the scope hereof. For example, one or more of locking fasteners 1405 and 1497 may be a set screw. When implementing each locking fastener 1405 as a set screw (or other form of screw recessed in clamp part 1440 or 1449), the bulk of locking fasteners 1405 extending out of connector 1404 is eliminated or at least reduced, which may provide additional freedom for placement of clamp 1404 relative to patient 170. Also without departing from the scope hereof, locking fasteners 1405 may be directed through connector 1404 at an oblique angle such that (a) finger holds of locking fasteners 1405 are angled away from patient 170 to reduce the risk of interference between locking fasteners 1405 and patient 170, or (b) if locking fasteners 1405 are implemented as set screws or other recessed screws, the tool(s) used to actuate locking fasteners 1405 is angled away from patient 170 to reduce the risk of interference between such tool(s) and patient 170.

In an alternate embodiment, locking fasteners 1405 access connector 1404 from surface 1448 of clamp part 1440, or from each of surface 1458 of clamp subpart 1450 and surface 1468 of clamp subpart 1460. Surfaces 1448, 1458, and 1468 generally face away from patient 170, such that this alternate embodiment eases access to locking fasteners 1405 and reduces the risk of interference between locking fasteners 1405 and patient 170. In this alternate embodiment, each locking fastener 1405 may include a right-angle gear or a worm gear (or another similar gear as known in the art) to translate actuation of locking fasteners 1405 to tightening of clamp part 1440 with clamp part 1449.

The orientation of coupler 1490 relative to the longitudinal axis of spinal surgery device 1493 may be flipped according to the surgical procedure performed and/or the preference of surgeon 180. In one exemplary use scenario, surgeon 180 uses monopedicular targeting system 1400 with the orientation to contralaterally target a surgery location 270, wherein the orientation of coupler 1490 relative to the longitudinal axis of spinal surgery device 1493 is as shown in FIG. 14A. This orientation advantageously allows for targeting surgery location 270 while positioning connector 1404 outside an anterior-posterior imaging pathway to surgery location 270. In another exemplary use scenario, the orientation of coupler 1490 relative to the longitudinal axis of spinal surgery device 1493 is flipped, as compared to that shown in FIG. 14A, to ipsilaterally target a surgery location 270 while positioning connector 1404 outside an anterior-posterior imaging pathway to surgery location 270. In a further use scenario, surgeon 180 may switch between the contralateral and ipsilateral procedures by disengaging coupler 1490 from spinal surgery device 1493 and flipping the orientation of coupler 1490 so as to perform each of these two procedures with monopedicular targeting system 1400 being attached to the same pedicle 176 and without monopedicular targeting system 1400 interfering with anterior-posterior imaging pathways to the associated surgery locations 270.

In an alternate embodiment, protrusion 1496 is permanently and rigidly coupled with spinal surgery device 1493 through connecting arm 1494 to form an integrated coupler-spinal surgery device. In one exemplary scenario, two different embodiments of this integrated coupler-spinal surgery device is supplied to surgeon 180 to allow both ipsilateral and contralateral procedures. These two different embodiments are equivalent to the two possible orientations of coupler 1490 as discussed above.

One or more portions of monopedicular targeting system 1400 and/or spinal surgery device 1493 may have anti-glare or glare reducing surfaces, as discussed above for monopedicular targeting system 900 and spinal surgery device 960. Furthermore, one or more portions of monopedicular targeting system 1400 or spinal surgery device 1493 may be translucent to radiation used for imaging of surgery location 270, such that these portions do not interfere with imaging-based visualization of surgery location 270.

Optionally, monopedicular targeting system 1400 includes a screwdriver 1470. Screwdriver 1470 fits through cannulation 1432, when locking driver 1480 is not located in cannulation 1432. Screwdriver 1470 may be used, through positioning arm 1402 to rigidly connect to fastener 1410 and screw fastener 1410 into pedicle 176. Screwdriver 1470 has a section 1474 of length 1476 sufficient to reach head 1412 through cannulation 1432. In one example, length 1476 is in the range between 3 and 6 inches. Screwdriver 1470 includes a locking bolt 1472 with an external thread configured to engage internal thread 1434 to apply pressure to a flange 1473 (at the top of section 1474) so as to rigidly couple screwdriver 1470 to fastener 1410. Although not shown in FIGS. 14A-C, monopedicular targeting system 1400 may include a tool for actuating screwdriver 1470 to screw fastener 1410 into pedicle 176. Locking bolt 1472 is free to rotate independently of section 1474 such that locking bolt 1472 may be unscrewed to disengage screwdriver 1470 from fastener 1410 without backing out fastener 1410. After disengaging screwdriver 1470 from fastener 1410, screwdriver 1470 may be removed from cylinder 1430, such that joint 1406 is free to rotate, and such that locking driver 1480 may be inserted into cylinder 1430.

In certain embodiments, monopedicular targeting system 1400 includes spinal surgery device 1493. Monopedicular targeting system 1400 may be provided to a user in assembled form or in a form that requires at least some assembly to be performed by a user.

Without departing from the scope hereof, connector 1404 may be supplied as a standalone item configured to cooperate with a third party percutaneous pedicle screw 212 and a third party spinal surgery device 150 to target surgery location 270. Connector 1404 is an embodiment of connector 200. In a similar fashion, spinal surgery device 1493 and coupler 1490 may be supplied as standalone items configured to cooperate with a third party spinal surgery systems.

Also without departing from the scope hereof, connector 1404 of monopedicular targeting system 1400 may be replaced by clamp 940, and clamp 940 of monopedicular targeting system 900 may be replaced by connector 1404. Likewise, monopedicular targeting system 1400 may utilize spinal surgery device 960 instead of spinal surgery device 1493 and coupler 1490, and monopedicular targeting system 900 may utilize spinal surgery device 1493 and coupler 1490 instead of spinal surgery device 960.

As discussed in further detail below in reference to FIGS. 56-59, monopedicular targeting system 1400 is readily extended to spine-anchored targeting systems that each have the same functionality as monopedicular targeting system 1400 but may be anchored to a different structure of spine 172 or to a pelvis of patient 170. Such spine-anchored targeting systems may be used in posterior spinal surgery of the cervical, thoracic, and/or lumbar spine of patient 170.

Figure 15B:
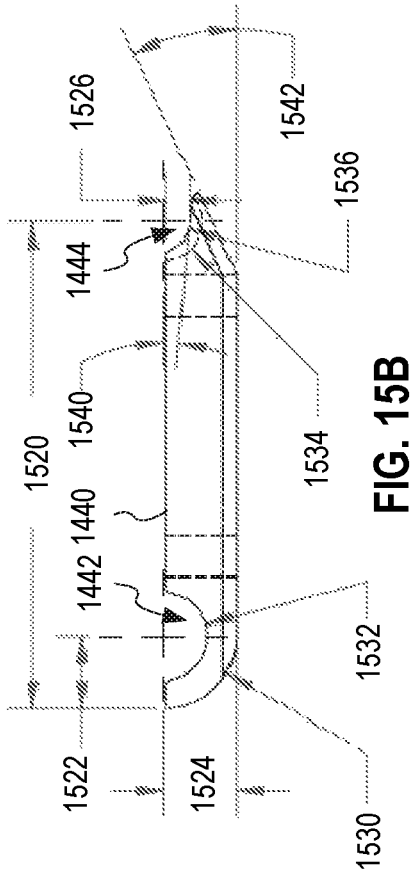
FIGS. 15A-D show, in further detail, one exemplary embodiment of a clamp part of the monopedicular targeting system of FIGS. 14A-C.
Figure 15D:
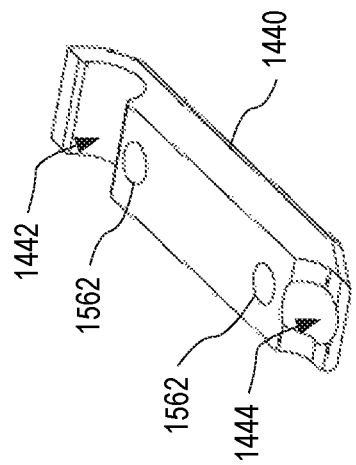
Figure 15A:
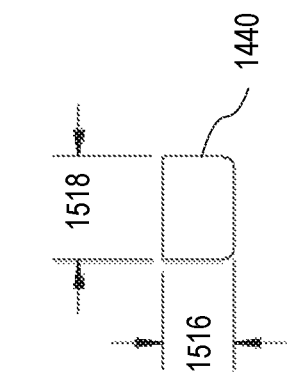
Figure 15C:
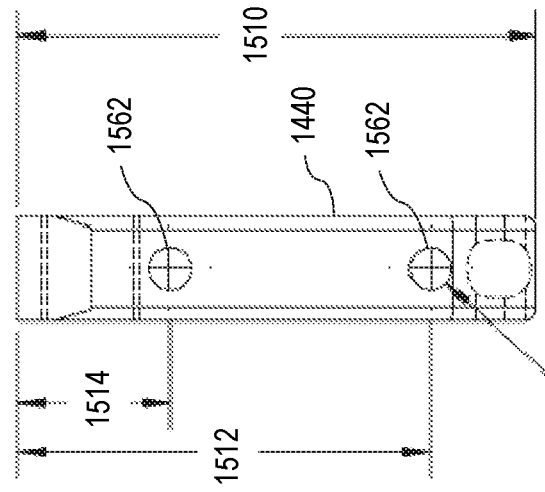

FIGS. 15A-D show one exemplary embodiment of clamp part 1440 in further detail. FIGS. 15A-C show orthogonal side views of clamp part 1440, while FIG. 15D shows clamp part 1440 in perspective view. FIGS. 15A-D are best viewed together.

Clamp part 1440 has length 1510 and cross-sectional dimensions 1516 and 1518. Clamp part 1440 includes threaded holes 1562 configured to engage locking fasteners 1405. Groove 1442 is cylindrical with the cylinder axis being placed slightly outside cross-sectional extent 1516 of clamp part 1440. This helps ensure that, when clamp part 1440 is brought together with clamp subpart 1460 around cylinder 1430, connector 1404 applies pressure to cylinder 1430 as opposed to only applying pressure between clamp part 1440 and clamp subpart 1460. Receptacle 1444 is of spherical shape. The center of the sphere is placed slightly outside extent 1516 to help ensure that, when clamp part 1440 is brought together with clamp subpart 1450 around protrusion 1496, connector 1404 applies pressure to protrusion 1496 as opposed to only applying pressure between clamp part 1440 and clamp subpart 1450.

In one embodiment, threaded holes 1562 are of type ¼-20NC, and each locking fastener 1405 has a corresponding external ¼-20NC thread. In one embodiment, dimensions 1510, 1512, 1514, 1516, 1518, 1520, 1522, 1524, and 1526 are 2.4850 inches, 1.9806 inches, 0.7309 inches, 0.3365 inches, 0.5000 inches, 2.3396 inches, 0.3488 inches, 0.3507 inches, and 0.1120 inches, respectively. The length of clamp part 1440 from the cylindrical center of groove 1442 to spherical center of receptacle 1444 (indicated in FIG. 15B as dimension 1520 minus dimension 1522) defines the distance between the cylindrical center of cylinder 1430 and the spherical center of protrusion 1496. In certain embodiments, this length is in the range from 50 millimeters to 70 millimeters, for example 60 millimeters, such that monopedicular targeting system 1400 may conveniently target surgery location 270 from a direction that is contralateral to pedicle 176. In one embodiment, radii of curvature 1530, 1532, 1534, and 1536 are 0.3490 inches, 0.2100 inches, 0.1875 inches, and 0.1467 inches, and angles 1540 and 1542 are 5 degrees and 25 degrees, respectively. Angle 1540 defines an angled opening into receptacle 1444. Without departing from the scope hereof, actual dimensions of clamp part 1440 may differ from those listed here.

Figure 16C:
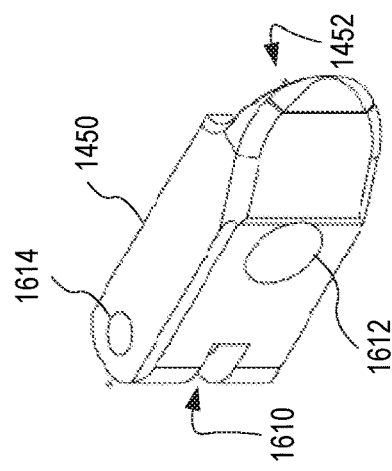
FIGS. 16A-C show, in further detail, one exemplary embodiment of a first clamp subpart of the monopedicular targeting system of FIGS. 14A-C.
Figure 16A:
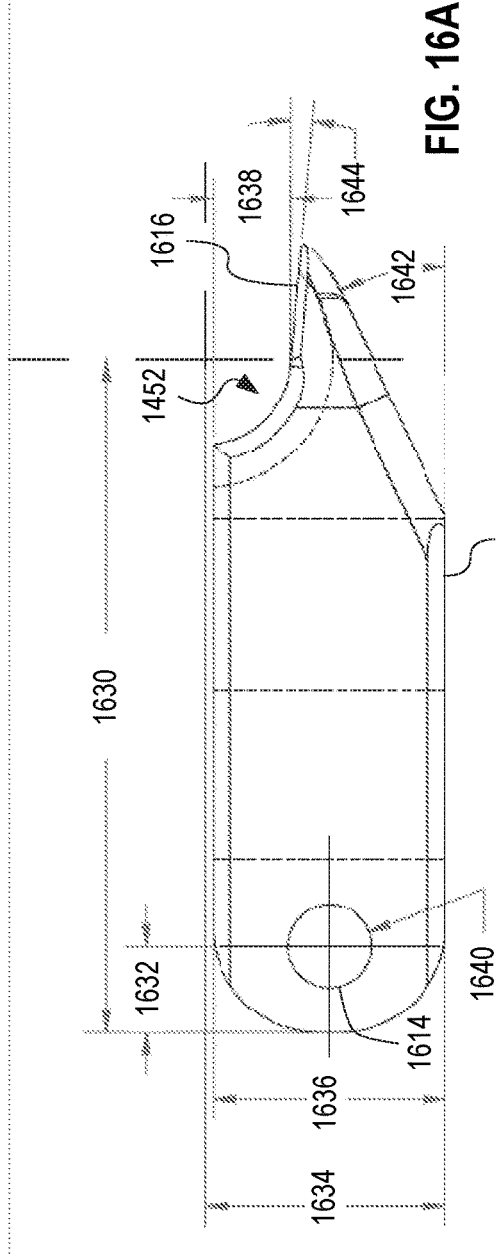
Figure 16B:
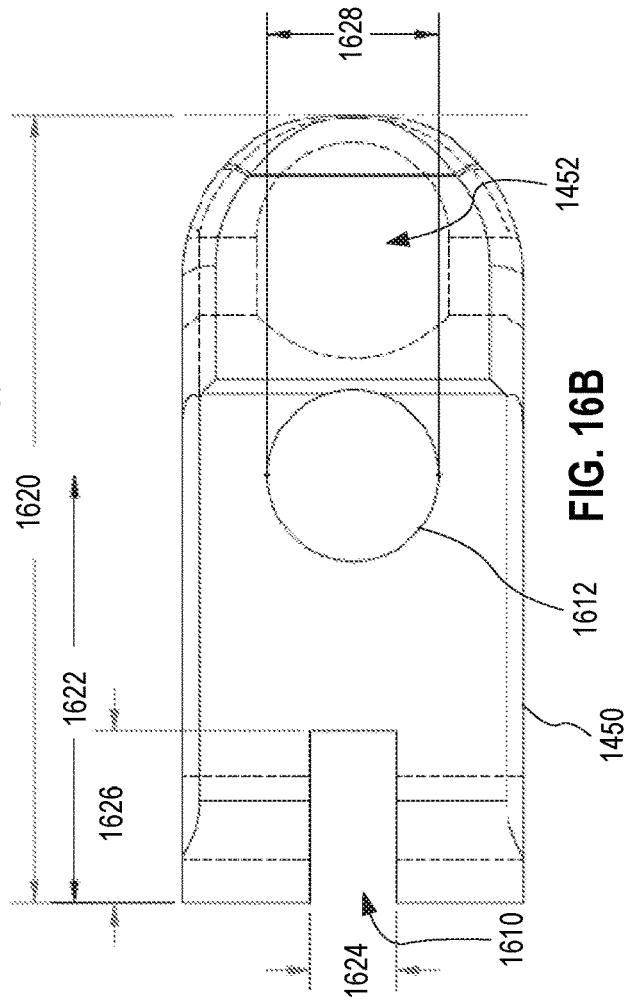

FIGS. 16A-C show one exemplary embodiment of clamp subpart 1450 in further detail. FIGS. 16A and 16B show orthogonal side views of clamp subpart 1450, while FIG. 16C shows clamp subpart 1450 in perspective view. FIGS. 16A-C are best viewed together.

Clamp subpart 1450 includes a slot 1610 and a through hole 1614, which cooperate with matching features of clamp subpart 1460 to form hinge 1455. Clamp subpart 1450 further includes a through hole 1612 configured to accept one of locking fasteners 1405. Receptacle 1452 is of spherical shape. The center of the sphere is placed slightly outside extent 1636 (as indicated by extent 1634) to help ensure that, when clamp part 1440 is brought together with clamp subpart 1450 around protrusion 1496, connector 1404 applies pressure to protrusion 1496 as opposed to only applying pressure between clamp part 1440 and clamp subpart 1450. Clamp subpart 1450 has an angled opening 1616 into receptacle 1452.

In one embodiment, dimensions 1620, 1622, 1624, 1626, 1628, 1630, 1632, 1634, 1634, 1636, and 1638 are 1.1531 inches, 0.6250 inches, 0.1250 inches, 0.2500 inches, 0.2500 inches, 0.9840 inches, 0.1250 inches, 0.3507 inches, 0.3382 inches, and 0.1120 inches, respectively. In one embodiment, diameter 1640 is 0.1220 inches. In one embodiment, angles 1642 and 1644 are 24.85 and 5 degrees, respectively. Receptacle 1452 may have radii of curvature similar to receptacle 1444. Without departing from the scope hereof, actual dimensions of clamp subpart 1450 may differ from those listed here.

Figure 17C:
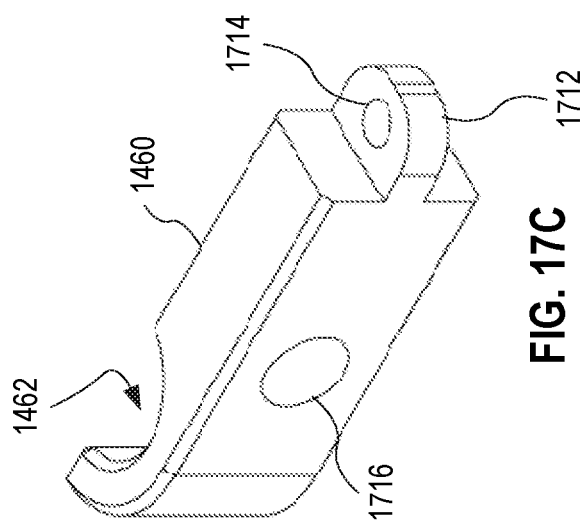
FIGS. 17A-C show, in further detail, one exemplary embodiment of a second clamp subpart of the monopedicular targeting system of FIGS. 14A-C.
Figure 17A:
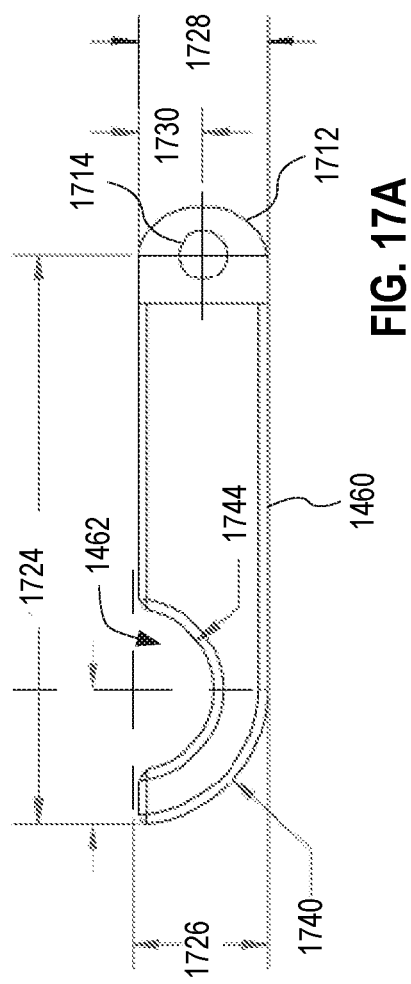
Figure 17B:
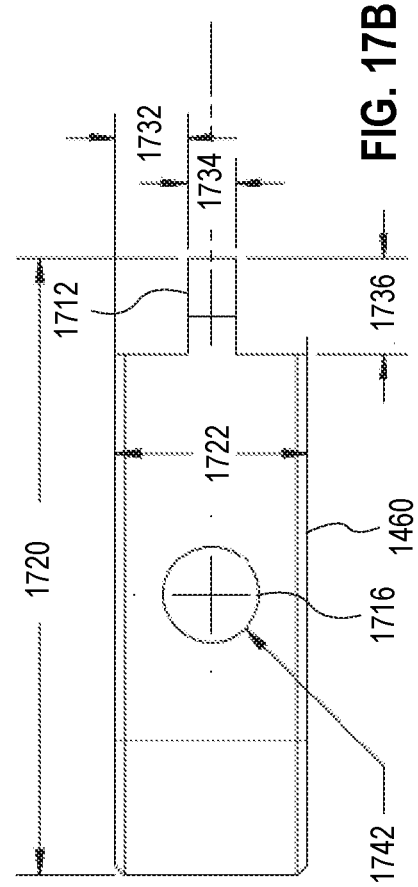

FIGS. 17A-C show one exemplary embodiment of clamp subpart 1460 in further detail. FIGS. 17A and 17B show orthogonal side views of clamp subpart 1460, while FIG. 17C shows clamp subpart 1460 in perspective view. FIGS. 17A-C are best viewed together.

Clamp subpart 1460 includes a bracket 1712 with a through hole 1714, which are configured to mate with slot 1610 and a pin passing through both through hole 1614 of clamp subpart 1450 and through hole 1714 to form hinge 1455. Clamp subpart 1460 further includes a through hole 1716 configured to accept one of locking fasteners 1405. Groove 1462 is of cylindrical shape. The center of the cylinder is placed slightly outside extent 1728 (as indicated by extent 1726) to help ensure that, when clamp part 1440 is brought together with clamp subpart 1460 around cylinder 1430, connector 1404 applies pressure to cylinder 1430 as opposed to only applying pressure between clamp part 1440 and clamp subpart 1460.

In one embodiment, dimensions 1720, 1722, 1724, 1726, 1728, 1730, 1732, 1734, and 1736 are 1.6056 inches, 0.5000 inches, 1.4806 inches, 0.3507 inches, 0.3382 inches, 0.1691 inches, 0.1875 inches, 0.1250 inches, and 0.2500 inches, respectively. In one embodiment, radii of curvature 1740 and 1744 are 0.3507 inches and 0.2102 inches, respectively. In one embodiment, diameter 1742 is 0.2500 inches. Without departing from the scope hereof, actual dimensions of clamp subpart 1460 may differ from those listed here.

Figure 18A:
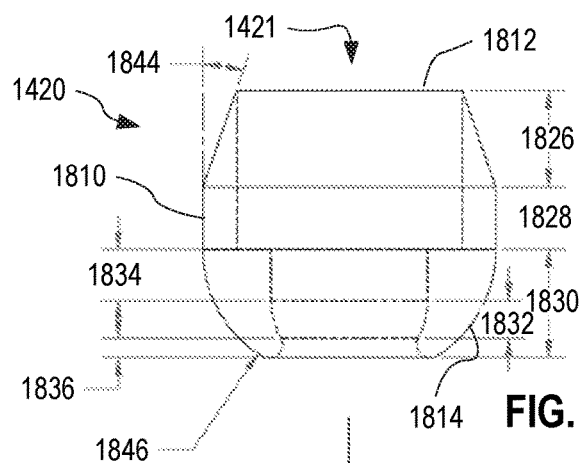
FIGS. 18A-E show, in further detail, one exemplary embodiment of a positioning arm of the monopedicular targeting system of FIGS. 14A-C.
Figure 18C:
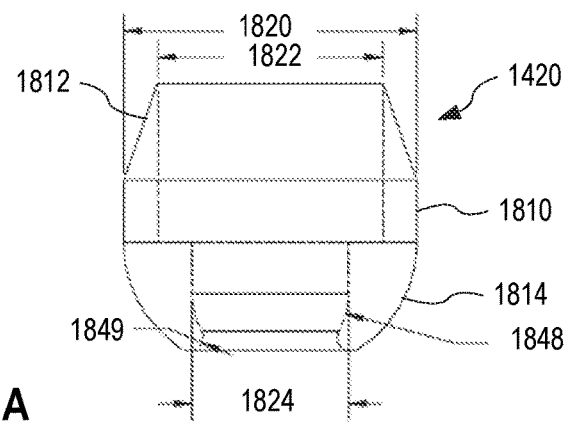
Figure 18B:
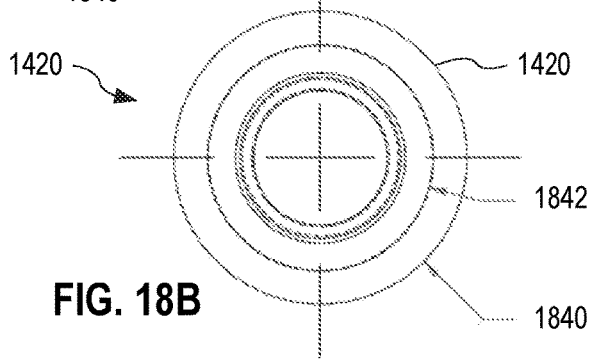
Figure 18D:
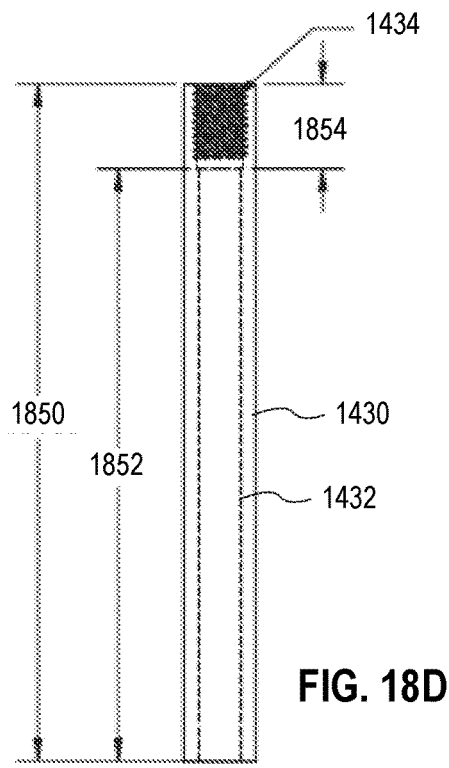
Figure 18E:
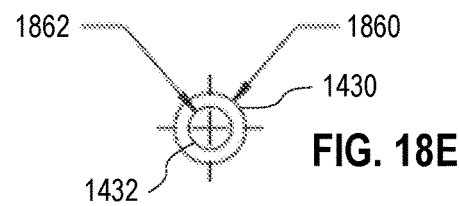

FIGS. 18A-E show one exemplary embodiment of positioning arm 1402 in further detail. FIGS. 18A-C show orthogonal side views of socket 1420 and FIGS. 18D and 18E shown orthogonal side views of cylinder 1430. FIGS. 18A-E are best viewed together.

Socket 1420 includes sections 1810, 1812, and 1814. Sections 1810 and 1812 include a cannulation of diameter 1822 such that sections 1810 and 1812 may hold cylinder 1430 of diameter 1860. Section 1814 is configured to have head 1412 seated therein. Section 1814 and head 1412 cooperate to form joint 1406. In the example shown in FIGS. 18A-E, the angular range of joint 1406 is 30 degrees (conically) in any direction orthogonal to the longitudinal axis of fastener 1410. However, section 1814 and/or head 1412 may be modified to provide a different angular range of joint 1406, without departing from the scope hereof. For example, the angular range of joint 1406 may be as discussed for joint 610 in reference to FIGS. 7C-E.

Diameters 1820, 1822, and 1824 are, for example, 0.5480 inches, 0.4205 inches, and 0.2929 inches, respectively. Dimensions 1826, 1828, 1830, 1832, 1834, and 1836 are, for example, 0.1815 inches, 0.1165 inches, 0.2020 inches, 0.0700 inches, 0.0950 inches, and 0.0370 inches, respectively. Diameters 1840 and 1842 are, for example, 0.5480 inches and 0.4205 inches, respectively. Radii of curvature 1846, 1848, and 1849 are, for example, 0.2349 inches, 0.1465 inches, and 0.0250 inches respectively. Angle 1844 is 19.00 degrees, for example.

Cylinder 1430 has length 1850. Length 1850 may be in the range between 70 millimeters and 120 millimeters such that cylinder 1430 has sufficient extent outside patient 170 for coupling connector 1404 thereto, without cylinder 1430 being unnecessarily long. In one example, length 1850 is 4.0 inches. Dimensions 1852 and 1854 may be 3.5 inches and 0.5 inches, respectively. Thread 1434 is a ⁵⁄₁₆-24 NF thread, for example. In one example, diameters 1860 and 1862 are 0.4205 inches and 0.2529, respectively.

Without departing from the scope hereof, actual dimensions of socket 1420 and cylinder 1430 may differ from those listed here.

FIGS. 19A-C show one exemplary embodiment of fastener 1410 in further detail. FIG. 19A is a side-view of fastener 1410. FIG. 19B is a cross-sectional view of fastener 1410 along line 19B-19B of FIG. 19A. FIG. 19C is a top view of fastener 1410. FIGS. 19A-C are best viewed together.

Head 1412 has a hexagonal recess 1910 for receiving a tool, such as screwdriver 1470, used to affix fastener 1410 to pedicle 176. Without departing from the scope hereof, recess 1910 may have a different shape, and/or be a protrusion, so as to engage with a different tool. Optionally, fastener 1410 has a cannulation 1912 for example used to insert fastener 1410 over a guide wire, or for inserting a guide wire through cannulation 1912 when fastener 1410 is in place in pedicle 176 such that the guide wire may be used subsequently for insertion of a pedicle screw. Embodiments of monopedicular targeting system 1400 supplied with a cannulated version of fastener 1410 may further be supplied with a plug that, when inserted into cannulation 1912 prevents debris from entering cannulation 1912.

Dimensions 1920, 1922, 1924, 1926, 1928, and 1940 are, for example, 1.7268 inches, 0.6524 inches, 0.1000 inches, 0.0865 inches, 0.0630 inches, and 0.1024 inches, respectively. Radius of curvature 1930 may be 0.1465 inches. Angles 1942, 1944, and 1946 are, for example, 64 degrees, 38 degrees, and 1.0 degree, respectively. Without departing from the scope hereof, actual dimensions of fastener 1410 may differ from those listed here.

Figure 20A:
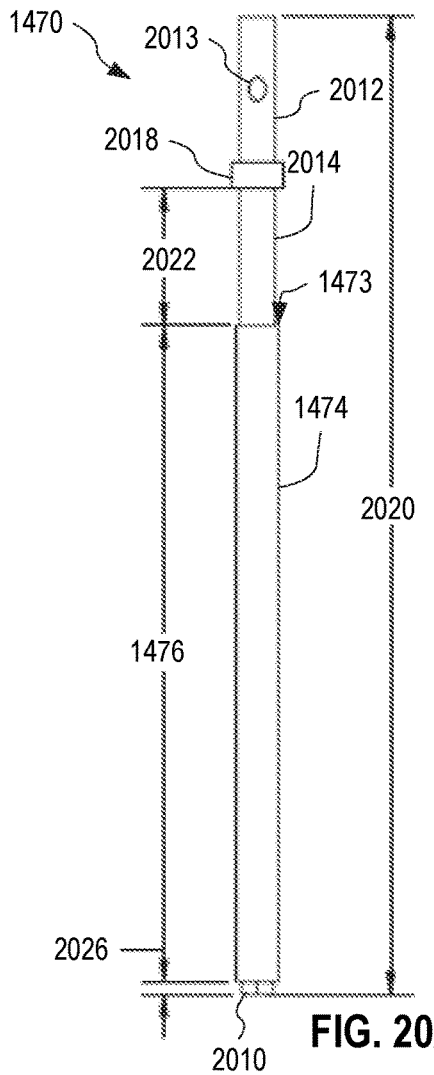
FIGS. 20A-H show, in further detail, one exemplary embodiment of a screwdriver of the monopedicular targeting system of FIGS. 14A-C.
Figure 20C:
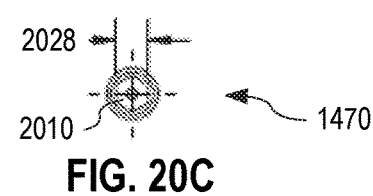
Figure 20B:
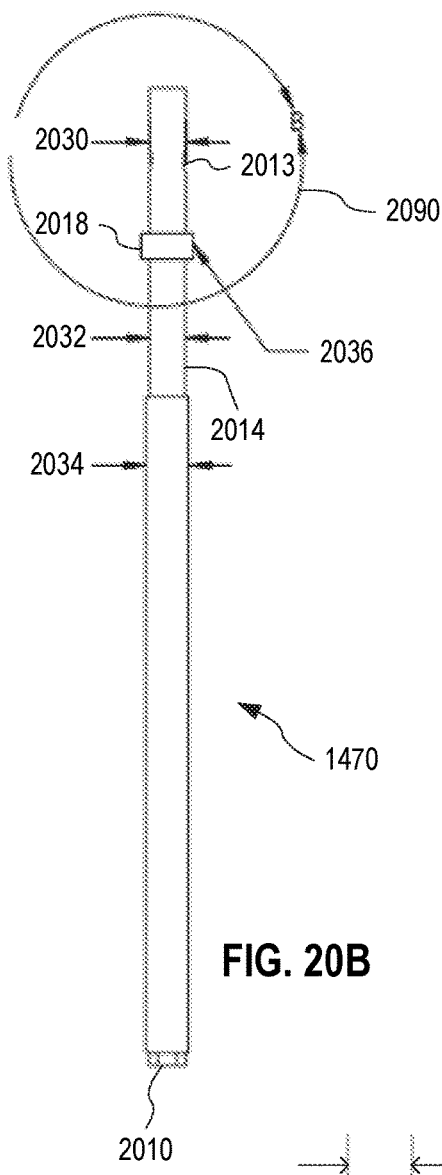
Figure 20D:
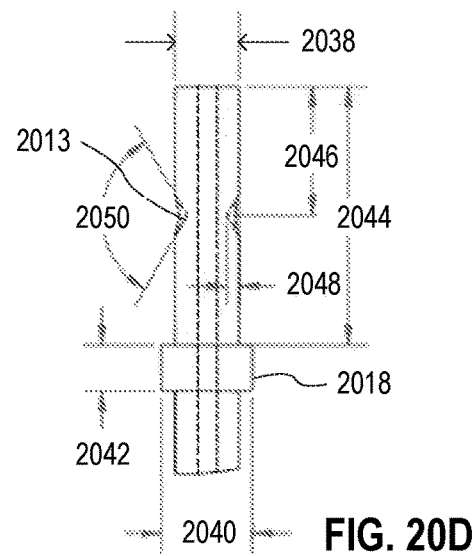
Figure 20E:
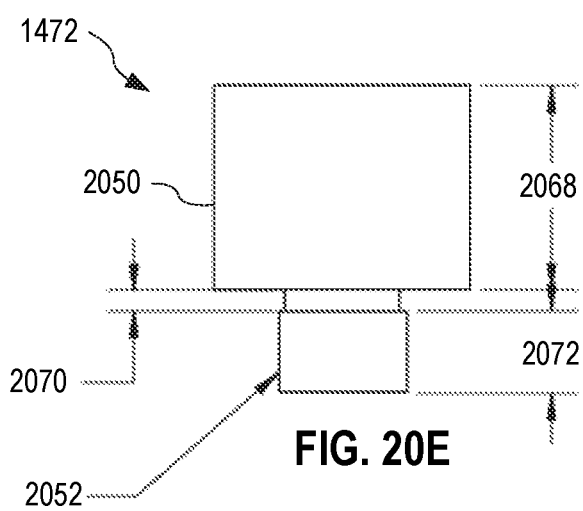
Figure 20F:
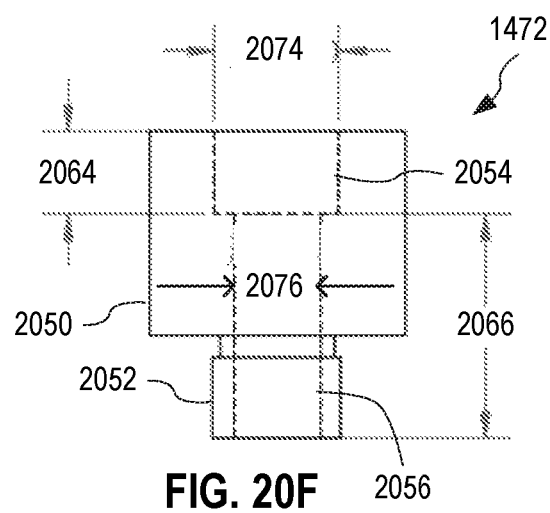
Figure 20G:
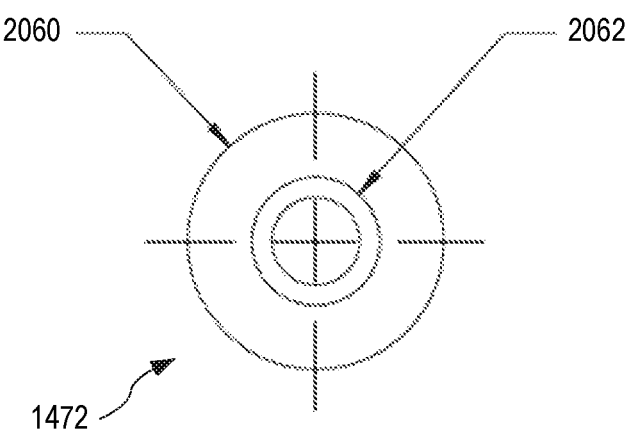
Figure 20H:
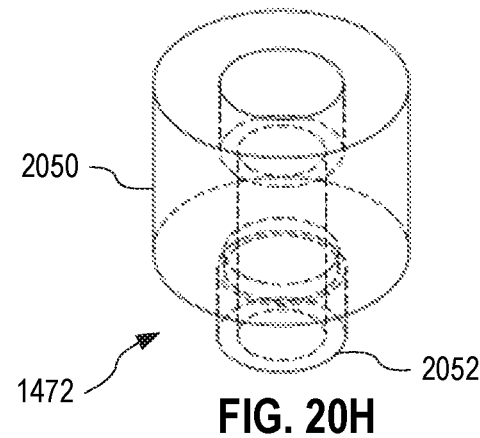

FIGS. 20A-H show one exemplary embodiment of screwdriver 1470 in further detail. FIGS. 20A-C are orthogonal side views of screwdriver 1470. FIG. 20D is a close-up of a portion 2090 of screwdriver 1470 indicated in FIG. 20B. FIGS. 20E-G are orthogonal side views of locking bolt 1472. FIG. 20H is a perspective view of locking bolt 1472. FIGS. 20A-H are best viewed together.

Screwdriver 1470 includes (a) section 1474, (b) hexagonal head 2010, (c) a smaller-diameter section 2014 adjacent section 1474, (d) a larger-diameter section 2018 adjacent section 2014, and (e) an actuator section 2012 most distant from head 2010. Section 2014 holds locking bolt 1472. Locking bolt 1472 is free to rotate about section 2014 but cannot slide beyond flange 1473. Section 2018 is a stop that ensures that locking bolt 1472 does not come off screwdriver 1470. Actuator section 2012 includes two indentations 2013 configured to engage a tool to drive fastener 1410 into pedicle 176 when screwdriver 1470 is locked into cylinder 1430 using locking bolt 1472.

Dimensions 2020, 2022, 1476, 2026, 2028, 2030, 2032, 2034, 2038, 2040, 2042, 2044, 2046, and 2048 are, for example, 5.7085 inches, 0.8000 inches, 3.8335 inches, 0.0720 inches, 0.1860 inches, 0.2105 inches, 0.2080 inches, 0.2475 inches, 0.2105 inches, 0.3000 inches, 0.1500 inches, 0.8530 inches, 0.4250 inches, and 0.0400 inches, respectively. Angle 2050 is 120 degrees, for example.

Locking bolt 1472 includes sections 2050 and 2052. Section 2050 provides a handhold for actuating locking bolt 1472. Section 2052 has an external thread that engages thread 1434. Locking bolt 1472 has cannulations 2054 and 2056. Cannulation 2054 is sized to accommodate at least a portion of section 2018. Cannulation 2056 is sized to accommodate section 2014. Diameters 2060, 2062, 2074, and 2076 are, for example, 0.6250 inches, 0.3125 inches, 0.3020 inches, and 0.2140 inches, respectively. Section 2052 may have a 5/16-24 NF thread. Dimensions 2064, 2066, 2068, 2070, and 2072 are, for example, 0.2000 inches, 0.5500 inches, 0.5000 inches, 0.0500 inches, and 0.2000 inches, respectively.

Without departing from the scope hereof, actual dimensions of screwdriver 1470 may differ from those listed here.

Figure 21A:
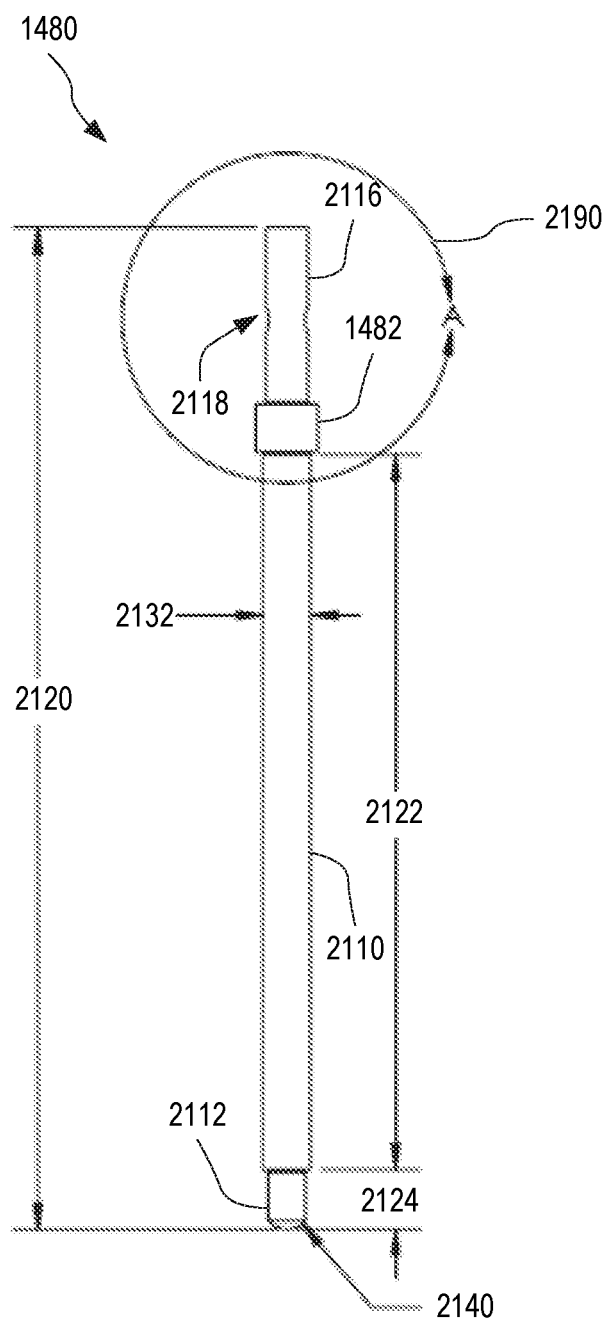
FIGS. 21A and 21B show, in further detail, one exemplary embodiment of a locking driver of the monopedicular targeting system of FIGS. 14A-C.
Figure 21B:
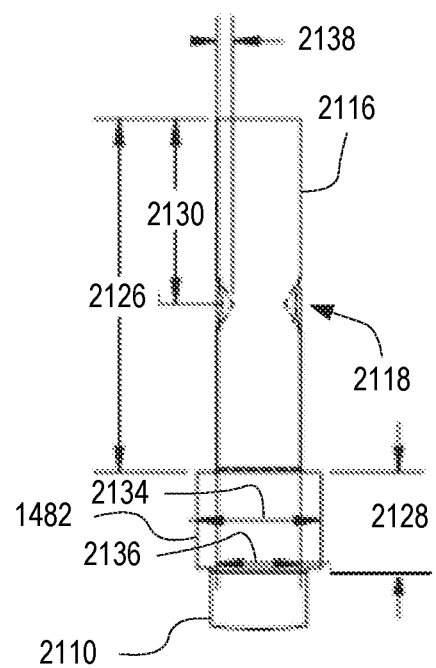

FIGS. 21A and 21B show one exemplary embodiment of locking driver 1480 in further detail. FIG. 21A is a side view of locking driver 2180. FIG. 21B is a close-up of a portion 2190 of locking driver 2180 indicated in FIG. 21A. FIGS. 21A and 21B are best viewed together.

Locking driver 1480 includes (a) a section 2112 with a rounded head 2140, (b) a section 2110 adjacent section 2112, (c) threaded section 1482 which may have a 5/16-24 NF thread, and (d) an actuating section 2116. Rounded head 2140 is configured to apply pressure on head 1412 when thread 1482 is threaded sufficiently far into thread 1434 of cylinder 1430. Actuating section 2116 may be hand actuated or include two indentations 2118 configured to engage with a tool for actuating locking driver 1480.

Dimensions 2120, 2122, 2124, 2126, 2128, 2130, and 2138 are, for example, 5.0660 inches, 3.6200 inches, 0.3000 inches, 0.8930 inches, 0.2430 inches, 0.4680 inches, and 0.0400 inches, respectively. Diameters 2132, 2134, and 2136 are, for example, 0.2430 inches, 0.3125 inches, and 0.2105 inches, respectively. Rounded head 2140 may have a radius of curvature of 0.1250 inches.

Without departing from the scope hereof, actual dimensions of locking driver 1480 may differ from those listed here.

Figure 22E:
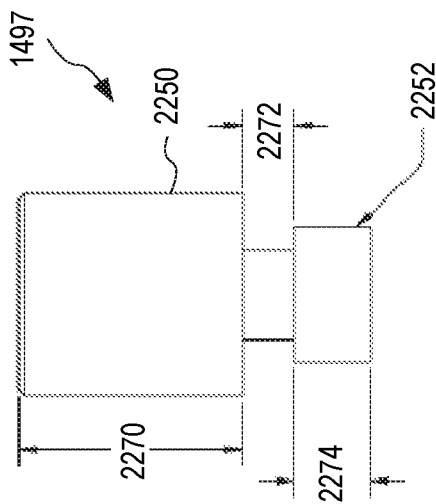
FIGS. 22A-F show, in further detail, one exemplary embodiment of a coupler of the monopedicular targeting system of FIGS. 14A-C.
Figure 22F:
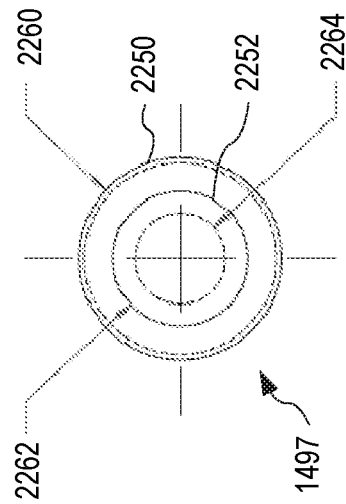
Figure 22C:
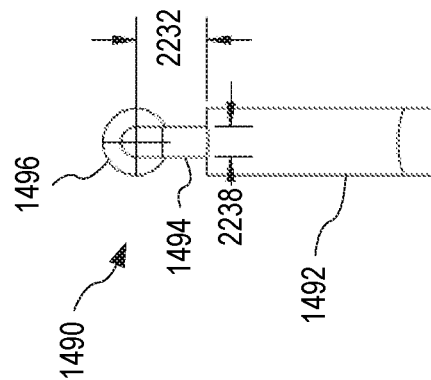
Figure 22D:
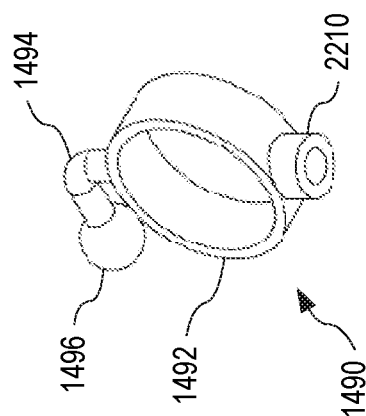
Figure 22A:
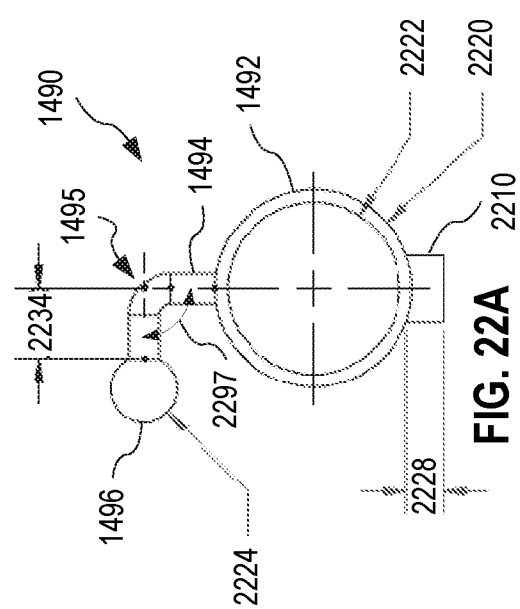
Figure 22B:
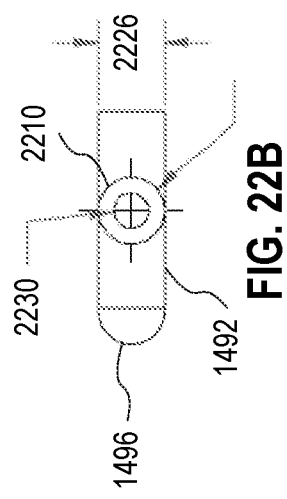
Figure 23A:
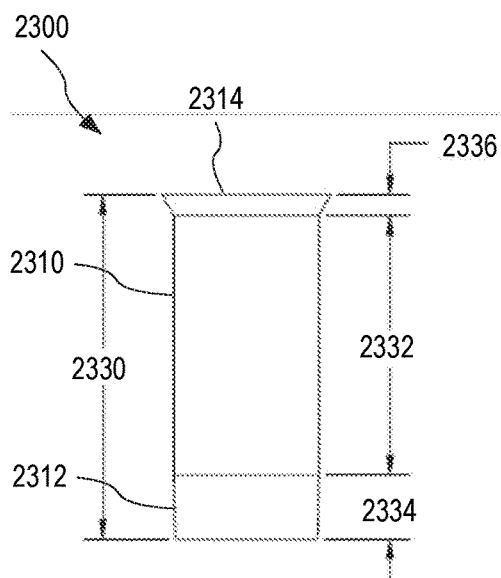
FIGS. 23A-D show a tubular retractor, according to an embodiment.
Figure 23C:
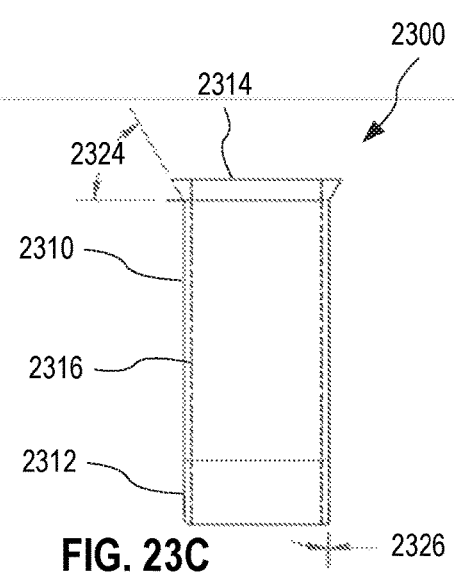
Figure 23B:
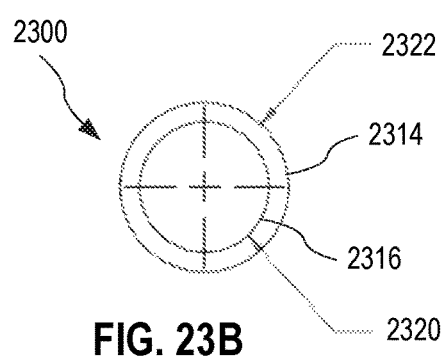
Figure 23D:
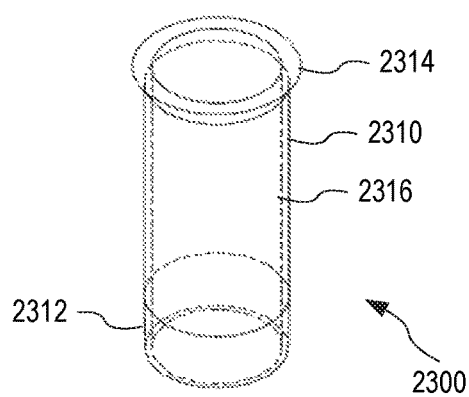

FIGS. 22A-F show one exemplary embodiment of coupler 1490 in further detail. FIGS. 22A-C are orthogonal side views of coupler 1490. FIG. 22D is a perspective view of coupler 1490. FIGS. 22E and 22F are orthogonal side views of locking fastener 1497. FIGS. 22A-F are best viewed together.

Coupler 1490 includes a receptacle 2210 with an internal thread 2230. Locking fastener 1497 includes a threaded section 2252 and an actuating section 2250. Threaded section 2252 is configured to thread into receptacle 2210 to engage internal thread 2230. Internal thread 2230 and threads of threaded section 2252 may be 1/4-20 NC. Ring 1492 has outer diameter 2220 and inner diameter 2222. Diameters 2220 and 2222 may be 1.1125 inches and 0.9700 inches, respectively. Protrusion 1496 may be a ball of radius 2224, for example 0.1875 inches. Dimensions 2226, 2228, 2232, 2234, and 2238 are, for example, 0.3750 inches, 0.2076 inches, 0.4000 inches, 0.4000 inches, 0.1755 inches, respectively. Dimensions 2270, 2272, and 2274 are, for example, 0.4150 inches, 0.0960 inches, and 0.1400 inches, respectively. Diameters 2260, 2262, and 2264 are, for example, 0.3750 inches, 0.2500 inches, and 0.1680 inches, respectively. Angle 2297 may be 90 degrees. Without departing from the scope hereof, actual dimensions of coupler 1490 may differ from those listed here, and the position, shape, and/or size of receptacle 2210 on ring 1492 may differ from that shown in FIGS. 22A-D. In addition, locking fastener 1497 may be replaced by a different type of fastener, such as a set screw.

FIGS. 23A-D show one exemplary tubular retractor 2300. Tubular retractor 2300 is an embodiment of spinal surgery device 1493. In one example, tubular retractor 2300 is intended for multiple use and is made of a material that may be easily cleaned between uses, for example a metal. In another example, tubular retractor 2300 is a disposable device intended for single use. In this example, tubular retractor 2300 may be made of a plastic such as delrin, another machineable polymer, or a moldable polymer.

Tubular retractor 2300 is configured to be accepted by coupler 1490. Tubular retractor 2300 includes a tapered section 2314 forming a lip that prevents tubular retractor 2300 from slipping through ring 1492. Tubular retractor further includes a straight cylindrical section 2310 and a tapered section 2312. Tapered section 2312 serves to ease insertion of tubular retractor 2300 into patient 170. A cannulation 2316 passes through tubular retractor 2300 and provides a pathway for surgeon 180 to access and operate on surgery location 270. Cannulation 2316 may be configured to match the shape and size of a dilator used to dilate the tissue of patient 170. This dilator is, for example, the largest dilator of a series of dilators used to dilate the tissue of patient 170 in a step-wise fashion. Without departing from the scope hereof, tapered section 2314 may be omitted or replaced by a straight section with same inner and outer diameter as straight cylindrical section 2310.

Dimensions 2330, 2332, 2334, and 2336 are, for example, 2.2940 inches, 1.7317 inches, 0.4250 inches, and 0.1373 inches. Diameters 2322 and 2320 are, for example, 1.1250 inches and 0.8661 inches, respectively. Taper angles 2324 and 2326 are, for example, 60 degrees and one degree. In an alternate embodiment, dimension 2330 is in the range between 30 and 90 millimeters (such as between 50 and 60 millimeters), diameter 2322 is in the range between 15 and 40 millimeters (for example, between 20 and 30 millimeters or between 16 and 26 millimeters), and diameter 2320 is approximately 1 to 3 millimeters less than diameter 2322.

Without departing from the scope hereof, actual dimensions of tubular retractor 2300 may differ from those listed here.

Figure 24:
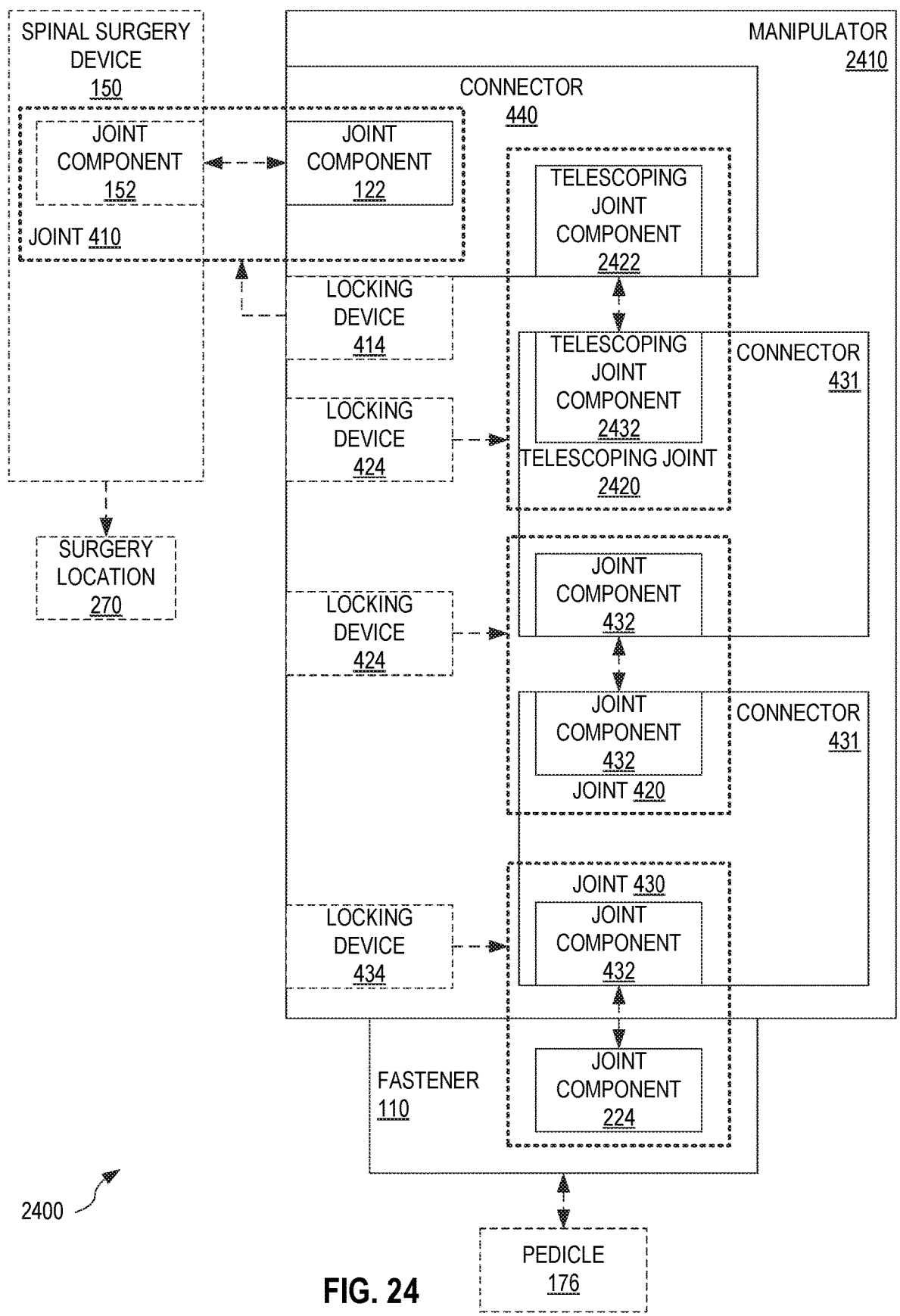
FIG. 24 illustrates a monopedicular targeting system, for posterior spinal surgery, including a manipulator with a telescoping joint, according to an embodiment.

FIG. 24 illustrates one exemplary monopedicular targeting system 2400, for posterior spinal surgery, including a manipulator 2410 with a telescoping joint 2420. Monopedicular targeting system 2400 is an embodiment of monopedicular targeting system 400, and manipulator 2410 is an embodiment of manipulator 410. Monopedicular targeting system 2400 is also an embodiment of monopedicular targeting system 490, and manipulator 2410 is an embodiment of percutaneous pedicle screw 212 and a portion of connector 460. Monopedicular targeting system 2400 may be used to perform any of methods 500, 501, 502, and 503.

Manipulator 2410 includes at least two connectors 431. Although not shown in FIG. 24, manipulator 2410 may implement more than two connectors 431 without departing from the scope hereof. Connector 440 of manipulator 2410 implements joint component 422 as a telescoping joint component 2422, and connector 431 adjacent connector 440 implements a telescoping joint component 2432. Telescoping joint components 2422 and 2432 are configured to mate to form telescoping joint 2420. In the context of monopedicular targeting system 490, this corresponds to joint components 472 of sub-connector 462 mating with another joint component 472 of connector 460 to form telescoping joint 2420. Telescoping joint 2420 allows for changing reach of manipulator 2410. Thus, manipulator 2410 is particularly useful in situations where flexible reach and/or long reach are required. In one use scenario, telescoping joint is used to contralaterally target a surgery location 270.

For comparison, embodiments of monopedicular targeting system 400 (or 490) that do not implement telescoping joint 2420 may instead be supplied to a user as a kit including several connectors 440 (or 460) having different respective reach and/or several of one or more of connectors 431 having different respective reach.

As discussed in further detail below in reference to FIGS. 56-59, monopedicular targeting system 2400 is readily extended to spine-anchored targeting systems that each have the same functionality as monopedicular targeting system 2400 but may be anchored to a different structure of spine 172 or to a pelvis of patient 170. Such spine-anchored targeting systems may be used in posterior spinal surgery of the cervical, thoracic, and/or lumbar spine of patient 170.

Figure 25:
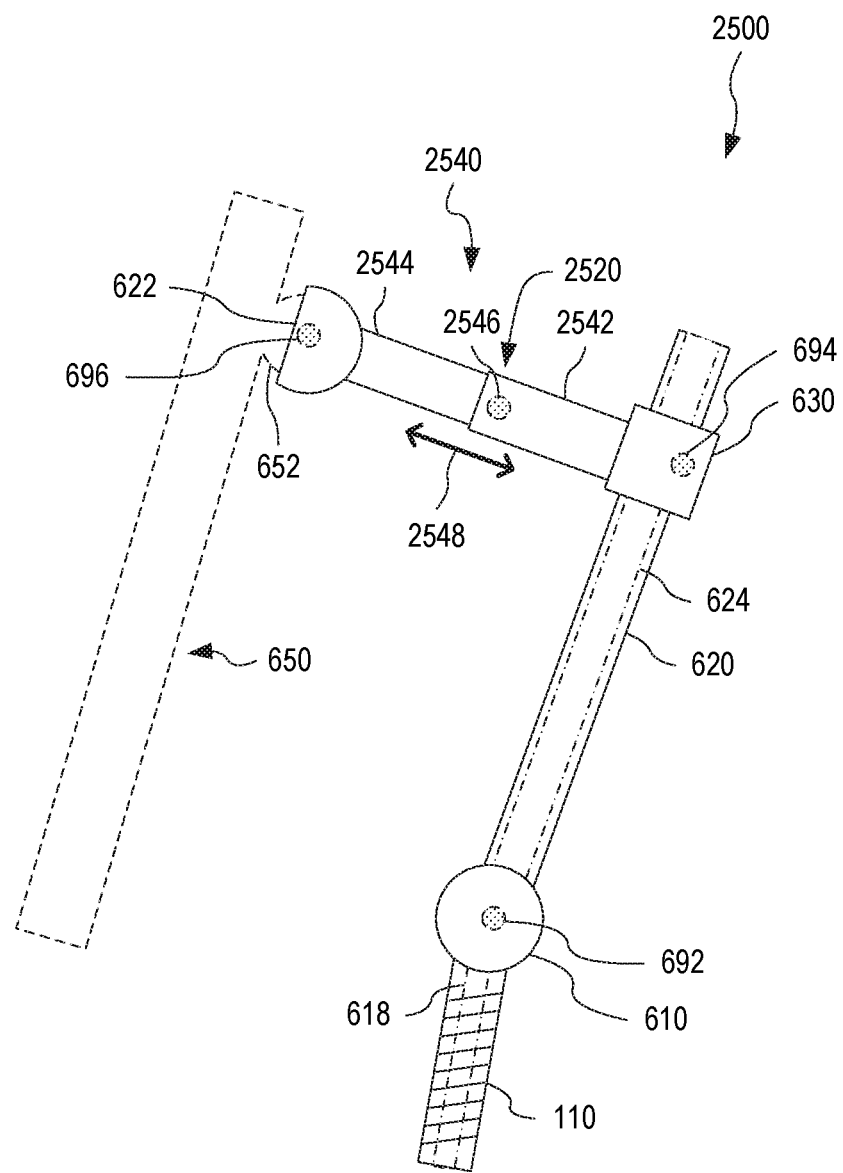
FIG. 25 illustrates another monopedicular targeting system, for posterior spinal surgery, including a manipulator with a telescoping joint, according to an embodiment.

FIG. 25 illustrates one exemplary monopedicular targeting system 2500 that, when assembled, forms (a) spherical joint 610, (b) joint 630 having at least a translational degree of freedom, (c) spherical joint component 622 configured to mate with a spherical joint component 652 of a spinal surgery device 650, and (d) a telescoping joint 2520. Telescoping joint 2520 is an embodiment of telescoping joint 2420. Monopedicular targeting system 2500 is an embodiment of monopedicular targeting system 2400. Monopedicular targeting system 2500 may be used to perform any of methods 500, 501, 502, and 503. Monopedicular targeting system 2500 is similar to monopedicular targeting system 600 except that connector 640 is replaced by a connector 2540 having two connectors 2542 and 2544 configured to mate to form telescoping joint 2520. Telescoping joint 2520 allows for changing the length of connector 2540 along a direction 2548, thereby facilitating changing the reach of monopedicular targeting system 2500. Connector 2544 is an embodiment of connector 440 of manipulator 2430, and connector 2542 is an embodiment of adjacent connector 431 of manipulator 2430.

Optionally, connector 2540 includes a locking device 2546 that may be engaged to lock telescoping joint 2520 in a desired configuration. Locking device 2546 is an embodiment of locking device 424 configured to lock telescoping joint 2420 of manipulator 2410.

Without departing from the scope hereof, fastener 110, joint 610, and positioning arm 620 of monopedicular targeting system 2500 may be replaced by percutaneous pedicle screw 212 or percutaneous pedicle screw 670. Also without departing from the scope hereof, connector 2540 may be supplied as a standalone item configured to couple with a third party percutaneous pedicle screw and a third party spinal surgery device 650 to target a surgery location 270. Connector 2540 is an embodiment of connector 460. Connector 2540 is also an embodiment of connector 200.

As discussed in further detail below in reference to FIGS. 56-59, monopedicular targeting system 2500 is readily extended to spine-anchored targeting systems that each have the same functionality as monopedicular targeting system 2500 but may be anchored to a different structure of spine 172 or to a pelvis of patient 170. Such spine-anchored targeting systems may be used in posterior spinal surgery of the cervical, thoracic, and/or lumbar spine of patient 170.

Figure 26:
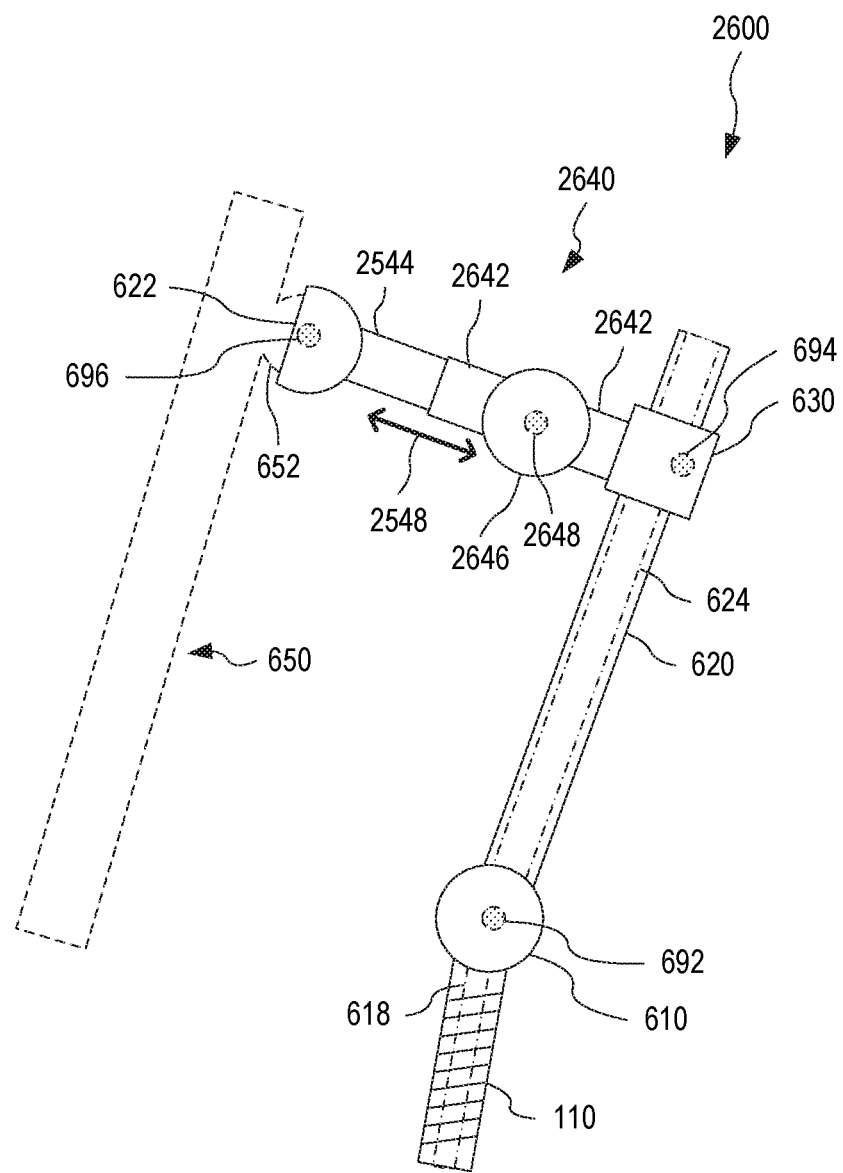
FIG. 26 illustrates a monopedicular targeting system that is an extension of the monopedicular targeting system of FIG. 25 further including an additional rotational joint, according to an embodiment.

FIG. 26 illustrates one exemplary monopedicular targeting system 2600 that is an extension of monopedicular targeting system 2500 including an additional rotational joint 2646. As compared to monopedicular targeting system 2500, connector 2540 is replaced by a connector 2640. Connector 2640 is similar to connector 2540 except that connector 2542 is replaced by a connector 2642 that includes rotational joint 2648. Rotational joint 2648 may have one, two, or three rotational degrees of freedom. Rotational joint 2648 allows for a change in angle of connector 2640, thus providing surgeon 180 additional flexibility to target surgery location 270 along a desired trajectory. Optionally, monopedicular targeting system 2600 includes a locking device 2648 that may be engaged to lock rotational joint 2646 in a desired configuration. Monopedicular targeting system 2600 may be used to perform any of methods 500, 501, 502, and 503.

Without departing from the scope hereof, fastener 110, joint 610, and positioning arm 620 of monopedicular targeting system 2600 may be replaced by percutaneous pedicle screw 212 or percutaneous pedicle screw 670. Also without departing from the scope hereof, connector 2640 may be supplied as a standalone item configured to couple with a third party percutaneous pedicle screw and a third party spinal surgery device 650 to target a surgery location 270. Connector 2640 is an embodiment of connector 460 and of connector 200.

As discussed in further detail below in reference to FIGS. 56-59, monopedicular targeting system 2600 is readily extended to spine-anchored targeting systems that each have the same functionality as monopedicular targeting system 2600 but may be anchored to a different structure of spine 172 or to a pelvis of patient 170. Such spine-anchored targeting systems may be used in posterior spinal surgery of the cervical, thoracic, and/or lumbar spine of patient 170.

Figure 27:
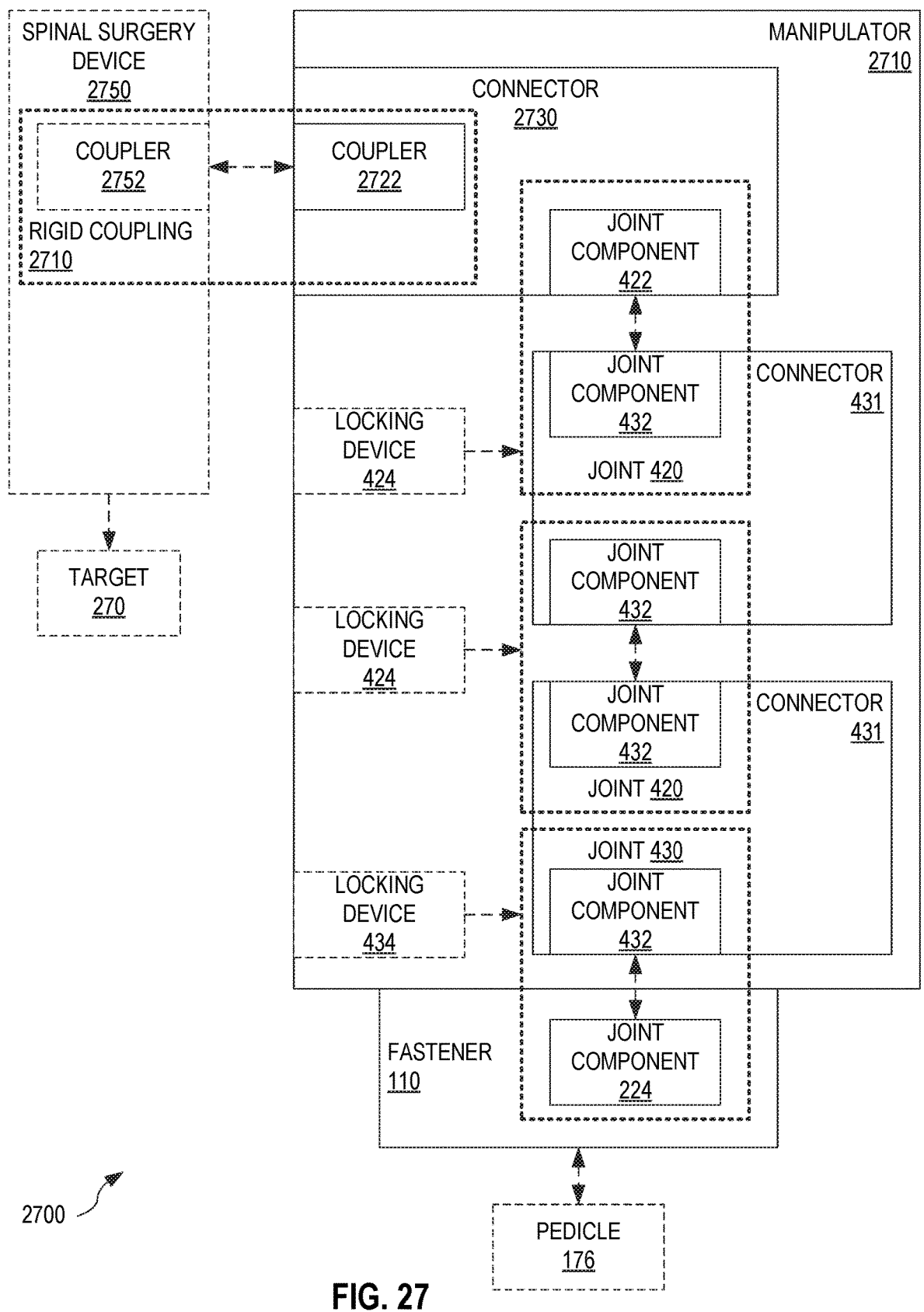
FIG. 27 illustrates a monopedicular targeting system, for posterior spinal surgery, which is configured to rigidly couple with a spinal surgery device, according to an embodiment.

FIG. 27 illustrates one exemplary monopedicular targeting system 2700, for posterior spinal surgery, which is configured to rigidly couple with a spinal surgery device 2750. Monopedicular targeting system 2700 is similar to monopedicular targeting system 2400 except that (a) manipulator 2410 is replaced by manipulator 2710 and (b) manipulator 2710 is configured to rigidly couple with spinal surgery device 2750. In certain embodiments, monopedicular targeting system 2700 includes spinal surgery device 2750. Monopedicular targeting system 2700 may be used to perform any of methods 500, 501, 502, and 503.

Manipulator 2710 is similar to manipulator 2710 and implements at least two connectors 431. Although not shown in FIG. 27, manipulator 2710 may implement more than two connectors 431 without departing from the scope hereof. As compared to manipulator 2410, manipulator 2710 replaces connector 440 with a connector 2730. Connector 2730 is similar to connector 440 except that joint component 122 is replaced by a rigid coupler 2722 configured to rigidly couple with a coupler 2752 of spinal surgery device 2750. Manipulator 2710 includes two joints 420 and forms a joint 430 with fastener 110. Joints 420 and joint 430 are configured such that, when assembled, monopedicular targeting system 2700 provides three translational degrees of freedom and three rotational degrees of freedom for spinal surgery device 2750 with respect to pedicle 176.

In one embodiment, joint 430 is a spherical joint, one joint 420 is a spherical joint, and another joint 420 has at least one translational degree of freedom, optionally in addition to other degrees of freedom.

Without departing from the scope hereof, fastener 110 and connector 431 coupled with fastener 110 may be replaced by percutaneous pedicle screw 212 or percutaneous pedicle screw 670.

As discussed in further detail below in reference to FIGS. 56-59, monopedicular targeting system 2700 is readily extended to spine-anchored targeting systems that each have the same functionality as monopedicular targeting system 2700 but may be anchored to a different structure of spine 172 or to a pelvis of patient 170. Such spine-anchored targeting systems may be used in posterior spinal surgery of the cervical, thoracic, and/or lumbar spine of patient 170.

Figure 28A:
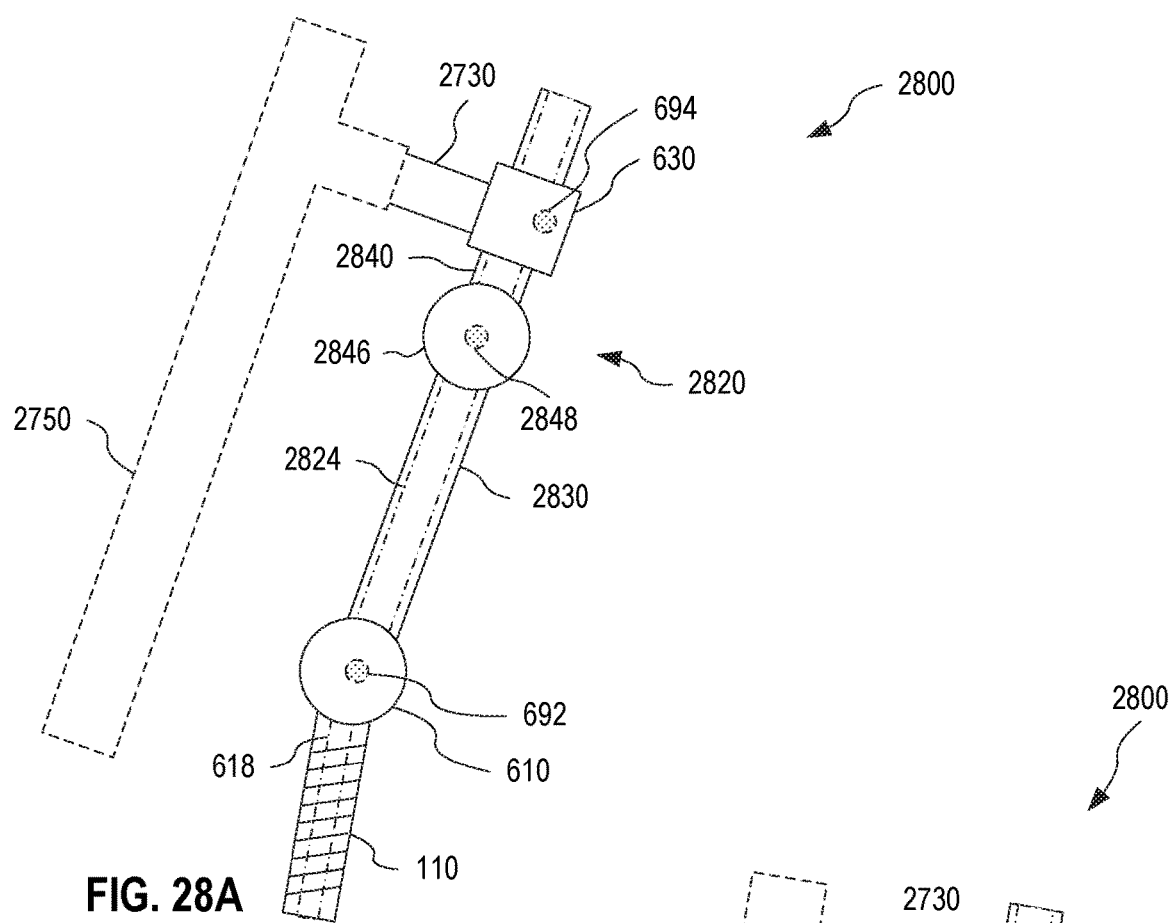
FIGS. 28A and 28B illustrate another monopedicular targeting system, for posterior spinal surgery, which is configured to rigidly couple with a spinal surgery device, according to an embodiment.
Figure 28B:
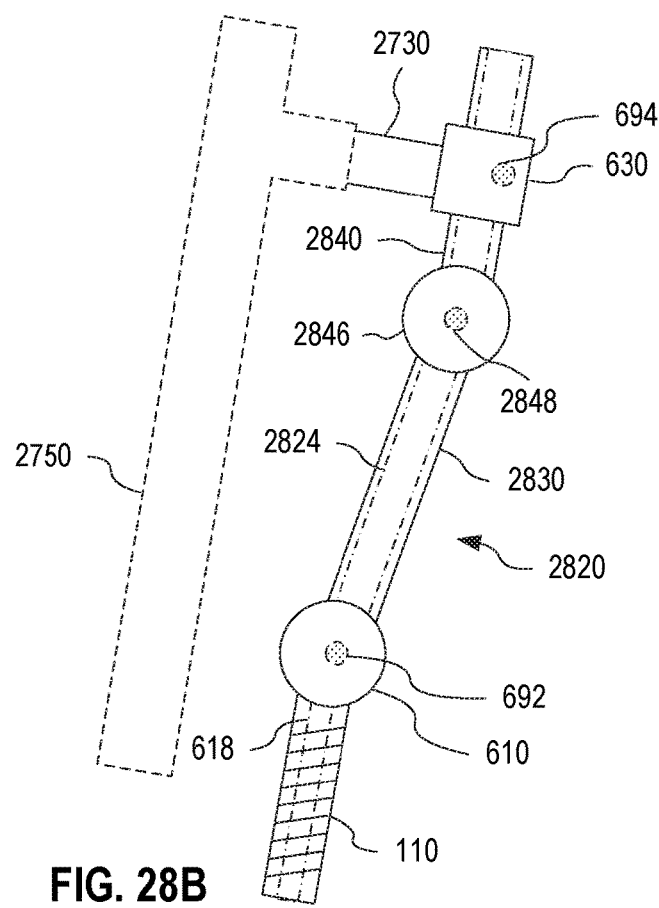

FIGS. 28A and 28B illustrate one exemplary monopedicular targeting system 2800 configured to rigidly couple with spinal surgery device 2750. Monopedicular targeting system 2800 is an embodiment of monopedicular targeting system 2700. Monopedicular targeting system 2800 may include spinal surgery device 2750. FIGS. 28A and 28B show two different states of monopedicular targeting system 2800. FIGS. 28A and 28B are best viewed together.

Monopedicular targeting system 2800 includes fastener 110, a positioning arm 2820, and connector 2730. Fastener 110 and positioning arm 2820 are configured to couple with each other via spherical joint 610, as discussed in reference to FIG. 6A for fastener 110 and positioning arm 620. Positioning arm 2820 and connector 2730 are configured to couple with each other via joint 630, as discussed in reference to FIG. 6A for positioning arm 620 and connector 640. Connector 2730 is configured to rigidly couple with spinal surgery device 2750 as discussed in reference to FIG. 27. Optionally, monopedicular targeting system 2800 includes one or both of locking devices 692 and 694.

Positioning arm 2820 includes two connectors 2830 and 2840 configured to couple with each other via a spherical joint 2846. Optionally, monopedicular targeting system 2800 includes a locking device 2848 that may be engaged to lock spherical joint 2846 in a desired configuration. Spherical joint 610, spherical joint 2846, and joint 630 cooperate to provide three translational degrees of freedom and three rotational degrees of freedom for spinal surgery device 2750 with respect to pedicle 176.

FIG. 28A shows positioning arm 2820 in a straight state with parallel connectors 2830 and 2840. FIG. 28B shows positioning arm 2820 in a kinked state with connectors 2830 and 2840 at an angle relative to each other.

In an embodiment, positioning arm 2820 includes a cannulation 2824 passing through the full length of positioning arm 2820 such that fastener 110 may be engaged through cannulation 2824, at least when connectors 2830 and 2840 are parallel as shown in FIG. 28A.

As discussed in further detail below in reference to FIGS. 56-59, monopedicular targeting system 2800 is readily extended to spine-anchored targeting systems that each have the same functionality as monopedicular targeting system 2800 but may be anchored to a different structure of spine 172 or to a pelvis of patient 170. Such spine-anchored targeting systems may be used in posterior spinal surgery of the cervical, thoracic, and/or lumbar spine of patient 170.

Figure 29A:
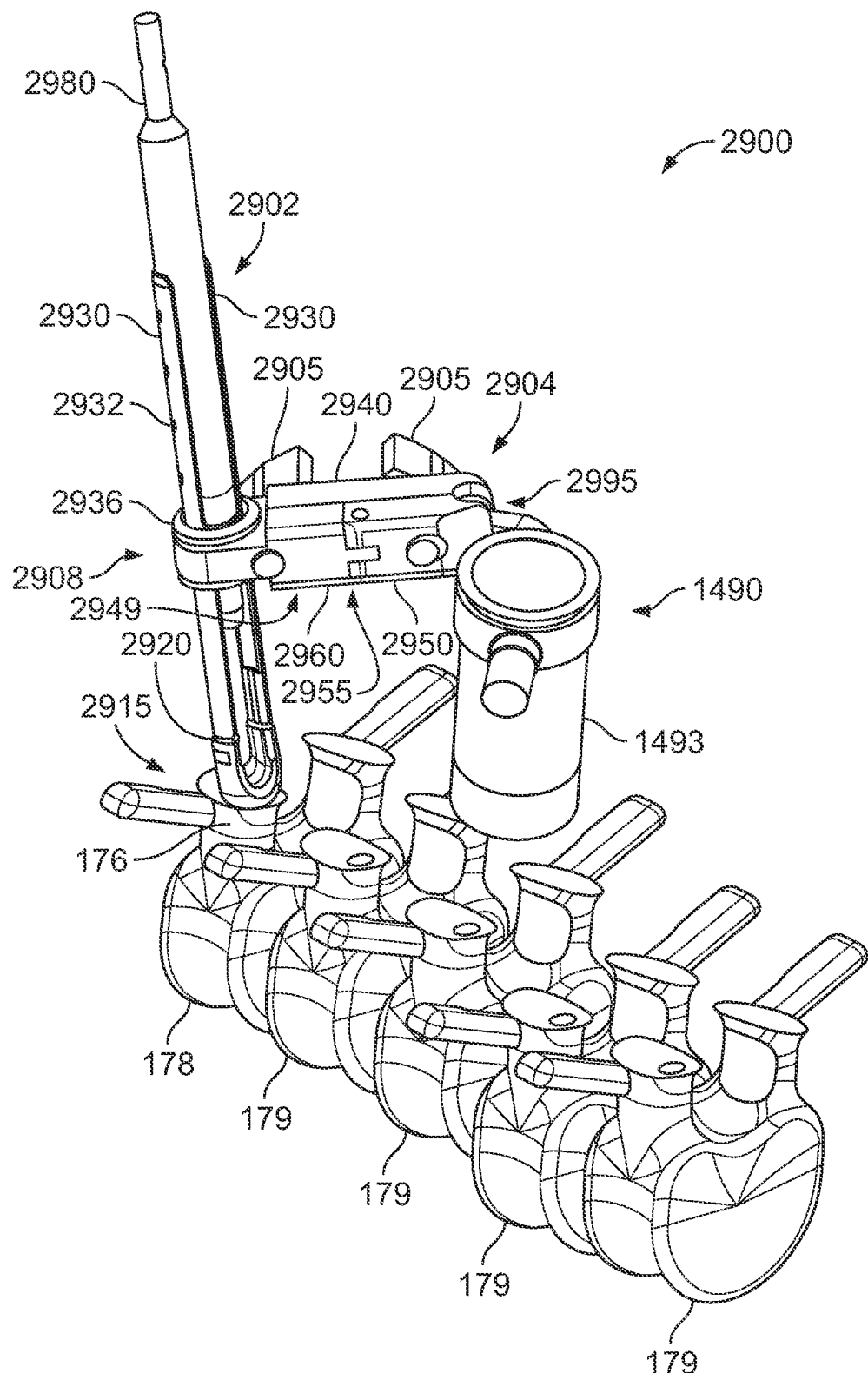
FIGS. 29A-C illustrate a monopedicular targeting system for posterior spinal surgery, which is based upon a percutaneous pedicle screw, according to an embodiment.
Figure 29B:
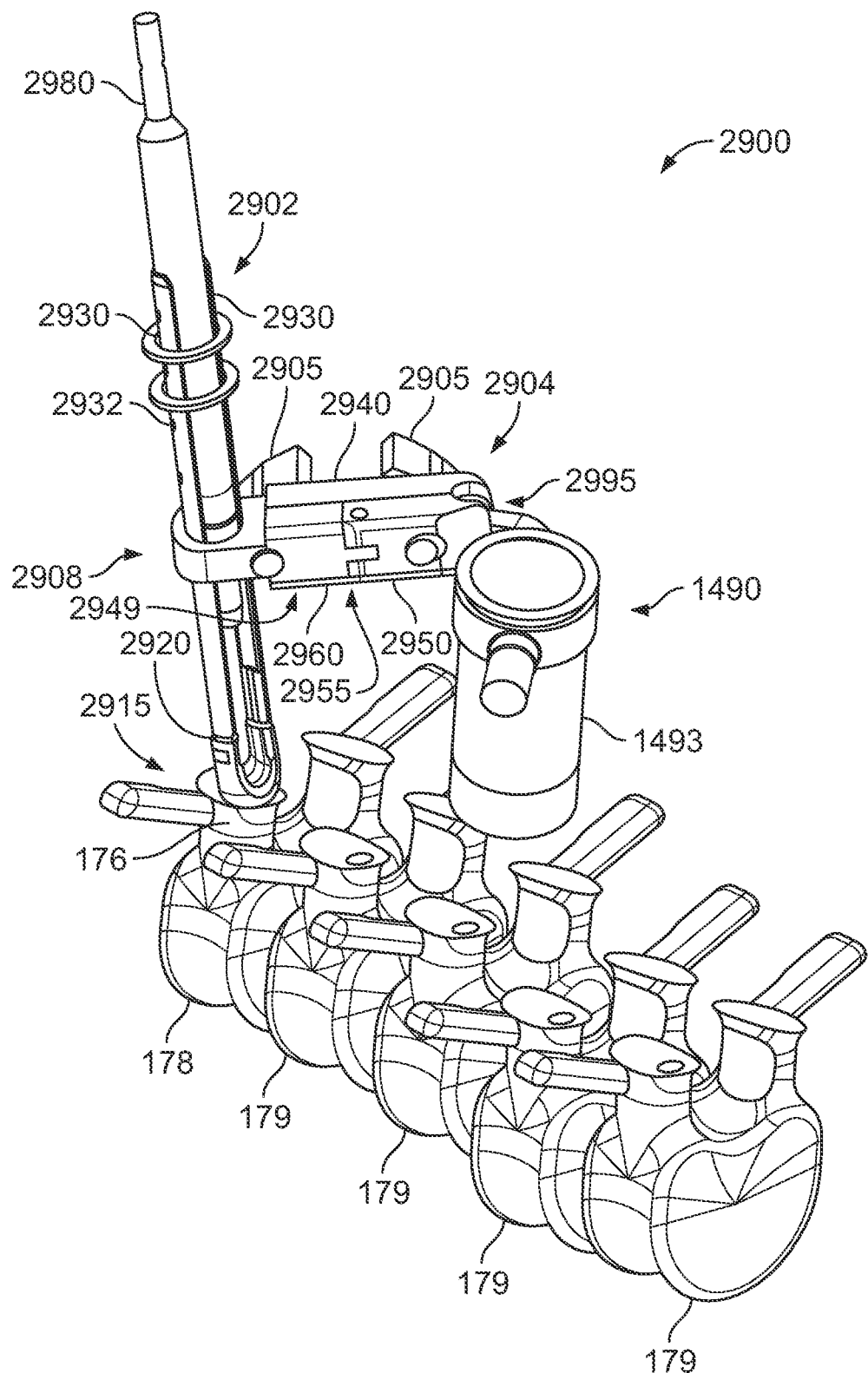
Figure 29C:
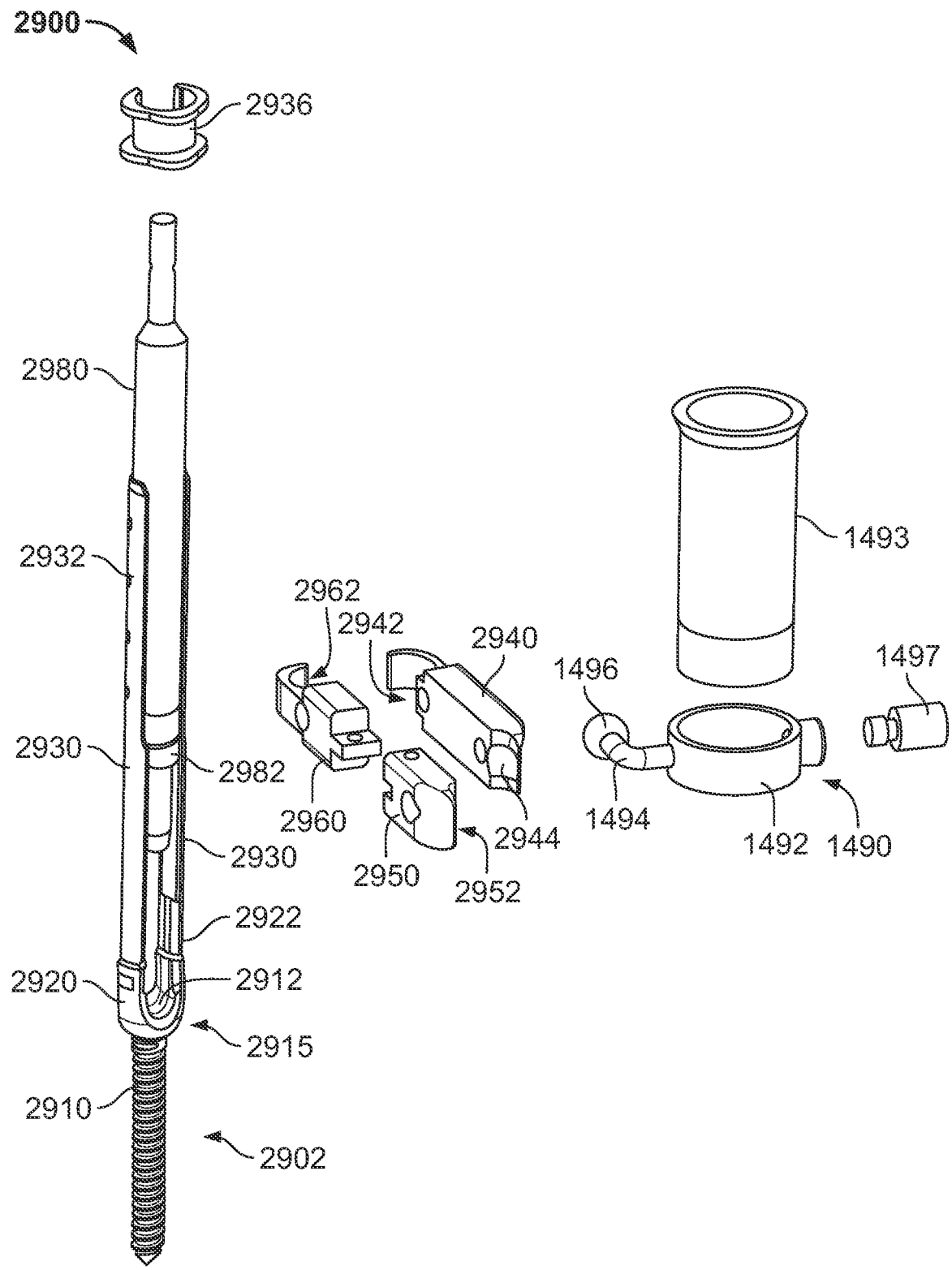

FIGS. 29A-C illustrate one exemplary monopedicular targeting system 2900 for posterior spinal surgery, which is based upon a percutaneous pedicle screw 2902. Monopedicular targeting system 2900 is an embodiment of monopedicular targeting system 602, and percutaneous pedicle screw 2902 is an embodiment of percutaneous pedicle screw 212. Monopedicular targeting system 2900 may be used to perform any of methods 500, 501, 502, and 503. Each of FIGS. 29A and 29B shows monopedicular targeting system 2900 in assembled form, inserted into pedicle 176, and coupled with spinal surgery device 1493 for targeting a surgery location 270 from a contralateral working direction. FIG. 29C shows monopedicular targeting system 2900 in exploded view. FIGS. 29A-C are best viewed together.

In the embodiment shown in FIGS. 29A-C, percutaneous pedicle screw 2902 is similar to the percutaneous pedicle screw of the ES2® Spinal System by Stryker. However, without departing from the scope hereof, percutaneous pedicle screw 2902 may be another off-the shelf percutaneous pedicle screw, or a custom made item. Exemplary vendors supplying percutaneous pedicle screw suitable for implementation as percutaneous pedicle screw 212 include, but are not limited to, Stryker, DePuy Synthes, NuVasive, Globus, K2 Medical, Medtronic, Biomet, and Zimmer Spine. Percutaneous pedicle screw 2902 includes (a) a pedicle screw 2910 for screwing into pedicle 176, (b) a socket 2920 that forms a spherical joint 2915 with the head 2912 of pedicle screw 2910, (c) two break-off blades 2930 having only a fragile connection with socket 2920, and (d) a stabilizing clip 2936. Break-off blades 2930 form an embodiment of removable guiding extension 240, socket 2920 is an embodiment of socket 230, pedicle screw 2910 is an embodiment of pedicle screw 220, and spherical joint 2915 is an embodiment of joint 680. Spherical joint 2915 may have angular range as discussed for joint 610 in reference to FIGS. 7C-7E. Without departing from the scope hereof, stabilizing clip 2936 need not be included in embodiments of monopedicular targeting system 2900 based upon a third party percutaneous pedicle screw that does not require a stabilizing clip. Likewise, monopedicular targeting system 2900 may be configured to cooperate with a percutaneous pedicle screw wherein break-off blades 2930 are replaced by another implementation of removable guiding extension 240.

Break-off blades 2930 may be broken off of socket 2920 when no longer needed. Stabilizing clip 2936 has lips configured to attach to each of break-off blades 2930 to stabilize the relative positions of break-off blades 2930, so as to prevent inadvertent detachment of break-off blades 2930 from socket 2920. Clip 2936 is removable from break-off blades 2930. Clip 2936 has spring loaded protrusions facing break-off blades 2930. Break-off blades 2930 have matching indentations 2932 placed at several different distances from socket 2920 such that clip 2936 may be stably coupled with break-off blades 2930 at these different distances from socket 2920. Without departing from the scope hereof, break-off blades 2930 may be configured differently from what is shown in FIGS. 29A-C, and/or clip 2936 may be replaced by another form of stabilizing clamp with features configured to interface with break-off blades 2930 to prevent inadvertent removal of break-off blades 2930 from socket 2920. In one such example, percutaneous pedicle screw 2902 includes more than two break-off blades and clip 2936 is replaced by a clamp that stabilizes the relative positioning of these break-off blades.

Percutaneous pedicle screw 2902 has internal threads 2922 placed at least on break-off blades 2930. Head 2912 of pedicle screw 2910 may be accessed with a tool through the cannulation formed by break-off blades 2930. In one embodiment, pedicle screw 2910 is cannulated, for example to accommodate a guide wire. In another embodiment, pedicle screw 2910 is not cannulated.

In addition to percutaneous pedicle screw 2902, monopedicular targeting system 2900 includes a connector 2904. Connector 2904 is an embodiment of connector 660 and of connector 200. Connector 2904 is similar to connector 1404, except for being adapted to couple with percutaneous pedicle screw 2902. Connector 2904 includes two clamp parts 2940 and 2949. Clamp part 2940 has a groove 2942, and clamp part 2949 has a groove 2962. Clamp parts 2940 and 2949 are configured to be brought together with grooves 2942 and 2962 around break-off blades 2930 (as shown in FIG. 29B), or around clip 2936 (as shown in FIG. 29A), to form a cylindrical joint 2908 therewith. Cylindrical joint 2908 is an embodiment of joint 630. In one implementation, connector 2904 may be mounted on break-off blades 2930 at any position along the length of break-off blades 2930, for example at a position closer to socket 2920 than clip 2936. Receptacles 2944 and 2952 of clamp parts 2940 and 2949, respectively, are configured to mate with a protrusion 1496 of coupler 1490 to form a spherical joint 2995. Coupler 1490 is configured to removably couple with spinal surgery device 1493.

Connector 2904, as shown in FIGS. 29A-C, has length compatible with contralaterally targeting a surgery location 270. However, connector 2904 may be shorter than shown in FIGS. 29A-C to ipsilaterally target a surgery location 270 at a spine segment adjacent pedicle 176, without departing from the scope hereof. Likewise, connector 2904 may be longer than shown in FIGS. 29A-C to target a more distant surgery location 270.

Without departing from the scope hereof, connector 2904 may have a protrusion, instead of grooves 2942 and 2962, that mates with a receptacle of coupler 1490, instead of protrusion 1496, to form spherical joint 2995.

Monopedicular targeting system 2900 further includes a locking driver 2980 that may be inserted into percutaneous pedicle screw 2902 between break-off blades 2930 and engage with internal threads 2922 to press on head 2912 through socket 2920. Locking driver 2980 has external threads 2982, such that locking driver 2980 may be threaded into internal threads 2922. Contact between internal threads 2922 and external threads 2982 cooperate with pressure between head 2912 and locking driver 2980 to lock spherical joint 2915. Locking driver 2980 is an embodiment of locking device 693. Although not shown in FIGS. 29A-C, monopedicular targeting system 2900 may include a tool for actuating locking driver 2980.

Monopedicular targeting system 2900 also includes two locking fasteners 2905 that may be inserted through one of clamp parts 2940 and 2949 to be screwed into another one of clamp parts 2940 and 2949 to tighten clamp parts 2940 and 2949 together over break-off blades 2930 and protrusion 1496, so as to lock both of joints 2908 and 2995. Locking fasteners 2905 implement locking devices 694 and 696 and are similar to locking fasteners 1405. Clamp part 2949 includes two clamp subparts 2950 and 2960 with a hinge 2955 therebetween. Clamp subpart 2950 includes receptacle 2952. Clamp subpart 2960 includes groove 2962. Hinge 2955 facilitates mutually independent locking of joints 2908 and 2995.

Without departing from the scope hereof, locking fasteners 2905 may be configured for actuation by a tool, as opposed to by use of finger holds, and/or be set screws or other recessed screws, as discussed in further detail for locking fasteners 1405. Likewise, locking fasteners 2905 may be directed through connector 2904 at an oblique angle, as discussed in further detail for locking fasteners 1405. Furthermore, locking fasteners 2905 may access connector 2904 from surfaces generally facing away from patient 170, as discussed in further detail for locking fasteners 1405, without departing from the scope hereof.

Connecting arm 1494 of coupler 1490 has a 90 degree angle that offers the same benefits for monopedicular targeting system 2900 as discussed for monopedicular targeting system 1400 above in reference to FIGS. 14A-C. Without departing from the scope hereof, ring 1492 may be replaced by a differently shaped element configured to couple with a spinal surgery device different from spinal surgery device 1493 shown in FIGS. 29A-C.

Monopedicular targeting system 2900 may utilize the two different orientations of coupler 1490 relative to the longitudinal axis of spinal surgery device 1493 to contralaterally or ipsilaterally target surgery location 270, as discussed above for monopedicular targeting system 1400.

In an alternate embodiment, protrusion 1496 is permanently and rigidly coupled with spinal surgery device 1493 through connecting arm 1494 to form an integrated coupler-spinal surgery device. In one exemplary scenario, two different embodiments of this integrated coupler-spinal surgery device is supplied to surgeon 180 to allow both ipsilateral and contralateral procedures. These two different embodiments are equivalent to the two possible orientations of coupler 1490 as discussed above.

One or more portions of monopedicular targeting system 2900 or spinal surgery device 1493 may have anti-glare or glare reducing surface, as discussed above for monopedicular targeting system 900 and spinal surgery device 960.

In certain embodiments, monopedicular targeting system 2900 includes spinal surgery device 1493.

Without departing from the scope hereof, connector 2904 may be supplied as a standalone item configured to cooperate with a third party percutaneous pedicle screw 212 and a third party spinal surgery device 150 to target surgery location 270. Connector 2904 is an embodiment of connector 200. Also without departing from the scope hereof, connector 2904 of monopedicular targeting system 2900 may be replaced by clamp 940, and clamp 940 of monopedicular targeting system 900 may be replaced by connector 2904. Likewise, monopedicular targeting system 2900 may utilize spinal surgery device 960 instead of spinal surgery device 1493 and coupler 1490.

In the ES2® Spinal System, the percutaneous pedicle screw has indentations providing four different positions for stable coupling between the break-off blades and a clip. However, break-off blades 2930 may have a different number of such indentations 2932 to provide a corresponding number of stable coupling positions, without departing from the scope hereof. For example, break-off blades 2930 may have more than four sets of indentations 2932 to provide more than four stable coupling positions, such as at least 6, 10, or 15 indentations 2932.

Figure 30B:
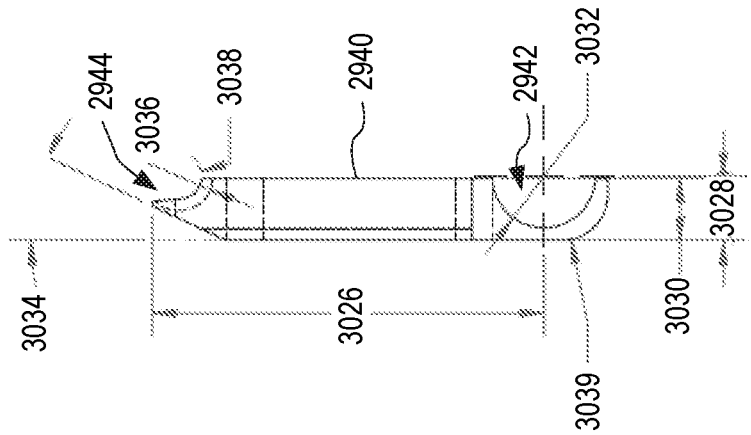
FIGS. 30A-C show, in further detail, one exemplary embodiment of a clamp part of the monopedicular targeting system of FIGS. 29A-C.
Figure 30C:
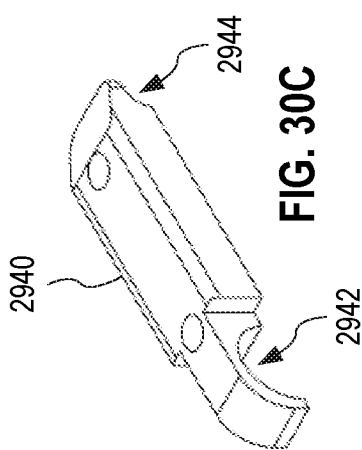
Figure 30A:
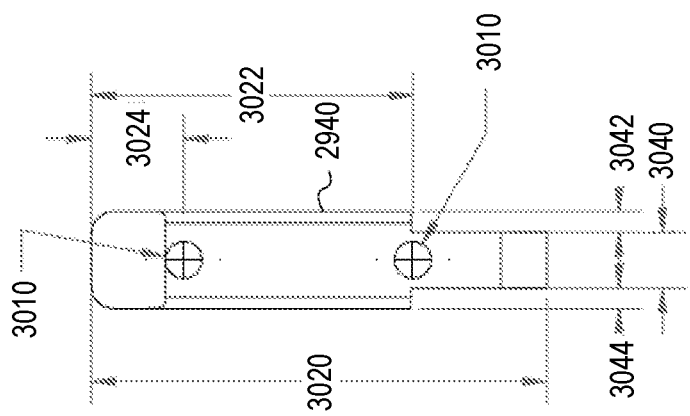

FIGS. 30A-C show one exemplary embodiment of clamp part 2940 in further detail. FIGS. 30A and 30B show orthogonal side views of clamp part 2940, while FIG. 30C shows clamp part 2940 in perspective view. FIGS. 30A-C are best viewed together.

Clamp part 2940 has length 3020, one cross-sectional dimension 3030, and an orthogonal cross-sectional dimension that is the sum of dimensions 3040, 3042, and 3044. Clamp part 2940 includes threaded holes 3010 configured to engage locking fasteners 2905. Groove 2942 is cylindrical with the cylinder axis being placed slightly outside cross-sectional extent 3030 of clamp part 2940. This helps ensure that, when clamp part 2940 is brought together with clamp subpart 2960 around break-off blades 2930 (or clip 2936), connector 2904 applies pressure to break-off blades 2930 (or clip 2936) as opposed to only applying pressure between clamp part 2940 and clamp subpart 2960. Receptacle 2944 is of spherical shape. The center of the sphere is placed slightly outside extent 3030 to help ensure that, when clamp part 2940 is brought together with clamp subpart 2950 around protrusion 1496, connector 2904 applies pressure to protrusion 1496 as opposed to only applying pressure between clamp part 2940 and clamp subpart 2950.

In one embodiment, threaded holes 3010 are of type ¼-20NC, and each corresponding locking fastener 2905 has a corresponding external ¼-20NC thread. In one embodiment, dimensions 3020, 3022, 3024, 3026, 3028, 3030, 3040, 3042, and 3044 are 2.4850 inches, 1.7544 inches, 0.5044 inches, 2.1362 inches, 0.3500 inches, 0.3375 inches, 0.3050 inches, 0.1125 inches, and 0.1125 inches, respectively. In one embodiment, radii of curvature 3032, 3036, 3038, and 3039 are 0.2813 inches, 0.1875 inches, 0.1250 inches, and 0.2500 inches, and angle 3034 is 25 degrees. Receptacle 2944 may have an angled opening similar to that of receptacle 1444. Without departing from the scope hereof, actual dimensions of clamp part 2940 may differ from those listed here.

Without departing from the scope hereof, actual dimensions of clamp part 2940 may differ from those listed here.

Figure 31A:
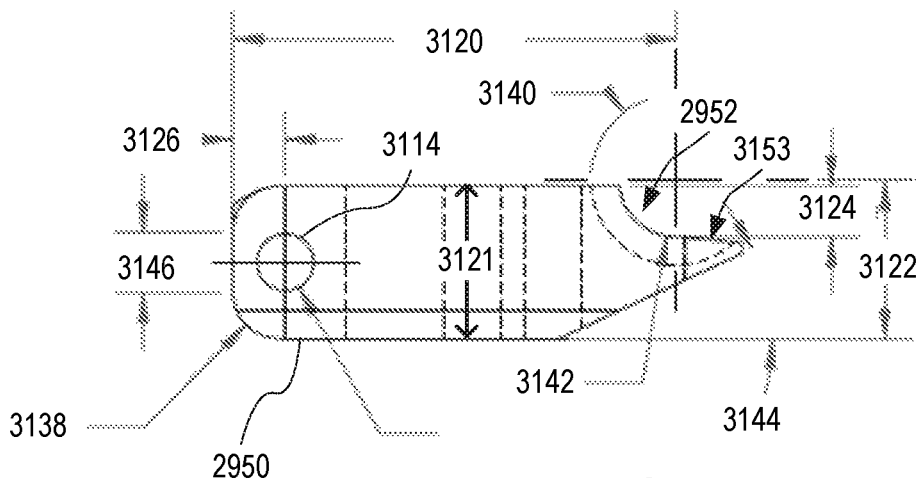
FIGS. 31A-C show, in further detail, one exemplary embodiment of a first clamp subpart of the monopedicular targeting system of FIGS. 29A-C.
Figure 31B:
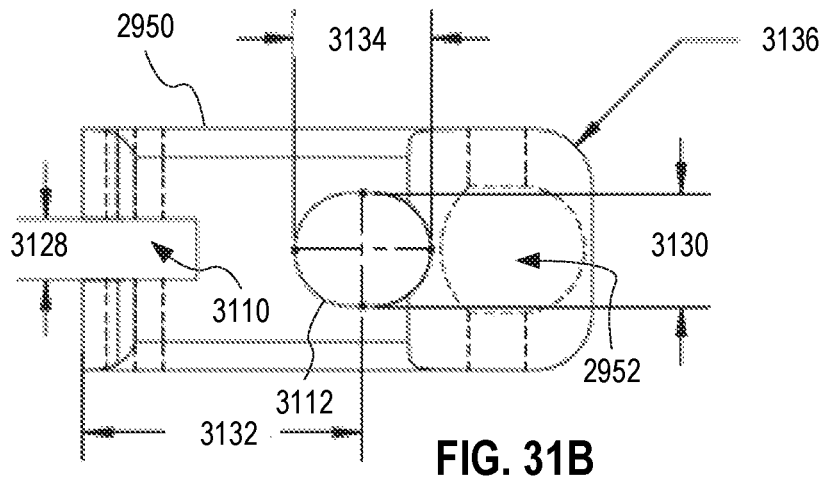
Figure 31C:
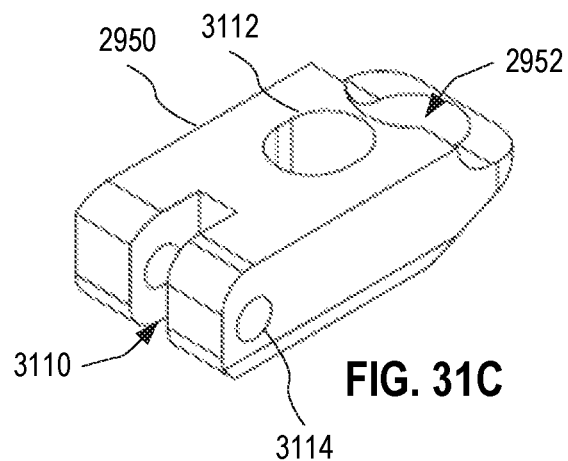

FIGS. 31A-C show one exemplary embodiment of clamp subpart 2950 in further detail. FIGS. 31A and 31B show orthogonal side views of clamp subpart 2950, while FIG. 31C shows clamp subpart 2950 in perspective view. FIGS. 31A-C are best viewed together.

Clamp subpart 2950 includes a slot 3110 and a through hole 3114, which cooperate with matching features of clamp subpart 2960 to form hinge 2955. Clamp subpart 2950 further includes a through hole 3112 configured to accept one locking fastener 2905. Receptacle 2952 is of spherical shape. The center of the sphere is placed slightly outside extent 3121 (as indicated by extent 3122) to help ensure that, when clamp part 2940 is brought together with clamp subpart 2950 around protrusion 1496, connector 2904 applies pressure to protrusion 1496 as opposed to only applying pressure between clamp part 2940 and clamp subpart 2950. Clamp subpart 2950 has an angled opening 3153 into receptacle 2952.

In one embodiment, dimensions 3120, 3121, 3122, 3124, 3126, 3128, 3130, 3132, 3134, and 3146 are 0.9746 inches, about 0.34 inches, 0.3500 inches, 0.1130 inches, 0.1156 inches, 0.1350 inches, 0.2500 inches, 0.6156 inches, 0.3000 inches, and 0.1339 inches, respectively. In one embodiment, the diameter of through hole 3114 is 0.1250 inches. In one embodiment, angle 3144 is 25 degrees. Radii of curvature 3138, 3140, and 3142 are, for example, 0.1000 inches, 0.1875 inches, and 0.1250 inches, respectively. Without departing from the scope hereof, actual dimensions of clamp subpart 2950 may differ from those listed here.

Without departing from the scope hereof, actual dimensions of clamp subpart 2950 may differ from those listed here.

FIGS. 32A-C show one exemplary embodiment of clamp subpart 2960 in further detail. FIGS. 32A and 32B show orthogonal side views of clamp subpart 2960, while FIG. 32C shows clamp subpart 2960 in perspective view. FIGS. 32A-C are best viewed together.

Clamp subpart 2960 includes a bracket 3210 with a through hole 3211, which are configured to mate with slot 3110 and a pin passing through both through hole 3114 of clamp subpart 2950 and through hole 3211 to form hinge 2955. Clamp subpart 2960 further includes a through hole 3212 configured to accept one locking fastener 2905. Groove 2962 is of cylindrical shape. The center of the cylinder may be placed slightly outside extent 3228 (as discussed for clamp subpart 1460) to help ensure that, when clamp part 2940 is brought together with clamp subpart 2960 around break-off blades 2930 (or clip 2936), connector 2904 applies pressure to break-off blades 2930 as opposed to only applying pressure between clamp part 2940 and clamp subpart 2960.

In one embodiment, dimensions 3220, 3222, 3224, 3226, 3228, 3230, 3232, and 3234 are 0.5300 inches, 0.3050 inches, 0.2500 inches, 0.1250 inches, 0.3375 inches, 0.1688 inches, 0.1294 inches, and 0.7390 inches, respectively. In one embodiment, diameter 3236 is 0.1250 inches. In one embodiment, radii of curvature 3240 and 3242 are 0.2500 inches and 0.2813 inches, respectively. Without departing from the scope hereof, actual dimensions of clamp subpart 2960 may differ from those listed here.

Without departing from the scope hereof, actual dimensions of clamp subpart 2960 may differ from those listed here.

FIGS. 33A-C illustrate one exemplary locking driver 3300 for use in an embodiment of monopedicular targeting system 2900 wherein percutaneous pedicle screw 2902 is the percutaneous pedicle screw of the ES2® Spinal System by Stryker. Locking driver 3300 is an embodiment of locking driver 2980. FIG. 33A shows a side view of locking driver 3300. FIG. 33B is a close-up of a portion 3390 of locking driver 3300 indicated in FIG. 33A. Portion 3390 includes an actuating section 3320 that is similar to actuating section 2116. FIG. 33C is a close-up of a portion 3392 of locking driver 3300 indicated in FIG. 33A. Portion 3392 includes a coupling section 3330. FIGS. 33A-C are best viewed together.

Locking driver 3300 is configured to be inserted into percutaneous pedicle screw 2902 between break-off blades 2930 and engage with internal threads 2922 to apply pressure on head 2912, so as to lock spherical joint 2915. Locking driver 3300 includes a section 3310 configured to have a snug fit inside break-off blades 2930. Section 3310 has constant diameter 3352 along its full length 3312. Section 3310 counteracts pressure by connector 2904, and/or the associated locking fastener 2905, on break-off blades 2930 to prevent inadvertent detachment of one or both of break-off blades 2930 when using locking fastener 2905 to tighten connector 2904 onto break-off blades 2930 (or clip 2936). The snug fit is ensured by the diameter 3352 of section 3310 being close to the inner diameter of the cannulation formed by break-off blades 2930.

Coupling section 3330 includes (a) a tip 3332 configured to contact head 2912 and (b) an external thread 2982 configured to engage with internal thread 2922. When external thread 2982 is threaded sufficiently far into internal thread 2922, tip 3332 applies pressure to head 2912 and locks spherical joint 2915.

Optionally, actuating section 3320 includes two indentations 3322 configured to couple with a tool to thread locking driver 3300 into percutaneous pedicle screw 2902. Alternatively, surgeon 180 may hand tighten locking driver 3300 into percutaneous pedicle screw 2902.

Dimensions 3312, 3350, 3354, 3356, 3358, 3360, 3362, 3366, 3368, and 3370 are, for example, 3.1795 inches, 5.7070 inches, 0.1250 inches, 0.3450 inches, 0.1500 inches, 0.6360 inches, 0.1432 inches, 0.0400 inches, 0.4250 inches, and 0.9180 inches, respectively. Diameters 3352, 3364, 3374, 3376, 3378, 3380, and 3382 are, for example, 0.4000 inches, 0.2100 inches, 0.3680 inches, 0.2850 inches, 0.3880 inches, 0.2850 inches, and 0.2200 inches, respectively. Angles 3372 and 3386 are, for example, 120 degrees and 60 degrees, respectively. Without departing from the scope hereof, actual dimensions of locking driver 3300 may differ from those listed here.

Without departing from the scope hereof, locking driver 3300 may be adapted to work with other percutaneous pedicle screws 2902, such as those supplied by Stryker, DePuy Synthes, NuVasive, Globus, K2 Medical, Medtronic, Biomet, and Zimmer Spine.

Figure 34A:
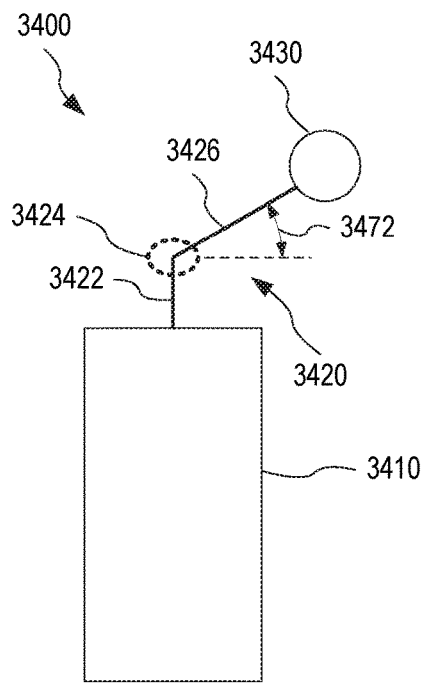
FIGS. 34A-D illustrate a tubular retractor having an angled connecting arm, according to an embodiment.
Figure 34B:
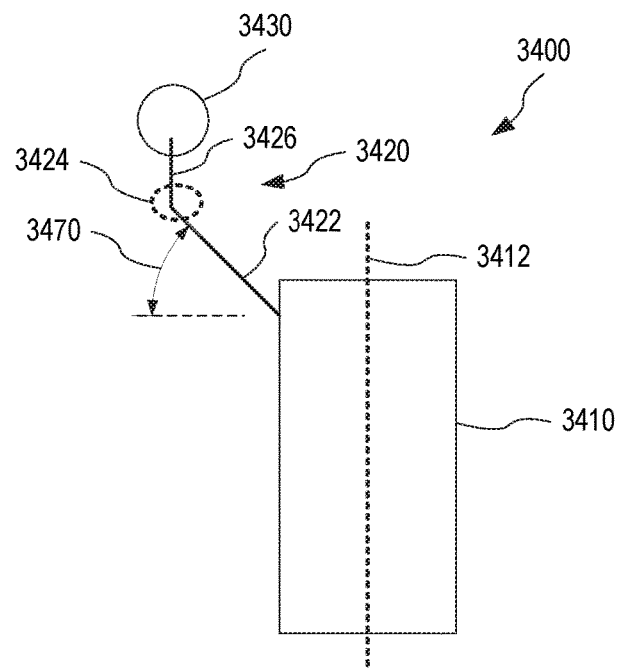
Figure 34C:
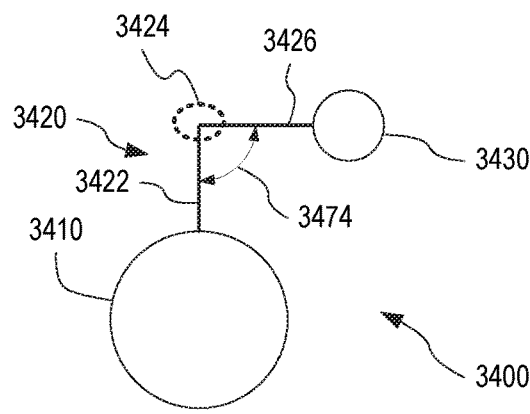
Figure 34D:
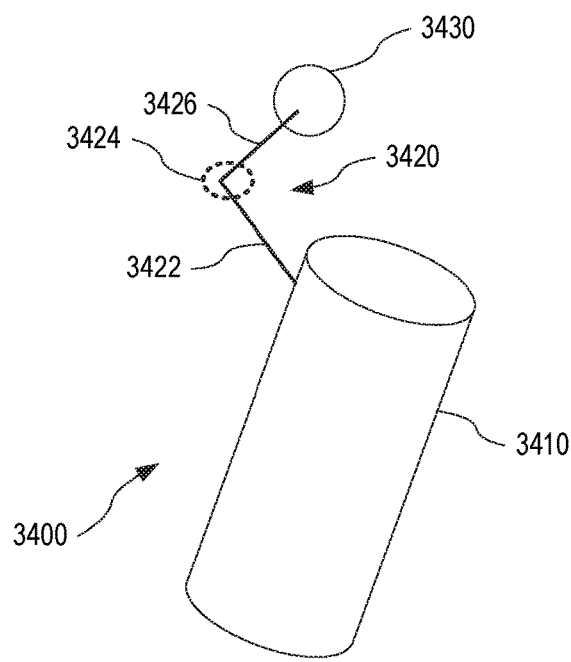

FIGS. 34A-D illustrate one exemplary tubular retractor 3400 having an angled connecting arm. Tubular retractor 3400 is configured to couple with monopedicular targeting system 100 to form a spherical joint with joint component 122. Tubular retractor 3400 includes a tube 3410, an angled connecting arm 3420, and a protrusion 3430. Connecting arm 3420 connects tube 3410 to protrusion 3430. FIGS. 34A-C show orthogonal side views of tubular retractor 3400. FIG. 34D is a perspective view of tubular retractor 3400. FIGS. 34A-D are best viewed together.

Connecting arm 3420 includes a straight section 3422 attached to tube 3410, a straight section 3426 connected to protrusion 3430, and an angled section 3424 connecting straight sections 3422 and 3426.

In certain embodiments, connecting arm 3420 is angled up relative to level orientation, wherein level orientation refers to a direction in the plane orthogonal to longitudinal axis 3412 of tube 3410. This may enhance the positioning flexibility of tube 3410 in patient 170 because an up-angled embodiment of connecting arm 3420 reduces potential interference between connecting arm 3420 and tissue of patient 170. The upwards angle of connecting arm 3420 may be achieved at angled section 3424 and/or at the point where connecting arm 3420 attaches to tube 3410. Without departing from the scope hereof, connecting arm 3420 may include one or more additional angled sections, for example adjacent to the point where connecting arm 3420 attaches to tube 3410.

Straight section 3422 is at an angle 3470 relative to level orientation, and straight section 3426 is at an angle 3472 relative to level orientation. Straight sections 3422 and 3426, when projected onto the plane orthogonal to longitudinal axis 3412, are at an angle 3474 relative to each other. In an embodiment, angle 3470 is in the range between zero and 90 degrees, for example in the range between zero and 60 degrees. In an embodiment, angle 3472 is in the range between zero and 90 degrees, for example in the range between zero and 60 degrees. In an embodiment, angle 3474 is in the range between 30 and 135 degrees, for example between 80 and 100 degrees.

In an alternate embodiment, connecting arm 3420 includes no straight sections or only one straight section. For example, connecting arm 3420 may be composed of angled section 3424 alone, wherein angled section 3424 (a) is directly coupled to tube 3410 and protrusion 3430 and (b) spans the distance otherwise collectively spanned by angled section 3424 and straight sections 3422 and 3426.

Tubular retractor 3400 is an embodiment of spinal surgery devices 150 and 650, and protrusion 3430 is an embodiment of joint components 152 and 652. Tubular retractor 3400 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Without departing from the scope hereof, tube 3410 may have non-circular cross section. For example, the cross section of tube 3410 may be elliptical or oval, or have shape of a polygon such as a triangle, a rectangle, a square, a pentagon, a hexagon, or an octagon. Additionally, tube 3410 may be composed of multiple separable pieces. In one such implementation, one of the multiple separable pieces may be removable, for example to change the shape and/or size of tube 3410 or to form a window in tube 3410. Although shown in FIGS. 34A and 34B as being a nearly complete sphere, protrusion 3430 may have a different shape, without departing from the scope hereof. For example, protrusion 3430 may be a smaller portion of a sphere.

Figure 35:
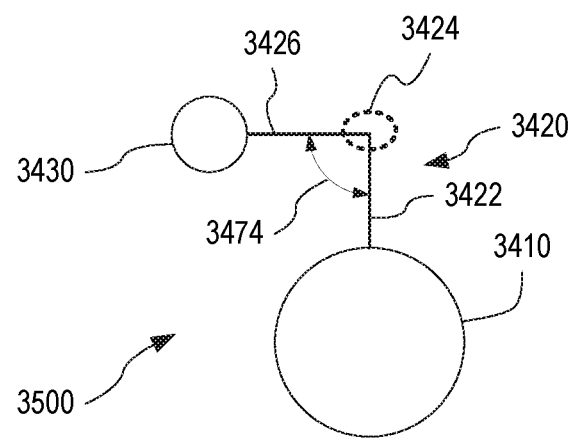
FIG. 35 illustrates another tubular retractor having an angled connecting arm, according to an embodiment.

FIG. 35 illustrates another exemplary tubular retractor 3500 having an angled connecting arm. Tubular retractor 3500 is similar to tubular retractor 3400 except for implementing connecting arm 3420 at an orientation, relative to longitudinal axis 3412, which is opposite of the orientation of connecting arm 3420 in tubular retractor 3400.

Referring collectively to FIGS. 34A-D and 35, each of tubular retractors 3400 and 3500, when coupled with manipulator 210, allows for respective positioning of both manipulator 210 and the tubular retractor outside an imaging-based anterior-posterior visualization pathway to surgery location 270. As compared to spinal surgery device 1490 (implemented as a tubular retractor) and coupler 1409, tubular retractors 3400 and 3500 may provide for more flexible positioning of the tube in patient 170 due to the absence of ring 1492 and fastener 1497. Instead of assembling spinal surgery device 1490 (implemented as a tubular retractor) with coupler 1409 in an appropriate one of the two possible orientations to optimally target surgery location 270 from a desired working direction, surgeon 180 may select an appropriate one of tubular retractors 3400 and 3500 to achieve the same goal.

Figure 36:
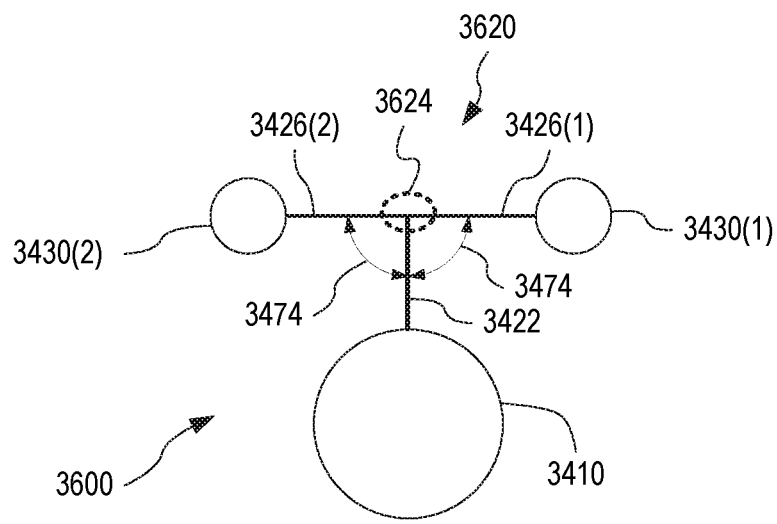
FIG. 36 illustrates a dual-mode tubular retractor having two joint components, each configured to couple with a monopedicular targeting system, according to an embodiment.

FIG. 36 illustrates one exemplary dual-mode tubular retractor 3600 having two joint components, each configured to couple with monopedicular targeting system 100 to form a spherical joint with joint component 122. Tubular retractor 3600 is similar to tubular retractor 3400 except for connecting arm being replaced by a dual-mode connecting arm 3620. Dual-mode connecting arm 3620 connects tube 3410 to two instances of protrusion 3430, indicated in FIGS. 36A and 36B as protrusions 3430(1) and 3430(2). FIG. 36 shows tubular retractor 3600 in the same view as that used in FIG. 34C.

Connecting arm 3620 includes straight section 3422, two instances of straight section 3426 indicated as straight sections 3426(1) and 3426 (2), and a junction 3624. Connecting arm 3620 connects tube 3410 to (a) protrusion 3430(1) via straight section 3426(1) and (b) protrusion 3430(2) via straight section 3426(2). Together, straight section 3422, a portion of junction 3624, and straight section 3426(1) implement connecting arm 3420 in the same orientation as in tubular retractor 3400. Likewise, straight section 3422, a portion of junction 3624, and straight section 3426(2) cooperate to implement connecting arm 3420 in the same orientation as in tubular retractor 3500. Thus, connecting arm 3620 simultaneously implements both of these two orientations of connecting arm 3420. Surgeon 180 may utilize protrusion 3430(1) to achieve the functionality of tubular retractor 3400 or, alternately, utilize protrusion 3430 (2) to achieve the functionality of tubular retractor 3500.

Tubular retractor 3600 is an embodiment of spinal surgery devices 150 and 650. Tubular retractor 3600 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Figure 37A:
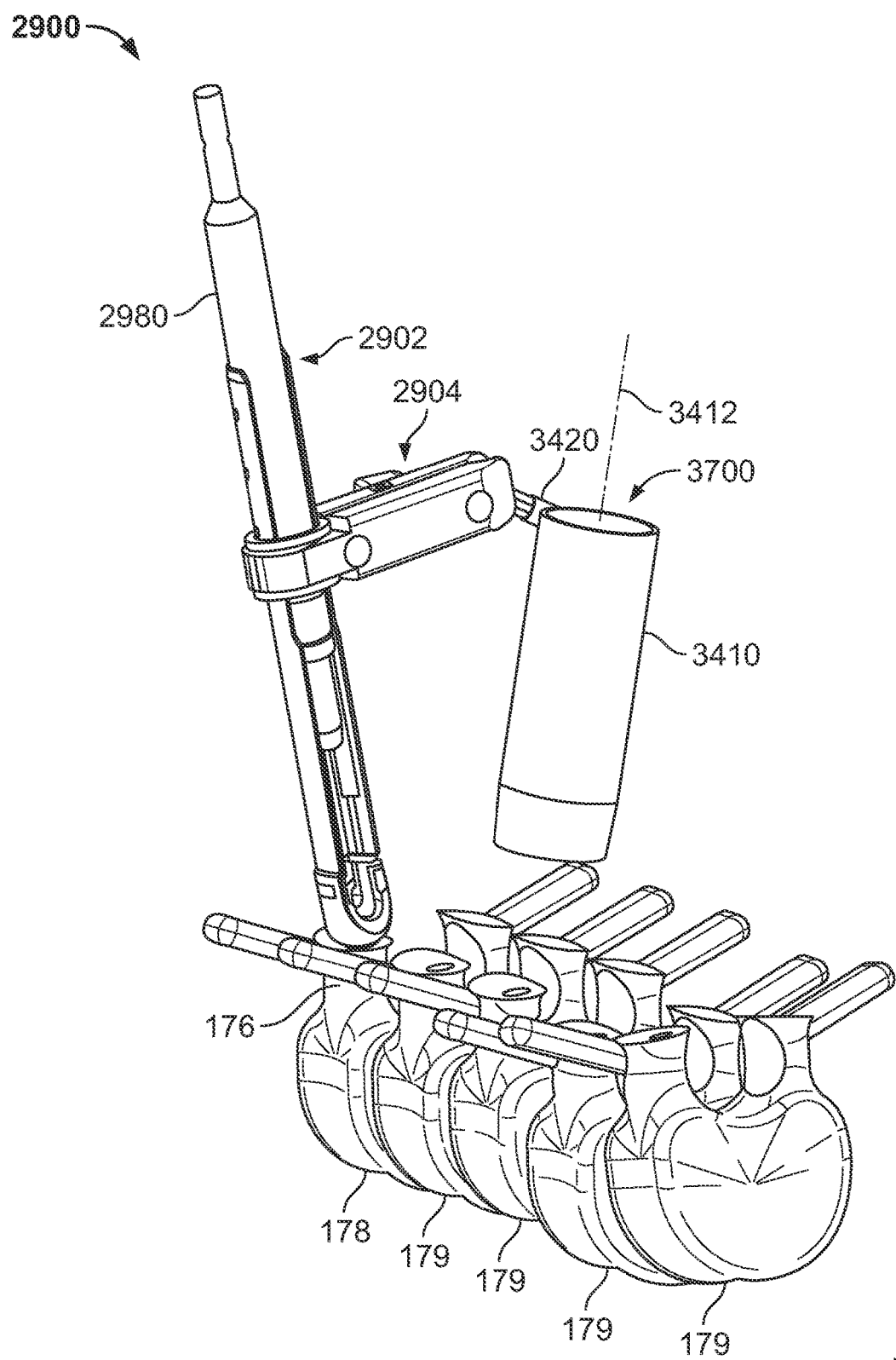
FIGS. 37A and 37B illustrate exemplary embodiments of the tubular retractors of FIGS. 34A-C and 35, respectively, in exemplary use scenarios.
Figure 37B:
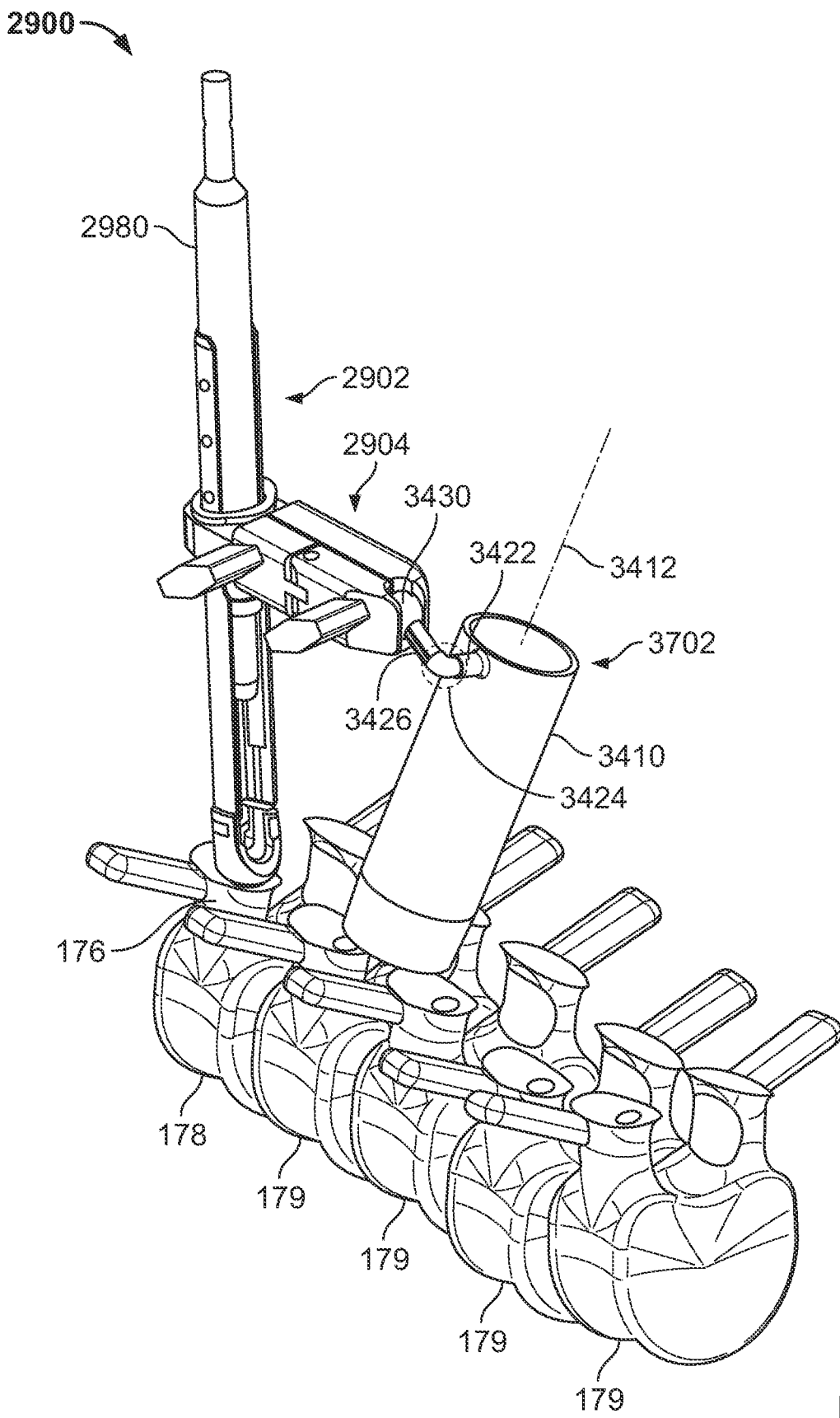

FIGS. 37A and 37B illustrate two exemplary embodiments of tubular retractors 3400 and 3500, respectively, in exemplary use scenarios. FIG. 37A shows one exemplary tubular retractor 3700 coupled with monopedicular targeting system 2900 to target surgery location 270 from a contralateral working direction. FIG. 37B shows one exemplary tubular retractor 3702 coupled with monopedicular targeting system 2900 to target surgery location 270 from an ipsilateral working direction. Tubular retractors 3700 and 3702 are embodiments of tubular retractors 3500 and 3400, respectively. FIGS. 37A and 37B are best viewed together.

As configured in FIGS. 37A and 37B, each of tubular retractors 3700 and 3702 allows for respective positioning of both connector 2904 and the tubular retractor outside an imaging-based anterior-posterior visualization pathway to surgery location 270. In each of tubular retractors 3700 and 3702, straight section 3426 is angled up relative to level orientation. This reduces potential interference between connecting arm 3420 and the tissue of patient 170 and thus improves the positioning flexibility of tubular retractors 3700 and 3702 as compared to a tubular retractor with a level connecting arm.

Tubular retractors 3700 and 3702 are embodiments of spinal surgery devices 150 and 650. Tubular retractors 3700 and 3702 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Figure 38A:
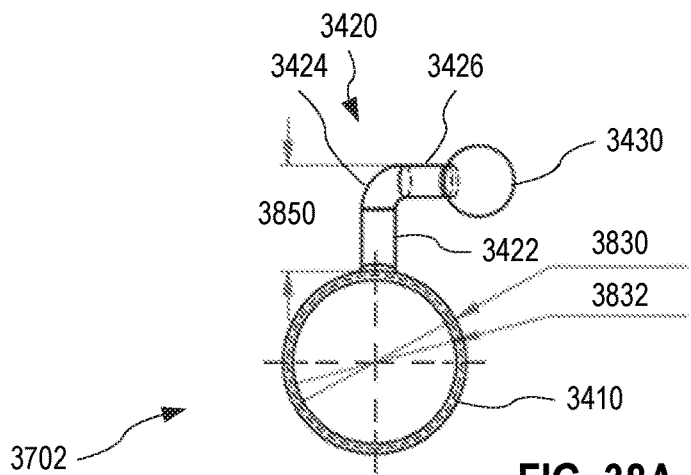
FIGS. 38A-C show the tubular retractor of FIG. 37B in further detail, according to an embodiment.
Figure 38B:
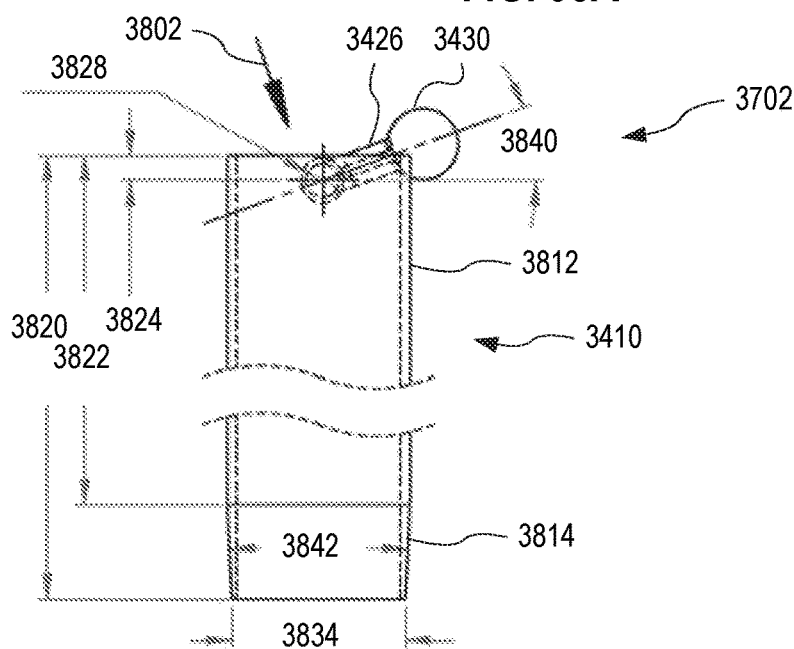
Figure 38C:
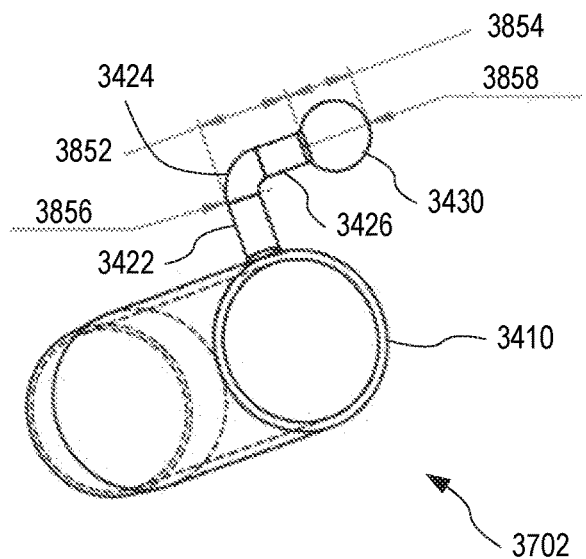

FIGS. 38A-C show tubular retractor 3702 in further detail. It is understood that tubular retractor 3700 has similar properties, apart from connecting arm 3420 having opposite orientation relative to longitudinal axis 3412, as compared to that shown in FIGS. 38A-C. FIG. 38A shows a top view of tubular retractor 3702 with the viewing direction being parallel to longitudinal axis 3412. FIG. 38B shows a side view of tubular retractor 3702 with the viewing direction being orthogonal to longitudinal axis 3412. FIG. 38C shows a perspective view of tubular retractor 3702 with the viewing direction being along direction 3802 indicated in FIG. 38B. FIGS. 38A-C are best viewed together.

In tubular retractor 3702, straight section 3422 is orthogonal to longitudinal axis 3412, and straight section 3426 is orthogonal to straight section 3422. However, straight section 3422 is angled up by an angle 3840. In one example, angle 3840 is in the range between 15 and 60 degrees, such as between 30 and 45 degrees. For clarity of illustration, longitudinal axis 3412 is not shown in FIGS. 38A-C. Tube 3410, as implemented in tubular retractor 3702, includes a straight section 3812 and a tapered section 3814. Tapered section 3814 may ease insertion of tube 3410 into the tissue of patient 170.

Length 3820 of tube 3410 may be in the range from 30 to 90 millimeters, such as between 50 and 60 millimeters. This value of length 3820 is suitable for retracting the tissue between spine 172 and the skin surface of patient 170, without extending so far above the skin surface of patient 170 that tube 3410 imposes unnecessary restriction of movement of surgery tools inserted through tube 3410 to operate on surgery location 270. In one example, length 3820 is 3.1496 inches. In an example, outer diameter 3830 of tube 3410 is in the range between 15 and 40 millimeters, for example between 20 and 30 millimeters or between 16 and 26 millimeters, and inner diameter 3832 of tube 3410 is approximately 1-3 millimeters less than outer diameter 3830.

In an embodiment, dimensions 3822, 3824, 3850, 3852, and 3854 are 2.6496 inches, 0.1331 inches, 0.5559 inches, 0.4878 inches, and 0.3532 inches, respectively. In an embodiment, diameters 3830, 3832, 3828, 3834, and 3858 are 0.9661 inches, 0.8661 inches, 0.1755 inches, 0.9161 inches, and 0.3750 inches, respectively. Angle 3840 is 20 degrees, for example. Radius of curvature 3856 of angled section 3424 may be 0.2378 inches. Taper angle 3842 may be 5.7248 degrees. However, taper angle 3842 may be zero without departing from the scope hereof.

Figure 39A:
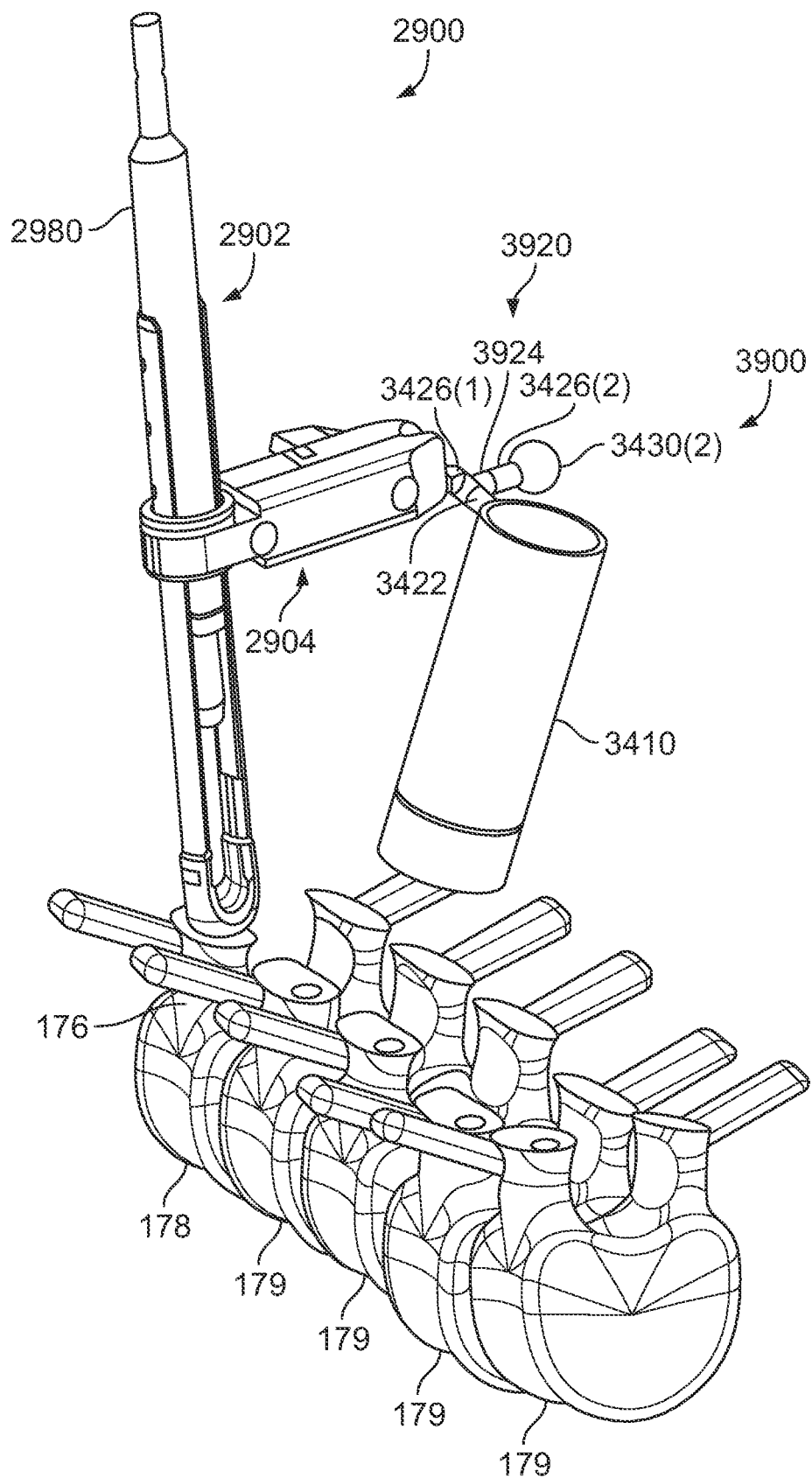
FIGS. 39A and 39B another dual-mode tubular retractor having two joint components, each configured to couple with a monopedicular targeting system, according to an embodiment.
Figure 39B:
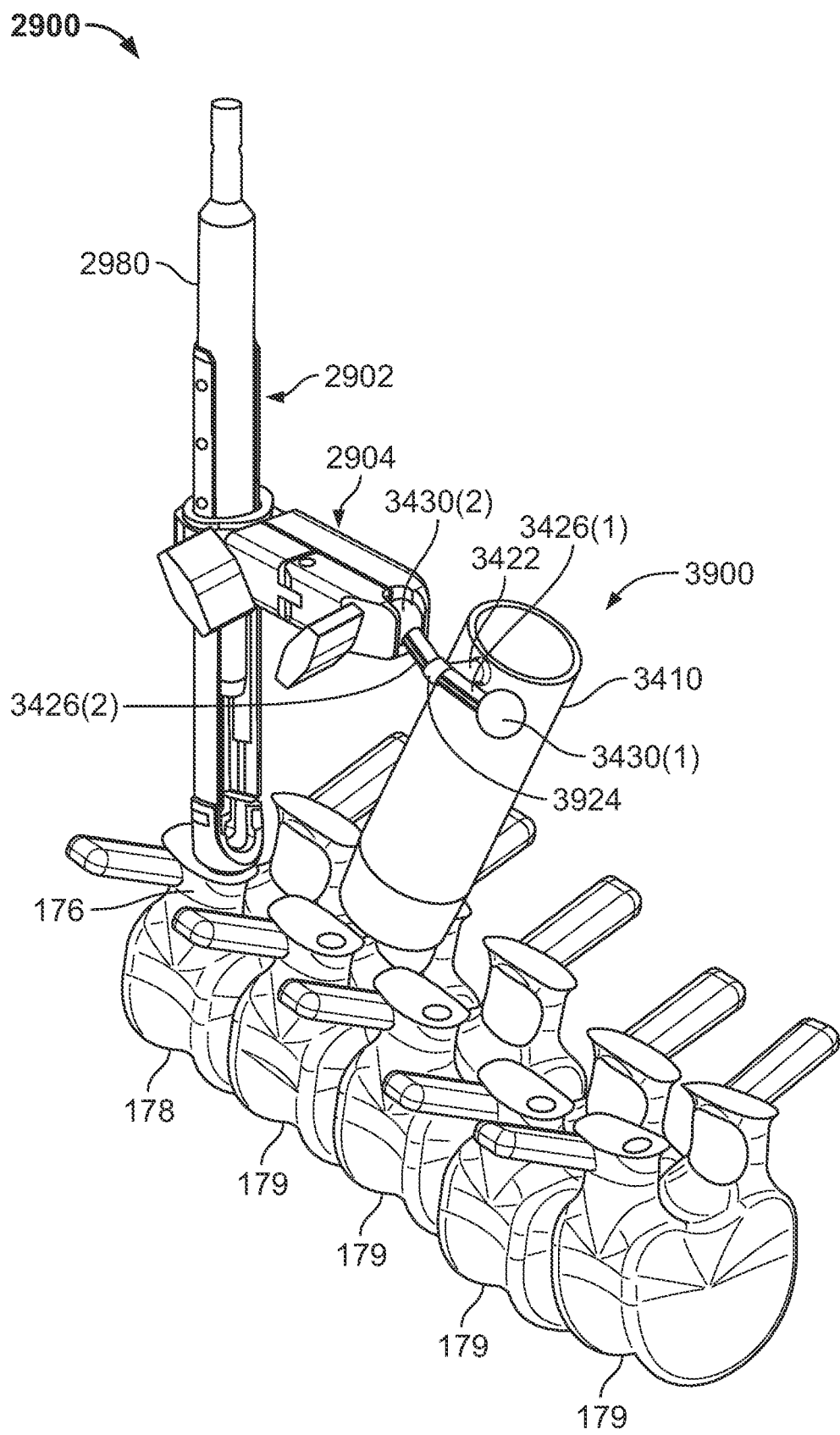

FIGS. 39A and 39B illustrate one exemplary dual-mode tubular retractor 3900 in two exemplary use scenarios, respectively. FIG. 39A shows tubular retractor 3900 coupled with monopedicular targeting system 2900 to target surgery location 270 from a contralateral working direction. FIG. 39B shows tubular retractor 3900 coupled with monopedicular targeting system 2900 to target surgery location 270 from an ipsilateral working direction. FIGS. 39A and 39B are best viewed together.

Tubular retractor 3900 is an extension of tubular retractor 3700, in the same manner that tubular retractor 3600 is an extension of tubular retractor 3400. Tubular retractor 3900 includes a dual-direction connecting arm 3920 and two protrusions 3430 indicated as protrusions 3430(1) and 3430 (2). Connecting arm 3920 includes straight section 3422, a junction 3924, two instances of straight section 3426 indicated as straight sections 3426(1) and 3426(2). Connecting arm 3920 connects tube 3410 to (a) protrusion 3430(1) via straight section 3426(1) and (b) protrusion 3430(2) via straight section 3426(2). Connecting arm 3920 and protrusions 3430(1) and 3430(2) thus cooperate to implement both (a) connecting arm 3420 and protrusion 3430 as configured in tubular retractor 3700 and (b) connecting arm 3420 and protrusion 3430 as configured in tubular retractor 3702. Hence, tubular retractor 3900 is capable of achieving the functionality of both of tubular retractors 3700 and 3702.

Tubular retractor 3900 is an embodiment of spinal surgery devices 150 and 650. Tubular retractor 3900 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Figure 40A:
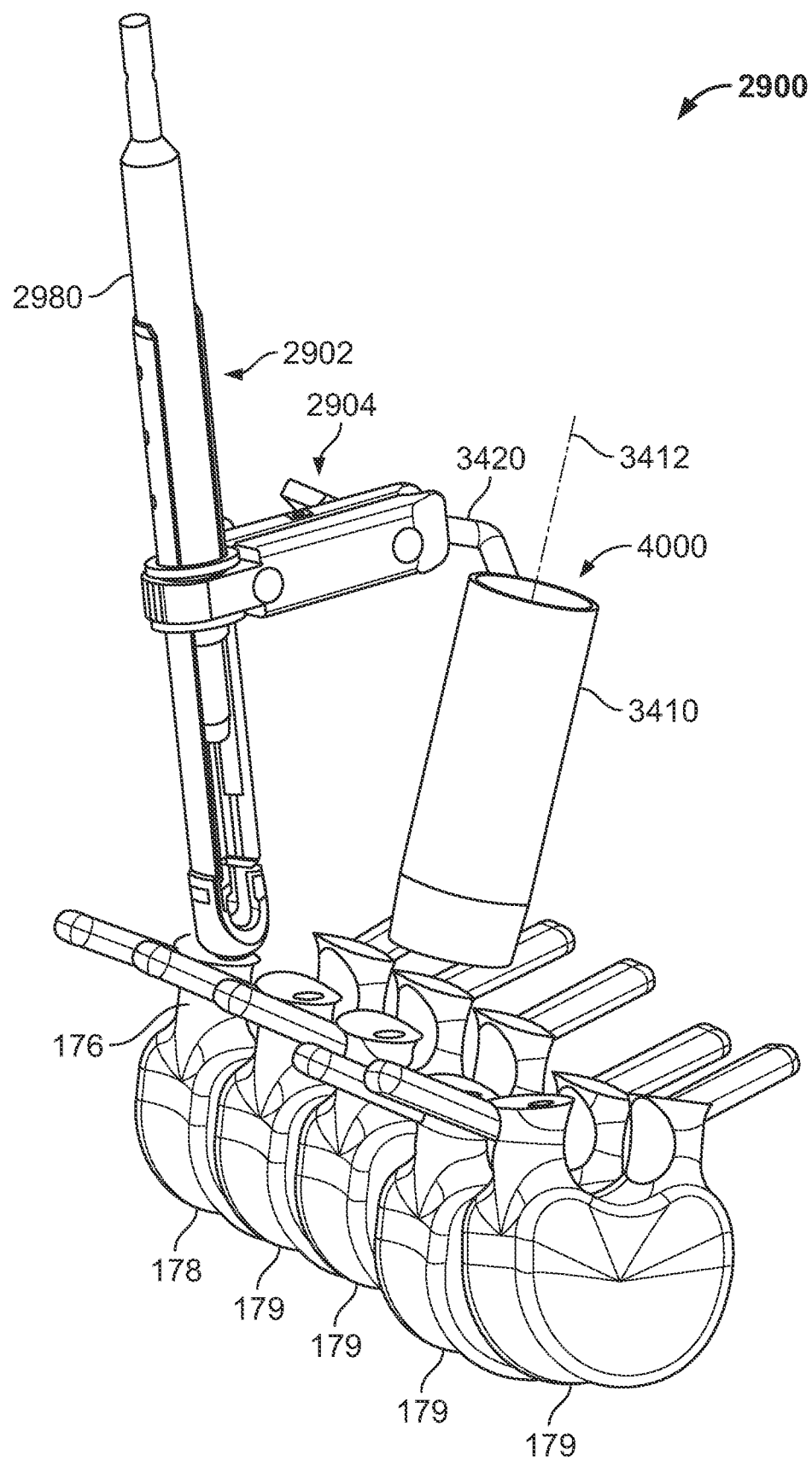
FIGS. 40A and 40B illustrate additional exemplary embodiments of the tubular retractors of FIGS. 34A-C and 35, respectively, in exemplary use scenarios.
Figure 40B:
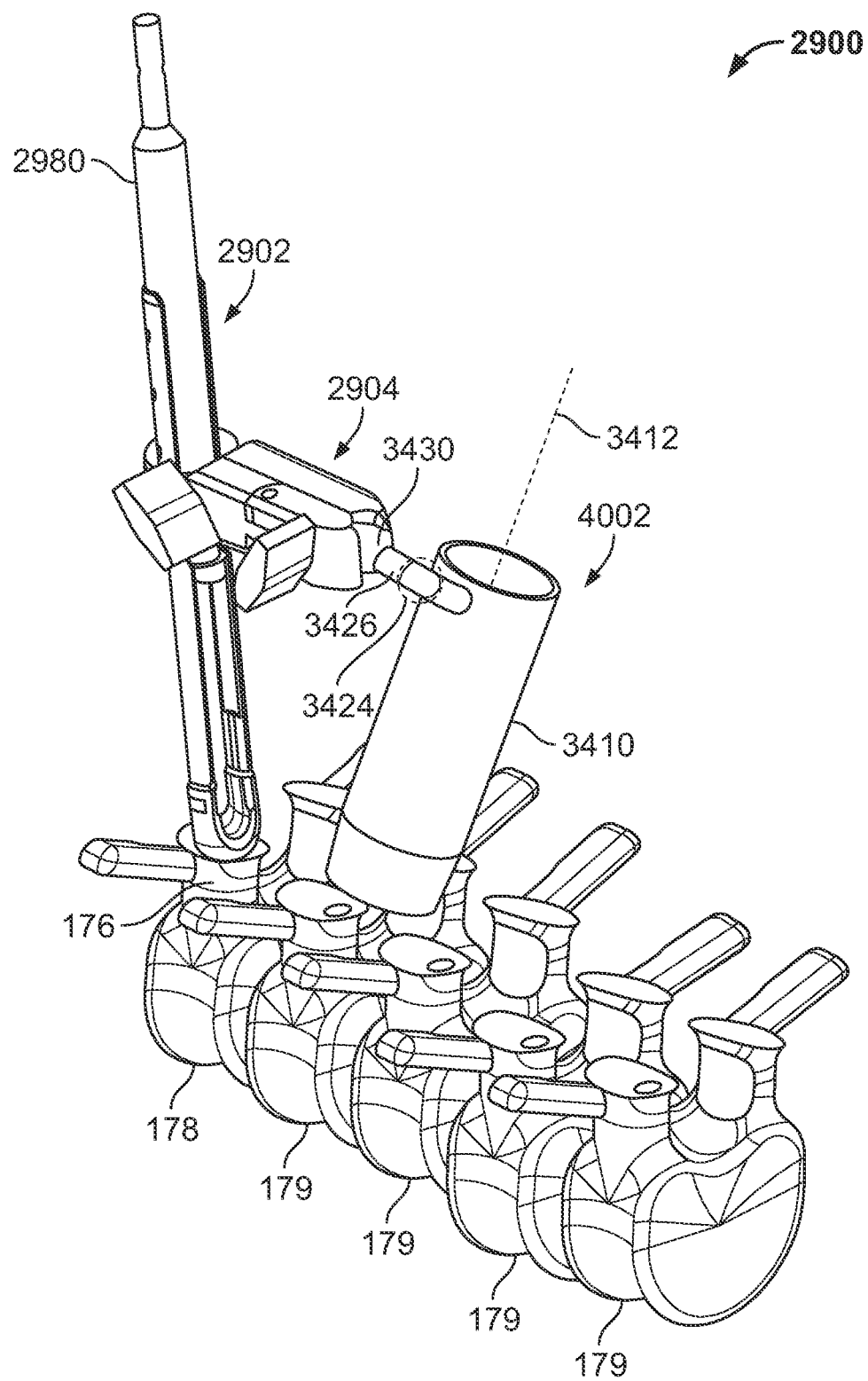

FIGS. 40A and 40B illustrate two exemplary embodiments of tubular retractors 3400 and 3500, respectively, in exemplary use scenarios. FIG. 40A shows one exemplary tubular retractor 4000 coupled with monopedicular targeting system 2900 to target surgery location 270 from a contralateral working direction. FIG. 40B shows one exemplary tubular retractor 4002 coupled with monopedicular targeting system 2900 to target surgery location 270 from an ipsilateral working direction. Tubular retractors 4000 and 4002 are embodiments of tubular retractors 3500 and 3400, respectively. FIGS. 40A and 40B are best viewed together.

As configured in FIGS. 40A and 40B, each of tubular retractors 4000 and 4002 allows for respective positioning of both connector 2904 and the tubular retractor outside an imaging-based anterior-posterior visualization pathway to surgery location 270. In each of tubular retractors 4000 and 4002, straight section 3422 is angled up relative to level orientation. This reduces potential interference between connecting arm 3420 and the tissue of patient 170 and thus improves the positioning flexibility of tubular retractors 4000 and 4002 as compared to a tubular retractor with a level connecting arm. Tubular retractor 4000 is similar to tubular retractor 3700 except that straight section 3422 (proximal tube 3410) is angled up in tubular retractor 4000 while straight section 3426 (proximal protrusion 3430) is angled up in tubular retractor 3700. Likewise, tubular retractor 4002 is similar to tubular retractor 3702 except that straight section 3422 (proximal tube 3410) is angled up in tubular retractor 4002 while straight section 3426 (proximal protrusion 3430) is angled up in tubular retractor 3702.

Tubular retractors 4000 and 4002 are embodiments of spinal surgery devices 150 and 650. Tubular retractors 4000 and 4002 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Figure 41A:
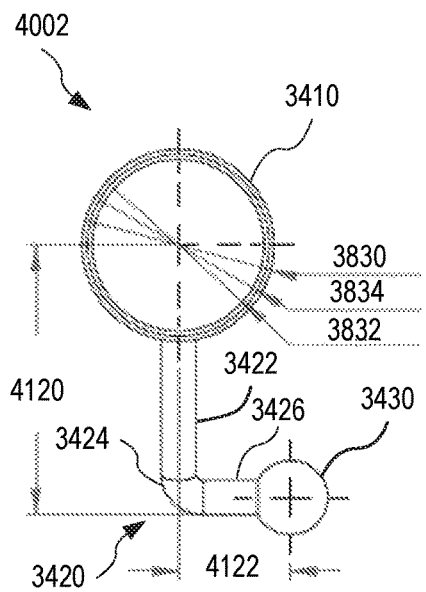
FIGS. 41A-D show the tubular retractor of FIG. 40B in further detail, according to an embodiment.
Figure 41B:
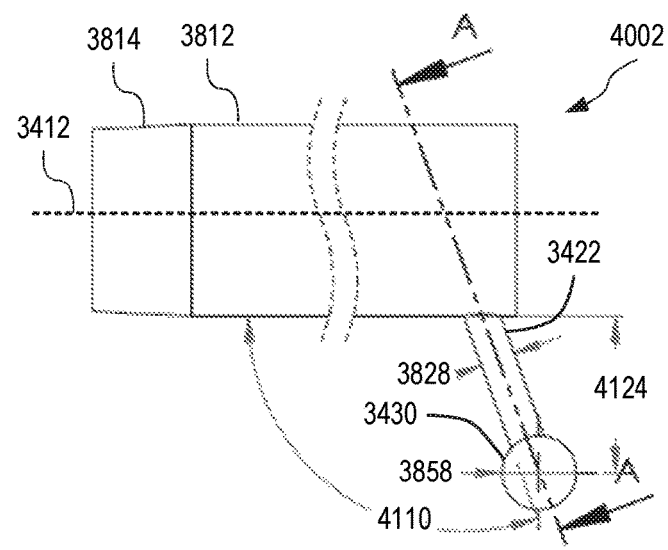
Figure 41C:
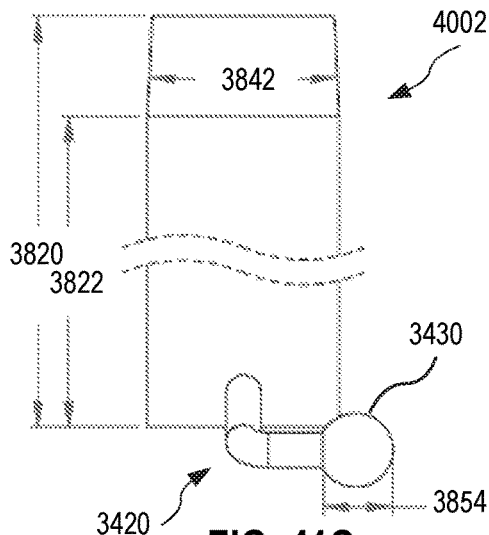
Figure 41D:
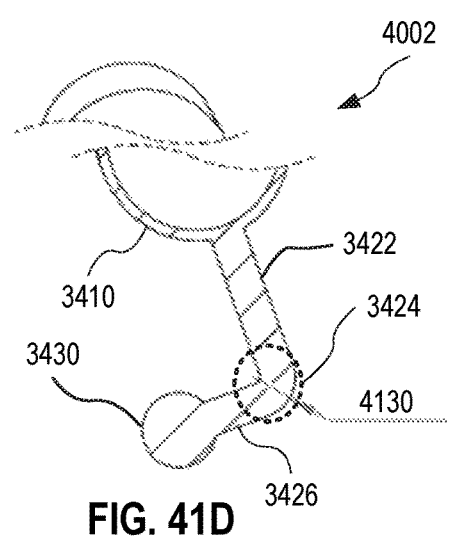

FIGS. 41A-C show tubular retractor 4002 in further detail. Tubular retractor 4002 is similar to tubular retractor 3702 except for connecting arm 3420 being implemented with different dimensions and angles. FIGS. 41A-C show orthogonal side views of tubular retractor 4002. FIG. 41D is a cross-sectional view of connecting arm 3420 and tube 3410 taken along line A-A indicated in FIG. 41B. FIGS. 41A-D are best viewed together.

In tubular retractor 4002, straight section 3422 is at a non-zero angle with respect to level orientation, wherein level orientation refers to directions orthogonal to longitudinal axis 3412. Straight section 3426 is level, that is, orthogonal to longitudinal axis 3412. Straight section 3426 is also orthogonal to straight section 3422. In one embodiment, angle 4110 of straight section 3422 relative to longitudinal axis 3412 is in the range from 110 to 150 degrees, such that the angle of straight section 3422 relative to level orientation is in the range from 20 to 60 degrees, for example between 30 and 50 degrees.

In one example, dimensions 4120, 4122, and 4124 are 1.3582 inches, 0.5657 inches, and 0.7874 inches, respectively. Radius of curvature 4130 of angled section 3424 may be 0.2128 inches.

Figure 42A:
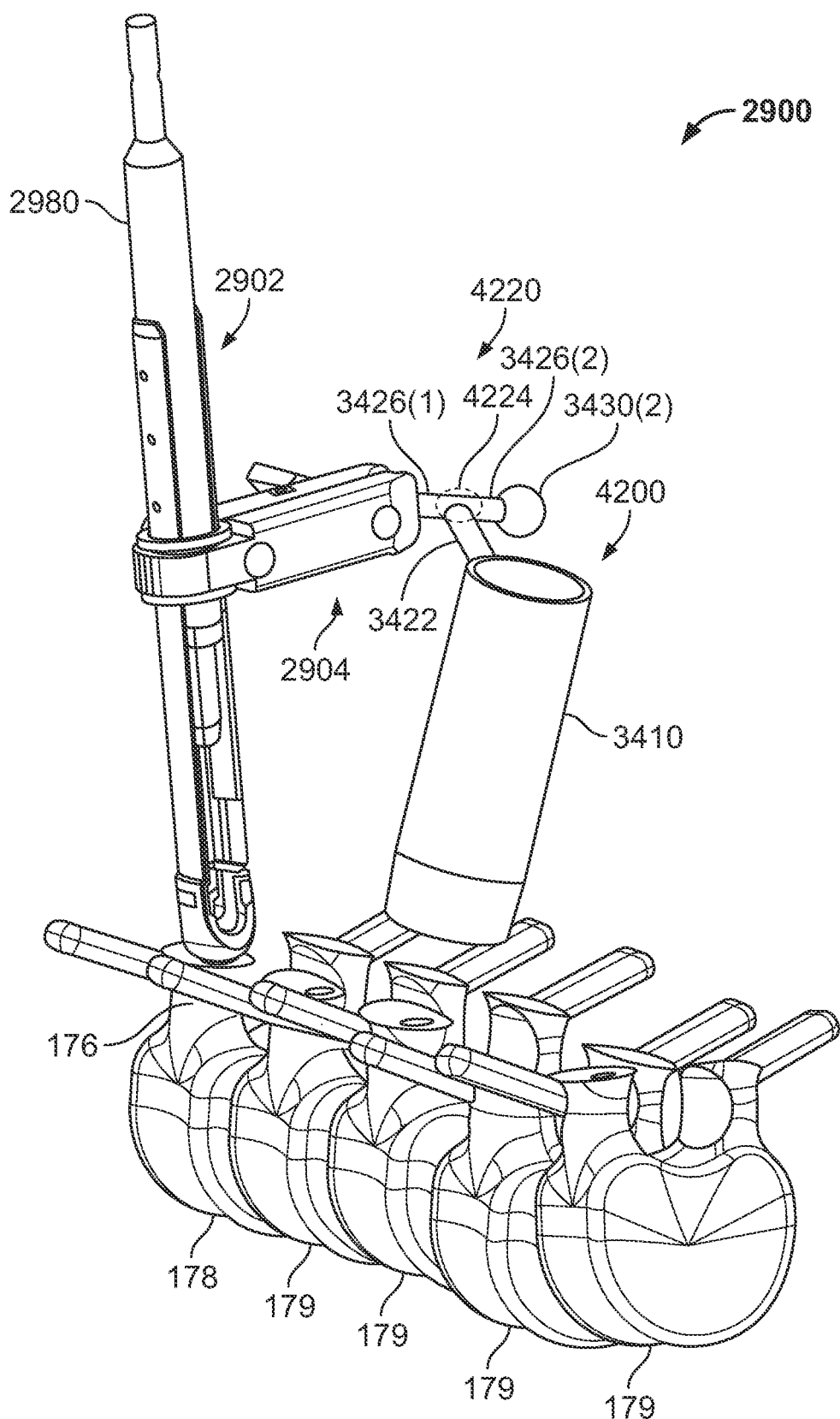
FIGS. 42A and 42B illustrate yet another dual-mode tubular retractor having two joint components, each configured to couple with a monopedicular targeting system, according to an embodiment.
Figure 42B:
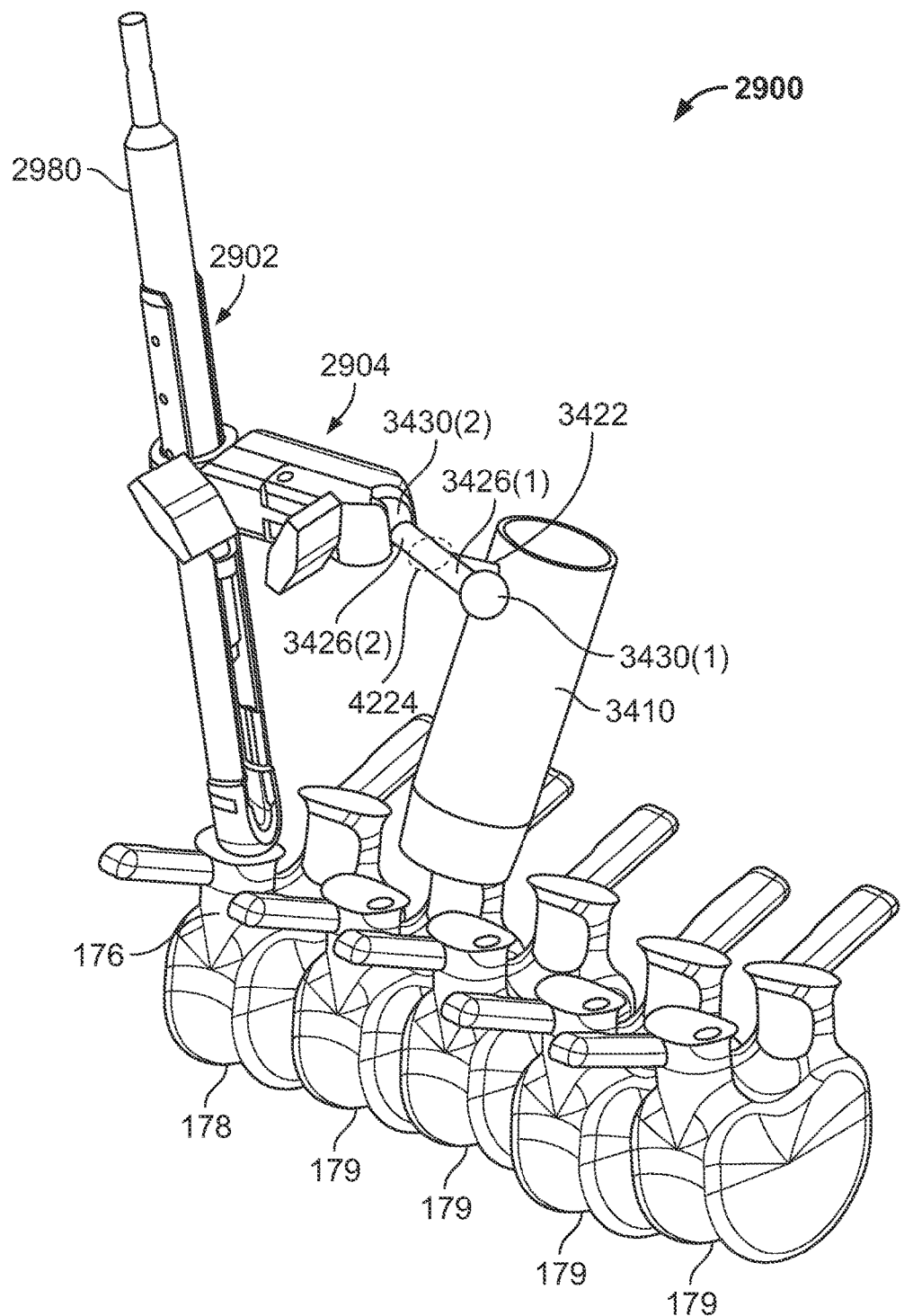

FIGS. 42A and 42B illustrate one exemplary dual-mode tubular retractor 4200 in two exemplary use scenarios, respectively. FIG. 42A shows tubular retractor 4200 coupled with monopedicular targeting system 2900 to target surgery location 270 from a contralateral working direction. FIG. 42B shows tubular retractor 4200 coupled with monopedicular targeting system 2900 to target surgery location 270 from an ipsilateral working direction. FIGS. 42A and 42B are best viewed together.

Tubular retractor 4200 is an extension of tubular retractor 4000, in the same manner that tubular retractor 3600 is an extension of tubular retractor 3400. Tubular retractor 4200 includes a dual-direction connecting arm 4220 and two protrusions 3430 indicated as protrusions 3430(1) and 3430(2). Connecting arm 4220 includes straight section 3422, a junction 3924, two instances of straight section 3426 indicated as straight sections 3426(1) and 3426(2). Connecting arm 4220 connects tube 3410 to (a) protrusion 3430(1) via straight section 3426(1) and (b) protrusion 3430(2) via straight section 3426(2). Connecting arm 4220 and protrusions 3430(1) and 3430(2) thus cooperate to implement both (a) connecting arm 3420 and protrusion 3430 as configured in tubular retractor 4000 and (b) connecting arm 3420 and protrusion 3430 as configured in tubular retractor 4002. Hence, tubular retractor 4200 is capable of achieving the functionality of both of tubular retractors 4000 and 4002.

Tubular retractor 4200 is an embodiment of spinal surgery devices 150 and 650. Tubular retractor 4200 may replace (a) spinal surgery device 960 in FIGS. 9 and 10, (b) spinal surgery device 1490 and coupler 1409 in FIGS. 14A and 14B, and (c) spinal surgery device 1490 and coupler 1409 in FIGS. 29A-C.

Figure 43A:
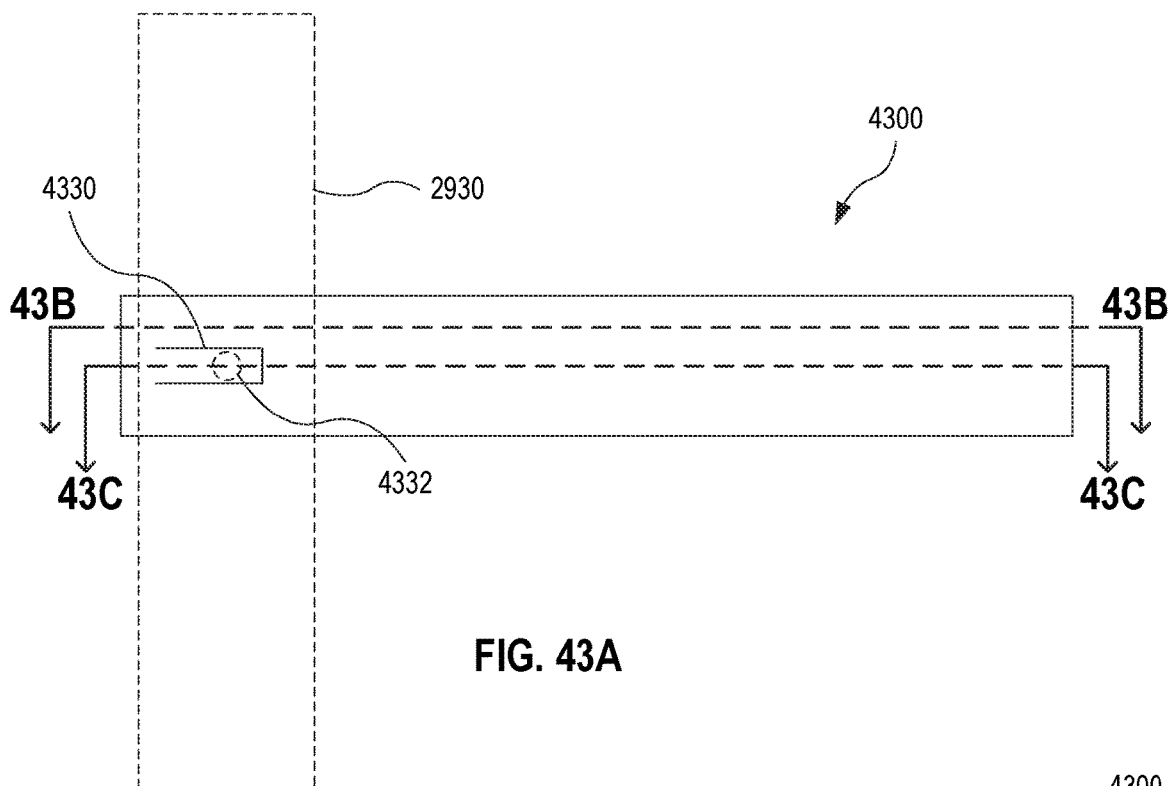
FIGS. 43A-C illustrate a connector for connecting a spinal surgery device to break-off blades of a percutaneous pedicle screw, according to an embodiment.
Figure 43B:
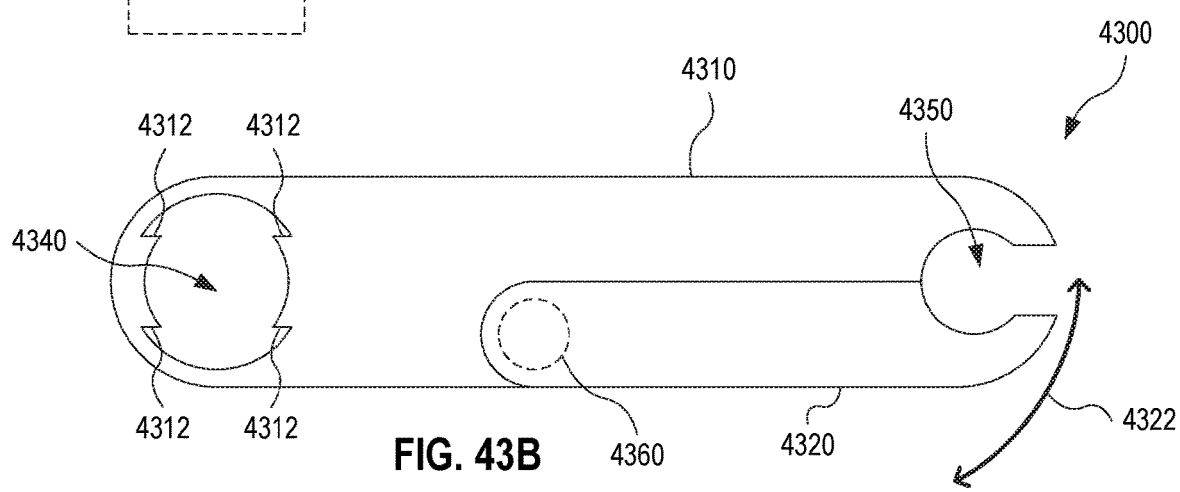
Figure 43C:
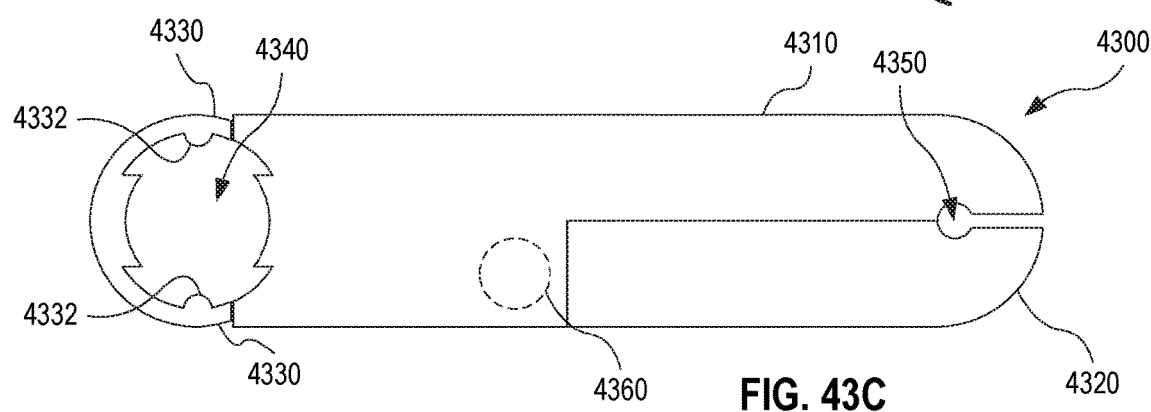

FIGS. 43A-C illustrate one exemplary connector 4300 for connecting spinal surgery device 150 to break-off blades 2930 of percutaneous pedicle screw 2902. Connector 4300 is an embodiment of connector 660 and may replace connector 2904 and clip 2936 of monopedicular targeting system 2900. Connector 4300 includes features for stabilizing break-off blades 2930 to prevent inadvertent detachment of break-off blades 2930 from socket 2920. Connector 4300 also includes features that allow for stable coupling of connector 4300 to indentations 2932 of break-off blades 2930. Thus, connector 4300 combines the functionality of connector 2904 and clip 2936 of monopedicular targeting system 2900. FIG. 43A shows connector 4300 in side view, wherein the viewing angle is orthogonal to the longitudinal axis of break-off blades 2930. FIGS. 43B and 43C are cross-sectional views of connector 4300 along respective lines 43B-43B and 43C-43C of FIG. 43A. FIGS. 43A-C are best viewed together.

Connector 4300 includes clamp parts 4310 and 4320. Clamp part 4320 is coupled to clamp part 4310 via a hinge 4360, such that clamp part 4320 may rotate along direction 4322. Clamp parts 4310 and 4320 cooperate to form a receptacle 4350 for a protrusion (e.g., protrusion 1496) of spinal surgery device 150. The joint formed between the protrusion of the spinal surgery device and connector 4300 is a spherical joint similar to that formed between joint components 622 and 652 of monopedicular targeting system 602. Hinge 4360 allows for opening of connector 4300 to insert the protrusion of the spinal surgery device into receptacle 4350. Connector 4300 also includes a receptacle 4340 that fits over break-off blades 2930. Connector 4300 may slide along break-off blades 2930 to a desired position. The joint formed between connector 2900 and break-off blades 2930 is an embodiment of joint 630. In an alternate embodiment, receptacle 4340 is configured to couple connector 4300 to another percutaneous pedicle screw wherein break-off blades 2930 are replaced by another implementation of removable guiding section 240.

Receptacle 4340 includes two pairs of lips 4312. Each pair of lips 4312 is configured to couple to the edges of a corresponding break-off blade 2930. Lips 4312 thus stabilize the relative positions of break-off blades 2930 and help prevent inadvertent detachment of break-off blades 2930 from socket 2920.

Clamp part 4310 includes two levers 4330. Each lever 4330 has a protrusion 4332. Levers 4330 provides spring loading of protrusions 4332 against break-off blades 2930 such that connector 4300 may be stably coupled to indentations 2932 of break-off blades 2930. Embodiments of percutaneous pedicle screw 2902 configured to couple with connector 4300 may be advantageously configured with a larger number of indentations 2932 than for example found in the percutaneous pedicle screw of the ES2® Spinal System by Stryker. A larger number of indentations 2932 may allow for finer adjustment of the distance along break-off blades 2930 from socket 2920 to connector 4300 and/or allow for a greater range of such distances. In one example, percutaneous pedicle screw 2902 has at least 6, 10, or 15 indentations 2932.

Without departing from the scope hereof, the size and shape of each of clamp parts 4310 and 4320, hinge 4360, receptacles 4340 and 4350, lips 4312, levers 4330, and protrusions 4332 may differ from what is shown in FIGS. 43A-C. In addition, without departing from the scope hereof, connector 4300 may be adapted for attachment to a different number of break-off blades and/or break-off blades of a different shape, in which case lips 4312, levers 4330, and/or protrusions 4332 may be modified accordingly or replaced with other appropriate functionality for attachment to the break-off blades.

Figure 44:
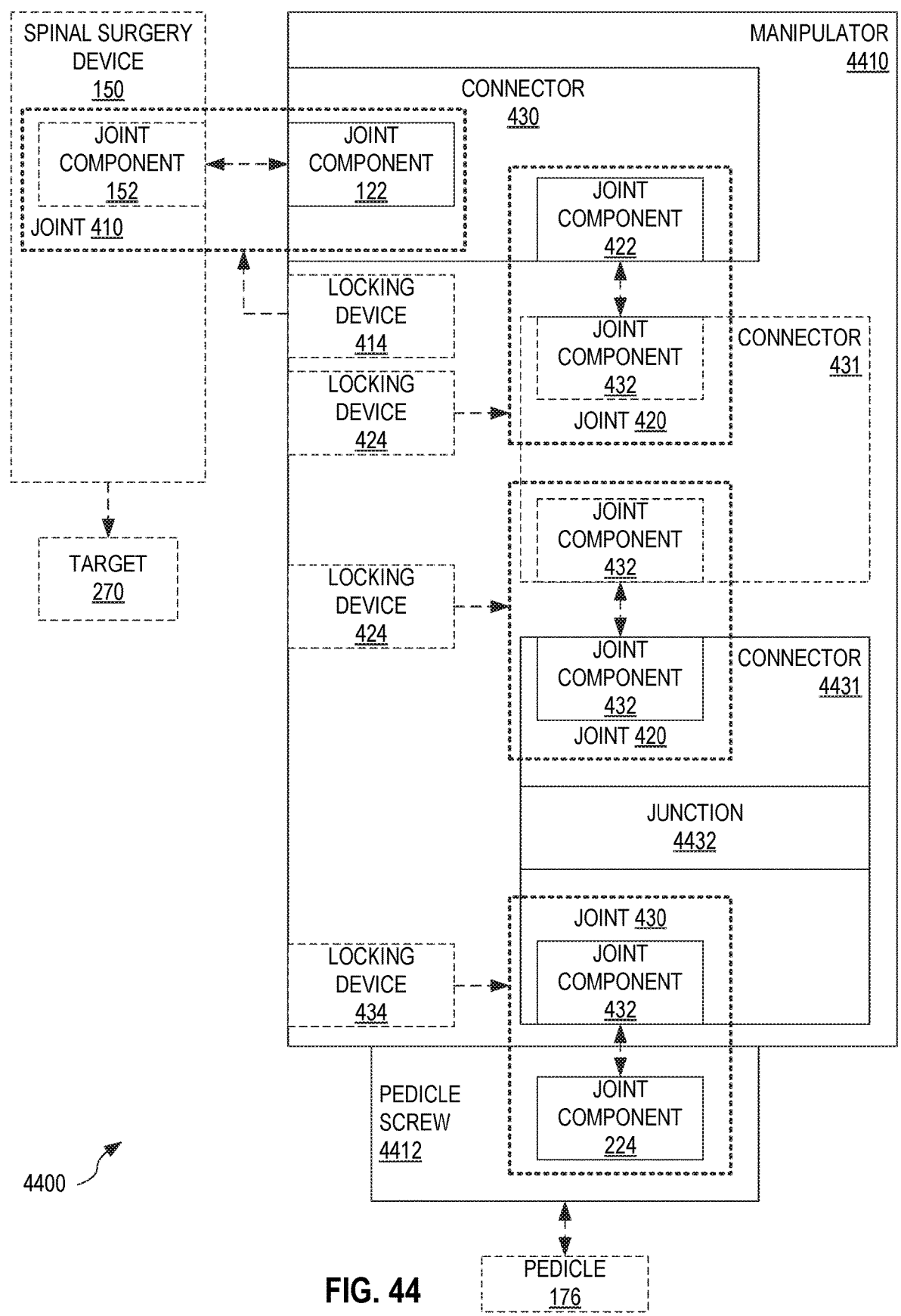
FIG. 44 illustrates a monopedicular targeting system, for posterior spinal surgery, including a manipulator and a pedicle screw, wherein the majority of the manipulator is detachable from the pedicle screw, according to an embodiment.

FIG. 44 illustrates one exemplary monopedicular targeting system 4400, for posterior spinal surgery, including a manipulator 4410 and a pedicle screw 4412, wherein the majority of manipulator 4410 is detachable from pedicle screw 4412. Pedicle screw 4412 may be left in pedicle 176 and used, for example, for stabilization of a spinal segment as part of transforaminal lumbar interbody fusion. Monopedicular targeting system 4400 is an embodiment of monopedicular targeting system 400, wherein fastener 110 is implemented as pedicle screw 4412. Monopedicular targeting system 4400 is also an embodiment of monopedicular targeting system 490.

In monopedicular targeting system 4400, connector 431 (adjacent fastener 110 in monopedicular targeting system 400) is implemented as connector 4431. Connector 4431 includes a junction 4432 between the two joint components 432 of connector 4431. Junction 4432 allows for separation of all of manipulator 4410, except joint component 432, from pedicle screw 4412. Furthermore, manipulator 4410 may be supplied to a user with junction 4432 disconnected. An example of junction 4432 is shown in FIG. 10 where positioning arm 920 is detachable from socket 1023. Monopedicular targeting system 900 may form an embodiment of monopedicular targeting system 4400. Another example of junction 4432 is a breakable connection between a socket and break-off tabs of a percutaneous pedicle screw.

Without departing from the scope hereof, manipulator 4410 may not include joint component 432 and pedicle screw 4412. In such cases, joint component 432 may instead be integrated in a third-party pedicle screw 4412 separate from monopedicular targeting system 4400.

Junction 4432 may be implemented in monopedicular targeting system 2700, without departing from the scope hereof.

Figure 45:
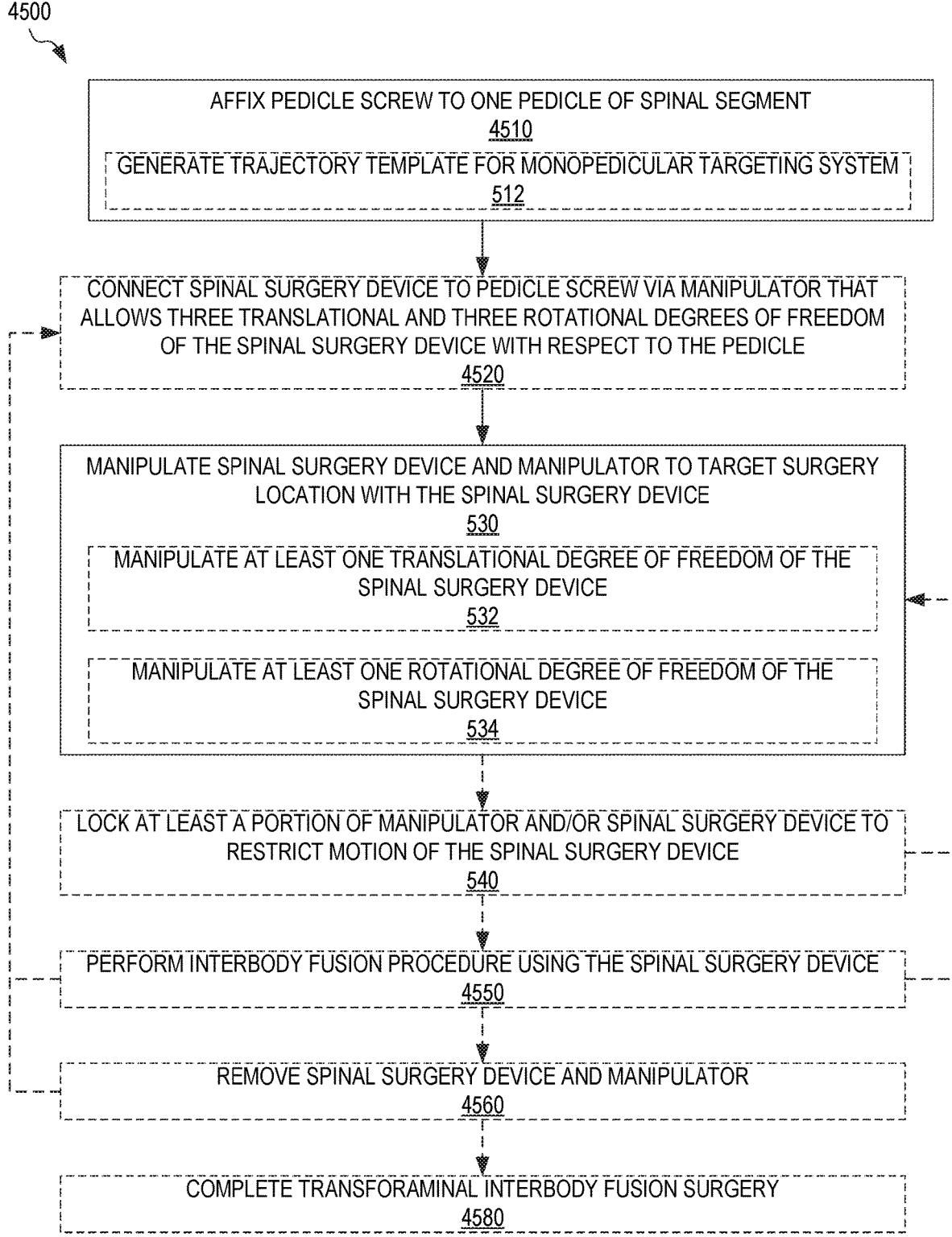
FIG. 45 illustrates a monopedicular targeting method for posterior spinal surgery, which utilizes a pedicle screw to affix a monopedicular targeting system to a pedicle, according to an embodiment.

FIG. 45 illustrates one exemplary monopedicular targeting method 4500 for posterior spinal surgery. Monopedicular targeting method 4500 is an embodiment of monopedicular targeting method 500, which uses a pedicle screw for attachment of a monopedicular targeting system to pedicle 176. In one example, monopedicular targeting method 4500 uses monopedicular targeting system 4500.

In a step 4510, a pedicle screw is affixed to pedicle 176 as discussed for a general fastener in reference to FIG. 5. Step 4510 is an embodiment of step 510 and may include step 512. In one example of step 4510, pedicle screw 4412 is affixed to pedicle 176.

In an optional step 4520, a spinal surgery device is connected to the pedicle screw of step 4510 via a manipulator that allows three translational degrees of freedom and three rotational degrees of freedom for the spinal surgery device with respect to pedicle 176. In one example of step 4520, spinal surgery device 150 is connected to pedicle screw 4412 via manipulator 4410. Step 4520 is an embodiment of step 520.

Subsequent to step 4510, and step 4520 if included, method 4500 performs step 530 as discussed in reference to FIG. 5A. In one example, step 4510 manipulates spinal surgery device 150 and manipulator 4410 to target surgery location 270. Method 4500 may include step 540 as discussed in reference to FIG. 5A.

In an optional step 4550 subsequent to step 530, and step 540 if included, surgeon 180 performs an interbody fusion procedure on spine 172 using the spinal surgery device affixed to pedicle 176 via the manipulator. At any time during either of steps 540 and 4550, method 4500 may revert to step 530 for readjustment of the positioning of spinal surgery device 150. Additionally, at any time during step 4550, method 4500 may revert to step 4520 to connect a different spinal surgery device to the manipulator. Step 4550 is an embodiment of step 550.

In an optional step 4560, the spinal surgery device and at least the majority of the manipulator are removed from the pedicle screw. In one example of step 45560, junction 4432 is separated. Step 4560 is an embodiment of step 560.

In an optional step 4580, surgeon 180 completes a transforaminal lumbar interbody fusion surgery. In one example of step 4580, additional pedicle screws are connected to spine 172. The pedicle screws may be interconnected with rods, as known in the art.

Without departing from the scope hereof, each of methods 501 and 502 may be modified in a similar manner to utilize a pedicle screw.

Without departing from the scope hereof, method 4500 may utilize a spine-anchored targeting system anchored to a different structure of spine 172 than pedicle 176, or to a pelvis of patient 170, to perform posterior spinal surgery of the cervical, thoracic, and/or lumbar spine of patient 170. Such spine-anchored targeting system are discussed further in reference to FIGS. 56-59 below.

Figure 46:
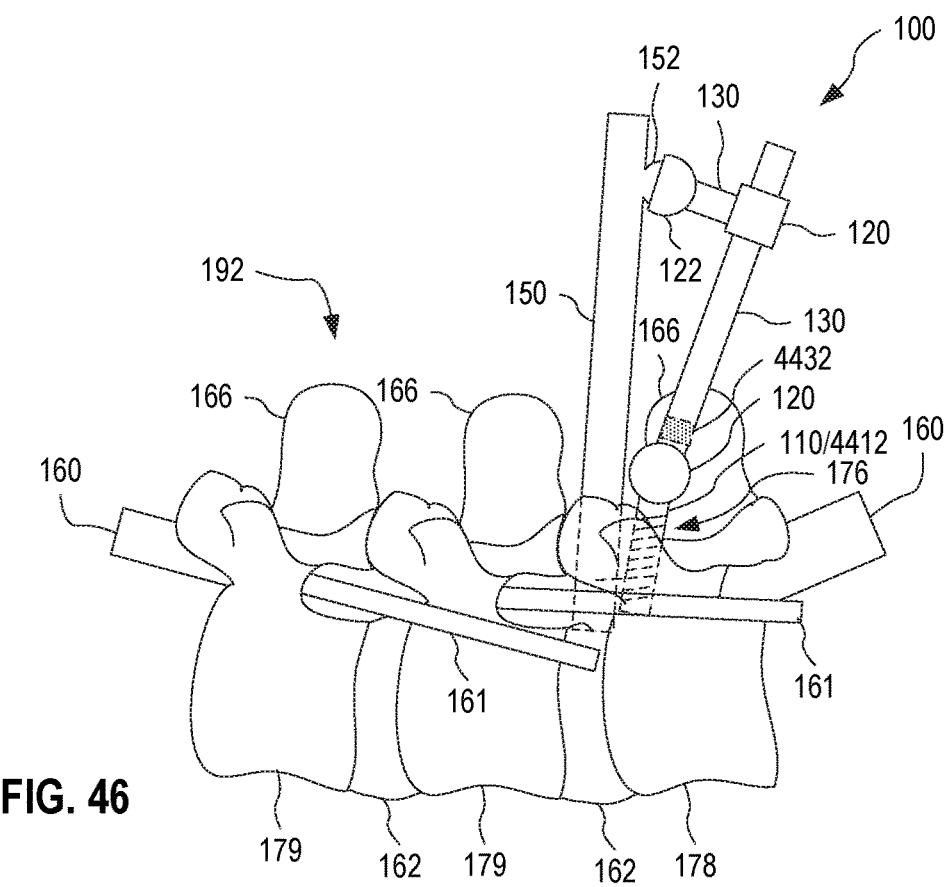
FIG. 46 illustrates one exemplary configuration of a monopedicular targeting system when performing an ipsilateral posterior spinal surgery procedure.

FIG. 46 illustrates one exemplary configuration of a monopedicular targeting system 100 when performing an ipsilateral posterior spinal surgery procedure. The configuration shown in FIG. 46 is applicable to embodiments of step 550 of methods 500, 501, and 502, and to embodiments of step 4550 of method 4500. In this configuration, monopedicular targeting system 100 is manipulated such that spinal surgery device 150 targets a surgery location 270 from the same side of spine 172 as pedicle 176, to which monopedicular targeting system 100 is affixed. In one scenario, monopedicular targeting system 100 is implemented with pedicle screw 4412 and junction 4432, such that pedicle screw 4412 may be left in pedicle 176. In another scenario, monopedicular targeting system 100 is implemented with percutaneous pedicle screw 212, such that pedicle screw 220 may be left in pedicle 176 after removing removable guiding section 240.

The configuration shown in FIG. 46 targets a surgery location 270 at intervertebral disc 162 adjacent pedicle 176. Without departing from the scope hereof, the configuration shown in FIG. 46 may target a surgery location 270 at another intervertebral disc 162 further from pedicle 176. In certain embodiments, monopedicular targeting system 100 is anchored to pedicle 176 inferior to surgery location 270 when performing an ipsilateral posterior spinal surgery procedure.

When performing method 500, 501, 502, or 503 using the configuration shown in FIG. 46, fastener 110 may be inserted into pedicle 176 through an incision used to access surgery location 270.

Figure 47:
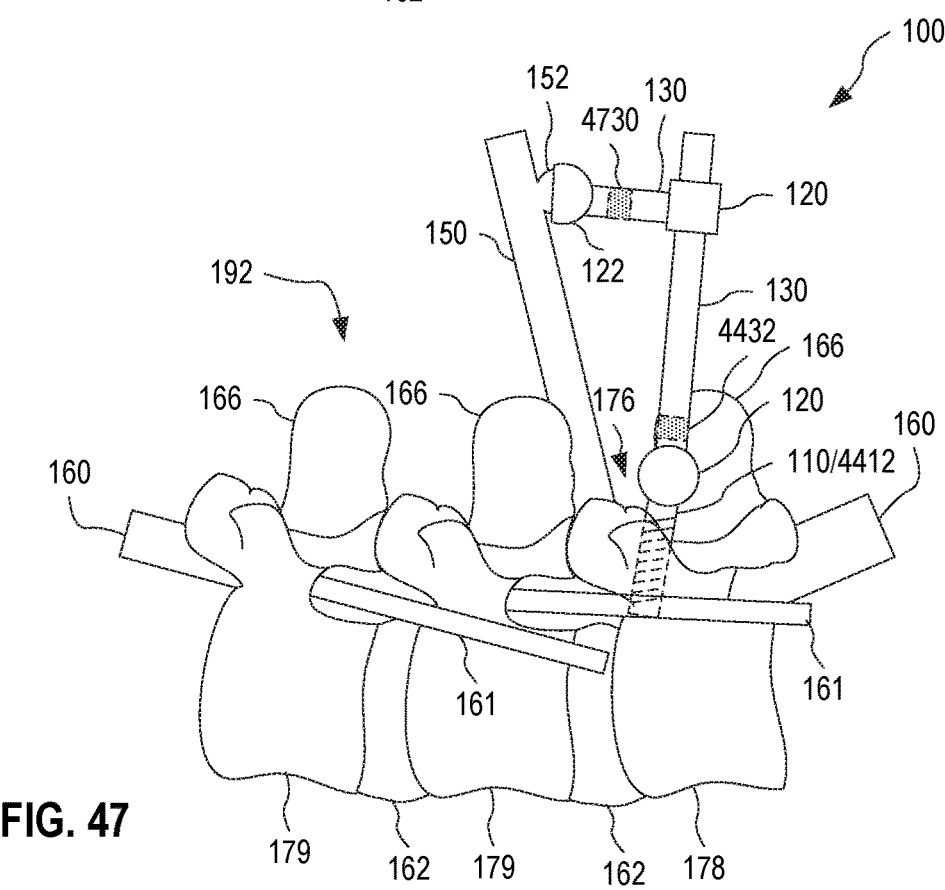
FIG. 47 illustrates one exemplary configuration of a monopedicular targeting system when performing a contralateral posterior spinal surgery procedure.

FIG. 47 illustrates one exemplary configuration of a monopedicular targeting system 100 when performing a contralateral posterior spinal surgery procedure. The configuration shown in FIG. 47 is applicable to embodiments of step 550 of methods 500, 501, and 502, and to embodiments of step 4550 of method 4500. In this configuration, monopedicular targeting system 100 is manipulated such that spinal surgery device 150 targets a surgery location 270 from the opposite side of spine 172 as pedicle 176, to which monopedicular targeting system 100 is affixed. In one scenario, monopedicular targeting system 100 is implemented with pedicle screw 4412 and junction 4432, such that pedicle screw 4412 may be left in pedicle 176. In another scenario, monopedicular targeting system 100 is implemented with percutaneous pedicle screw 212, such that pedicle screw 220 may be left in pedicle 176 after removing removable guiding section 240. Additionally, monopedicular targeting system 100 may implement a telescoping joint 4730. Telescoping joint 4730 is an embodiment of telescoping joint 2420. Telescoping joint 4730 may aid surgeon 180 reach the contralateral side of spine 172. Furthermore, connector 130 associated with the scenario shown in FIG. 47 may be longer than connector 130 associated with the scenario shown in FIG. 47 to extend the reach of monopedicular targeting system 100.

The configuration of FIG. 47 may allow surgeon 180 more working room to manipulate monopedicular targeting system 100 and spinal surgery device 150, as compared to the configuration shown in FIG. 46, since elements of monopedicular targeting system 100 near pedicle 176 are less likely to limit the maneuverability of spinal surgery device 150. At the same time, surgeon 180 may benefit from reuse of the hole formed in pedicle 176, and optionally pedicle screw 3812, thus minimizing adverse impact on patient 170.

The configuration shown in FIG. 47 targets a surgery location 270 at intervertebral disc 162 adjacent pedicle 176. Without departing from the scope hereof, the configuration shown in FIG. 47 may target a surgery location 270 another intervertebral disc 162 further from pedicle 176.

Figure 48A:
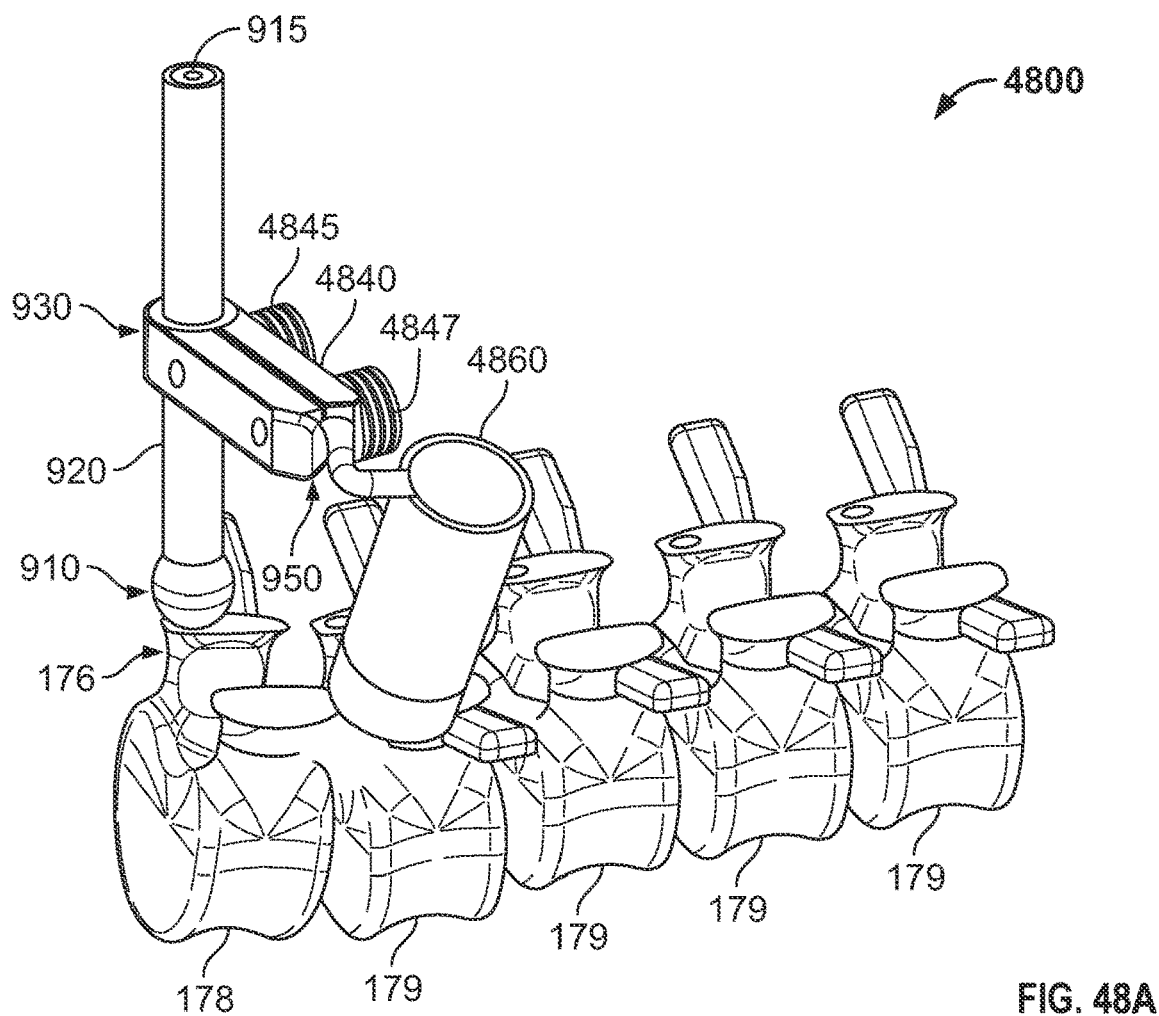
FIGS. 48A and 48B illustrate a monopedicular targeting system adapted for contralateral posterior spinal surgery, according to an embodiment.
Figure 48B:
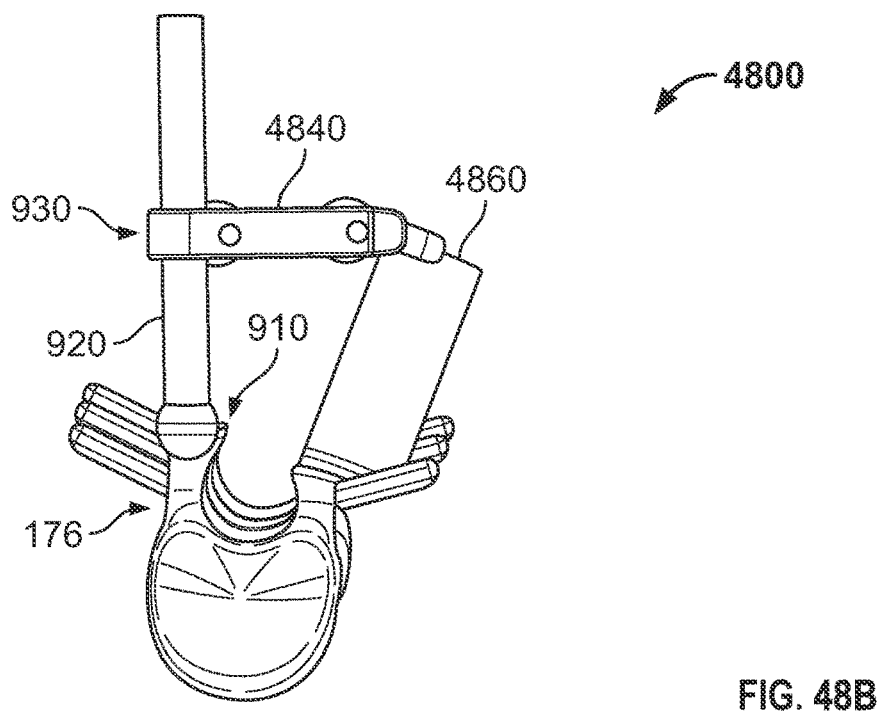

FIGS. 48A and 48B illustrate one exemplary monopedicular targeting system 4800 adapted for contralateral posterior spinal surgery. Monopedicular targeting system 4800 is an embodiment of monopedicular targeting system 100. FIGS. 48A and 48B show two different perspective views of monopedicular targeting system 4800 as configured for contralateral posterior spinal surgery on spine 172. FIGS. 48A and 48B are best viewed together.

Monopedicular targeting system 4800 is similar to monopedicular targeting system 900 except for clamp 940 being replaced by a connector 4840. Connector 4840 has longer reach than clamp 940 so as to more easily reach the contralateral side of spine 172 with a spinal surgery device 4860. Additionally, connector 4840 includes two locking devices 4845 and 4847 that may be engaged to lock joints 930 and 950, respectively. Locking devices 4845 and 4847 may be implemented according to a variety of configurations, such as those discussed above in reference to locking fasteners 1405.

Although FIGS. 48A and 48B show spinal surgery device 4860 as a tubular retractor, spinal surgery device 4860 may be another spinal surgery device without departing from the scope hereof. The tubular retractor shown in FIGS. 48A and 48B is similar to that shown in FIG. 9, except for having an angled arm configured to connect with connector 4840. The angled arm provides improved angular range of the joint between connector 4840 and spinal surgery device 960, as well as allows for placing connector 4840 away from an optical pathway use to image surgery location 270. Without departing from the scope hereof, monopedicular targeting system 4800 may be used with the tubular retractor shown in FIG. 9 or another retractor. Likewise, monopedicular targeting system 4800 may be used with a coupler such as coupler 1490 and a spinal surgery device attached thereto. Without departing from the scope hereof, tubular retractor 4260 may be replaced by either one of tubular retractors 3400, 3500, 3600, 3700, 3702, 3900, 4000, 4002, and 4200.

As discussed in further detail below in reference to FIGS. 56-59, monopedicular targeting system 4800 is readily extended to spine-anchored targeting systems that each have the same functionality as monopedicular targeting system 4800 but may be anchored to a different structure of spine 172 or to a pelvis of patient 170. Such spine-anchored targeting systems may be used in posterior spinal surgery of the cervical, thoracic, and/or lumbar spine of patient 170.

Figure 49A:
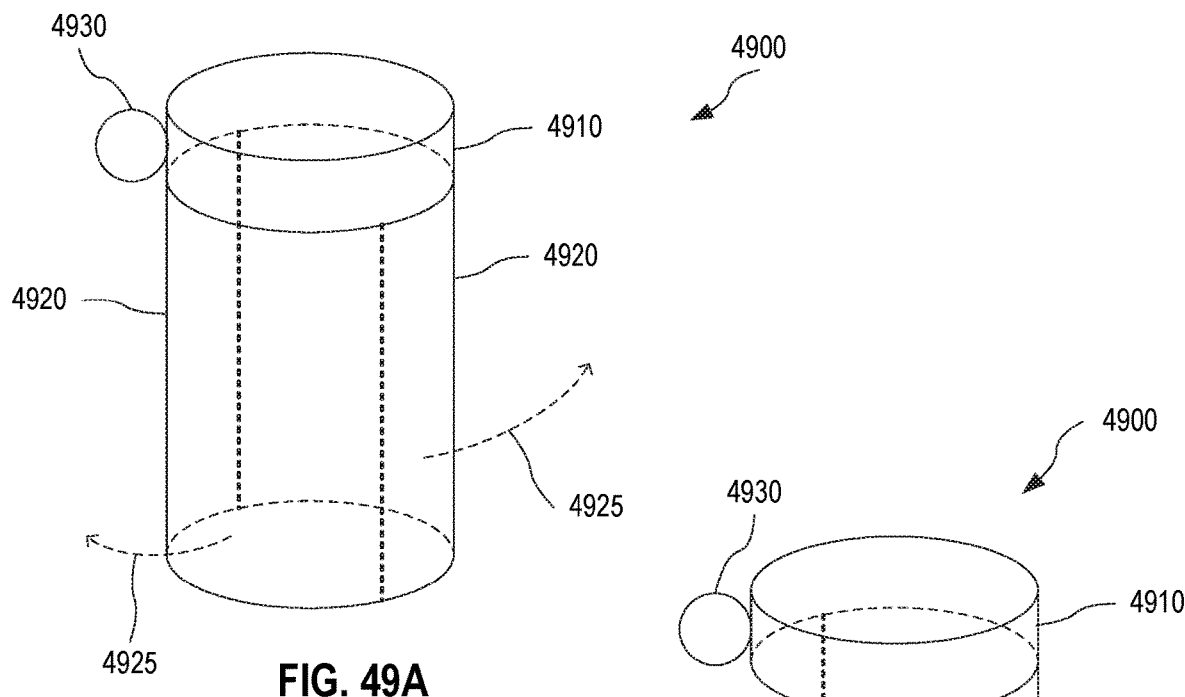
FIGS. 49A-C illustrate two-piece tubular retractors, according to embodiments.

FIG. 49A illustrates one exemplary two-piece tubular retractor 4900. Tubular retractor 4900 is an embodiment of spinal surgery device 150 and is similar to tubular retractor 1360. Tubular retractor 4900 has dimensions similar to those of spinal surgery device 1360 (implemented as a tubular retractor) or similar to tubular retractor 2300.

Tubular retractor 4900 includes two semi-cylindrical blades 4920, a ring 4910 that holds semi-cylindrical blades 4920, and a spherical joint component 4930 attached to ring 4910. Spherical joint component 4930 is an embodiment of protrusion 962. Although depicted in FIGS. 49A-C as a ball, spherical joint component 4930 may have a different shape. For example, spherical joint component 4930 may be shaped as a portion of a ball. Furthermore, spherical joint component 4930 may be connected to ring 4910 via an angled arm, such as connecting arm 1494, connecting arm 3420, or a portion of either one of connecting arms 3620, 3920, and 4220. In addition, spherical joint component 4930 may be connected to ring 4910 via an angled arm and a ring, such as connecting arm 1494 and ring 1492.

Without departing from the scope hereof, the cross section of tubular retractor 4900 may be non-circular such that semi-cylindrical blades 4920 are not necessarily semi-cylindrical. For example, each semi-cylindrical blade 4920 may have a V-shaped cross section such that semi-cylindrical blades 4920, when brought together, form an elongated hollow shape with rectangular cross section rather than circular cross section. In another example, semi-cylindrical blades 4920, when brought together, form an elongated hollow shape with elliptical cross section. Regardless of the cross sectional shape of tubular retractor 4900, ring 4910 may be adapted to fit around tubular retractor 4900, without departing from the scope hereof. Furthermore, ring 4910 may be replaced by another component that need not be configured to wrap around tubular retractor 4900 but may attach to tubular retractor 4900 through other means. For example, ring 4910 may be replaced by a component that is screwed onto tubular retractor 4900, or press fit into an appropriate receptacle of tubular retractor 4900.

Figure 49B:
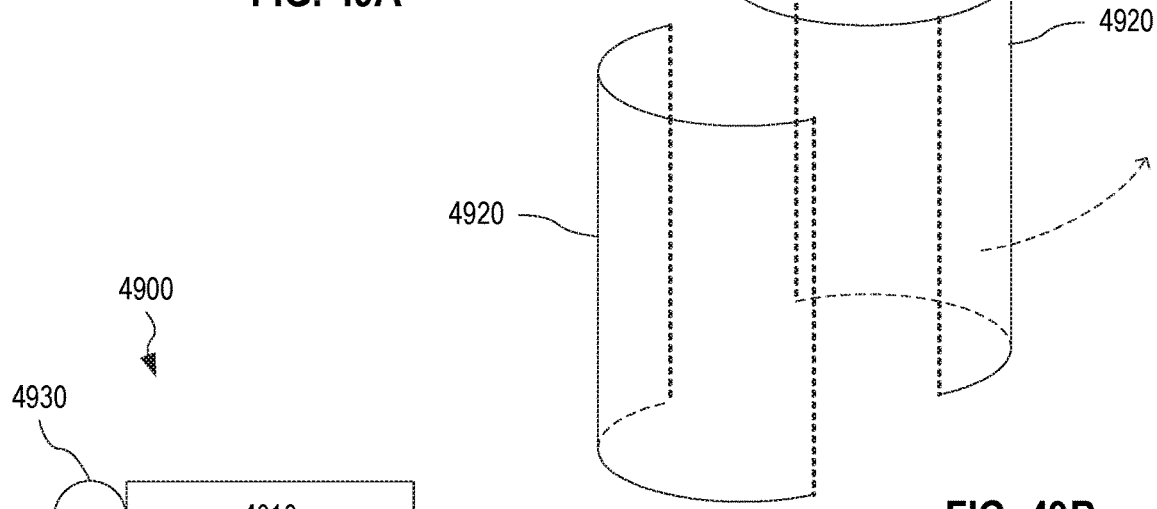

FIG. 49B illustrates one exemplary implementation of tubular retractor 4900, wherein one of semi-cylindrical blades 4920 is detachable from ring 4910. This implementation may be used to provide more open access to a spinal surgery location after retraction of tissue using both of semi-cylindrical blades 4920.

Figure 49C:
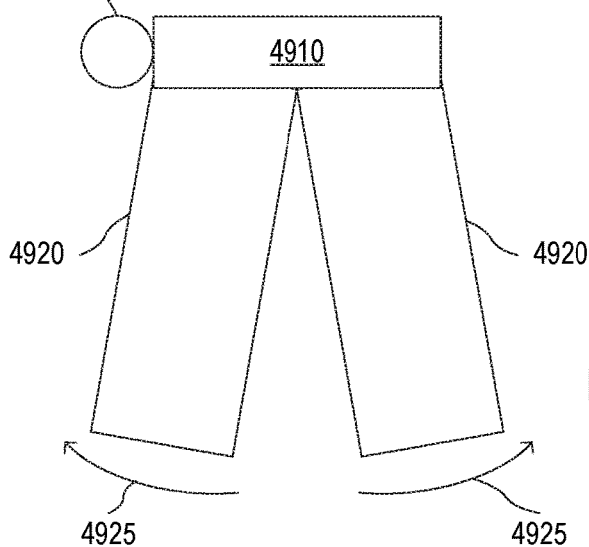

FIG. 49C illustrates another exemplary implementation of tubular retractor 4900, wherein one or both of semi-cylindrical blades 4920 may be articulated outwards along respective directions 4925. Directions 4925 are also indicated in FIG. 49A. This articulation may help further retract tissue of patient 170.

Without departing from the scope hereof, tubular retractor 4900 may be implemented with semi-cylindrical blades 4920 that are both articulating and detachable, or with one semi-cylindrical blade 4920 that is articulating and another semi-cylindrical blade 4920 that is detachable.

Figure 50:
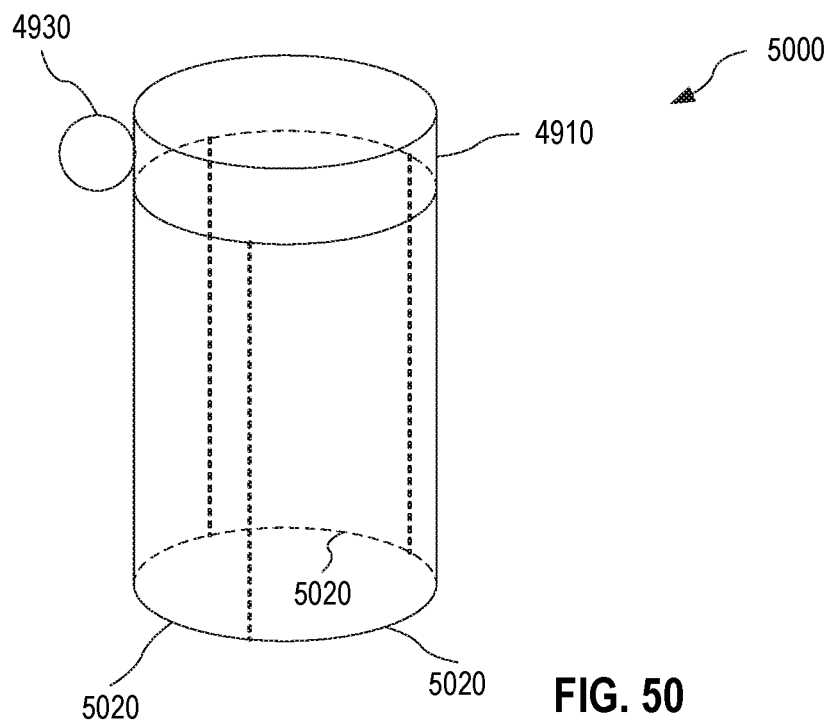
FIG. 50 illustrates a three-piece tubular retractor, according to an embodiment.

FIG. 50 illustrates one exemplary three-piece tubular retractor 5000. Tubular retractor 5000 is similar to tubular retractor 4900 except for having three blades 5020 instead of two. Each of blades 5020 is a longitudinal portion of the same cylindrical shape. As discussed in reference to FIGS. 49B and 49C, one or more of blades 5020 may be articulating and/or detachable. Additionally, as discussed in reference to FIG. 49, the cross section of tubular retractor 5000 need not be circular.

Figure 51:
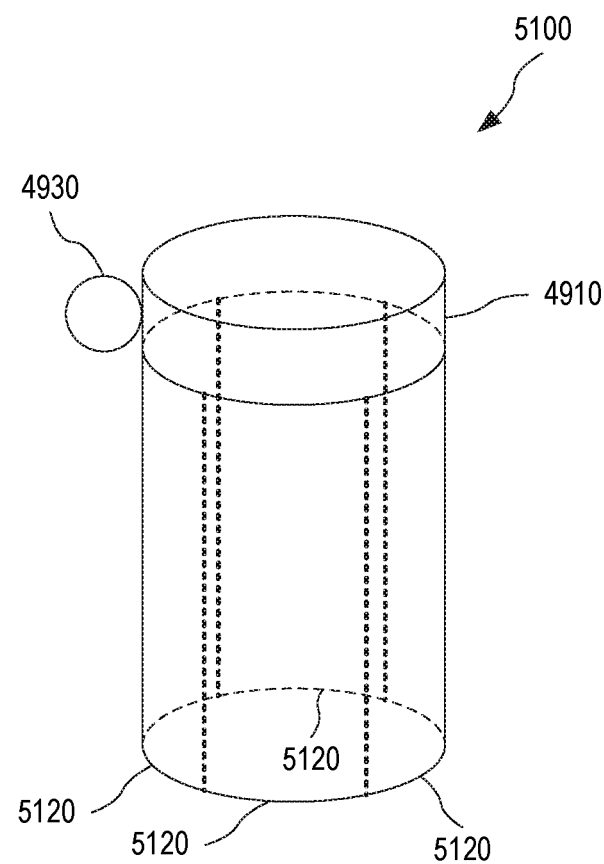
FIG. 51 illustrates a four-piece tubular retractor, according to an embodiment.

FIG. 51 illustrates one exemplary four-piece tubular retractor 5100. Tubular retractor 5100 is similar to tubular retractor 5000 except for having four blades 5120 instead of three. Each of blades 5120 is a longitudinal portion of the same cylindrical shape. As discussed in reference to FIGS. 49B and 49C, one or more of blades 4120 may be articulating and/or detachable. Tubular retractor 4100 may be extended to includes any number of blades 4120 that form a longitudinal portion of the same cylindrical shape. Additionally, as discussed in reference to FIG. 49, the cross section of tubular retractor 5100 need not be circular.

Figure 52:
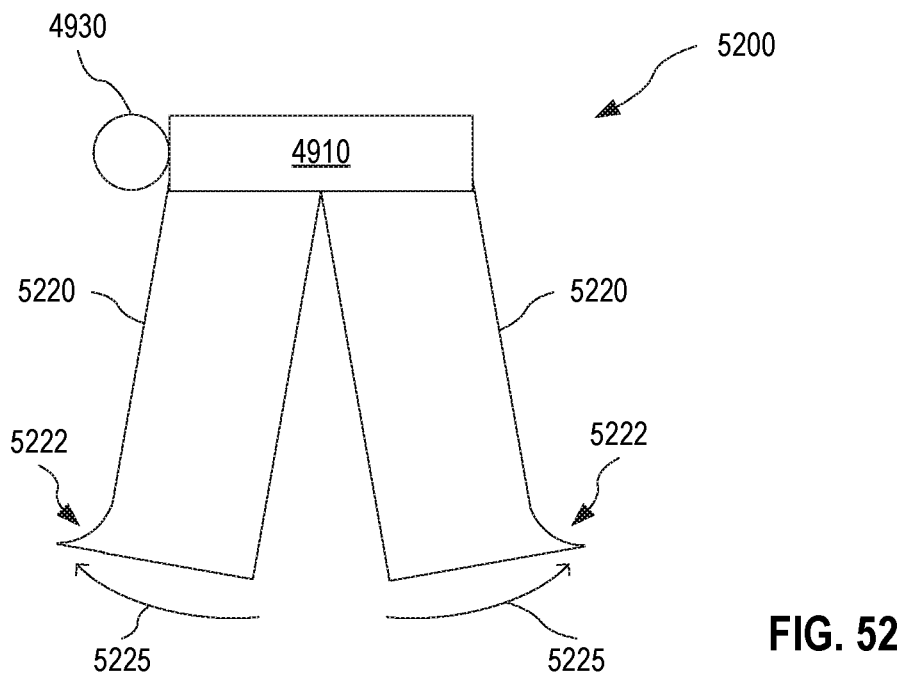
FIG. 52 illustrates a two-piece tubular retractor with hook-shaped blades, according to an embodiment.

FIG. 52 illustrates one exemplary two-piece tubular retractor 5200 with two semi-cylindrical hook-shaped blades 5220. Tubular retractor 5200 is an embodiment of tubular retractor 4900. Each blade 5220 is an embodiment of semi-cylindrical blade 4920 and includes a hook-shaped portion 5222 furthest from ring 4910. Hook-shaped portion 5222 may aid surgeon 180 grab tissue of patient 170 when retracting such tissue. Each blade 5220 may be configured to articulate along direction 5225 and/or detach from ring 4910.

Without departing from the scope hereof, one of blades 5220 may be implemented without hook-shaped portion 5222. Also without departing from the scope hereof, tubular retractors 5000 and 5100 may implement one or more of blades 5020 and 5120, respectively, as blade 5220.

Figure 53:
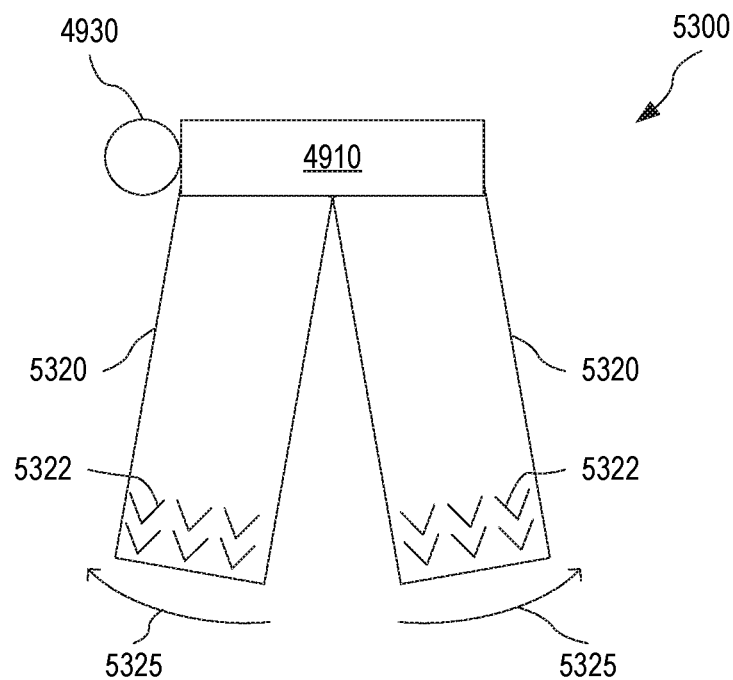
FIG. 53 illustrates a two-piece tubular retractor with teethed blades, according to an embodiment.

FIG. 53 illustrates one exemplary two-piece tubular retractor 5300 with two semi-cylindrical teethed blades 5320. Tubular retractor 5300 is an embodiment of tubular retractor 4900. Each blade 5320 is an embodiment of semi-cylindrical blade 4920 and includes a plurality of teeth 5322. Teeth 5322 may aid surgeon 180 grab tissue of patient 170 when retracting such tissue. For clarity of illustration, not all teeth 5322 are labeled in FIG. 53. Each blade 5320 may include more or fewer teeth 5322 than shown in FIG. 53, without departing from the scope hereof. Likewise, teeth 5322 may have shape and/or size different from those shown in FIG. 5333. Each blade 5320 may be configured to articulate along direction 4925 and/or detach from ring 4910.

Without departing from the scope hereof, one of blades 5320 may be implemented without teeth 5322. Also without departing from the scope hereof, tubular retractors 5000 and 5100 may implement one or more of blades 5020 and 5120, respectively, as blade 5320.

Figure 54:
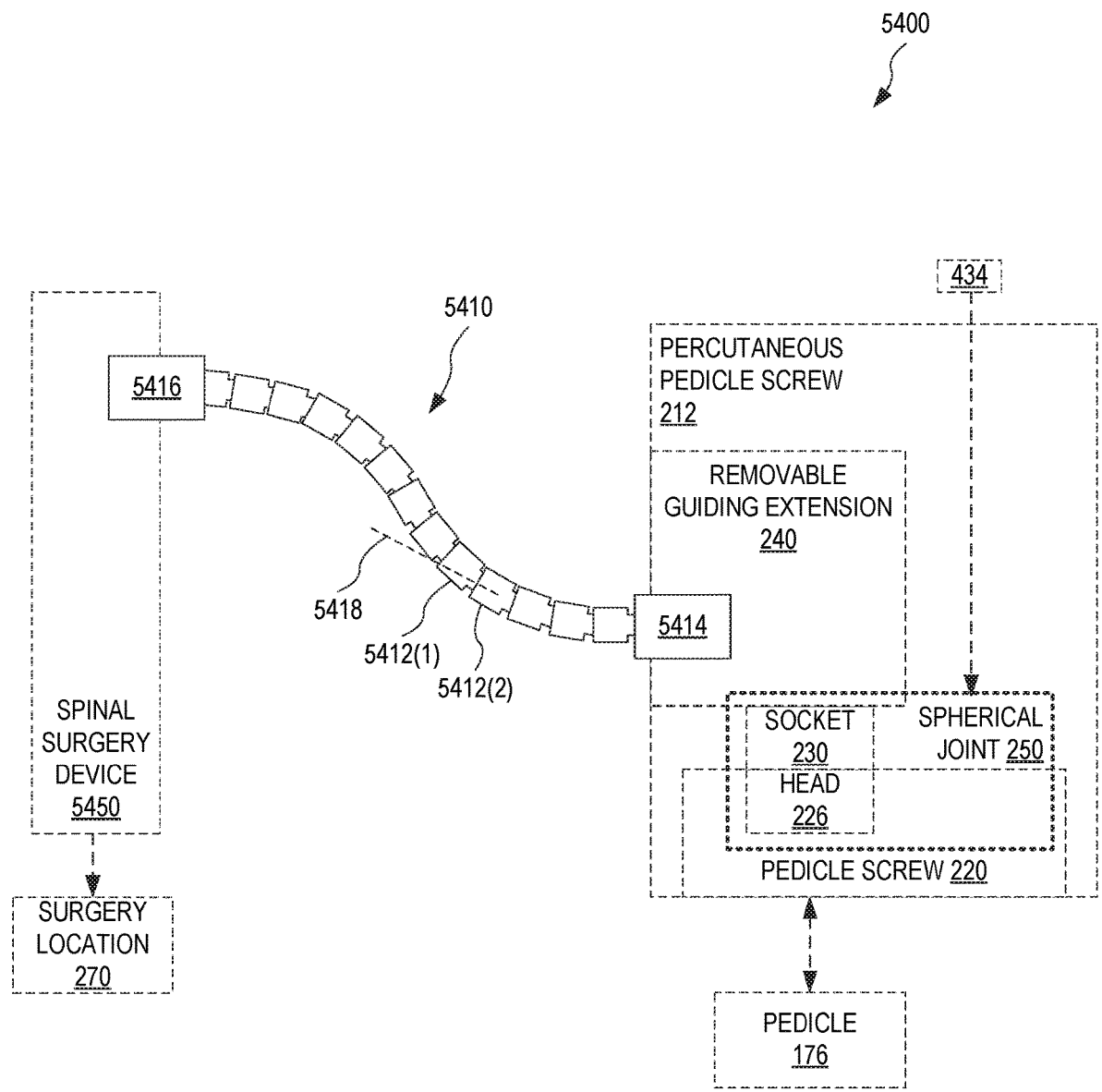
FIG. 54 illustrates a monopedicular targeting system that utilizes a snake-arm connector to couple a spinal surgery device to a removable guiding section of percutaneous pedicle screw, according to an embodiment.

FIG. 54 illustrates one exemplary monopedicular targeting system 5400 that utilizes a snake-arm connector 5410 to couple a spinal surgery device 5450 to removable guiding section 240 of percutaneous pedicle screw 212. Monopedicular targeting system 5400 is similar to monopedicular targeting system 490. In the following, only differences between monopedicular targeting system 5400 and monopedicular targeting system 490 are discussed.

Monopedicular targeting system 5400 replaces connector 460 with a snake-arm connector 5410. Snake-arm connector 5410 is an embodiment of connector 460, wherein a plurality of elements 5412 are connected to each other and wherein each element 5412 is free to articulate relative to adjacent elements 5412. Snake-arm connector 5410 may include any number of elements 5412 greater than one, such as between 5 and one hundred elements 5412. For clarity of illustration, not all elements 5412 are labeled in FIG. 54. In embodiment, each element 5412 forms a joint with a preceding element 5412, such that element 5412 may rotate about any axis orthogonal to a longitudinal axis 5418 of the adjacent element 5412. For example, element 5412(1) is free to rotate about any axis orthogonal to longitudinal axis 5418 of element 5412(2).

Snake-arm connector 5410 is connected to removable guiding extension 240 via a connector 5414 and to spinal surgery device 5450 via a connector 5416. By virtue of the high flexibility of snake-arm connector 5410, connectors 5414 and 5414 may form rigid connections with removable guiding extension 240 and spinal surgery device 5450, respectively. Connector 5414 may include features similar to those of connector 4300 at the interface between connector 4300 and break-off blades 2930.

Snake-arm connector 5410 is highly flexible and may be bent to place spinal surgery device 5450 with three translational degrees of freedom and three rotational degrees of freedom with respect to pedicle 176, so as to target surgery location 270. Snake-arm connector 5410 may be useful for targeting surgery locations 270 at a variety of distances from pedicle 176. In certain embodiments, the friction between adjacent elements 5412 is sufficient to maintain a stable configuration of snake-arm connector 5410 after placing spinal surgery device 5450 at a desired position and orientation.

Without departing from the scope hereof, percutaneous pedicle screw 212 may be replaced by fastener 110 and positioning arm 620, or by fastener 110 and connector 431. Also without departing from the scope hereof, spherical joint 250 may be replaced by a rigid connection or a joint with fewer degrees of freedom. Furthermore, snake-arm connector 5410 may be used with positioning arm 620 or a positioning arm that is not a portion of a percutaneous pedicle screw, without departing from the scope hereof. In an alternate embodiment, snake-arm connector 5410 is connected directly to pedicle screw 220. In this embodiment, snake-arm connector 5410 (optionally in cooperation with a joint between pedicle screw 220 and snake-arm connector 5410) provides three translational degrees of freedom and three rotational degrees of freedom for placement of spinal surgery device 5450 with respect to pedicle 176.

As discussed in further detail below in reference to FIGS. 56-59, monopedicular targeting system 5400 is readily extended to spine-anchored targeting systems that each have the same functionality as monopedicular targeting system 5400 but may be anchored to a different structure of spine 172 or to a pelvis of patient 170. Such spine-anchored targeting systems may be used in posterior spinal surgery of the cervical, thoracic, and/or lumbar spine of patient 170.

Figure 55:
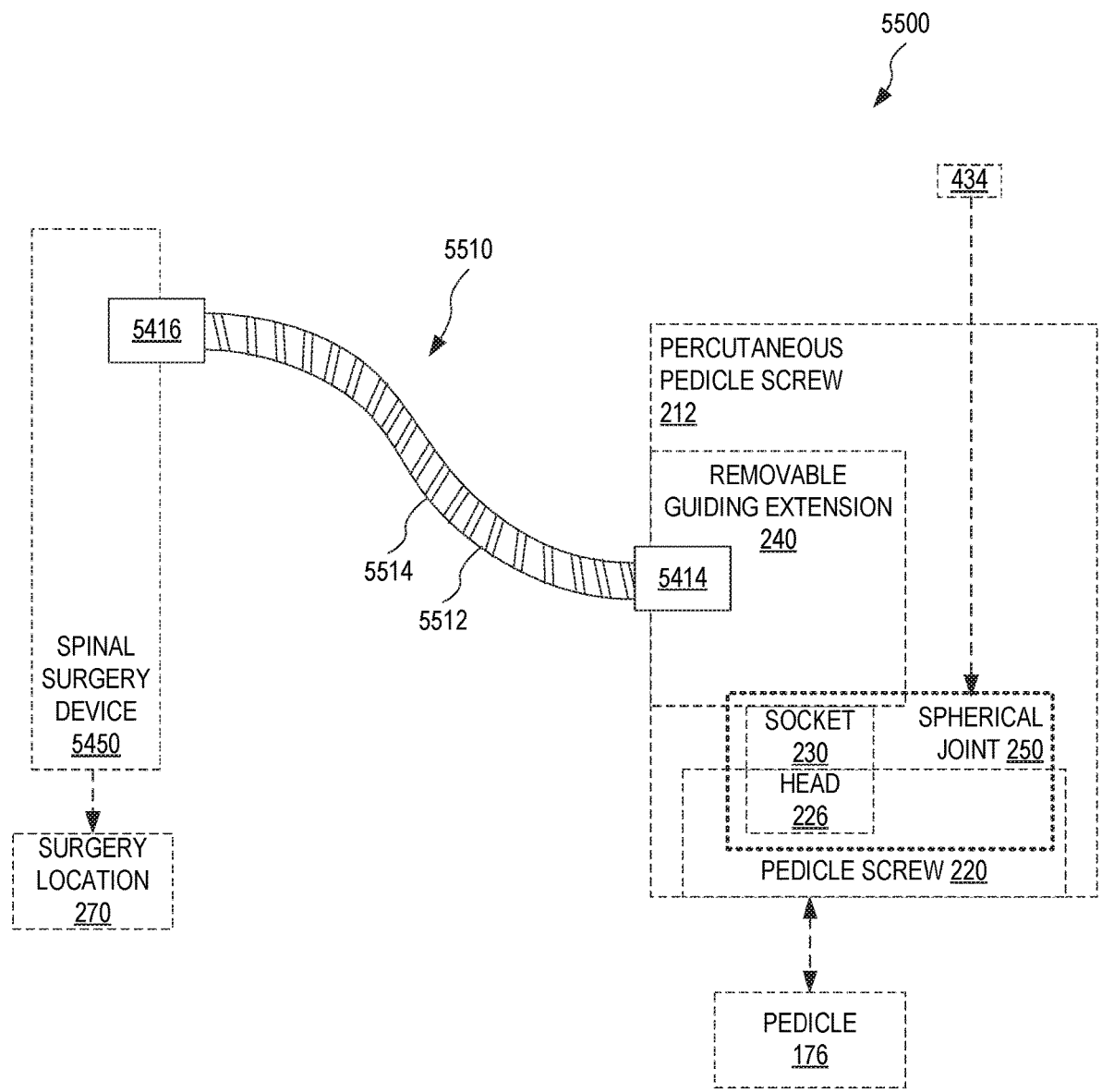
FIG. 55 illustrates another monopedicular targeting system that utilizes a snake-arm connector to couple a spinal surgery device to a removable guiding section of percutaneous pedicle screw, according to an embodiment.

FIG. 55 illustrates another exemplary monopedicular targeting system 5500 that utilizes a snake-arm connector 5510 to couple spinal surgery device 5450 to removable guiding section 240 of percutaneous pedicle screw 212. Monopedicular targeting system 5500 is similar to monopedicular targeting system 5400 except for snake-arm connector 5410 being replaced by snake-arm connector 5510. Snake-arm connector 5510 includes two interlocking spirals 5512 and 5514 that form a continuous joint between connectors 5414 and 5416.

As discussed in further detail below in reference to FIGS. 56-59, monopedicular targeting system 5500 is readily extended to spine-anchored targeting systems that each have the same functionality as monopedicular targeting system 5500 but may be anchored to a different structure of spine 172 or to a pelvis of patient 170. Such spine-anchored targeting systems may be used in posterior spinal surgery of the cervical, thoracic, and/or lumbar spine of patient 170.

Figure 56:
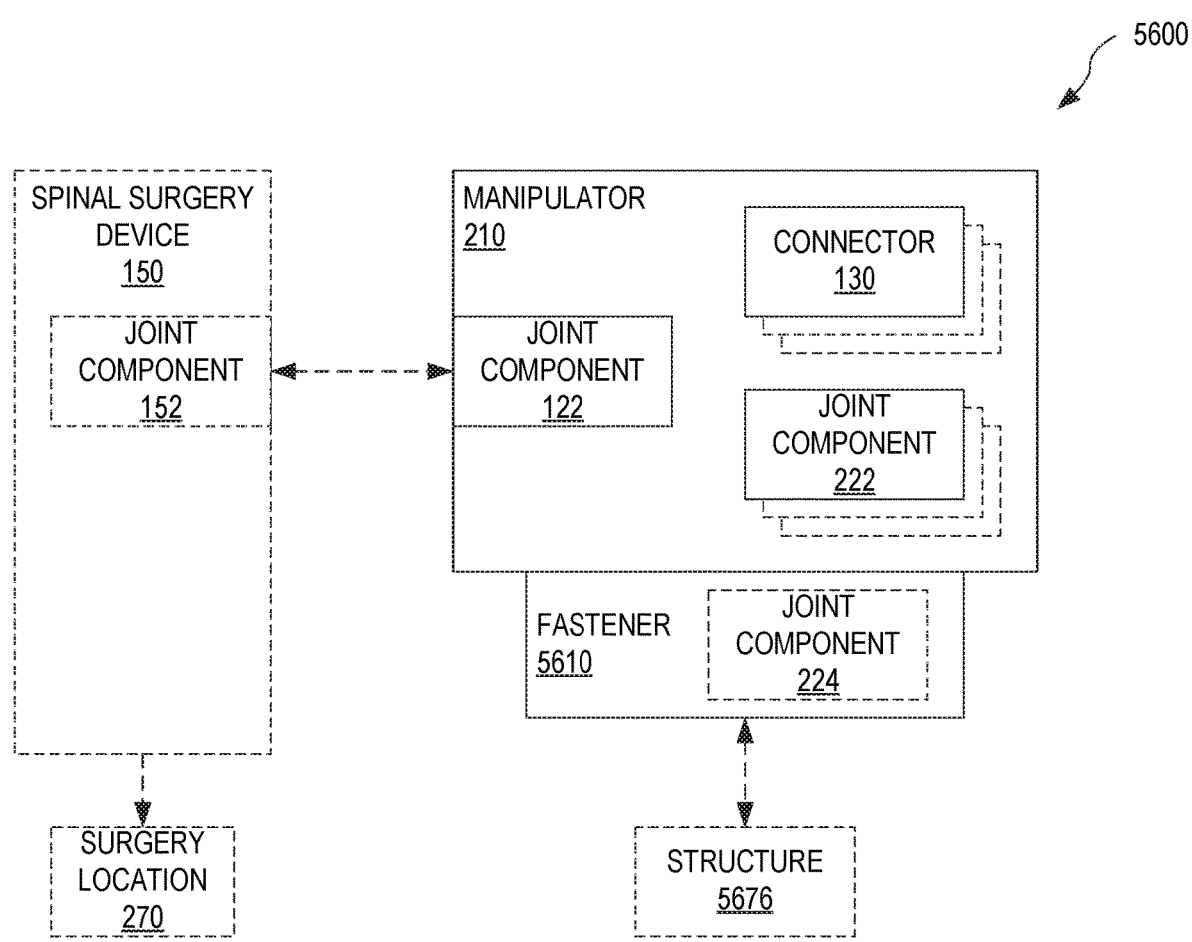
FIG. 56 is a block diagram illustrating a spine-anchored targeting system configured to be affixed to a structure of a spine or to a pelvis, according to an embodiment.

FIG. 56 is a block diagram illustrating a spine-anchored targeting system 5600. Spine-anchored targeting system 5600 is an extension of monopedicular targeting system 100. As compared to monopedicular targeting system 100, fastener 110 is replaced by a fastener 5610 configured to be affixed to an anatomic structure 5676 of patient 170. Anatomic structure 5676 is a structure of spine 172 or a pelvis of patient 170.

In one embodiment, anatomic structure 5676 is a single spinous process 166 of vertebra 178, wherein the single spinous process 166 is a spinous process of the cervical, thoracic, lumbar, or sacral spine of patient 170. In this embodiment, fastener 5676 may be a clamp that is removably clamped onto the single spinous process 166. In a similar embodiment, anatomic structure 5676 is two adjacent spinous processes 166 of spine 172, wherein these adjacent spinous processes 166 are located in the cervical, thoracic, lumbar, and/or sacral spine of patient 170. This embodiment of spine-anchored targeting system 5600 may be used to target a surgery location 270 in the cervical, thoracic, and/or lumbar spine or at the sacrum. In another embodiment, spine-anchored targeting system 5600 is configured to be affixed to a pelvis of patient 170. In this embodiment, anatomic structure 5676 may be the iliac crest of the pelvis, for example the posterior superior iliac crest, and fastener 5676 may be a screw or pin that is affixed to the iliac crest. This embodiment may be advantageous for targeting a segment of the lumbar spine or the L5-S1 segment of spine 172. In yet another embodiment, spine-anchored targeting system 5600 is configured to be affixed via a screw or a pin to the sacrum of patient 170. In this embodiment, anatomic structure 5676 may be a pedicle or the ala of the sacrum. In a further embodiment, anatomic structure 5676 is the lamina of vertebra 178, a facet of vertebra 178, a transverse process of vertebra 178, or another structure of spine 172. In this embodiment, anatomic structure 5676 may be a structure in the cervical, thoracic, or lumbar spine of patient 170, or in the sacrum of patient 170, and fastener 5610 is a screw for example. This embodiment of spine-anchored targeting system 5600 may be used to target a surgery location 270 in the cervical, thoracic, and/or lumbar spine or at the sacrum.

Spine-anchored targeting system 5600 may be utilized in any one of methods 501, 502, 503, 800, 850, and 4500.

Without departing from the scope hereof, spine-anchored targeting system 5600 may be indirectly affixed to spine 172 (and/or a pelvis of patient 170) via other mechanical hardware affixed to spine 172 (and/or the pelvis). In one such example, spine-anchored targeting system 5600 is mounted onto a rod connected to two pedicle screws and used to stabilize a segment of spine 172. In embodiments of spine-anchored targeting system 5600 configured for mounting to mechanical hardware affixed to spine 172 (and/or a pelvis of patient 170), fastener 5610 is replaced by a coupler that mounts manipulator 210 to this mechanical hardware. In scenarios where the mechanical hardware affixed to spine 172 (and/or a pelvis of patient 170) includes one or more joints that provide at least one degree of freedom for positioning of spinal surgery device 150, the coupler and manipulator 210 may cooperate with the degree(s) of freedom provided by this mechanical hardware to provide three translational and three rotational degrees of freedom for positioning of spinal surgery device 150.

Figure 57:
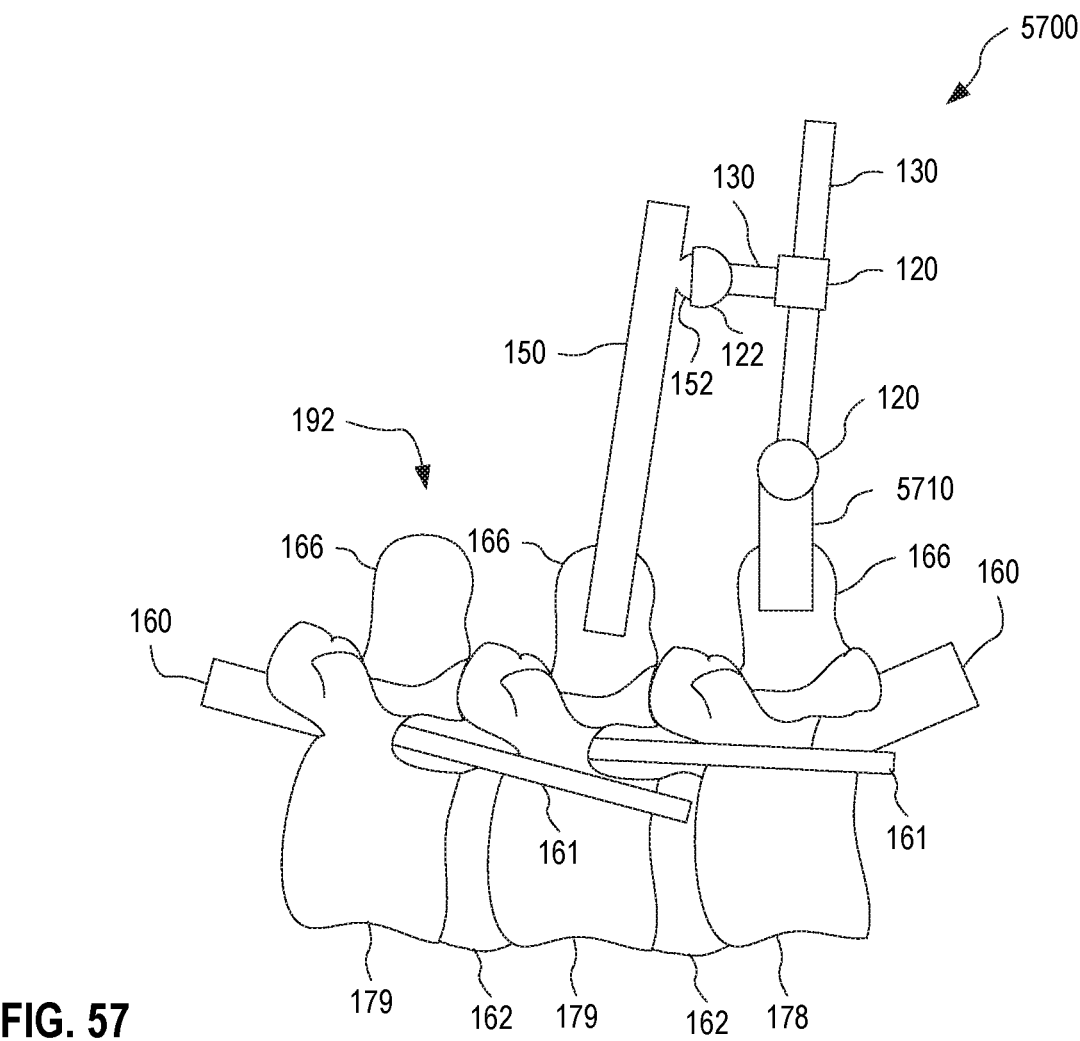
FIG. 57 illustrates a spine-anchored targeting system configured to be anchored to a spinous process, according to an embodiment.

FIG. 57 illustrates one exemplary spine-anchored targeting system 5700 configured to be anchored to a spinous process 166 of spine 172. Spine-anchored targeting system 5700 is an embodiment of spine-anchored targeting system 5600. Spine-anchored targeting system 5700 is an extension of monopedicular targeting system 100, wherein fastener 110 is replaced by a clamp 5710 that clamps onto spinous process 166.

In the exemplary embodiment shown in FIG. 57, spine-anchored targeting system 5700 includes two joints 120 and two connectors 130. A first connector 130 is configured to connect with fastener 5710 via a first joint 120, and a second connector 130 is configured to mate with the first connector 130 via a second joint 120. In one example of this embodiment, joint 120 between fastener 5710 and the first connector 130 has three rotational degrees of freedom, joint 120 between the first and second connectors 130 has a translational degree of freedom, and the joint formed by joint components 122 and 152 has three rotational degrees of freedom.

It is understood that spine-anchored targeting system 5700 is not limited to the particular embodiment shown in FIG. 57. For example, spine-anchored targeting system 5700 may include a different number of joints 120 and connectors 130 to provide three translational degrees of freedom and three rotational degrees of freedom for spinal surgery device 150 with respect to pedicle 176. In certain embodiments, spine-anchored targeting system 5700 is configured in a manner similar to any one of monopedicular targeting systems 400, 600, 900, 1400, 2400, 2500, 2600, 2700, 2800, and 4800, with fastener 110 implemented as clamp 5710. Additionally, spine-anchored targeting system 5700 may be configured in a manner similar to either one of monopedicular targeting systems 5400 and 5500 with percutaneous pedicle screw 212 replaced by clamp 5710 and positioning arm 620.

Figure 58:
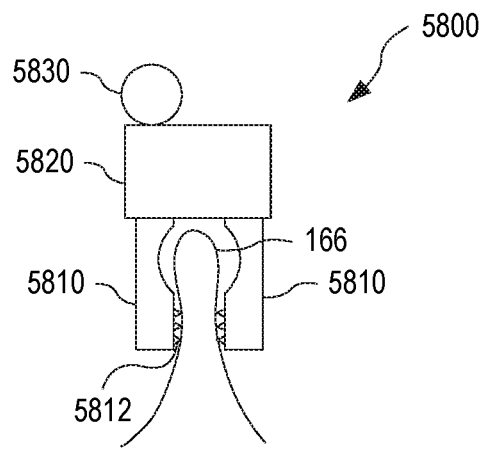
FIG. 58 illustrates a clamp for clamping the spine-anchored targeting system of FIG. 57 onto a spinous process, according to an embodiment.

FIG. 58 schematically illustrates one exemplary clamp 5800 for clamping spine-anchored targeting system 5700 onto a spinous process 166. Clamp 5800 is an embodiment of clamp 5710. Clamp 5800 includes two clamp portions 5810, an actuator unit 5820, and a spherical joint component 5830. Spherical joint component 5830 is an embodiment of joint component 224 (see FIG. 56) and forms a portion of joint 120 between clamp 5800 and connector 130 (see FIG. 57). FIG. 58 shows spinous process in a superior view. In use, surgeon 180 operates actuator unit 5820 to press clamp portions 5810 against respective sides of spinous process 166. Actuator unit 5820 may include mechanisms known in the art to move clamp portions 5810 to secure clamp 5800 to spinous process 166. One or both of clamp portions 5810 may include protrusions 5812, such as teeth or ribs, or have a rough surface, so as to improve the grip of clamp portions 5810 onto spinous process 166. For clarity of illustration, not all protrusions 5812 are labeled in FIG. 58.

Without departing from the scope hereof, clamp 5800 may have size and/or shape different from that shown in FIG. 58. Also without departing from the scope hereof, spherical joint component 5830 may be located on a different portion of actuator unit 5820 (for example on a lateral side of actuator unit relative to spine 172), be indirectly connected to actuator unit 5830, or be located on one of clamp portions 5810.

Figure 59:
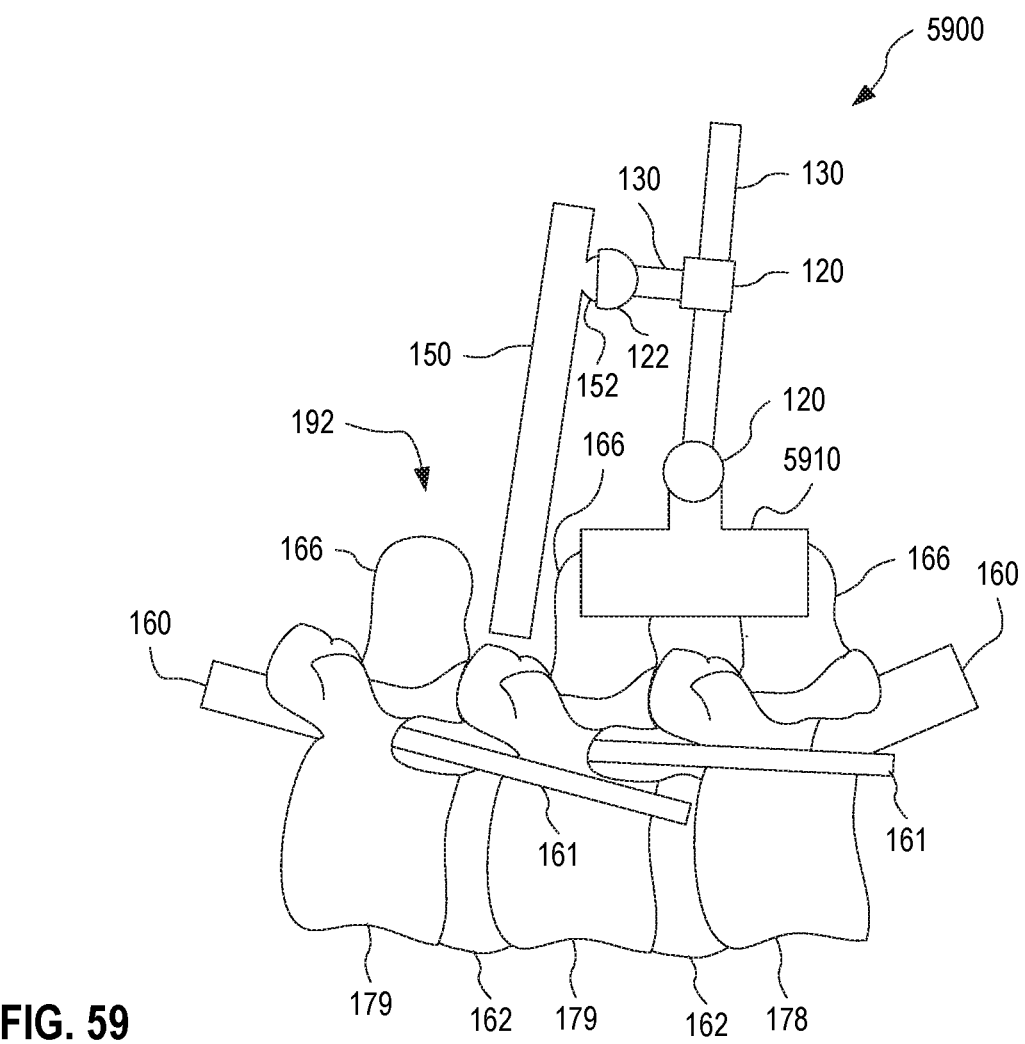
FIG. 59 illustrates a spine-anchored targeting system configured to be anchored to two adjacent spinous processes, according to an embodiment.

FIG. 59 illustrates one exemplary spine-anchored targeting system 5900 configured to be anchored to two adjacent spinous processes 166 of spine 172. Spine-anchored targeting system 5900 is an embodiment of spine-anchored targeting system 5600. Spine-anchored targeting system 5900 is similar to spine-anchored targeting system 5700, except for clamp 5710 being replaced by a clamp 5910 configured to clamp onto two adjacent spinous processes 166. Clamp 5910 may be similar to clamp 5800 except for clamp portions 5810 being sized to contact two adjacent spinous processes 166.

Figure 60:
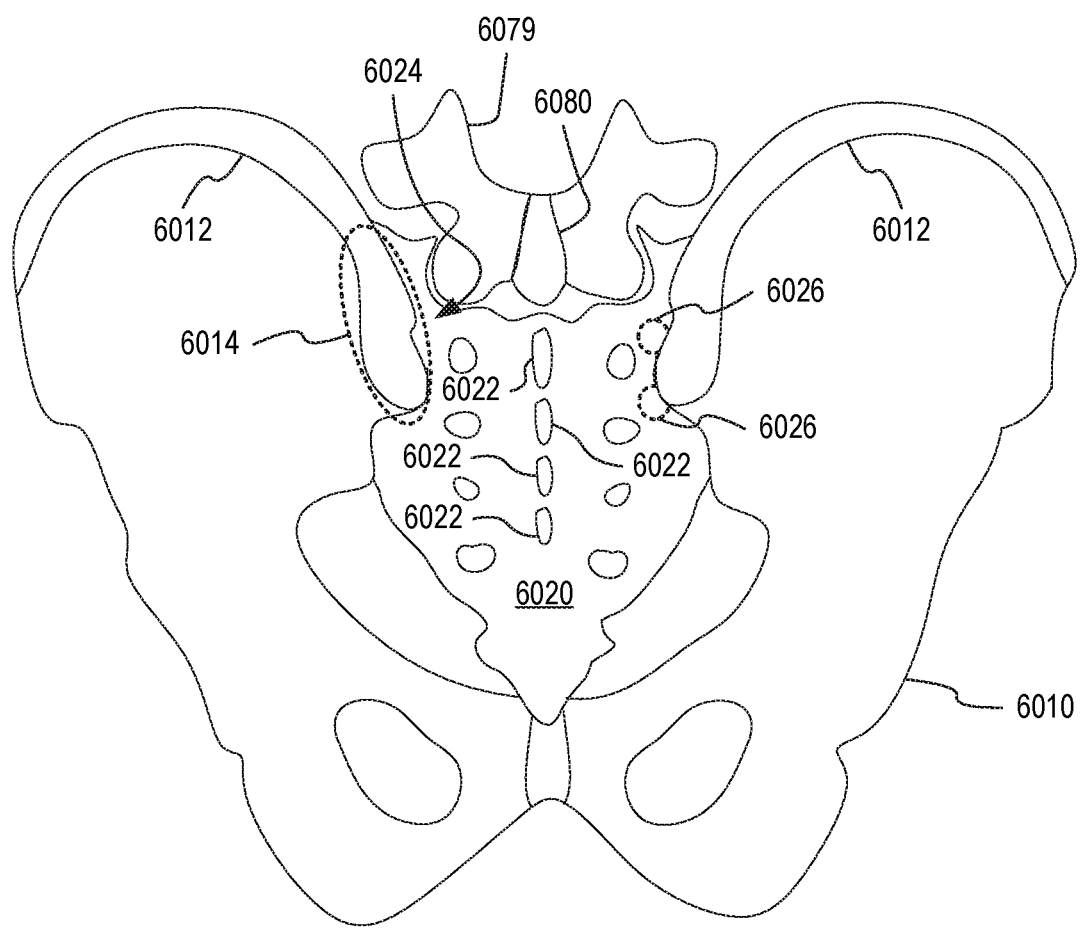
FIG. 60 shows exemplary fixation points for the spine-anchored targeting system of FIG. 56 in the pelvis and sacrum of a patient.

FIG. 60 shows exemplary fixation points for spine-anchored targeting system 5600 in the pelvis 6010 and sacrum 6020 of patient 170.

In one embodiment, spine-anchored targeting system 5600 is affixed to an iliac crest 6012 of pelvis 6010, for example a posterior superior iliac crest 6012 indicated in FIG. 60 by oval 6014. For clarity of illustration, the posterior superior iliac crest 6012 is indicated only for the left side of patient 170. In one example of this embodiment, fastener 5610 is a pin such as a percutaneous pin as known in the art. This pin may include a threaded portion. In another example of this embodiment, fastener 5610 is similar to fastener 1010 but adapted for fixation to the iliac crest.

In another embodiment, spine-anchored targeting system 5600 is affixed to a pedicle 6026 of sacrum 6020, as discussed above in reference to monopedicular targeting system 100. For clarity of illustration, not all pedicles 6026 of sacrum 6020 are indicated in FIG. 60.

In yet another embodiment, spine-anchored targeting system 5600 is affixed, via a screw or a pin, to another portion of sacrum 6020 such as ala 6024. In FIG. 60, alas 6024 of sacrum 6020 are partly hidden from view by pelvis 6010. For clarity of illustration, only the left ala 6024 is indicated in FIG. 60. This embodiment may implement a fastener 5610 similar to those discussed for fixation to the iliac crest but adapted for fixation to sacrum 6020.

In a further embodiment, spine-anchored targeting system 5600 is implemented as spine-anchored targeting system 5700 or spine-anchored targeting system 5900 and is affixed to (a) one or two spinous processes 6022 of sacrum 6020 or (b) spinous process 6080 of L5 vertebra 6079 and spinous process 6022 adjacent spinous process 6080.

Combinations of Features

Features described above as well as those claimed below may be combined in various ways without departing from the scope hereof. For example, it will be appreciated that aspects of one spine-anchored targeting system or method described herein may incorporate or swap features of another spine-anchored targeting system or method described herein. The following examples illustrate possible, non-limiting combinations of embodiments described above. It should be clear that many other changes and modifications may be made to the methods and devices herein without departing from the spirit and scope of this invention:

(A1) A monopedicular targeting system for posterior spinal surgery may include a first joint component, a fastener for affixing the first joint component to a single pedicle of a vertebra, a positioning arm having a second joint component for mating with the first joint component to form a first joint having three rotational degrees of freedom, and a connector for coupling a spinal surgery device to the positioning arm, the connector having a third joint component that mates with a fourth joint component, for mounting to the spinal surgery device to form a second joint having three rotational degrees of freedom.

(A2) In the monopedicular targeting system denoted as (A1), the first joint component may be a protrusion, the second joint component may be a receptacle located at a first end of the positioning arm, and the positioning arm may have a cannulation from the receptacle to a second end of the positioning arm opposite the first end, such that the protrusion is accessible through the cannulation.

(A3) The monopedicular targeting system denoted as (A2) may further include a locking driver for locking the first joint by (a) inserting the locking driver from the second end of the positioning arm into the cannulation and (b) affixing the locking driver to the positioning arm to press on the protrusion through the receptacle.

(A4) In the monopedicular targeting system denoted as (A3), the cannulation may have an internal thread and the locking driver may have an external thread, such that contact between the internal thread and the external thread cooperates with pressure between the protrusion and the locking driver to fix the locking driver in the cannulation so as to lock the first joint.

(A5) In the monopedicular targeting system denoted as (A2), the cannulation may have an internal thread at the second end of the positioning arm, and the monopedicular targeting system may further include a locking device for locking the first joint, wherein the locking device includes a locking driver for inserting into the cannulation from the second end of the positioning arm, and wherein the locking driver has an external thread configured to thread into the internal thread of the cannulation to apply pressure on the protrusion, so as to lock the first joint.

(A6) In any of the monopedicular targeting systems denoted as (A1) through (A5), the connector may be movable along the positioning arm to vary distance between the connector and the first joint so as to provide translational degree of freedom of the spinal surgery device along the positioning arm.

(A7) In the monopedicular targeting system denoted as (A6), the translational degree of freedom, the three rotational degrees of freedom of the first joint, and the three rotational degrees of freedom of the second joint may cooperate to provide six degrees of freedom for position and orientation of the spinal surgery device.

(A8) In the monopedicular targeting system denoted as (A6), the translational degree of freedom, the three rotational degrees of freedom of the first joint, and the three rotational degrees of freedom of the second joint may cooperate to provide (a) six degrees of freedom for positioning of the spinal surgery device and (b) a rotational degree of freedom for the third joint component, such that each possible position of the third joint component is associated with a range of possible orientations of the third joint component.

(A9) In any of the monopedicular targeting systems denoted as (A1) through (A8), the connector may include a clamp that clamps onto the positioning arm and the spinal surgery device.

(A10) In the monopedicular targeting system denoted as (A9), the connector may further include at least one locking fastener for locking (a) position of the clamp on the positioning arm and (b) the second joint.

(A11) In the monopedicular targeting system denoted as (A10), the clamp may include a first clamp part and a second clamp part each forming (a) a portion of the third joint component and (b) a portion of a cylindrical joint component for mating with the positioning arm, such that the first clamp part and the second clamp part may be brought together to clamp onto the fourth joint component and the positioning arm.

(A12) In the monopedicular targeting system denoted as (A11), the at least one locking fastener may include a first locking fastener for locking position of the clamp on the positioning arm and a second locking fastener for locking the second joint, and one of the first clamp part and the second clamp part may include a hinge to separate locking of the clamp on the positioning arm by the first locking fastener from locking of the second joint by the second locking fastener.

(A13) In any of the monopedicular targeting systems denoted as (A1) through (A12), the positioning arm may include a section for mounting of the connector thereto, wherein the section has constant cross section through a range of distances from the first joint.

(A14) In the monopedicular targeting system denote as (A13), the cross section may be circular such that the connector may be mounted to the section at any orientation in plane of the cross section to provide a rotational degree of freedom of the connector about axis of the section.

(A15) In any of the monopedicular targeting systems denoted as (A1) through (A14), the fastener may include a threaded member.

(A16) In the monopedicular targeting system denoted as (A15), the threaded member may include an awl portion furthest from the first joint component, and a tap portion between the awl portion and the first joint component.

(A17) In either or both of the monopedicular targeting systems denoted as (A15) and (A16), the second joint component may be a receptacle located at a first end of the positioning arm, the positioning arm may have a cannulation from the receptacle to a second end of the positioning arm opposite the first end, wherein the threaded member includes a head for receiving a driver through the cannulation to screw the threaded member into the pedicle.

(A18) Any of the monopedicular targeting systems denoted as (A1) through (A17) may further include the spinal surgery device.

(A19) In the monopedicular targeting system denoted as (A18), the spinal surgery device may include a retractor for retracting tissue to provide access to a spinal surgery location.

(A20) In the monopedicular targeting system denoted as (A19), the retractor may be a tubular retractor.

(A21) In any of the monopedicular targeting systems denoted as (A1) through (A20), the connector may include a telescoping joint for adjusting reach of the monopedicular targeting system.

(A22) In any of the monopedicular targeting systems denoted as (A1) through (A21), the connector may include a rotational joint for adjusting angle of the connector with respect to the positioning arm.

(A23) In any of the monopedicular targeting systems denoted as (A1) through (A22), the positioning arm may include a rotational joint for bending the positioning arm.

(A24) Any of the monopedicular targeting systems denoted as (A1) through (A23) may further include (i) the fourth joint component, (ii) a connecting arm having a first end and a second end, wherein the first end is connected to the fourth joint component, and (iii) a coupler connected the second end and configured to attach to the spinal surgery device.

(A25) In the monopedicular targeting system denoted as (A24), the coupler may be configured to attach to a retractor and including a locking fastener for affixing the coupler to the retractor.

(A26) In the monopedicular targeting system denoted as (A25), the retractor may be a tubular retractor, and the coupler may include a ring configured to attach to the outside of the tubular retractor.

(A27) In any of the monopedicular targeting systems denoted as (A24) through (A26), the fourth joint component may be a male spherical joint component.

(A28) In any of the monopedicular targeting systems denoted as (A24) through (A27), the connecting arm may be angled to place the first end at an angle to the second end, wherein the angle is in the range from 45 to 135 degrees, to accommodate an imaging path to an intervertebral disc space.

(A29) In any of the monopedicular targeting systems denoted as (A1) through (A28), angular range of the first joint may, away from longitudinal axis of the fastener, may be between 20 degrees and 30 degrees.

(A30) In any of the monopedicular targeting systems denoted as (A1) through (A29), the first joint may have at least 35 degrees angular range away from longitudinal axis of the fastener.

(A31) In any of the monopedicular targeting systems denoted as (A1) through (A30), the first joint may be an asymmetric joint having expanded angular range in one range of directions orthogonal to longitudinal axis of the fastener, as compared to angular range in another range of directions orthogonal to the longitudinal axis.

(A32) In any of the monopedicular targeting systems denoted as (A1) through (A31), the connector may include a snake-arm.

(A33) In the monopedicular targeting system denoted as (A32), the snake-arm may include a plurality of joints coupled in series.

(A34) In the monopedicular targeting system denoted as (A33), the snake-arm may include two interlocking spirals forming a continuous joint therebetween.

(A35) Any of the monopedicular targeting systems denoted as (A1) through (A34) may be adapted for anchoring to a different structure than a pedicle, such as a different structure of the patient's spine or a pelvis of the patient.

(B1) A monopedicular targeting method for posterior spinal surgery, may include affixing a fastener to a single pedicle of a vertebra, anchoring a spinal surgery device to the pedicle via a manipulator attached to the fastener, and adjusting the manipulator to define, with three translational degrees of freedom and three rotational degrees of freedom relative to the pedicle, position and orientation of the spinal surgery device to posteriorly target a surgery location.

(B2) In the monopedicular targeting method denoted as (B1), the fastener may include a threaded member, and the step of affixing may include screwing the threaded member into the pedicle.

(B3) In either or both of the monopedicular targeting methods denoted as (B1) and (B2), the step of adjusting may include (a) manipulating a first joint between the fastener and a positioning arm, wherein the first joint has three rotational degrees of freedom, (b) manipulating a translational degree of freedom of a second joint coupled between the positioning arm and a connector for connecting the spinal surgery device to the positioning arm, and (c) manipulating a third joint between the spinal surgery device and the connector, wherein the third joint has three rotational degrees of freedom.

(B4) The monopedicular targeting method denoted as (B3) may further include locking position and orientation of the spinal surgery device with respect to the pedicle.

(B5) In the monopedicular targeting method denoted as (B4), the step of locking may include (a) tightening a locking driver, inserted through a cannulation of the positioning arm, to the positioning arm to press on a protrusion of the fastener through a receptacle of the positioning arm, wherein the protrusion and the receptacle form the first joint, and (b) tightening a clamp forming a portion of each of the second joint and the third joint.

(B6) In the monopedicular targeting method denoted as (B5), the step of locking may further include inserting the locking driver into the cannulation of the positioning arm through an end of the positioning arm facing away from the fastener.

(B7) In any of the monopedicular targeting methods denoted as (B3) through (B6), the fastener may include a threaded member, and the step of affixing may include screwing the threaded member into the pedicle by actuating the threaded member through a cannulation of the positioning arm.

(B8) Any of the monopedicular targeting methods denoted as (B1) through (B7) may include performing the step of anchoring prior to completing the step of adjusting.

(B9) Any of the monopedicular targeting methods denoted as (B1) through (B8) may further include (i) prior to the step of anchoring, placing the spinal surgery device at the position and the orientation, and (ii) after the step of placing, performing the step of anchoring while performing the step of adjusting according to the position and the orientation of the spinal surgery device.

(B10) In the monopedicular targeting method denoted as (B9), the step of anchoring may include assembling and adjusting the manipulator to anchor the spinal surgery device to the pedicle, according to the position and the orientation of the spinal surgery device.

(B11) In the monopedicular targeting method denoted as (B10), the step of assembling and adjusting may include assembling a second joint of the manipulator having a translational degree of freedom, and manipulating (a) a first joint located between the second joint and the pedicle and having (i) fixed location relative to pedicle and (ii) three rotational degrees of freedom, and (b) the second joint, to assemble a third joint, having three rotational degrees of freedom, to couple the spinal surgery device to the manipulator, so as to anchor the spinal surgery device to the pedicle.

(B12) In the monopedicular targeting method denoted as (B11), the step of affixing may include affixing a percutaneous pedicle screw to the pedicle, and in the step of adjusting, the percutaneous pedicle screw may include a removable guiding extension of the percutaneous pedicle screw, wherein the first joint is a spherical joint between (a) head of a first pedicle screw of the percutaneous pedicle screw and (b) a socket attaching the removable guiding extension to the first pedicle screw.

(B13) The monopedicular targeting method denoted as (B12) may further include mating a first cylindrical joint component of the connector to the removable guiding extension to form the second joint, and mating a second spherical joint component of the connector with a third spherical joint component coupled with the spinal surgery device to form the third joint.

(B14) The monopedicular targeting method denoted as (B13) may further include adjusting the first joint, the second joint, and the third joint to target a surgery location with the spinal surgery device.

(B15) The monopedicular targeting method denoted as (B14) may further include locking the first joint by screwing a locking driver into to the removable guiding extension to apply pressure on the head, locking the second joint by clamping two clamp parts of the connector onto the removable guiding extension, and locking the third joint by clamping the two clamp parts tight onto the third spherical joint component.

(B16) In any of the monopedicular targeting methods denoted as (B13) through (B15), the step of mating a first cylindrical joint component may include mating the first cylindrical joint component directly with break-off blades of the removable guiding extension.

(B17) In any of the monopedicular targeting methods denoted as (B13) through (B15), the step of mating a first cylindrical joint component may include mating the first cylindrical joint component with a stabilizing clamp configured to prevent inadvertent detachment of the break-off blades from the socket.

(B18) In the monopedicular targeting method denoted as (B7), the removable guiding extension may be two break-off blades, and the stabilizing clamp may be a clip with lips configured to attach to each of the break-off blades to stabilize the break-off blades.

(B19) In any of the monopedicular targeting methods denoted as (B13) through (B15), the step of mating a first cylindrical joint component may include mating the first cylindrical joint component with each of a plurality of break-off blades of the removable guiding extension, and stabilizing relative position of the break-off blades.

(B20) Any of the monopedicular targeting methods denoted as (B12) through (B19) may further include detaching the connector from the percutaneous pedicle screw, and connecting a rod to the percutaneous pedicle screw and a second percutaneous pedicle screw to stabilize a spine segment.

(B21) In any of the monopedicular targeting methods denoted as (B1) through (B20), the step of anchoring may include anchoring the spinal surgery device to the pedicle via a snake-arm attached to the fastener, and the step of adjusting may include adjusting the snake-arm to posteriorly target a surgery location.

(B22) Any of the monopedicular targeting methods denoted as (B1) through (B21) may be adapted for anchoring the spinal surgery device to a different structure than a pedicle, such as a different structure of the patient's spine or a pelvis of the patient.

(C1) A monopedicular targeting system for posterior spinal surgery may include a manipulator for holding a spinal surgery device and manipulating three translational and three rotational degrees of freedom of the spinal surgery device with respect to an anchoring location of the manipulator, and a fastener for anchoring the manipulator to a single pedicle of a vertebra.

(C2) In the monopedicular targeting system denoted as (C1), the manipulator may include a first spherical joint component for mating with a spherical joint component of the spinal surgery device to provide three rotational degrees of freedom for the spinal surgery device with respect to the manipulator.

(C3) In either or both of the monopedicular targeting systems denoted as (C1) and (C2), the manipulator may include a second spherical joint component for mating with a spherical joint component of the fastener to provide three rotational degrees of freedom for the manipulator with respect to the fastener.

(C4) In any of the monopedicular targeting systems denoted as (C1) through (C3), the manipulator and fastener may be cooperatively configured to form a second spherical joint.

(C5) In the monopedicular targeting system denoted as (C4), angular range of the second spherical joint, away from longitudinal axis of the fastener, may be between 20 degrees and 30 degrees.

(C6) In the monopedicular targeting system denoted as (C4), the second spherical joint may be at least 35 degrees angular range away from longitudinal axis of the fastener.

(C7) In any of the monopedicular targeting systems denoted as (C4) through (C6), the second spherical joint may be an asymmetric joint having expanded angular range in one range of directions orthogonal to longitudinal axis of the fastener, as compared to angular range in another range of directions orthogonal to the longitudinal axis.

(C8) In any of the monopedicular targeting systems denoted as (C3) through (C7), the manipulator may include a translational joint for adjusting distance between the first spherical joint component and the second spherical joint component.

(C9) In any of the monopedicular targeting systems denoted as (C1) through (C8), the manipulator may include a snake-arm.

(C10) In the monopedicular targeting system denoted as (C9), the snake-arm may include a plurality of joints coupled in series.

(C11) In the monopedicular targeting system denoted as (C9), the snake-arm may include two interlocking spirals forming a continuous joint therebetween.

(C12) In any of the monopedicular targeting systems denoted as (C1) through (C11), the manipulator may include a first spherical joint component for mating with a spherical joint component of the spinal surgery device to provide three rotational degrees of freedom for the spinal surgery device with respect to the manipulator.

(C13) Any of the monopedicular targeting systems denoted as (C1) through (C12) may be adapted for anchoring to a different structure than a pedicle, such as a different structure of the patient's spine or a pelvis of the patient.

(D1) A monopedicular targeting system may cooperate with a percutaneous pedicle screw to anchor, to a single pedicle of a vertebra, a spinal surgery device for posterior spinal surgery, wherein the percutaneous pedicle screw has (i) a first pedicle screw, (ii) a socket that forms a first spherical joint with a head of the first pedicle screw, and (iii) a removable guiding extension attached to the socket, and wherein the monopedicular targeting system includes a connector for (a) mating with the removable guiding extension at a variable distance from the socket to form a first joint having at least a translational degree of freedom and (b) mating with a first spherical joint component, configured for mounting to the spinal surgery device, to form a second spherical joint, such that the connector is capable of cooperating with the first spherical joint component and the percutaneous pedicle screw to provide three translational and three rotational degrees of freedom of the spinal surgery device with respect to the pedicle.

(D2) In the monopedicular targeting system denoted as (D1), the connector may include a first joint component configured to mate with the removable guiding extension at a variable distance from the socket to form the first joint, and a second spherical joint component mechanically coupled with the first joint component and configured to mate with the first spherical joint component to form a second spherical joint.

(D3) In the monopedicular targeting system denoted as (D2), the first joint component may be configured to mate directly with the removable guiding extension and form a cylindrical joint therewith.

(D4) In the monopedicular targeting system denoted as (D3), the first joint component may be of cylindrical shape and capable of attaching to the removable guiding extension at a continuous range of distances from the socket.

(D5) In either or both of the monopedicular targeting systems denoted as (D3) and (D4), the first joint component may be configured to mate with a stabilizing clamp, for preventing inadvertent detachment of a plurality of break-off blades of the removable guiding extension, at a variable orientation, relative to longitudinal axis of the removable guiding extension, to form a cylindrical joint between the connector and the guiding extension.

(D6) In any of the monopedicular targeting systems denoted as (D3) through (D5), the first joint component may be configured to attach to each of a plurality of break-off blades of the removable guiding extension, at a variable distance from the socket, so as to form a translational joint with the break-off blades and prevent inadvertent detachment of the break-off blades from the socket.

(D7) In the monopedicular targeting system denoted as (D6), the first joint component may have at least one spring-loaded protrusion that matches each of several instances of at least one respective indentation in the break-off blades to preferably seat the first joint component at one of several discrete distances from the socket.

(D8) In either or both of the monopedicular targeting systems denoted as (D6) and (D7), the plurality of break-off blades may be two break-off blades, the first joint component including two pairs of lips for respectively attaching to the two break-off blades so as to stabilize relative positions of the break-off blades.

(D9) In any of the monopedicular targeting systems denoted as (D2) through (D8), the connector may include a first clamp part and a second clamp part, each forming a portion of the first joint component and a portion of the second spherical joint component such that the first clamp part and the second clamp part may be brought together to clamp the connector onto the removable guiding extension and the first spherical joint component.

(D10) In the monopedicular targeting system denoted as (D9), the connector may further include at least one locking fastener for coupling the first clamp part and the second clamp part.

(D11) In the monopedicular targeting system denoted as (D10), the at least one locking fastener may be configured to lock the first joint and the second spherical joint.

(D12) The monopedicular targeting system denoted as (D11) may further include a locking driver for locking the first spherical joint by (a) inserting the locking driver into the percutaneous pedicle screw through the removable guiding section and (b) screwing the locking driver into the socket to apply pressure to the head.

(D13) In the monopedicular targeting system denoted as (D12), the removable guiding section may include a plurality of break-off blades, wherein the locking driver is configured for insertion into the percutaneous pedicle screw between the break-off blades and having size sufficient to prevent break-off of the break-off blades when locking the first joint using the at least one locking fastener.

(D14) In any of the monopedicular targeting systems denoted as (D11) through (D13), the at least one locking fastener may include a first locking fastener for locking the first joint and a second locking fastener for locking the second spherical joint, and one of the first clamp part and the second clamp part may include a hinge to separate locking of the first joint by the first locking fastener from locking of the second spherical joint by the second locking fastener.

(D15) Any of the monopedicular targeting systems denoted as (D1) through (D14) may further include the first spherical joint component, a connecting arm having a first end and a second end, the first end being connected to the first spherical joint component, and a coupler connected the second end, wherein the coupler is configured to attach to the spinal surgery device.

(D16) In the monopedicular targeting system denoted as (D15), the coupler may be configured to attach to a retractor and including a locking fastener for affixing the coupler to the retractor.

(D17) In the monopedicular targeting system denoted as (D16), the retractor may be a tubular retractor, and the coupler may include a ring configured to attach to the outside of the tubular retractor.

(D18) In any of the monopedicular targeting systems denoted as (D15) through (D17), the first spherical joint component may be a male spherical joint component.

(D19) In any of the monopedicular targeting systems denoted as (D15) through (D18), the connecting arm may be angled to place the first end at an angle to the second end, and the angle may be in the range from 45 to 135 degrees, to accommodate an imaging path to an intervertebral disc space.

(D20) Any of the monopedicular targeting systems denoted as (D1) through (D19) may further include the percutaneous pedicle screw, and the first spherical joint may have rotational range, about any axis orthogonal to axis of the first pedicle screw, of at least 70 degrees.

(D21) In any of the monopedicular targeting systems denoted as (D1) through (D20), the connector may include a snake-arm.

(D22) In the monopedicular targeting system denoted as (D21), the snake-arm may include a plurality of joints coupled in series.

(D23) In the monopedicular targeting system denoted as (D21), the snake-arm may include two interlocking spirals forming a continuous joint therebetween.

(D24) Any of the monopedicular targeting systems denoted as (D1) through (D23) may be adapted for anchoring to a different structure than a pedicle, such as a different structure of the patient's spine or a pelvis of the patient.

(E1) A monopedicular targeting method for posterior spinal surgery may include coupling a spinal surgery device to a percutaneous pedicle screw via a connector, to anchor the spinal surgery device to a single pedicle of a vertebra.

(E2) In the monopedicular targeting method denoted as (E1), the step of coupling may include forming a first joint between the percutaneous pedicle screw and the connector, wherein the first joint has at least a translational degree of freedom, and forming a second joint between the connector and the spinal surgery device.

(E3) In the monopedicular targeting method denoted as (E2), the step of forming a first joint may include attaching the connector to a removable guiding extension of the percutaneous pedicle screw.

(E4) In the monopedicular targeting method denoted as (E3), the step of attaching may include clamping the connector around the removable guiding extension.

(E5) In the monopedicular targeting method denoted as (E4), the step of attaching may include clamping the connector around a plurality of break-off blades of the removable guiding extension.

(E6) In the monopedicular targeting method denoted as (E5), the step of attaching may further include stabilizing relative position of the break-off blades using the connector.

(E7) In the monopedicular targeting method denoted as (E6), the step of attaching may include attaching the connector to a stabilizing clamp configured to prevent inadvertent detachment of a plurality of break-off blades of the removable guiding section.

(E8) In any of the monopedicular targeting methods denoted as (E2) through (E3), the step of coupling may include bringing together a first clamp part and a second clamp part to form the first joint and the second joint, wherein each of the first clamp part and the second clamp part includes joint components forming a portion of each of the first joint and the second joint.

(E9) Any of the monopedicular targeting methods denoted as (E2) through (E8), may further include locking the first joint and the second joint using at least one locking fastener of the connector.

(E10) Any of the monopedicular targeting methods denoted as (E1) through (E9) may be adapted for anchoring the spinal surgery device to a different structure than a pedicle, such as a different structure of the patient's spine or a pelvis of the patient.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present devices and methods, which, as a matter of language, might be said to fall therebetween.

What is claimed is:

1. A surgical positioning system, comprising:
    a cannulated surgical access device having first and second blades having an inner surface, an outer surface, and a sidewall, the sidewall extending between the inner and outer surface, the inner surface of each blade defining an access channel for accessing a surgery location therethrough with surgical tools; and
    a support arm having first and second connectors and a first joint, the first connector having an anchoring end configured to connect to a bone fastener, the second connector having a working end configured to connect to the cannulated surgical access device, and the first joint being disposed at the working end, the anchoring end, or between the first and second connector such that, when the cannulated surgical access device is connected to the working end and the anchoring end is connected to the bone fastener in bone, the cannulated surgical access device is moveable in multiple degrees of freedom upon manipulation of the first joint,
    wherein the first and second blades are configured to move relative to each other while the support arm is connected to the surgical access device.

2. The system of claim 1, wherein the first joint is a ball joint.

3. The system of claim 1, wherein the first connector includes a first arm member and the second connector includes a second arm member, the first arm member includes the anchoring end and the second arm member includes the working end, the first and second arm members are connected by a second joint having at least two degrees of freedom.

4. The system of claim 3, wherein the second arm member extends in a direction transverse to the first arm member.

5. The system of claim 3, wherein the first and second arm members can be locked in relative position so as to support the cannulated surgical access device adjacent a predesignated surgical site.

6. The system of claim 3, wherein the second joint is a sliding joint that slides axially along a length of the first arm member such and the second arm member is coupled to the second joint such that the second arm member is movable along with the second joint.

7. The system of claim 6, wherein the cannulated surgical access device is connected to the second arm member such that sliding the second joint along the first arm member correspondingly moves the cannulated surgical access device along the length of the first arm member.

8. The system of claim 1, wherein the bone fastener is a pedicle screw and the support arm extends posteriorly from the pedicle screw when the pedicle screw is in a vertebra.

9. The system of claim 1, wherein the surgical access device includes a connecting arm extending from the outer surface of one of the first and second blades.

10. The system of claim 9, wherein the surgical access device has first and second ends and the connecting arm is positioned between the first and second ends of the surgical access device.

11. The system of claim 1, wherein the first and second blades are moveable between a first configuration and a second configuration such that respective ends of the blades are positioned closer to each other in the first configuration than in the second configuration.

12. A surgical positioning system, comprising:
 a fastener configured to connect to a bony structure of a mammalian subject;
 a cannulated surgical access device having a sidewall defining a channel extending along a length of the cannulated surgical access device for accessing a surgical location through soft tissue with surgical tools; and
 a support arm having a plurality of connectors being moveably connected, a first connector of the plurality of connectors having a first arm member and being configured to connect to the fastener, a second connector of the plurality of connectors having a second arm member and being configured to connect to the cannulated surgical access device, the first arm member having a channel extending along the length thereof from a first end to a second end thereof for access of the fastener positioned at the second end of the first arm member,
 wherein the surgical access device is moveable in multiple degrees of freedom relative to the fastener upon relative movement of the arm members when the first connector is connected to the fastener, the fastener is connected to the bony structure, and the second connector is connected to the surgical access device, and
 wherein the channel of the cannulated surgical access device has a larger cross-sectional dimension than the channel of the first arm member and is sufficiently large allow passage of an interbody implant therethrough to a disc space for performing an interbody fusion procedure using the surgical access device, wherein the cannulated surgical access device has a longitudinal length substantially longer than the first connector.

13. The system of claim 12, wherein the fastener is a pedicle screw.

14. The system of claim 12, wherein the first and second arm members are connected to each other by a joint having at least two degrees of freedom.

15. A method of supporting a retractor positioned adjacent to a surgical site, comprising:
 connecting a support arm to a fastener that is connected to a first bony structure of a mammalian subject;
 connecting a retractor to the support arm;
 moving the retractor in multiple degrees of freedom relative to the fastener by manipulating arm members of the support arm to position the retractor in a predetermined location relative to the mammalian subject such that the retractor is positioned above a second bony structure without being connected thereto;
 retracting soft tissue over the predetermined location with the retractor;
 performing a surgical procedure on the mammalian subject through the retractor; and
 removing the support arm and retractor from the mammalian subject, wherein the retracting step includes moving blades of the retractor from a first configuration to a second configuration in which respective ends of the blades are positioned further from each other than in the first configuration.

16. The method of claim 15, further comprising:
 connecting the fastener to one of a vertebra and pelvic bone.

17. The method of claim 15, further comprising:
 locking the arm members relative to one another so as to hold the retractor in the predetermined location such that the retractor is supported by the support arm.

18. The method of claim 15, wherein connecting the support arm to the fastener includes connecting a first arm member of the arm members to the fastener such that the first arm member extends away from the first bony structure and a second arm member of the arm members extends transverse to the first arm member.

* * * * *